United States Patent
Ohkura et al.

(10) Patent No.: US 6,777,414 B1
(45) Date of Patent: Aug. 17, 2004

(54) NITROGEN-CONTAINING HETEROCYCLIC COMPOUNDS AND BENAMIDE COMPOUNDS AND DRUGS CONTAINING THE SAME

(75) Inventors: Naoto Ohkura, Yokohama (JP); Yukiko Hiraiwa, Yokohama (JP); Tetsuya Matsushima, Yokohama (JP); Kazue Sasaki, Yokohama (JP); Takehiro Yamamoto, Yokohama (JP); Masaharu Shiotani, Yokohama (JP); Shigeki Suzuki, Yokohama (JP); Yuuko Nakatani, Yokohama (JP); Chizuko Kuroda, Yokohama (JP); Mieko Nagasawa, Yokohama (JP); Kiyoaki Katano, Yokohama (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 0 days.

(21) Appl. No.: 09/958,296
(22) PCT Filed: Apr. 10, 2000
(86) PCT No.: PCT/JP00/02329
§ 371 (c)(1), (2), (4) Date: Oct. 5, 2001
(87) PCT Pub. No.: WO00/61556
PCT Pub. Date: Oct. 19, 2000

(30) Foreign Application Priority Data

Apr. 9, 1999 (JP) .......................... 11/102559
Apr. 26, 1999 (JP) .......................... 11/118490
Apr. 27, 1999 (JP) .......................... 11/119043

(51) Int. Cl.$^7$ .................. C07D 209/46; C07D 213/81; C07D 217/22; A61P 43/00; A61K 31/495
(52) U.S. Cl. .............................. 514/252.13; 514/254.11; 514/255.03; 544/375; 544/392; 544/393
(58) Field of Search ................. 514/252.13, 254.11, 514/255.03; 544/375, 392, 393

(56) References Cited

FOREIGN PATENT DOCUMENTS

| JP | 2000-502355 | 1/1999 |
| JP | 11-500442 | 2/2000 |
| WO | 96/26205 | 8/1996 |
| WO | 97/26240 | 7/1997 |

Primary Examiner—Bruck Kifle
(74) Attorney, Agent, or Firm—Wenderoth, Lind & Ponack, L.L.P.

(57) ABSTRACT

Disclosed are compounds represented by formula (I) which have triglyceride biosynthesis inhibitory activity in the liver and inhibitory activity against the secretion of apolipoprotein B-containing lipoprotein from the liver and particularly have excellent inhibitory activity against the secretion of apolipoprotein B-containing lipoprotein, are free from side effect of accumulation of lipids in the liver, and are useful for the treatment and prevention of hyperlipidemia and arteriosclerotic diseases. In formula (I), $R^1$ and $R^2$ represent alkyl, alkoxy, cycloalkyl, phenyl, alkenyl, alkynyl, or a five- or six-membered saturated or unsaturated heterocyclic ring, or $R^1$ and $R^2$, together with a nitrogen atom to which $R^1$ and $R^2$ are attached, may form a ring; $R^3$ and $R^4$ represent a hydrogen atom, alkyl, a halogen atom, hydroxyl, nitrile, alkoxycarbonyl, alkoxy, or carboxyl; or $R^2$ and $R^3$ may be attached to each other to form —$(CH_2)_m$—, —N=CH—, —CH=N—, or —$(C_{1-6}$ alkyl$)C$=N—; A, D, E, and G each represent a carbon atom, or any one of A, D, E, and G represents a nitrogen atom with the other three each representing a carbon atom; Q represents a nitrogen atom or a carbon atom; Y represents a group represented by formula (II) wherein X represents a hydrogen atom, group —C(=O)N($R^5$)$R^6$ or group —C(=O)O$R^7$, $R^8$ is absent or represents a bond, an oxygen atom, a sulfur atom, —$SO_2$—, —SO—, —$CH_2$—$CH_2$—, or —CH=CH—, and $R^9$ and $R^{10}$ represent a hydrogen atom, alkyl, alkoxy, a halogen atom, or hydroxyl; and Z represents —$(CH_2)_n$—, —O—$(CH_2)_i$—, or —C(=O)NH—$(CH_2)_i$—.

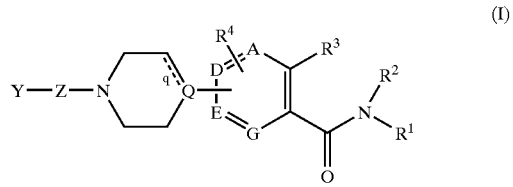

(I)

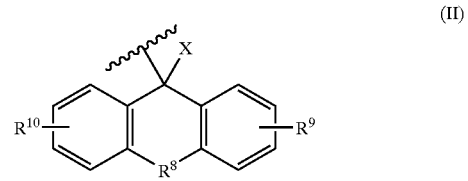

(II)

13 Claims, No Drawings

NITROGEN-CONTAINING HETEROCYCLIC COMPOUNDS AND BENAMIDE COMPOUNDS AND DRUGS CONTAINING THE SAME

This application is a 371 of PTC/JP00/02329 filed Apr. 10, 2000.

BACKGROUND OF THE INVENTION

1. Field of the Invention

The present invention relates to novel compounds having inhibitory activity against the biosynthesis of triglycerides and inhibitory activity against the secretion of apolipoprotein B-containing lipoproteins, and pharmaceuticals comprising the compounds as an active component, especially prophylactic or therapeutic agents for hyperlipidemia.

2. Background Art

A change in dietary habits and an increase in population of persons of advanced age has lead to an increase in arteriosclerotic diseases. An abnormal increase in the level of cholesterol and triglycerides which are serum lipids (hyperlipidemia) may be one major risk factor of this group of diseases. For example, the proportion of patients suffering from familial combined hyperlipidemia (FCHL) among patients suffering from cardiac infarction is about 30%, which is a higher frequency than the case of other underlying diseases. Furthermore, the familial combined hyperlipidemia (FCHL) is known as an underlying disease which has a high risk of onset of ischemic hear diseases (Lipid, 2, 373 (1991)).

Hyperlipidemia, which takes place with high frequency as the complication of obesity and diabetes mellitus, is also recognized as a risk factor of arteriosclerosis (Diabetes, 37, 1595 (1988) and Int. J. Obesity, 15, 1 (1991)).

Further, it is also known that among hyperlipidemia, hypertriglyceridemia leads to pancreatitis and the like (Medical Practice, 12, 957 (1995)).

Therefore, the treatment of hyperlipidemia is important for the prevention and treatment of arteriosclerotic diseases, such as ischemic hear diseases and cerebrovascular diseases. Further, it has been pointed out that there is a possibility that hyperlipidemia attended with renal diseases evolves the renal disorder (Molecular Medicine, 31, 536 (1994)). For this reason, the necessity of treating hyperlipidemia has been proposed.

For the treatment or prevention of hyperlipidemia and arteriosclerotic diseases, statin compounds, such as Lovastatin, as agents for inhibiting the biosynthesis of cholesterol, particularly as agents for inhibiting 3-hydroxy-3-methylglutaryl-coenzyme A reductase, and fibrate compounds, such as Bezafibrate, as agents for lowering the level of triglycerides, have been clinically used as pharmaceuticals.

Further, in recent years, reducing the level of triglycerides in serum and the level of apolipoprotein B-containing lipoprotein in serum, which is considered to induce arteriosclerosis, is expected to be useful for the prevention and treatment of the above diseases (Arterioscler. Thromb., 12, 1284 (1992) and Circulation, 85, 37 (1992)). One reason for this is that patients suffering from abetalipoproteinemia, in which apolipoprotein B-containing lipoprotein is not detected in blood, do not cause arteriosclerosis (Clin. Chem., 34, B9–12 (1988)).

Compounds known to have such activity include pyrrolecarboxylic acid derivatives, sulfonamide derivatives, phenylpiperazine derivatives, and biphenyl-2-carboxylic acid derivatives. Further, isoindolone derivatives having a substituent only in the nitrogen atom at the 2-position are also known (EP 643057 and WO 96/26205).

On the other hand, compounds having piperazine on the benzene ring in isoindolone and isoquinolone skeletons are known (WO 96/26187). These compounds, however, are different from the compounds of the present invention in the substituent of nitrogen at the 2-position and, in addition, acts as fibrinogen receptor antagonist. Thus, the above compounds are different from the compounds of the present invention in idea.

The present inventors have previously disclosed, in WO 98/54135, compounds which have piperazine on a benzene ring of isoindolone and isoquinolone skeletons and inhibit the secretion of apolipoprotain B-containing lipoprotein.

On the other hand, benzamide compounds are not known which have piperazine on a benzene ring and have two substituents other than a hydrogen atom on a nitrogen atom and, at the same time, inhibit the biosynthesis of triglycerides and inhibit the secretion of apolipoprotain B-containing lipoprotein.

Further, compounds having piperazine on a naphthyridinone skeleton are not also known. Furthermore, compounds are also not known which have piperazine on a pyridine skeleton and, in addition, have an N,N-di-substituted carbamoyl group.

Furthermore, compounds are not also known which have piperazine on naphthyridinone and pyridine skeletons and inhibit the secretion of apolipoprotein B-containing lipoproteins.

Agents, which have the activity of lowering serum triglyceride level and have the activity of lowering blood apolipoprotein B-containing lipoprotein level based on a new mechanism of action and, at the same time, do not cause, as side effect, the accumulation of some lipids within the liver which is found in abetalipoproteinemia, have been desired to be developed as prophylactic or therapeutic agents for hyperlipidemia or arteriosclerotic diseases (The Metabolic Basis of Inherited Disease, Sixth Edition, 1139 (1989)).

SUMMARY OF THE INVENTION

The present inventors disclose herein novel nitrogen-containing heterocyclic compounds, which have piperazine or piperidine on a benzene or pyridine ring of an isoindolone or isoquinolone skeleton and a skeleton similar to this skeleton, such as a quinazolinone, phthalazinone, or naphthyridinone skeleton, and further disclose benzamide compounds or amide-substituted pyridine compounds which have at least two substituents on a benzene or pyridine ring one of which is a substituent through piperazine or piperidine and another substituent is an amide having two substituents other than hydrogen atoms on the nitrogen atom. These compounds have high activity of lowering the blood triglyceride level and high activity of lowering the blood apolipoprotein B-containing lipoprotein level through high activity of lowering the blood lipid level, particularly inhibitory activity against the biosynthesis of triglycerides in the liver and inhibitory activity against the secretion of apolipoprotein B-containing lipoprotein from the liver, and are useful as therapeutic and prophylactic agents for hyperlipidemia and arteriosclerotic diseases.

Accordingly, an object of the present invention is to provide compounds which have inhibitory activity against the biosynthesis of triglycerides in the liver and, in addition, have inhibitory activity against the secretion of apolipoprotein B-containing lipoprotein from the liver, and are particularly excellent in inhibitory activity against the secretion of apolipoprotein B-containing lipoprotein, are free from the side effect of accumulation of the lipids within the liver. Thus, they are useful for the treatment and prevention of hyperlipidemia and arteriosclerotic diseases.

According to the present invention, there is provided a compound represented by formula (I) or a pharmacologically acceptable salt or solvate thereof:

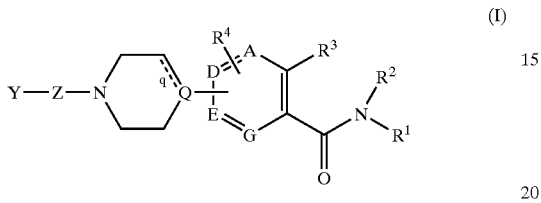

wherein $R^1$ and $R^2$, which may be the same or different, represent
optionally substituted alkyl having 1 to 6 carbon atoms,
optionally substituted alkoxy having 1 to 6 carbon atoms,
optionally substituted cycloalkyl having 3 to 8 carbon atoms,
optionally substituted phenyl,
optionally substituted alkenyl having 2 to 6 carbon atoms,
optionally substituted alkynyl having 2 to 6 carbon atoms, or
an optionally substituted five- or six-membered saturated or unsaturated heterocyclic ring containing not more than 2 hetero-atoms, or
$R^1$ and $R^2$, together with a nitrogen atom to which $R^1$ and $R^2$ are attached, may form a five- or six-membered monocyclic ring which may further contain one hetero-atom or may be substituted or an eight- to ten-membered condensed ring which may further contain one hetero-atom or may be substituted;
$R^3$ and $R^4$, which may be the same or different, represent
a hydrogen atom,
optionally substituted alkyl having 1 to 6 carbon atoms,
a halogen atom,
hydroxyl,
nitrile,
alkoxycarbonyl having 2 to 5 carbon atoms,
alkoxy having 1 to 6 carbon atoms, or
carboxyl, or
$R^2$ and $R^3$ may be attached to each other to form group —$(CH_2)_m$—, wherein m is 1 or 2, —N=CH—, —CH=N—, or —$(C_{1-6}$ alkyl$)$C=N—;
A, D, E, and G each represent a carbon atom, or any one of A, D, E, and G represents a nitrogen atom with the other three each representing a carbon atom,
Q represents a nitrogen atom or a carbon atom,
q, when Q represents a nitrogen atom, represents a single bond and, when Q represents a carbon atom, represents a single bond or a double bond;

Y represents a group represented by formula (II):

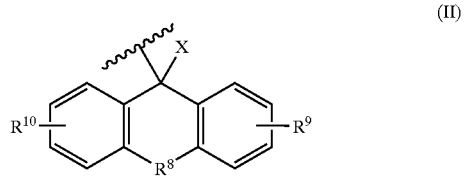

wherein
X represents a hydrogen atom; group —C(=O)N($R^5$)$R^6$ wherein $R^5$ and $R^6$, which may be the same or different, represent a hydrogen atom, optionally substituted alkyl having 1 to 6 carbon atoms, optionally substituted cycloalkyl having 3 to 8 carbon atoms, optionally substituted phenyl, optionally substituted alkenyl having 2 to 6 carbon atoms, or optionally substituted alkynyl having 2 to 6 carbon atoms; or group —C(=O)O$R^7$ wherein $R^7$ represents a hydrogen atom or optionally substituted alkyl having 1 to 6 carbon atoms,
$R^8$ is absent or represents a bond, an oxygen atom, a sulfur atom, —$SO_2$—, —SO—, —$CH_2$—$CH_2$—, or —CH=CH—, and
$R^9$ and $R^{10}$, which may be the same or different, represent a hydrogen atom, optionally substituted alkyl having 1 to 6 carbon atoms, alkoxy having 1 to 6 carbon atoms, a halogen atom, or hydroxyl; and
Z represents —$(CH_2)_n$—, wherein n is an integer of 0 to 6, —O—$(CH_2)_i$—, or —C(=O)NH—$(CH_2)_i$— wherein i is an integer of 1 to 6, excluding the case where
$R^2$ and $R^3$ are attached to each other to form group $(CH_2)_m$— wherein m is 1 or 2; A, D, E, and G each represent a carbon atom; Q represents a nitrogen atom; Y represents a group represented by formula (II) wherein X represents a hydrogen atom and $R^8$ is absent; and Z represents —$(CH_2)_n$—.

DETAILED DESCRIPTION OF THE INVENTION

Definition

As used herein, the term "alkyl" and the term "alkoxy" as a group or a part of a substituent respectively mean straight chain or branched chain alkyl and straight chain or branched chain alkoxy. Further, the term "aryl" as a group or a part of a substituent means a six- to fourteen-membered (mono- to tricyclic, preferably mono- or bicyclic) aromatic ring, such as phenyl, 1-naphthyl, 2-naphthyl, biphenyl, or 2-anthrylnaphthyl. The term "halogen atom" means a fluorine, chlorine, bromine, or iodine atom. The term "hetero-atom" means a nitrogen, oxygen, or sulfur atom.

Compounds of Formula (I)

In formula (I), alkyl having 1 to 6 carbon atoms represented by $R^1$, $R^2$, $R^3$, $R^4$, $R^5$, $R^6$, $R^7$, $R^9$, or $R^{10}$ is preferably alkyl having 1 to 4 carbon atoms. One or more hydrogen atoms on alkyl represented by $R^1$, $R^2$, $R^3$, $R^4$, $R^5$, $R^6$, $R^7$, $R^9$, or $R^{10}$ may be substituted. In this case, examples of substituents include: hydroxyl; halogen atoms, preferably fluorine, chlorine, and bromine atoms; amino; alkoxys having 1 to 6 carbon atoms, preferably methoxy and ethoxy; alkoxycarbonyls having 2 to 5 carbon atoms, preferably methoxycarbonyl and ethoxycarbonyl; $C_{3-8}$ cycloalkyls; phenyl; biphenyl; amino substituted by alkyl having 1 to 6, preferably 1 to 4, carbon atoms; and five- or six-membered saturated or unsaturated heteroaromatic rings containing one hetero-atom (preferably a nitrogen, oxygen, or sulfur atom), for example, tetrahydropyranyl, pyridyl, piperazinyl, furyl, and thienyl.

Alkoxy having 1 to 6 carbon atoms represented by $R^1$, $R^2$, $R^3$, $R^4$, $R^9$, or $R^{10}$ is preferably alkoxy having 1 to 4 carbon atoms. One or more hydrogen atoms on alkoxy represented by $R^1$, $R^2$, $R^3$, $R^4$, $R^9$, or $R^{10}$ may be substituted. In this case, examples of substituents include: hydroxyl; halogen atoms, preferably fluorine, chlorine, and bromine atoms; amino; alkoxys having 1 to 6 carbon atoms, preferably methoxy and ethoxy; alkoxycarbonyls having 2 to 5 carbon atoms, preferably methoxycarbonyl and ethoxycarbonyl; $C_{3-8}$ cycloalkyls; phenyl; biphenyl; amino substituted by alkyl having 1 to 6, preferably 1 to 4, carbon atoms; and five- or six-membered saturated or unsaturated heteroaromatic rings containing one hetero-atom (preferably a nitrogen, oxygen, or sulfur atom), for example, tetrahydropyranyl, pyridyl, piperazinyl, furyl, and thienyl.

Cycloalkyl having 3 to 8 carbon atoms represented by $R^1$, $R^2$, $R^5$ or $R^6$ is preferably cycloalkyl having 3 to 6 carbon atoms. One or more hydrogen atoms on cycloalkyl represented by $R^1$, $R^2$, $R^5$, or $R^6$ may be substituted. In this case, examples of substituents include: alkyls having 1 to 6 carbon atoms; hydroxyl; halogen atoms, preferably fluorine, chlorine, and bromine atoms; amino; alkoxys having 1 to 6 carbon atoms, preferably methoxy and ethoxy; alkoxycarbonyls having 2 to 5 carbon atoms, preferably methoxycarbonyl and ethoxycarbonyl; $C_{3-8}$ cycloalkyls; phenyl; benzyl; and alkylcarbonyloxys having 2 to 5 carbon atoms, preferably acetoxy and ethylcarbonyloxy.

One or more hydrogen atoms on phenyl represented by $R^1$, $R^2$, $R^5$, or $R^6$ may be substituted. In this case, examples of substituents include: alkyls having 1 to 6 carbon atoms; hydroxyl; halogen atoms, preferably fluorine, chlorine, and bromine atoms; amino; alkoxys having 1 to 6 carbon atoms, preferably methoxy and ethoxy; alkylcarbonyls having 2 to 5 carbon atoms, preferably acetyl and ethylcarbonyl; alkoxycarbonyls having 2 to 5 carbon atoms, preferably methoxycarbonyl and ethoxycarbonyl; $C_{3-8}$ cycloalkyls; phenyl; biphenyl; amino substituted by alkyl having 1 to 6, preferably 1 to 4, carbon atoms; five- or six-membered saturated or unsaturated heteroaromatic rings containing one hetero-atom (preferably a nitrogen, oxygen, or sulfur atom), for example, tetrahydropyranyl, pyridyl, piperazinyl, furyl, and thienyl; trifluoromethyl; and nitro.

Alkenyl having 2 to 6 carbon atoms represented by $R^1$, $R^2$, $R^5$, or $R^6$ is preferably alkenyl having 2 to 4 carbon atoms. One or more hydrogen atoms on alkenyl represented by $R^1$, $R^2$, $R^5$, or $R^6$ may be substituted. In this case, examples of substituents include: hydroxyl; halogen atoms, preferably fluorine, chlorine, and bromine atoms; amino; alkoxys having 1 to 6 carbon atoms, preferably methoxy and ethoxy, alkoxycarbonyls having 2 to 5 carbon atoms, preferably methoxycarbonyl and ethoxycarbonyl; $C_{3-8}$ cycloalkyls; phenyl; biphenyl; amino substituted by alkyl having 1 to 6, preferably 1 to 4, carbon atoms; and five- or six-membered saturated or unsaturated heteroaromatic rings containing one hetero-atom (preferably a nitrogen, oxygen, or sulfur atom), for example, tetrahydropyranyl, pyridyl, piperazinyl, furyl, and thienyl.

Alkynyl having 2 to 6 carbon atoms represented by $R^1$, $R^2$, $R^5$, or $R^6$ is preferably alkynyl having 2 to 4 carbon atoms. One or more hydrogen atoms on alkynyl represented by $R^1$, $R^2$, $R^5$, or $R^6$ may be substituted. In this case, examples of substituents include: hydroxyl; halogen atoms, preferably fluorine, chlorine, and bromine atoms; amino; alkoxy having 1 to 6 carbon atoms, preferably methoxy and ethoxy; alkoxycarbonyls having 2 to 5 carbon atoms, preferably methoxycarbonyl and ethoxycarbonyl; $C_{3-8}$ cycloalkyls; phenyl; biphenyl; amino substituted by alkyl having 1 to 6, preferably 1 to 4, carbon atoms; and five- or six-membered saturated or unsaturated heteroaromatic rings containing one hetero-atom (preferably a nitrogen, oxygen, or sulfur atom), for example, tetrahydropyranyl, pyridyl, piperazinyl, furyl, and thienyl.

The five- or six-membered saturated or unsaturated heterocyclic ring containing not more than two hetero-atoms represented by $R^1$ or $R^2$ is a ring selected from the group consisting of pyridine, thiophene, pyrrole, furan, pyrazole, imidazole, oxazole, thiazole, pyran, pyridazine, pyrimidine, pyrazine, and oxane, and preferred examples thereof include pyridine, thiophene, furan, imidazole, oxazole, thiazole, and oxane. One or more hydrogen atoms on the five- or six-membered saturated or unsaturated heterocyclic ring containing not more than two hetero-atoms represented by $R^1$ or $R^2$ may be substituted. In this case, examples of substituents include: alkyls having 1 to 6 carbon atoms; hydroxyl; halogen atoms, preferably fluorine, chlorine, and bromine atoms; amino; alkoxys having 1 to 6 carbon atoms, preferably methoxy and ethoxy; alkoxycarbonyls having 2 to 5 carbon atoms, preferably methoxycarbonyl and ethoxycarbonyl; $C_{3-8}$ cycloalkyls; and benzyl.

An example of the ring formed by $R^1$ and $R^2$ together with a nitrogen atom to which $R^1$ and $R^2$ are attached is a ring selected from the group consisting of piperazine, piperidine, and 3,4-dihydro-1H-isoquinolinone rings, and preferred examples thereof include piperidine and 3,4-dihydro-1H-isoquinolinone rings. One or more hydrogen atoms on this ring may be substituted. In this case, examples of substituents include: alkyls having 1 to 6 carbon atoms; hydroxyl; halogen atoms, preferably fluorine, chlorine, and bromine atoms; amino; alkoxys having 1 to 6 carbon atoms, preferably methoxy and ethoxy; alkoxycarbonyls having 2 to 5 carbon atoms, preferably methoxycarbonyl and ethoxycarbonyl; $C_{3-8}$ cycloalkyls; and benzyl.

The absence of $R^8$ in the group represented by formula (II) means that the group has a structure represented by formula

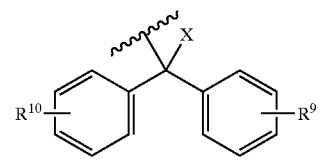

According to a preferred embodiment of the present invention, examples of preferred groups represented by $R^1$ or $R^2$ include optionally substituted alkyl having 1 to 6 carbon atoms, alkoxy having 1 to 6 carbon atoms, optionally substituted cycloalkyl having 3 to 8 carbon atoms, optionally substituted phenyl, optionally substituted alkenyl having 2 to 6 carbon atoms, optionally substituted alkynyl having 2 to 6 carbon atoms, or optionally substituted five- or six-membered saturated or unsaturated heterocyclic ring containing not more than two hetero-atoms, and five- or six-membered monocyclic or eight- to ten-membered condensed ring formed by $R^1$ and $R^2$ together with a nitrogen atom to which $R^1$ and $R^2$ are attached.

According to a preferred embodiment of the present invention, examples of preferred groups represented by $R^3$ or $R^4$ include a hydrogen atom, optionally substituted alkyl having 1 to 6 carbon atoms, a halogen atom, hydroxyl, nitrile, alkoxycarbonyl having 2 to 5 carbon atoms, alkoxy having 1 to 6 carbon atoms, and carboxyl.

The group formed by the combination of $R^2$ and $R^3$ together is preferably —$(CH_2)_m$—, wherein m is 1 or 2, or —N=CH—.

Preferably, A, D, E, and G each represent a carbon atom.

Q preferably represents a nitrogen atom.

Y is preferably a group represented by formula (II) wherein

X represents group —C(=O)N($R^5$)$R^6$ wherein $R^5$ and $R^6$, which may be the same or different, represent a hydrogen atom, optionally substituted alkyl having 1 to 6 carbon atoms, optionally substituted cycloalkyl having 3 to 8 carbon atoms, optionally substituted phenyl, optionally substituted alkenyl having 2 to 6 carbon atoms, or alkynyl having 2 to 6 carbon atoms, preferably a hydrogen atom or optionally substituted alkyl having 1 to 6 carbon atoms; $R^8$ represents a bond, an oxygen atom, a sulfur atom, —$SO_2$—, —SO—, —$CH_2$—$CH_2$—, or —CH=CH—, preferably a bond or an oxygen atom; and $R^9$ and $R^{10}$, which may be the same or different, represent a hydrogen atom, optionally substituted alkyl having 1 to 6 carbon atoms, alkoxy having 1 to 6 carbon atoms, a halogen atom, or hydroxyl, preferably a hydrogen atom or a halogen atom, or a group represented by formula (II) wherein X represents a hydrogen atom; $R^8$ is absent; $R^9$ and $R^{10}$, which may be the same or different, represent a hydrogen atom, optionally substituted alkyl having 1 to 6 carbon atoms, alkoxy having 1 to 6 carbon atoms, a halogen atom, or hydroxyl, preferably a hydrogen atom or a halogen atom.

Z preferably represents —$(CH_2)_n$— wherein n is an integer of 0 to 6.

Examples of preferred groups represented by group Y—Z— include optionally substituted carbamoyldibenzosuberanylalkyl, optionally substituted carbamoyldibenzosuberenylalkyl, optionally substituted carbamoylxanthenylalkyl, optionally substituted carbamoylthioxanthenylalkyl, and optionally substituted carbamoylfluorenylalkyl.

Compound Group A

Among the compounds represented by formula (I), a group of preferred compounds are those wherein $R^1$ represents optionally substituted alkyl having 1 to 6 carbon atoms, optionally substituted cycloalkyl having 3 to 8 carbon atoms, optionally substituted phenyl, optionally substituted alkenyl having 2 to 6 carbon atoms, or optionally substituted a five- or six-membered saturated or unsaturated heterocyclic ring containing not more than two hetero-atoms, $R^2$ and $R^3$ are attached to each other to represent group —$(CH_2)_m$— wherein m is 1 or 2, $R^4$ represents a hydrogen atom or a halogen atom, A, D, E, and G each represent a carbon atom, Q represents a nitrogen atom, q represents a single bond, Y represents a group represented by formula (II) wherein X represents group —C(=O)N($R^5$)$R^6$, wherein $R^5$ and $R^6$, which may be the same or different, represent a hydrogen atom, optionally substituted alkyl having 1 to 6 carbon atoms, optionally substituted cycloalkyl having 3 to 8 carbon atoms, optionally substituted phenyl, optionally substituted alkenyl having 2 to 6 carbon atoms, or alkynyl having 2 to 6 carbon atoms, or group —C(=O)O$R^7$ wherein $R^7$ represents a hydrogen atom or optionally substituted alkyl having 1 to 6 carbon atoms; $R^8$ is absent or represents a bond, an oxygen atom, a sulfur atom, —$SO_2$—, —SO—, —$CH_2$—$CH_2$—, or —CH=CH—; and $R^9$ and $R^{10}$, which may be the same or different, represent a hydrogen atom, optionally substituted alkyl having 1 to 6 carbon atoms, alkoxy having 1 to 6 carbon atoms, a halogen atom, or hydroxyl, and Z represents —$(CH_2)_n$—, wherein n is an integer of 0 to 6, —O—$(CH_2)_i$—, or —C(=O)NH—$(CH_2)_i$— wherein i is an integer of 1 to 6. A group of more preferred compounds are those wherein $R^1$ represents optionally substituted alkyl having 1 to 6 carbon atoms, cycloalkyl having 3 to 8 carbon atoms, phenyl, alkenyl having 2 to 6 carbon atoms, or optionally substituted a five- or six-membered saturated or unsaturated heterocyclic ring containing not more than two hetero-atoms, $R^2$ and $R^3$ are attached to each other to represent group —$(CH_2)_m$— wherein m is 1 or 2, $R^4$ represents a hydrogen atom or a halogen atom, A, D, E, and G each represent a carbon atom, Q represents a nitrogen atom, q represents a single bond, Y represents a group represented by formula (II) wherein X represents group —C(=O)N($R^5$)$R^6$, wherein $R^5$ and $R^6$, which may be the same or different, represent a hydrogen atom, optionally substituted alkyl having 1 to 6 carbon atoms or alkenyl having 2 to 6 carbon atoms; $R^8$ represents a bond, an oxygen atom, a sulfur atom, —$SO_2$—, —SO—, or —$CH_2$—$CH_2$—; and $R^9$ and $R^{10}$, which may be the same or different, represent a hydrogen atom or a halogen atom, Z represents —$(CH_2)_n$—, wherein n is an integer of 0 to 6, —O—$(CH_2)_i$—, or —C(=O)NH—$(CH_2)_i$— wherein i is an integer of 1 to 6, and Q and E are attached to each other.

Among these compounds, a group of still more preferred compounds are those wherein $R^1$ represents cycloalkyl having 5 or 6 carbon atoms or alkyl having 1 to 6 carbon atoms in which one or more hydrogen atoms on the alkyl may be substituted by phenyl or a five- or six-membered heteroaromatic ring containing one hetero-atom (preferably an oxygen or nitrogen atom).

Further, in formula (II) represented by Y, X preferably represents group —C(=O)N($R^5$)$R^6$ wherein $R^5$ represents a hydrogen atom and $R^6$ represents alkyl having 1 to 6 carbon atoms, preferably 1 to 4 carbon atoms, substituted by a halogen, preferably fluorine.

Z preferably represents —$(CH_2)_n$— wherein n is 3 or 4.

Compound Group B

Another group of preferred compounds according to the present invention are those wherein $R^1$ and $R^2$, which may be the same or different, represent optionally substituted alkyl having 1 to 6 carbon atoms,
optionally substituted alkoxy having 1 to 6 carbon atoms,
optionally substituted cycloalkyl having 3 to 8 carbon atoms,
optionally substituted phenyl,
optionally substituted alkenyl having 2 to 6 carbon atoms,
alkynyl having 2 to 6 carbon atoms, or
an optionally substituted five- or six-membered saturated or unsaturated heterocyclic ring containing not more than two hetero-atoms, or $R^1$ and $R^2$, together with a nitrogen atom to which $R^1$ and $R^2$ are attached, may form a five- or six-membered monocyclic ring which may further contain one hetero-atom or may be substituted or an eight- to ten-membered condensed ring which may further contain one hetero-atom or may be substituted;

$R^3$ and $R^4$, which may be the same or different, represent a hydrogen atom,
optionally substituted alkyl having 1 to 6 carbon atoms,
a halogen atom,
hydroxyl,
nitrile,
alkoxycarbonyl having 2 to 5 carbon atoms,
alkoxy having 1 to 6 carbon atoms, or
carboxyl, or $R^2$ and $R^3$ are attached to each other to represent group —N=CH—, —CH=N—, or —($C_{1-6}$ alkyl)C=N—;

A, D, E, and G each represent a carbon atom,
Q represents a nitrogen atom or a carbon atom,
q, when Q represents a nitrogen atom, represents a single bond and, when Q represents a carbon atom, represents a single bond or a double bond;
Y represents a group represented by formula (II) wherein X represents a hydrogen atom, group —C(=O)N($R^5$)$R^6$ wherein $R^5$ and $R^6$, which may be the same or different, represent a hydrogen atom, optionally substituted alkyl having 1 to 6 carbon atoms, optionally substituted cycloalkyl having 3 to 8 carbon atoms, optionally substituted phenyl, optionally substituted alkenyl having 2 to 6 carbon atoms, or alkynyl having 2 to 6 carbon atoms, or group —C(=O)O$R^7$ wherein $R^7$ represents a hydrogen atom or optionally substituted alkyl having 1 to 6 carbon atoms; $R^8$ is absent or represents a bond, an oxygen atom, a sulfur atom, —$SO_2$—, —SO—, —$CH_2$—$CH_2$—, or —CH=CH—; and $R^9$ and $R^{10}$, which may be the same or different, represent a hydrogen atom, optionally substituted alkyl having 1 to 6 carbon atoms, alkoxy having 1 to 6 carbon atoms, a halogen atom, or hydroxyl; and Z represents —$(CH_2)_n$— wherein n is an integer of 0 to 6.

A group of more preferred compounds are those wherein
$R^1$ represents optionally substituted alkyl having 1 to 6 carbon atoms,
optionally substituted cycloalkyl having 3 to 8 carbon atoms,
optionally substituted phenyl,
optionally substituted alkenyl having 2 to 6 carbon atoms,
alkynyl having 2 to 6 carbon atoms, or
an optionally substituted five- or six-membered saturated or unsaturated heterocyclic ring containing not more than two hetero-atoms, $R^2$ and $R^3$ are attached to each other to represent group —N=CH—, —CH=N—, or —($C_{1-6}$ alkyl)C=N—, $R^4$ represents a hydrogen atom,
optionally substituted alkyl having 1 to 6 carbon atoms,
a halogen atom,
hydroxyl,
nitrile,
alkoxycarbonyl having 2 to 5 carbon atoms,
alkoxy having 1 to 6 carbon atoms, or
carboxyl, A, D, E, and G each represent a carbon atom,
Q represents a nitrogen atom or a carbon atom,
q, when Q represents a nitrogen atom, represents a single bond and, when Q represents a carbon atom, represents a single bond or a double bond,
Y represents a group represented by formula (II) wherein X represents a hydrogen atom, group —C(=O)N($R^5$)$R^6$, wherein $R^5$ and $R^6$, which may be the same or different, represent a hydrogen atom, optionally substituted alkyl having 1 to 6 carbon atoms, optionally substituted cycloalkyl having 3 to 8 carbon atoms, optionally substituted phenyl, optionally substituted alkenyl having 2 to 6 carbon atoms, or alkynyl having 2 to 6 carbon atoms, or group —C(=O)O$R^7$ wherein $R^7$ represents a hydrogen atom or optionally substituted alkyl having 1 to 6 carbon atoms; $R^8$ is absent or represents a bond, an oxygen atom, a sulfur atom, —$SO_2$—, —SO—, —$CH_2$—$CH_2$—, or —CH=CH—; and $R^9$ and $R^{10}$, which may be the same or different, represent a hydrogen atom, optionally substituted alkyl having 1 to 6 carbon atoms, alkoxy having 1 to 6 carbon atoms, a halogen atom, or hydroxyl, and Z represents —$(CH_2)_n$—, wherein n is an integer of 0 to 6.

Among these compounds, a group of still more preferred compounds are those wherein Y is a group represented by formula (II) wherein $R^8$ is absent and X represents a hydrogen atom; and $R^3$ represents a hydrogen atom, a halogen atom, preferably a fluorine or chlorine atom, alkyl having 1 to 6 carbon atoms, preferably 1 to 4 carbon atoms, alkoxy having 1 to 6 carbon atoms, preferably 1 to 4 carbon atoms, or nitrile.

Another examples of still more preferred compounds are those wherein $R^1$ represents alkyl having 1 to 6 carbon atoms, preferably 1 to 4 carbon atoms, in which one or more hydrogen atoms on the alkyl may be substituted by a halogen atom (preferably a fluorine atom), phenyl (optionally substituted by phenyl optionally substituted by a halogen atom), a five- or six-membered saturated heteroaromatic ring containing one hetero-atom (preferably an oxygen atom), cycloalkyl having 5 or 6 carbon atoms, amino substituted by alkyl having 1 to 6 (preferably 1 to 4) carbon atoms, or a five- or six-membered saturated or unsaturated heteroaromatic ring (optionally substituted by benzyl) containing one hetero-atom (preferably a nitrogen atom), alkoxy having 1 to 6 carbon atoms, preferably 1 to 4 carbon atoms, alkenyl having 2 to 6 carbon atoms which may be substituted by phenyl, alkynyl having 2 to 6 carbon atoms, cycloalkyl having 3 to 8 carbon atoms, preferably 3 to 6 carbon atoms, in which one or more hydrogen atoms on the cycloalkyl may be substituted by hydroxyl, or phenyl in which one or more hydrogen atoms on the phenyl may be substituted by a halogen atom or alkyl having 1 to 6 carbon atoms, preferably 1 to 4 carbon atoms, or alkyl having 1 to 6 carbon atoms in which one or more hydrogen atoms on the alkyl may be substituted by phenyl, a five- or six-membered saturated heteroaromatic ring containing one hetero-atom, preferably an oxygen atom, or a five- or six-membered unsaturated heteroaromatic ring containing one hetero-atom, preferably a nitrogen atom.

Further examples of still more preferred compounds are those wherein $R^2$ and $R^3$ are attached to each other to represent group —N=CH—, —CH=N—, or —($C_{1-6}$ alkyl)C=N—; and, in formula (II) represented by Y, X represents a hydrogen atom or group —C(=O)N($R^5$)$R^6$ wherein $R^6$ represents a hydrogen atom and $R^6$ represents alkyl having 1 to 6 carbon atoms, preferably 1 to 4 carbon atoms, substituted by a halogen, preferably fluorine. Another examples of still more preferred compounds are those wherein $R^1$ represents alkyl having 1 to 6 carbon atoms in which one or more hydrogen atoms on the alkyl may be substituted by phenyl (optionally substituted by alkyl having 1 to 6 carbon atoms, preferably 1 to 4 carbon atoms, or a halogen atom); a five- or six-membered saturated heteroaromatic ring containing one hetero-atom, preferably an oxygen atom; or a five- or six-membered unsaturated heteroaromatic ring containing one hetero-atom, preferably a nitrogen atom.

Z preferably represents —($CH_2$)$_n$— wherein n is 3 or 4.

Another group of more preferred compounds are those wherein $R^1$ represents optionally substituted alkyl having 1 to 6 carbon atoms, optionally substituted cycloalkyl having 3 to 8 carbon atoms, optionally substituted phenyl, optionally substituted alkenyl having 2 to 6 carbon atoms, alkynyl having 2 to 6 carbon atoms, or an optionally substituted five- or six-membered saturated or unsaturated heterocyclic ring containing not more than two hetero-atoms, $R^2$ and $R^3$ are attached to each other to represent group —N=CH—, —CH=N—, or —($C_{1-6}$ alkyl)C=N—, $R^4$ represents a hydrogen atom, optionally substituted alkyl having 1 to 6 carbon atoms, a halogen atom, hydroxyl, nitrile, alkoxycarbonyl having 2 to 5 carbon atoms, alkoxy having 1 to 6 carbon atoms, or carboxyl, A, D, E, and G each represent a carbon atom, Q represents a nitrogen atom or a carbon atom, q, when Q represents a nitrogen atom, represents a single bond and, when Q represents a carbon atom, represents a single bond or a double bond, Y represents a group represented by formula (II)

wherein

X represents group —C(=O)N($R^5$)$R^6$ wherein $R^5$ and $R^6$, which may be the same or different, represent a hydrogen atom, optionally substituted alkyl having 1 to 6 carbon atoms, optionally substituted cycloalkyl having 3 to 8 carbon atoms, optionally substituted phenyl, optionally substituted alkenyl having 2 to 6 carbon atoms, or alkynyl having 2 to 6 carbon atoms;

$R^8$ represents a bond, an oxygen atom, a sulfur atom, —$SO_2$—, —SO—, —$CH_2$—$CH_2$—, or —CH=CH—; and $R^9$ and $R^{10}$, which may be the same or different, represent a hydrogen atom, optionally substituted alkyl having 1 to 6 carbon atoms, alkoxy having 1 to 6 carbon atoms, a halogen atom, or hydroxyl, and Z represents —($CH_2$)$_n$— wherein n is an integer of 0 to 6.

Still another examples of more preferred compounds are those wherein $R^1$ and $R^2$, which may be the same or different, represent optionally substituted alkyl having 1 to 6 carbon atoms, alkoxy, optionally substituted cycloalkyl having 3 to 8 carbon atoms, optionally substituted phenyl, optionally substituted alkenyl having 2 to 6 carbon atoms, alkynyl having 2 to 6 carbon atoms, or $R^1$ and $R^2$, together with a nitrogen atom to which $R^1$ and $R^2$ are attached, may form a five- or six-membered monocyclic ring which may further contain one heteroatom or may be substituted or an eight- to ten-membered condensed ring which may further contain one hetero-atom or may be substituted;

$R^3$ and $R^4$, which may be the same or different, represent a hydrogen atom, optionally substituted alkyl having 1 to 6 carbon atoms, a halogen atom, hydroxyl, nitrile, alkoxycarbonyl having 2 to 5 carbon atoms, alkoxy having 1 to 6 carbon atoms, or carboxyl, or $R^2$ and $R^3$ are attached to each other to represent group —N=CH—, —CH=N—, or —($C_{1-6}$ alkyl)C=N—;

A, D, E, and G each represent a carbon atom,

Q represents a nitrogen atom or a carbon atom, q, when Q represents a nitrogen atom, represents a single bond and, when Q represents a carbon atom, represents a single bond or a double bond;

Y represents a group represented by formula (II)

wherein

X represents a hydrogen atom, group —C(=O)N($R^5$) $R^6$ wherein $R^5$ and $R^6$, which may be the same or different, represent a hydrogen atom, optionally substituted alkyl having 1 to 6 carbon atoms, or group —C(=O)O$R^7$ wherein $R^7$ represents a hydrogen atom or alkyl having 1 to 6 carbon atoms; $R^8$ is absent or represents a bond or an oxygen atom; and $R^9$ and $R^{10}$, which may be the same or different, represent a hydrogen atom or a halogen atom; and Z represents —$(CH_2)_n$— wherein n is an integer of 0 to 6.

Compound Group C

Still another group of preferred compounds according to the present invention are those wherein $R^1$ and $R^2$, which may be the same or different, represent optionally substituted alkyl having 1 to 6 carbon atoms, optionally substituted alkoxy having 1 to 6 carbon atoms, optionally substituted cycloalkyl having 3 to 8 carbon atoms, optionally substituted phenyl, optionally substituted alkenyl having 2 to 6 carbon atoms, alkynyl having 2 to 6 carbon atoms, or an optionally substituted five- or six-membered saturated or unsaturated heterocyclic ring containing not more than two hetero-atoms, or $R^1$ and $R^2$, together with a nitrogen atom to which $R^1$ and $R^2$ are attached, may form a five- or six-membered monocyclic ring which may further contain one hetero-atom or may be substituted or an eight- to ten-membered condensed ring which may further contain one hetero-atom or may be substituted;

$R^3$ and $R^4$, which may be the same or different, represent a hydrogen atom, optionally substituted alkyl having 1 to 6 carbon atoms, a halogen atom, hydroxyl, nitrile, alkoxycarbonyl having 2 to 5 carbon atoms, alkoxy having 1 to 6 carbon atoms, or carboxyl;

A, D, E, and G each represent a carbon atom,

Q represents a nitrogen atom or a carbon atom, q, when Q represents a nitrogen atom, represents a single bond and, when Q represents a carbon atom, represents a single bond or a double bond;

Y represents a group represented by formula (II) wherein

X represents group —$C(=O)N(R^5)R^6$ wherein $R^5$ and $R^6$, which may be the same or different, represent a hydrogen atom, optionally substituted alkyl having 1 to 6 carbon atoms, optionally substituted cycloalkyl having 3 to 8 carbon atoms, optionally substituted phenyl, optionally substituted alkenyl having 2 to 6 carbon atoms, or alkynyl having 2 to 6 carbon atoms;

$R^8$ represents a bond, an oxygen atom, a sulfur atom, —$SO_2$—, —$SO$—, —$CH_2$—$CH_2$—, or —$CH=CH$—; and $R^9$ and $R^{10}$, which may be the same or different, represent a hydrogen atom, optionally substituted alkyl having 1 to 6 carbon atoms, alkoxy having 1 to 6 carbon atoms, a halogen atom, or hydroxyl; and Z represents —$(CH_2)_n$— wherein n is an integer of 0 to 6.

Among these compounds, a group of more preferred compounds are those wherein $R^1$ represents alkyl having 1 to 6 carbon atoms, preferably 1 to 4 carbon atoms, in which one or more hydrogen atoms on the alkyl may be substituted by phenyl, cycloalkyl having 5 or 6 carbon atoms, or a five- or six-membered saturated or unsaturated heteroaromatic ring containing one hetero-atom, preferably a nitrogen, oxygen, or sulfur atom, alkenyl having 2 to 6 carbon atoms, or cycloalkyl having 3 to 8 carbon atoms, preferably 5 or 6 carbon atoms.

Z preferably represents —$(CH_2)_n$— wherein n is 3 or 4.

Compound Group D

A further group of preferred compounds according to the present invention are those wherein $R^1$ and $R^2$, which may be the same or different, represent optionally substituted alkyl having 1 to 6 carbon atoms, optionally substituted alkoxy having 1 to 6 carbon atoms, optionally substituted cycloalkyl having 3 to 8 carbon atoms, optionally substituted phenyl, optionally substituted alkenyl having 2 to 6 carbon atoms, alkynyl having 2 to 6 carbon atoms, or an optionally substituted five- or six-membered saturated or unsaturated heterocyclic ring containing not more than two hetero-atoms, or $R^1$ and $R^2$, together with a nitrogen atom to which $R^1$ and $R^2$ are attached, may form a five- or six-membered monocyclic ring which may further contain one hetero-atom or may be substituted or an eight- to ten-membered condensed ring which may further contain one hetero-atom or may be substituted;

$R^3$ and $R^4$, which may be the same or different, represent a hydrogen atom, optionally substituted alkyl having 1 to 6 carbon atoms, a halogen atom, hydroxyl, nitrile, alkoxycarbonyl having 2 to 5 carbon atoms, alkoxy having 1 to 6 carbon atoms, or carboxyl;

A, D, E, and G each represent a carbon atom,

Q represents a nitrogen atom or a carbon atom, q, when Q represents a nitrogen atom, represents a single bond and, when Q represents a carbon atom, represents a single bond or a double bond;

Y represents a group represented by formula (II) wherein

X represents a hydrogen atom; $R^8$ is absent; $R^9$ and $R^{10}$, which may be the same or different, represent a hydrogen atom, optionally substituted alkyl having 1 to 6 carbon atoms, alkoxy having 1 to 6 carbon atoms, a halogen atom, or hydroxyl; and Z represents —$(CH_2)_n$— wherein n is an integer of 0 to 6.

Among these compounds, a group of more preferred compounds are those wherein $R^1$ represents alkyl having 1 to 6 carbon atoms, preferably 1 to 4 carbon atoms, in which one or more hydrogen atoms on the alkyl may be substituted by a halogen atom (preferably a fluorine atom), phenyl (optionally substituted by phenyl optionally substituted by a halogen atom), a five- or six-membered saturated heteroaromatic ring containing one hetero-atom (preferably an oxygen atom), cycloalkyl having 5 or 6 carbon atoms, amino substituted by alkyl having 1 to 6 (preferably 1 to 4) carbon atoms, or a five- or six-membered saturated or unsaturated heteroaromatic ring (optionally substituted by benzyl) containing one hetero-atom (preferably a nitrogen atom), alkoxy having 1 to 6 carbon atoms, preferably 1 to 4 carbon atoms, alkenyl having 2 to 6 carbon atoms which may be substituted by phenyl, alkynyl having 2 to 6 carbon atoms, cycloalkyl having 3 to 8 carbon atoms, preferably 3 to 6 carbon atoms, in which one or more hydrogen atoms on the cycloalkyl may be substituted by hydroxyl, or phenyl in which one or more hydrogen atoms on the phenyl may be substituted by a halogen atom or alkyl having 1 to 6 carbon atoms, preferably 1 to 4 carbon atoms, or alkyl having 1 to 6 carbon atoms in which one or more hydrogen atoms on the alkyl may be substituted by phenyl, a five- or six-membered saturated heteroaromatic ring containing one hetero-atom, preferably an oxygen atom, or a five- or six-membered unsaturated heteroaromatic ring containing one hetero-atom, preferably a nitrogen atom.

Compound Group E

Another group of preferred compounds according to the present invention are those wherein $R^1$ and $R^2$, which may be the same or different, represent optionally substituted alkyl having 1 to 6 carbon atoms, alkoxy, optionally substituted cycloalkyl having 3 to 8 carbon atoms, optionally substituted phenyl, optionally substituted alkenyl having 2 to 6 carbon atoms, alkynyl having 2 to 6 carbon atoms, or an optionally substituted five- or six-membered saturated or unsaturated heterocyclic ring containing not more than two hetero-atoms, or $R^1$ and $R^2$, together with a nitrogen atom to which $R^1$ and $R^2$ are attached, may form a five- or six-membered monocyclic ring which may further contain one hetero-atom or may be substituted or an eight- to ten-membered condensed ring which may further contain one hetero-atom or may be substituted;

$R^3$ and $R^4$, which may be the same or different, represent a hydrogen atom, optionally substituted alkyl having 1 to 6 carbon atoms, a halogen atom, hydroxyl, nitrile, alkoxycarbonyl having 2 to 5 carbon atoms, alkoxy having 1 to 6 carbon atoms, or carboxyl, or $R^2$ and $R^3$ are attached to each other to represent group —N=CH—, —CH=N—, or —($C_{1-6}$ alkyl)C=N—;

any one of A, D, E, and G represents a nitrogen atom with the other three each representing a carbon atom, Q represents a nitrogen atom or a carbon atom, q, when Q represents a nitrogen atom, represents a single bond and, when Q represents a carbon atom, represents a single bond or a double bond;

Y represents a group represented by formula (II) wherein

X represents a hydrogen atom, group —C(=O)N($R^5$)$R^6$ wherein $R^5$ and $R^6$, which may be the same or different, represent a hydrogen atom, optionally substituted alkyl having 1 to 6 carbon atoms, or group —C(=O)O$R^7$ wherein $R^7$ represents a hydrogen atom or alkyl having 1 to 6 carbon atoms; $R^8$ is absent or represents a bond or an oxygen atom; and $R^9$ and $R^{10}$, which may be the same or different, represent a hydrogen atom or a halogen atom; and Z represents —$(CH_2)_n$— wherein n is an integer of 0 to 6.

A group of more preferred compounds are those wherein $R^1$ and $R^2$, which may be the same or different, represent optionally substituted alkyl having 1 to 6 carbon atoms, optionally substituted alkoxy having 1 to 6 carbon atoms, optionally substituted cycloalkyl having 3 to 8 carbon atoms, or optionally substituted alkenyl having 2 to 6 carbon atoms;

$R^3$ and $R^4$, which may be the same or different, represent a hydrogen atom, optionally substituted alkyl having 1 to 6 carbon atoms, or a halogen atom, or $R^2$ and $R^3$ are attached to each other to represent group —$(CH_2)_m$— wherein m is 1 or 2;

any one of A, D, E, and G represents a nitrogen atom with the other three each representing a carbon atom;

Q represents a nitrogen atom;

q represents a single bond;

Y represents a group represented by formula (II) wherein

X represents a hydrogen atom or group —C(=O)N($R^5$)$R^6$ wherein $R^5$ and $R^6$, which may be the same or different, represent a hydrogen atom, optionally substituted alkyl having 1 to 6 carbon atoms, optionally substituted cycloalkyl having 3 to 8 carbon atoms, optionally substituted phenyl, optionally substituted alkenyl having 2 to 6 carbon atoms, or alkynyl having 2 to 6 carbon atoms; $R^8$ is absent or represents a bond or an oxygen atom; and $R^9$ and $R^{10}$, which may be the same or different, represent a hydrogen atom, optionally substituted alkyl having 1 to 6 carbon atoms, alkoxy having 1 to 6 carbon atoms, a halogen atom, or hydroxyl; and Z represents —$(CH_2)_n$— wherein n is an integer of 0 to 6.

Still more preferred compounds are those wherein $R^1$ and $R^2$, which may be the same or different, represent optionally substituted alkyl having 1 to 6 carbon atoms, alkoxy having 1 to 6 carbon atoms, cycloalkyl having 3 to 8 carbon atoms, or alkenyl having 2 to 6 carbon atoms;

$R^3$ and $R^4$, which may be the same or different, represent a hydrogen atom, alkyl having 1 to 6 carbon atoms, or a halogen atom, or $R^2$ and $R^3$ are attached to each other to represent group —$(CH_2)_m$— wherein m is 1 or 2;

any one of A, D, E, and G represents a nitrogen atom with the other three each representing a carbon atom;

Q represents a nitrogen atom;

q represents a single bond;

Y represents a group represented by formula (II) wherein

X represents a hydrogen atom or group —C(=O)N($R^5$)$R^6$ wherein $R^5$ and $R^6$, which may be the same or different, represent a hydrogen atom or optionally substituted alkyl having 1 to 6 carbon atoms; $R^8$ is absent or represents a bond or an oxygen atom; and $R^9$ and $R^{10}$ each represent a hydrogen atom; and Z represents —$(CH_2)_n$— wherein n is an integer of 0 to 6.

Among these compounds, a group of more preferred compounds are those wherein $R^1$ represents alkyl having 1 to 6 carbon atoms, preferably 1 to 4 carbon atoms, in which one or more hydrogen atoms on the alkyl may be substituted by a halogen atom (preferably a fluorine atom), phenyl (optionally substituted by phenyl optionally substituted by a halogen atom), a five- or six-membered saturated heteroaromatic ring containing one hetero-atom (preferably an oxygen atom), cycloalkyl having 5 or 6 carbon atoms, amino substituted by alkyl having 1 to 6 (preferably 1 to 4) carbon atoms, or a five- or six-membered saturated or unsaturated heteroaromatic ring (optionally substituted by benzyl) containing one hetero-atom (preferably a nitrogen atom), alkoxy having 1 to 6 carbon atoms, preferably 1 to 4 carbon atoms, alkenyl having 2 to 6 carbon atoms which may be substituted by phenyl, alkynyl having 2 to 6 carbon atoms, cycloalkyl having 3 to 8 carbon atoms, preferably 3 to 6 carbon atoms, in which one or more hydrogen atoms on the cycloalkyl may be substituted by hydroxyl, phenyl in which one or more hydrogen atoms on the phenyl may be substituted by a halogen atom or alkyl having 1 to 6 carbon atoms, preferably 1 to 4 carbon atoms, or alkyl having 1 to 6 carbon atoms in which one or more hydrogen atoms on the alkyl may be substituted by phenyl, a five- or six-membered saturated heteroaromatic ring containing one hetero-atom, preferably an oxygen atom, or a five- or six-membered unsaturated heteroaromatic ring containing one hetero-atom, preferably a nitrogen atom.

In the case of compounds where any one of A, D, E, and G represents a nitrogen atom with the other three each representing a carbon atom, Y preferably represents a group represented by formula (II) wherein $R^8$ is absent. Further, $R^1$ preferably represents alkyl having 1 to 6 carbon atoms, preferably 1 to 4 carbon atoms in which one or more hydrogen atoms on the alkyl may be substituted by phenyl, alkenyl having 2 to 6 carbon atoms, or cycloalkyl having 3 to 8 carbon atoms, preferably 5 or 6 carbon atoms.

Z is preferably —$(CH_2)_n$— wherein n is 2.

Specific examples of preferred compounds represented by formula (I) include 2-cyclohexyl-6-[4-[4-[9-(2,2,2-trifluoroethylcarbamoyl)-9H-fluoren-9-yl]butyl]piperazin-1-yl]-2,3-dihydro-1H-isoindol-1-one, 2-cyclohexyl-6-[4-[3-[9-(2,2,2-trifluoroethylcarbamoyl)-9H-fluoren-9-yl]propyl]piperazin-1-yl]-2,3-dihydro-1H-isoindol-1-one, 2-cyclohexyl-6-[4-[4-[9-(2,2,2-trifluoroethylcarbamoyl)-9H-xanthen-9-yl]butyl]piperazin-1-yl]-2,3-dihydro-1H-isoindol-1-one, 2-cyclohexyl-6-[4-[3-[9-(2,2,2-trifluoroethylcarbamoyl)-9H-xanthen-9-yl]propyl]piperazin-1-yl]-2,3-dihydro-1H-isoindol-1-one, 2-cyclohexyl-6-[4-[4-[9-(2,2,2-trifluoroethylcarbamoyl)-9H-thioxanthen-9-yl]butyl]piperazin-1-yl]-2,3-dihydro-1H-isoindol-1-one, 2-cyclohexyl-6-[4-[3-[9-(2,2,2-trifluoroethylcarbamoyl)-9H-thioxanthen-9-yl]propyl]piperazin-1-yl]-2,3-dihydro-1H-isoindol-1-one, 2-cyclohexyl-6-[4-[4-(9-ethylcarbamoyl-9H-fluoren-9-yl)butyl]piperazin-1-yl]-2,3-dihydro-1H-isoindol-1-one, 2-cyclohexyl-6-[4-[3-(9-ethylcarbamoyl-9H-fluoren-9-yl)propyl]piperazin-1-yl]-2,3-dihydro-1H-isoindol-1-one, 2-cyclohexyl-6-[4-[4-(9-ethylcarbamoyl-9H-xanthen-9-yl)butyl]piperazin-1-yl]-2,3-dihydro-1H-isoindol-1-one, 2-cyclohexyl-6-[4-[3-(9-ethylcarbamoyl-9H-xanthen-9-yl)propyl]piperazin-1-yl]-2,3-dihydro-1H-isoindol-1-one, 2-cyclohexyl-6-[4-[4-(9-ethylcarbamoyl-9H-thioxanthen-9-yl)butyl]piperazin-1-yl]-2,3-dihydro-1H-isoindol-1-one, 2-cyclohexyl-6-[4-[3-(9-ethylcarbamoyl-9H-thioxanthen-9-yl)propyl]piperazin-1-yl]-2,3-dihydro-1H-isoindol-1-one, 2-(tetrahydropyran-2-yl)methyl-6-[4-[4-[9-(2,2,2-trifluoroethylcarbamoyl)-9H-fluoren-9-yl]butyl]piperazin-1-yl]-2,3-dihydro-1H-isoindol-1-one, 2-(tetrahydropyran-2-yl)methyl-6-[4-[3-[9-(2,2,2-trifluoroethylcarbamoyl)-9H-fluoren-9-yl]propyl]piperazin-1-yl]-2,3-dihydro-1H-isoindol-1-one, 2-(tetrahydropyran-2-yl)methyl-6-[4-[4-[9-(2,2,2-trifluoroethylcarbamoyl)-9H-xanthen-9-yl]butyl]piperazin-1-yl]-2,3-dihydro-1H-isoindol-1-one, 2-(tetrahydropyran-2-yl)methyl-6-[4-[3-[9-(2,2,2-trifluoroethylcarbamoyl)-9H-xanthen-9-yl]propyl]piperazin-1-yl]-2,3-dihydro-1H-isoindol-1-one, 2-(tetrahydropyran-2-yl)methyl-6-[4-[4-[9-(2,2,2-trifluoroethylcarbamoyl)-9H-thioxanthen-9-yl]butyl]piperazin-1-yl]-2,3-dihydro-1H-isoindol-1-one, 2-(tetrahydropyran-2-yl)methyl-6-[4-[3-[9-(2,2,2-trifluoroethylcarbamoyl)-9H-thioxanthen-9-yl]propyl]piperazin-1-yl]-2,3-dihydro-1H-isoindol-1-one, 6-[4-[4-(9-ethylcarbamoyl-9H-fluoren-9-yl)butyl]piperazin-1-yl]-2-(tetrahydropyran-2-yl)methyl-2,3-dihydro-1H-isoindol-1-one, 6-[4-[3-(9-ethylcarbamoyl-9H-fluoren-9-yl)propyl]piperazin-1-yl]-2-(tetrahydropyran-2-yl)methyl-2,3-dihydro-1H-isoindol-1-one, 6-[4-[4-(9-ethylcarbamoyl-9H-xanthen-9-yl)butyl]piperazin-1-yl]-2-(tetrahydropyran-2-yl)methyl-2,3-dihydro-1H-isoindol-1-one, 6-[4-[3-(9-ethylcarbamoyl-9H-xanthen-9-yl)propyl]piperazin-1-yl]-2-(tetrahydropyran-2-yl)methyl-2,3-dihydro-1H-isoindol-1-one, 6-[4-[4-(9-ethylcarbamoyl-9H-thioxanthen-9-yl)butyl]
piperazin-1-yl]-2-(tetrahydropyran-2-yl)methyl-2,3-
dihydro-1H-isoindol-1-one, 6-[4-[3-(9-ethylcarbamoyl-9H-thioxanthen-9-yl)propyl]
piperazin-1-yl]-2-(tetrahydropyran-2-yl)methyl-2,3-
dihydro-1H-isoindol-1-one, 2-benzyl-6-[4-[4-[9-(2,2,2-trifluoroethylcarbamoyl)-9H-
fluoren-9-yl]butyl]piperazin-1-yl]-2,3-dihydro-1H-
isoindol-1-one, 2-benzyl-6-[4-[3-[9-(2,2,2-trifluoroethylcarbamoyl)-9H-
fluoren-9-yl]propyl]piperazin-1-yl]-2,3-dihydro-1H-
isoindol-1-one, 2-benzyl-6-[4-[4-[9-(2,2,2-trifluoroethylcarbamoyl)-9H-
xanthen-9-yl]butyl]piperazin-1-yl]-2,3-dihydro-1H-
isoindol-1-one, 2-benzyl-6-[4-[3-[9-(2,2,2-trifluoroethylcarbamoyl)-9H-
xanthen-9-yl]propyl]piperazin-1-yl]-2,3-dihydro-1H-
isoindol-1-one, 2-benzyl-6-[4-[4-[9-(2,2,2-trifluoroethylcarbamoyl)-9H-
thioxanthen-9-yl]butyl]piperazin-1-yl]-2,3-dihydro-
1H-isoindol-1-one, 2-benzyl-6-[4-[3-[9-(2,2,2-trifluoroethylcarbamoyl)-9H-
thioxanthen-9-yl]propyl]piperazin-1-yl]-2,3-dihydro-
1H-isoindol-1-one, 2-benzyl-6-[4-[4-(9-ethylcarbamoyl-9H-fluoren-9-yl)
butyl]piperazin-1-yl]-2,3-dihydro-1H-isoindol-1-one, 2-benzyl-6-[4-[3-(9-ethylcarbamoyl-9H-fluoren-9-yl)
propyl]piperazin-1-yl]-2,3-dihydro-1H-isoindol-1-one, 2-benzyl-6-[4-[4-(9-ethylcarbamoyl-9H-xanthen-9-yl)
butyl]piperazin-1-yl]-2,3-dihydro-1H-isoindol-1-one, 2-benzyl-6-[4-[3-(9-ethylcarbamoyl-9H-xanthen-9-yl)
propyl]piperazin-1-yl]-2,3-dihydro-1H-isoindol-1-one, 2-benzyl-6-[4-[4-(9-ethylcarbamoyl-9H-thioxanthen-9-
yl)butyl]piperazin-1-yl]-2,3-dihydro-1H-isoindol-1-
one, 2-benzyl-6-[4-[3-(9-ethylcarbamoyl-9H-thioxanthen-9-
yl)propyl]piperazin-1-yl]-2,3-dihydro-1H-isoindol-1-
one, 2-(3-fluorobenzyl)-6-[4-[4-[9-(2,2,2-
trifluoroethylcarbamoyl)-9H-fluoren-9-yl]butyl]
piperazin-1-yl]-2,3-dihydro-1H-isoindol-1-one, 2-(3-fluorobenzyl)-6-[4-[3-[9-(2,2,2-
trifluoroethylcarbamoyl)-9H-fluoren-9-yl]propyl]
piperazin-1-yl]-2,3-dihydro-1H-isoindol-1-one, 2-(3-fluorobenzyl)-6-[4-[4-[9-(2,2,2-
trifluoroethylcarbamoyl)-9H-xanthen-9-yl]butyl]
piperazin-1-yl]-2,3-dihydro-1H-isoindol-1-one, 2-(3-fluorobenzyl)-6-[4-[3-[9-(2,2,2-
trifluoroethylcarbamoyl)-9H-xanthen-9-yl]propyl]
piperazin-1-yl]-2,3-dihydro-1H-isoindol-1-one, 2-(3-fluorobenzyl)-6-[4-[4-[9-(2,2,2-
trifluoroethylcarbamoyl)-9H-thioxanthen-9-yl]butyl]
piperazin-1-yl]-2,3-dihydro-1H-isoindol-1-one, 2-(3-fluorobenzyl)-6-[4-[3-[9-(2,2,2-
trifluoroethylcarbamoyl)-9H-thioxanthen-9-yl]propyl]
piperazin-1-yl]-2,3-dihydro-1H-isoindol-1-one, 6-[4-[4-(9-ethylcarbamoyl-9H-fluoren-9-yl)butyl]
piperazin-1-yl]-2-(3-fluorobenzyl)-2,3-dihydro-1H-
isoindol-1-one, 6-[4-[3-(9-ethylcarbamoyl-9H-fluoren-9-yl)propyl]
piperazin-1-yl]-2-(3-fluorobenzyl)-2,3-dihydro-1H-
isoindol-1-one, 6-[4-[4-(9-ethylcarbamoyl-9H-xanthen-9-yl)butyl]
piperazin-1-yl]-2-(3-fluorobenzyl)-2,3-dihydro-1H-
isoindol-1-one, 6-[4-[3-(9-ethylcarbamoyl-9H-xanthen-9-yl)propyl]
piperazin-1-yl]-2-(3-fluorobenzyl)-2,3-dihydro-1H-
isoindol-1-one, 6-[4-[4-(9-ethylcarbamoyl-9H-thioxanthen-9-yl)butyl]
piperazin-1-yl]-2-(3-fluorobenzyl)-2,3-dihydro-1H-
isoindol-1-one, 6-[4-[3-(9-ethylcarbamoyl-9H-thioxanthen-9-yl)propyl]
piperazin-1-yl]-2-(3-fluorobenzyl)-2,3-dihydro-1H-
isoindol-1-one, 2-(3-chlorobenzyl)-6-[4-[4-[9-(2,2,2-
trifluoroethylcarbamoyl)-9H-fluoren-9-yl]butyl]
piperazin-1-yl]-2,3-dihydro-1H-isoindol-1-one, 2-(3-chlorobenzyl)-6-[4-[3-[9-(2,2,2-
trifluoroethylcarbamoyl)-9H-fluoren-9-yl]propyl]
piperazin-1-yl]-2,3-dihydro-1H-isoindol-1-one, 2-(3-chlorobenzyl)-6-[4-[4-[9-(2,2,2-
trifluoroethylcarbamoyl)-9H-xanthen-9-yl]butyl]
piperazin-1-yl]-2,3-dihydro-1H-isoindol-1-one, 2-(3-chlorobenzyl)-6-[4-[3-[9-(2,2,2-
trifluoroethylcarbamoyl)-9H-xanthen-9-yl]propyl]
piperazin-1-yl]-2,3-dihydro-1H-isoindol-1-one, 2-(3-chlorobenzyl)-6-[4-[4-[9-(2,2,2-
trifluoroethylcarbamoyl)-9H-thioxanthen-9-yl]butyl]
piperazin-1-yl]-2,3-dihydro-1H-isoindol-1-one, 2-(3-chlorobenzyl)-6-[4-[3-[9-(2,2,2-
trifluoroethylcarbamoyl)-9H-thioxanthen-9-yl]propyl]
piperazin-1-yl]-2,3-dihydro-1H-isoindol-1-one, 2-(3-chlorobenzyl)-6-[4-[4-(9-ethylcarbamoyl-9H-
fluoren-9-yl)butyl]piperazin-1-yl]-2,3-dihydro-1H-
isoindol-1-one, 2-(3-chlorobenzyl)-6-[4-[3-(9-ethylcarbamoyl-9H-
fluoren-9-yl)propyl]piperazin-1-yl]-2,3-dihydro-1H-
isoindol-1-one, 2-(3-chlorobenzyl)-6-[4-[4-(9-ethylcarbamoyl-9H-
xanthen-9-yl)butyl]piperazin-1-yl]-2,3-dihydro-1H-
isoindol-1-one, 2-(3-chlorobenzyl)-6-[4-[3-(9-ethylcarbamoyl-9H-
xanthen-9-yl)propyl]piperazin-1-yl]-2,3-dihydro-1H-
isoindol-1-one, 2-(3-chlorobenzyl)-6-[4-[4-(9-ethylcarbamoyl-9H-
thioxanthen-9-yl)butyl]piperazin-1-yl]-2,3-dihydro-
1H-isoindol-1-one, 2-(3-chlorobenzyl)-6-[4-[3-(9-ethylcarbamoyl-9H-
thioxanthen-9-yl)propyl]piperazin-1-yl]-2,3-dihydro-
1H-isoindol-1-one, 2-(3-methoxybenzyl)-6-[4-[4-[9-(2,2,2-
trifluoroethylcarbamoyl)-9H-fluoren-9-yl]butyl]
piperazin-1-yl]-2,3-dihydro-1H-isoindol-1-one, 2-(3-methoxybenzyl)-6-[4-[3-[9-(2,2,2-
trifluoroethylcarbamoyl)-9H-fluoren-9-yl]propyl]
piperazin-1-yl]-2,3-dihydro-1H-isoindol-1-one, 2-(3-methoxybenzyl)-6-[4-[4-[9-(2,2,2-
trifluoroethylcarbamoyl)-9H-xanthen-9-yl]butyl]
piperazin-1-yl]-2,3-dihydro-1H-isoindol-1-one, 2-(3-methoxybenzyl)-6-[4-[3-[9-(2,2,2-
trifluoroethylcarbamoyl)-9H-xanthen-9-yl]propyl]
piperazin-1-yl]-2,3-dihydro-1H-isoindol-1-one, 2-(3-methoxybenzyl)-6-[4-[4-[9-(2,2,2-
trifluoroethylcarbamoyl)-9H-thioxanthen-9-yl]butyl]
piperazin-1-yl]-2,3-dihydro-1H-isoindol-1-one, 2-(3-methoxybenzyl)-6-[4-[3-[9-(2,2,2-
trifluoroethylcarbamoyl)-9H-thioxanthen-9-yl]propyl]
piperazin-1-yl]-2,3-dihydro-1H-isoindol-1-one, 6-[4-[4-(9-ethylcarbamoyl-9H-fluoren-9-yl)butyl]
piperazin-1-yl]-2-(3-methoxybenzyl)-2,3-dihydro-1H-
isoindol-1-one, 6-[4-[3-(9-ethylcarbamoyl-9H-fluoren-9-yl)propyl]
piperazin-1-yl]-2-(3-methoxybenzyl)-2,3-dihydro-1H-
isoindol-1-one, 6-[4-[4-(9-ethylcarbamoyl-9H-xanthen-9-yl)butyl]
piperazin-1-yl]-2-(3-methoxybenzyl)-2,3-dihydro-1H-
isoindol-1-one, 6-[4-[3-(9-ethylcarbamoyl-9H-xanthen-9-yl)propyl]
piperazin-1-yl]-2-(3-methoxybenzyl)-2,3-dihydro-1H-
isoindol-1-one, 6-[4-[4-(9-ethylcarbamoyl-9H-thioxanthen-9-yl)butyl]
piperazin-1-yl]-2-(3-methoxybenzyl)-2,3-dihydro-1H-
isoindol-1-one, 6-[4-[3-(9-ethylcarbamoyl-9H-thioxanthen-9-yl)propyl]
piperazin-1-yl]-2-(3-methoxybenzyl)-2,3-dihydro-1H-
isoindol-1-one, 2-(3-methylbenzyl)-6-[4-[4-[9-(2,2,2-
trifluoroethylcarbamoyl)-9H-fluoren-9-yl]butyl]
piperazin-1-yl]-2,3-dihydro-1H-isoindol-1-one, 2-(3-methylbenzyl)-6-[4-[3-[9-(2,2,2-
trifluoroethylcarbamoyl)-9H-fluoren-9-yl]propyl]
piperazin-1-yl]-2,3-dihydro-1H-isoindol-1-one, 2-(3-methylbenzyl)-6-[4-[4-[9-(2,2,2-
trifluoroethylcarbamoyl)-9H-xanthen-9-yl]butyl]
piperazin-1-yl]-2,3-dihydro-1H-isoindol-1-one, 2-(3-methylbenzyl)-6-[4-[3-[9-(2,2,2-
trifluoroethylcarbamoyl)-9H-xanthen-9-yl]propyl]
piperazin-1-yl]-2,3-dihydro-1H-isoindol-1-one, 2-(3-methylbenzyl)-6-[4-[4-[9-(2,2,2-
trifluoroethylcarbamoyl)-9H-thioxanthen-9-yl]butyl]
piperazin-1-yl]-2,3-dihydro-1H-isoindol-1-one, 2-(3-methylbenzyl)-6-[4-[3-[9-(2,2,2-
trifluoroethylcarbamoyl)-9H-thioxanthen-9-yl]propyl]
piperazin-1-yl]-2,3-dihydro-1H-isoindol-1-one, 6-[4-[4-(9-ethylcarbamoyl-9H-fluoren-9-yl)butyl]
piperazin-1-yl]-2-(3-methylbenzyl)-2,3-dihydro-1H-
isoindol-1-one, 6-[4-[3-(9-ethylcarbamoyl-9H-fluoren-9-yl)propyl]
piperazin-1-yl]-2-(3-methylbenzyl)-2,3-dihydro-1H-
isoindol-1-one, 6-[4-[4-(9-ethylcarbamoyl-9H-xanthen-9-yl)butyl]
piperazin-1-yl]-2-(3-methylbenzyl)-2,3-dihydro-1H-
isoindol-1-one, 6-[4-[3-(9-ethylcarbamoyl-9H-xanthen-9-yl)propyl]
piperazin-1-yl]-2-(3-methylbenzyl)-2,3-dihydro-1H-
isoindol-1-one, 6-[4-[4-(9-ethylcarbamoyl-9H-thioxanthen-9-yl)butyl]
piperazin-1-yl]-2-(3-methylbenzyl)-2,3-dihydro-1H-
isoindol-1-one, 6-[4-[3-(9-ethylcarbamoyl-9H-thioxanthen-9-yl)propyl]
piperazin-1-yl]-2-(3-methylbenzyl)-2,3-dihydro-1H-
isoindol-1-one, 2-(α-methylbenzyl)-6-[4-[4-[9-(2,2,2-
trifluoroethylcarbamoyl)-9H-fluoren-9-yl]butyl]
piperazin-1-yl]-2,3-dihydro-1H-isoindol-1-one, 2-(α-methylbenzyl)-6-[4-[3-[9-(2,2,2-
trifluoroethylcarbamoyl)-9H-fluoren-9-yl]propyl]
piperazin-1-yl]-2,3-dihydro-1H-isoindol-1-one, 2-(α-methylbenzyl)-6-[4-[4-[9-(2,2,2-
trifluoroethylcarbamoyl)-9H-xanthen-9-yl]butyl]
piperazin-1-yl]-2,3-dihydro-1H-isoindol-1-one, 2-(α-methylbenzyl)-6-[4-[3-[9-(2,2,2-
trifluoroethylcarbamoyl)-9H-xanthen-9-yl]propyl]
piperazin-1-yl]-2,3-dihydro-1H-isoindol-1-one, 2-(α-methylbenzyl)-6-[4-[4-[9-(2,2,2-
trifluoroethylcarbamoyl)-9H-thioxanthen-9-yl]butyl]
piperazin-1-yl]-2,3-dihydro-1H-isoindol-1-one, 2-(α-methylbenzyl)-6-[4-[3-[9-(2,2,2-
trifluoroethylcarbamoyl)-9H-thioxanthen-9-yl]propyl]
piperazin-1-yl]-2,3-dihydro-1H-isoindol-1-one, 6-[4-[4-(9-ethylcarbamoyl-9H-fluoren-9-yl)butyl]
piperazin-1-yl]-2-(α-methylbenzyl)-2,3-dihydro-1H-
isoindol-1-one, 6-[4-[3-(9-ethylcarbamoyl-9H-fluoren-9-yl)propyl]
piperazin-1-yl]-2-(α-methylbenzyl)-2,3-dihydro-1H-
isoindol-1-one, 6-[4-[4-(9-ethylcarbamoyl-9H-xanthen-9-yl)butyl]
piperazin-1-yl]-2-(α-methylbenzyl)-2,3-dihydro-1H-
isoindol-1-one, 6-[4-[3-(9-ethylcarbamoyl-9H-xanthen-9-yl)propyl]
piperazin-1-yl]-2-(α-methylbenzyl)-2,3-dihydro-1H-
isoindol-1-one, 6-[4-[4-(9-ethylcarbamoyl-9H-thioxanthen-9-yl)butyl]
piperazin-1-yl]-2-(α-methylbenzyl)-2,3-dihydro-1H-
isoindol-1-one, 6-[4-[3-(9-ethylcarbamoyl-9H-thioxanthen-9-yl)propyl]
piperazin-1-yl]-2-(α-methylbenzyl)-2,3-dihydro-1H-
isoindol-1-one, 2-cyclohexyl-7-[4-[4-[9-(2,2,2-trifluoroethylcarbamoyl)-
9H-fluoren-9-yl]butyl]piperazin-1-yl]-3,4-dihydro-
2H-isoquinolin-1-one, 2-cyclohexyl-7-[4-[3-[9-(2,2,2-trifluoroethylcarbamoyl)-
9H-fluoren-9-yl]propyl]piperazin-1-yl]-3,4-dihydro-
2H-isoquinolin-1-one, 2-cyclohexyl-7-[4-[4-[9-(2,2,2-trifluoroethylcarbamoyl)-
9H-xanthen-9-yl]butyl]piperazin-1-yl]-3,4-dihydro-
2H-isoquinolin-1-one, 2-cyclohexyl-7-[4-[3-[9-(2,2,2-trifluoroethylcarbamoyl)-
9H-xanthen-9-yl]propyl]piperazin-1-yl]-3,4-dihydro-
2H-isoquinolin-1-one, 2-cyclohexyl-7-[4-[4-[9-(2,2,2-trifluoroethylcarbamoyl)-
9H-thioxanthen-9-yl]butyl]piperazin-1-yl]-3,4-
dihydro-2H-isoquinolin-1-one, 2-cyclohexyl-7-[4-[3-[9-(2,2,2-trifluoroethylcarbamoyl)-
9H-thioxanthen-9-yl]propyl]piperazin-1-yl]-3,4-
dihydro-2H-isoquinolin-1-one, 2-cyclohexyl-7-[4-[4-(9-ethylcarbamoyl-9H-fluoren-9-
yl)butyl]piperazin-1-yl]-3,4-dihydro-2H-isoquinolin-
1-one, 2-cyclohexyl-7-[4-[3-(9-ethylcarbamoyl-9H-fluoren-9-
yl)propyl]piperazin-1-yl]-3,4-dihydro-2H-isoquinolin-
1-one, 2-cyclohexyl-7-[4-[4-(9-ethylcarbamoyl-9H-xanthen-9-
yl)butyl]piperazin-1-yl]-3,4-dihydro-2H-isoquinolin-
1-one, 2-cyclohexyl-7-[4-[3-(9-ethylcarbamoyl-9H-xanthen-9-
yl)propyl]piperazin-1-yl]-3,4-dihydro-2H-isoquinolin-
1-one, 2-cyclohexyl-7-[4-[4-(9-ethylcarbamoyl-9H-
thioxanthen-9-yl)butyl]piperazin-1-yl]-3,4-dihydro-
2H-isoquinolin-1-one, 2-cyclohexyl-7-[4-[3-(9-ethylcarbamoyl-9H-
thioxanthen-9-yl)propyl]piperazin-1-yl]-3,4-dihydro-
2H-isoquinolin-1-one, 2-(tetrahydropyran-2-yl)methyl-7-[4-[4-[9-(2,2,2-trifluoroethylcarbamoyl)-9H-fluoren-9-yl]butyl]piperazin-1-yl]-3,4-dihydro-2H-isoquinolin-1-one, 2-(tetrahydropyran-2-yl)methyl-7-[4-[3-[9-(2,2,2-trifluoroethylcarbamoyl)-9H-fluoren-9-yl]propyl]piperazin-1-yl]-3,4-dihydro-2H-isoquinolin-1-one, 2-(tetrahydropyran-2-yl)methyl-7-[4-[4-[9-(2,2,2-trifluoroethylcarbamoyl)-9H-xanthen-9-yl]butyl]piperazin-1-yl]-3,4-dihydro-2H-isoquinolin-1-one, 2-(tetrahydropyran-2-yl)methyl-7-[4-[3-[9-(2,2,2-trifluoroethylcarbamoyl)-9H-xanthen-9-yl]propyl]piperazin-1-yl]-3,4-dihydro-2H-isoquinolin-1-one, 2-(tetrahydropyran-2-yl)methyl-7-[4-[4-[9-(2,2,2-trifluoroethylcarbamoyl)-9H-thioxanthen-9-yl]butyl]piperazin-1-yl]-3,4-dihydro-2H-isoquinolin-1-one, 2-(tetrahydropyran-2-yl)methyl-7-[4-[3-[9-(2,2,2-trifluoroethylcarbamoyl)-9H-thioxanthen-9-yl]propyl]piperazin-1-yl]-3,4-dihydro-2H-isoquinolin-1-one, 7-[4-[4-(9-ethylcarbamoyl-9H-fluoren-9-yl)butyl]piperazin-1-yl]-2-(tetrahydropyran-2-yl)methyl-3,4-dihydro-2H-isoquinolin-1-one, 7-[4-[3-(9-ethylcarbamoyl-9H-fluoren-9-yl)propyl]piperazin-1-yl]-2-(tetrahydropyran-2-yl)methyl-3,4-dihydro-2H-isoquinolin-1-one, 7-[4-[4-(9-ethylcarbamoyl-9H-xanthen-9-yl)butyl]piperazin-1-yl]-2-(tetrahydropyran-2-yl)methyl-3,4-dihydro-2H-isoquinolin-1-one, 7-[4-[3-(9-ethylcarbamoyl-9H-xanthen-9-yl)propyl]piperazin-1-yl]-2-(tetrahydropyran-2-yl)methyl-3,4-dihydro-2H-isoquinolin-1-one, 7-[4-[4-(9-ethylcarbamoyl-9H-thioxanthen-9-yl)butyl]piperazin-1-yl]-2-(tetrahydropyran-2-yl)methyl-3,4-dihydro-2H-isoquinolin-1-one, 7-[4-[3-(9-ethylcarbamoyl-9H-thioxanthen-9-yl)propyl]piperazin-1-yl]-2-(tetrahydropyran-2-yl)methyl-3,4-dihydro-2H-isoquinolin-1-one, 2-benzyl-7-[4-[4-[9-(2,2,2-trifluoroethylcarbamoyl)-9H-fluoren-9-yl]butyl]piperazin-1-yl]-3,4-dihydro-2H-isoquinolin-1-one, 2-benzyl-7-[4-[3-[9-(2,2,2-trifluoroethylcarbamoyl)-9H-fluoren-9-yl]propyl]piperazin-1-yl]-3,4-dihydro-2H-isoquinolin-1-one, 2-benzyl-7-[4-[4-[9-(2,2,2-trifluoroethylcarbamoyl)-9H-xanthen-9-yl]butyl]piperazin-1-yl]-3,4-dihydro-2H-isoquinolin-1-one, 2-benzyl-7-[4-[3-[9-(2,2,2-trifluoroethylcarbamoyl)-9H-xanthen-9-yl]propyl]piperazin-1-yl]-3,4-dihydro-2H-isoquinolin-1-one, 2-benzyl-7-[4-[4-[9-(2,2,2-trifluoroethylcarbamoyl)-9H-thioxanthen-9-yl]butyl]piperazin-1-yl]-3,4-dihydro-2H-isoquinolin-1-one, 2-benzyl-7-[4-[3-[9-(2,2,2-trifluoroethylcarbamoyl)-9H-thioxanthen-9-yl]propyl]piperazin-1-yl]-3,4-dihydro-2H-isoquinolin-1-one, 2-benzyl-7-[4-[4-(9-ethylcarbamoyl-9H-fluoren-9-yl)butyl]piperazin-1-yl]-3,4-dihydro-2H-isoquinolin-1-one, 2-benzyl-7-[4-[3-(9-ethylcarbamoyl-9H-fluoren-9-yl)propyl]piperazin-1-yl]-3,4-dihydro-2H-isoquinolin-1-one, 2-benzyl-7-[4-[4-(9-ethylcarbamoyl-9H-xanthen-9-yl)butyl]piperazin-1-yl]-3,4-dihydro-2H-isoquinolin-1-one, 2-benzyl-7-[4-[3-(9-ethylcarbamoyl-9H-xanthen-9-yl)propyl]piperazin-1-yl]-3,4-dihydro-2H-isoquinolin-1-one, 2-benzyl-7-[4-[4-(9-ethylcarbamoyl-9H-thioxanthen-9-yl)butyl]piperazin-1-yl]-3,4-dihydro-2H-isoquinolin-1-one, 2-benzyl-7-[4-[3-(9-ethylcarbamoyl-9H-thioxanthen-9-yl)propyl]piperazin-1-yl]-3,4-dihydro-2H-isoquinolin-1-one, 2-(3-fluorobenzyl)-7-[4-[4-[9-(2,2,2-trifluoroethylcarbamoyl)-9H-fluoren-9-yl]butyl]piperazin-1-yl]-3,4-dihydro-2H-isoquinolin-1-one, 2-(3-fluorobenzyl)-7-[4-[3-[9-(2,2,2-trifluoroethylcarbamoyl)-9H-fluoren-9-yl]propyl]piperazin-1-yl]-3,4-dihydro-2H-isoquinolin-1-one, 2-(3-fluorobenzyl)-7-[4-[4-[9-(2,2,2-trifluoroethylcarbamoyl)-9H-xanthen-9-yl]butyl]piperazin-1-yl]-3,4-dihydro-2H-isoquinolin-1-one, 2-(3-fluorobenzyl)-7-[4-[3-[9-(2,2,2-trifluoroethylcarbamoyl)-9H-xanthen-9-yl]propyl]piperazin-1-yl]-3,4-dihydro-2H-isoquinolin-1-one, 2-(3-fluorobenzyl)-7-[4-[4-[9-(2,2,2-trifluoroethylcarbamoyl)-9H-thioxanthen-9-yl]butyl]piperazin-1-yl]-3,4-dihydro-2H-isoquinolin-1-one, 2-(3-fluorobenzyl)-7-[4-[3-[9-(2,2,2-trifluoroethylcarbamoyl)-9H-thioxanthen-9-yl]propyl]piperazin-1-yl]-3,4-dihydro-2H-isoquinolin-1-one, 7-[4-[4-(9-ethylcarbamoyl-9H-fluoren-9-yl)butyl]piperazin-1-yl]-2-(3-fluorobenzyl)-3,4-dihydro-2H-isoquinolin-1-one, 7-[4-[3-(9-ethylcarbamoyl-9H-fluoren-9-yl)propyl]piperazin-1-yl]-2-(3-fluorobenzyl)-3,4-dihydro-2H-isoquinolin-1-one, 7-[4-[4-(9-ethylcarbamoyl-9H-xanthen-9-yl)butyl]piperazin-1-yl]-2-(3-fluorobenzyl)-3,4-dihydro-2H-isoquinolin-1-one, 7-[4-[3-(9-ethylcarbamoyl-9H-xanthen-9-yl)propyl]piperazin-1-yl]-2-(3-fluorobenzyl)-3,4-dihydro-2H-isoquinolin-1-one, 7-[4-[4-(9-ethylcarbamoyl-9H-thioxanthen-9-yl)butyl]piperazin-1-yl]-2-(3-fluorobenzyl)-3,4-dihydro-2H-isoquinolin-1-one, 7-[4-[3-(9-ethylcarbamoyl-9H-thioxanthen-9-yl)propyl]piperazin-1-yl]-2-(3-fluorobenzyl)-3,4-dihydro-2H-isoquinolin-1-one, 2-(3-chlorobenzyl)-7-[4-[4-[9-(2,2,2-trifluoroethylcarbamoyl)-9H-fluoren-9-yl]butyl]piperazin-1-yl]-3,4-dihydro-2H-isoquinolin-1-one, 2-(3-chlorobenzyl)-7-[4-[3-[9-(2,2,2-trifluoroethylcarbamoyl)-9H-fluoren-9-yl]propyl]piperazin-1-yl]-3,4-dihydro-2H-isoquinolin-1-one, 2-(3-chlorobenzyl)-7-[4-[4-[9-(2,2,2-trifluoroethylcarbamoyl)-9H-xanthen-9-yl]butyl]piperazin-1-yl]-3,4-dihydro-2H-isoquinolin-1-one, 2-(3-chlorobenzyl)-7-[4-[3-[9-(2,2,2-trifluoroethylcarbamoyl)-9H-xanthen-9-yl]propyl]piperazin-1-yl]-3,4-dihydro-2H-isoquinolin-1-one, 2-(3-chlorobenzyl)-7-[4-[4-[9-(2,2,2-trifluoroethylcarbamoyl)-9H-thioxanthen-9-yl]butyl]piperazin-1-yl]-3,4-dihydro-2H-isoquinolin-1-one, 2-(3-chlorobenzyl)-7-[4-[3-[9-(2,2,2-trifluoroethylcarbamoyl)-9H-thioxanthen-9-yl]propyl]piperazin-1-yl]-3,4-dihydro-2H-isoquinolin-1-one, 2-(3-chlorobenzyl)-7-[4-[4-(9-ethylcarbamoyl-9H-fluoren-9-yl)butyl]piperazin-1-yl]-3,4-dihydro-2H-isoquinolin-1-one, 2-(3-chlorobenzyl)-7-[4-[3-(9-ethylcarbamoyl-9H-fluoren-9-yl)propyl]piperazin-1-yl]-3,4-dihydro-2H-isoquinolin-1-one, 2-(3-chlorobenzyl)-7-[4-[4-(9-ethylcarbamoyl-9H-xanthen-9-yl)butyl]piperazin-1-yl]-3,4-dihydro-2H-isoquinolin-1-one, 2-(3-chlorobenzyl)-7-[4-[3-(9-ethylcarbamoyl-9H-xanthen-9-yl)propyl]piperazin-1-yl]-3,4-dihydro-2H-isoquinolin-1-one, 2-(3-chlorobenzyl)-7-[4-[4-(9-ethylcarbamoyl-9H-thioxanthen-9-yl)butyl]piperazin-1-yl]-3,4-dihydro-2H-isoquinolin-1-one, 2-(3-chlorobenzyl)-7-[4-[3-(9-ethylcarbamoyl-9H-thioxanthen-9-yl)propyl]piperazin-1-yl]-3,4-dihydro-2H-isoquinolin-1-one, 2-(3-methoxybenzyl)-7-[4-[4-[9-(2,2,2-trifluoroethylcarbamoyl)-9H-fluoren-9-yl]butyl]piperazin-1-yl]-3,4-dihydro-2H-isoquinolin-1-one, 2-(3-methoxybenzyl)-7-[4-[3-[9-(2,2,2-trifluoroethylcarbamoyl)-9H-fluoren-9-yl]propyl]piperazin-1-yl]-3,4-dihydro-2H-isoquinolin-1-one, 2-(3-methoxybenzyl)-7-[4-[4-[9-(2,2,2-trifluoroethylcarbamoyl)-9H-xanthen-9-yl]butyl]piperazin-1-yl]-3,4-dihydro-2H-isoquinolin-1-one, 2-(3-methoxybenzyl)-7-[4-[3-[9-(2,2,2-trifluoroethylcarbamoyl)-9H-xanthen-9-yl]propyl]piperazin-1-yl]-3,4-dihydro-2H-isoquinolin-1-one, 2-(3-methoxybenzyl)-7-[4-[4-[9-(2,2,2-trifluoroethylcarbamoyl)-9H-thioxanthen-9-yl]butyl]piperazin-1-yl]-3,4-dihydro-2H-isoquinolin-1-one, 2-(3-methoxybenzyl)-7-[4-[3-[9-(2,2,2-trifluoroethylcarbamoyl)-9H-thioxanthen-9-yl]propyl]piperazin-1-yl]-3,4-dihydro-2H-isoquinolin-1-one, 7-[4-[4-(9-ethylcarbamoyl-9H-fluoren-9-yl)butyl]piperazin-1-yl]-2-(3-methoxybenzyl)-3,4-dihydro-2H-isoquinolin-1-one, 7-[4-[3-(9-ethylcarbamoyl-9H-fluoren-9-yl)propyl]piperazin-1-yl]-2-(3-methoxybenzyl)-3,4-dihydro-2H-isoquinolin-1-one, 7-[4-[4-(9-ethylcarbamoyl-9H-xanthen-9-yl)butyl]piperazin-1-yl]-2-(3-methoxybenzyl)-3,4-dihydro-2H-isoquinolin-1-one, 7-[4-[3-(9-ethylcarbamoyl-9H-xanthen-9-yl)propyl]piperazin-1-yl]-2-(3-methoxybenzyl)-3,4-dihydro-2H-isoquinolin-1-one, 7-[4-[4-(9-ethylcarbamoyl-9H-thioxanthen-9-yl)butyl]piperazin-1-yl]-2(3-methoxybenzyl)-3,4-dihydro-2H-isoquinolin-1-one, 7-[4-[3-(9-ethylcarbamoyl-9H-thioxanthen-9-yl)propyl]piperazin-1-yl]-2-(3-methoxybenzyl)-3,4-dihydro-2H-isoquinolin-1-one, 2-(3-methylbenzyl)-7-[4-[4-[9-(2,2,2-trifluoroethylcarbamoyl)-9H-fluoren-9-yl]butyl]piperazin-1-yl]-3,4-dihydro-2H-isoquinolin-1-one, 2-(3-methylbenzyl)-7-[4-[3-[9-(2,2,2-trifluoroethylcarbamoyl)-9H-fluoren-9-yl]propyl]piperazin-1-yl]-3,4-dihydro-2H-isoquinolin-1-one, 2-(3-methylbenzyl)-7-[4-[4-[9-(2,2,2-trifluoroethylcarbamoyl)-9H-xanthen-9-yl]butyl]piperazin-1-yl]-3,4-dihydro-2H-isoquinolin-1-one, 2-(3-methylbenzyl)-7-[4-[3-[9-(2,2,2-trifluoroethylcarbamoyl)-9H-xanthen-9-yl]propyl]piperazin-1-yl]-3,4-dihydro-2H-isoquinolin-1-one, 2-(3-methylbenzyl)-7-[4-[4-[9-(2,2,2-trifluoroethylcarbamoyl)-9H-thioxanthen-9-yl]butyl]piperazin-1-yl]-3,4-dihydro-2H-isoquinolin-1-one, 2-(3-methylbenzyl)-7-[4-[3-[9-(2,2,2-trifluoroethylcarbamoyl)-9H-thioxanthen-9-yl]propyl]piperazin-1-yl]-3,4-dihydro-2H-isoquinolin-1-one, 7-[4-[4-(9-ethylcarbamoyl-9H-fluoren-9-yl)butyl]piperazin-1-yl]-2-(3-methylbenzyl)-3,4-dihydro-2H-isoquinolin-1-one, 7-[4-[3-(9-ethylcarbamoyl-9H-fluoren-9-yl)propyl]piperazin-1-yl]-2-(3-methylbenzyl)-3,4-dihydro-2H-isoquinolin-1-one, 7-[4-[4-(9-ethylcarbamoyl-9H-xanthen-9-yl)butyl]piperazin-1-yl]-2-(3-methylbenzyl)-3,4-dihydro-2H-isoquinolin-1-one, 7-[4-[3-(9-ethylcarbamoyl-9H-xanthen-9-yl)propyl]piperazin-1-yl]-2-(3-methylbenzyl)-3,4-dihydro-2H-isoquinolin-1-one, 7-[4-[4-(9-ethylcarbamoyl-9H-thioxanthen-9-yl)butyl]piperazin-1-yl]-2-(3-methylbenzyl)-3,4-dihydro-2H-isoquinolin-1-one, 7-[4-[3-(9-ethylcarbamoyl-9H-thioxanthen-9-yl)propyl]piperazin-1-yl]-2-(3-methylbenzyl)-3,4-dihydro-2H-isoquinolin-1-one, 2-(α-methylbenzyl)-7-[4-[4-[9-(2,2,2-trifluoroethylcarbamoyl)-9H-fluoren-9-yl]butyl]piperazin-1-yl]-3,4-dihydro-2H-isoquinolin-1-one, 2-(α-methylbenzyl)-7-[4-[3-[9-(2,2,2-trifluoroethylcarbamoyl)-9H-fluoren-9-yl]propyl]piperazin-1-yl]-3,4-dihydro-2H-isoquinolin-1-one, 2-(α-methylbenzyl)-7-[4-[4-[9-(2,2,2-trifluoroethylcarbamoyl)-9H-xanthen-9-yl]butyl]piperazin-1-yl]-3,4-dihydro-2H-isoquinolin-1-one, 2-(α-methylbenzyl)-7-[4-[3-[9-(2,2,2-trifluoroethylcarbamoyl)-9H-xanthen-9-yl]propyl]piperazin-1-yl]-3,4-dihydro-2H-isoquinolin-1-one, 2-(α-methylbenzyl)-7-[4-[4-[9-(2,2,2-trifluoroethylcarbamoyl)-9H-thioxanthen-9-yl]butyl]piperazin-1-yl]-3,4-dihydro-2H-isoquinolin-1-one, 2-(α-methylbenzyl)-7-[4-[3-[9-(2,2,2-trifluoroethylcarbamoyl)-9H-thioxanthen-9-yl]propyl]piperazin-1-yl]-3,4-dihydro-2H-isoquinolin-1-one, 7-[4-[4-(9-ethylcarbamoyl-9H-fluoren-9-yl)butyl]piperazin-1-yl]-2-(α-methylbenzyl)-3,4-dihydro-2H-isoquinolin-1-one, 7-[4-[3-(9-ethylcarbamoyl-9H-fluoren-9-yl)propyl]piperazin-1-yl]-2-(α-methylbenzyl)-3,4-dihydro-2H-isoquinolin-1-one, 7-[4-[4-(9-ethylcarbamoyl-9H-xanthen-9-yl)butyl]piperazin-1-yl]-2-(α-methylbenzyl)-3,4-dihydro-2H-isoquinolin-1-one, 7-[4-[3-(9-ethylcarbamoyl-9H-xanthen-9-yl)propyl]piperazin-1-yl]-2-(α-methylbenzyl)-3,4-dihydro-2H-isoquinolin-1-one, 7-[4-[4-(9-ethylcarbamoyl-9H-thioxanthen-9-yl)butyl]piperazin-1-yl]-2-(α-methylbenzyl)-3,4-dihydro-2H-isoquinolin-1-one, 7-[4-[3-(9-ethylcarbamoyl-9H-thioxanthen-9-yl)propyl]piperazin-1-yl]-2-(α-methylbenzyl)-3,4-dihydro-2H-isoquinolin-1-one, N-benzyl-3-[4-(3,3-diphenyl-1-propyl)piperazin-1-yl]-N-methylbenzamide,
N-benzyl-N-cyclohexyl-3-[4-(3,3-diphenyl-1-propyl)piperazin-1-yl]benzamide,
N-benzyl-3-[4-(3,3-diphenyl-1-propyl)piperazin-1-yl]-N-isopropylbenzamide,
(3,4-dihydro-1H-isoquinolin-2-yl)-[3-[4-(3,3-diphenyl-1-propyl)piperazin-1-yl]phenyl]methanone,
N,N-diisopropyl-3-[4-(3,3-diphenyl-1-propyl)piperazin-1-yl]benzamide,
(4-benzyl-piperidin-1-yl)-[3-[4-(3,3-diphenyl-1-propyl)piperazin-1-yl]phenyl]methanone,
N-cyclohexyl-3-[4-(3,3-diphenyl-1-propyl)piperazin-1-yl]-N-methylbenzamide,
N-benzyl-3-[4-(3,3-diphenyl-1-propyl)piperazin-1-yl]-N-phenylbenzamide,
N,N-dibenzyl-3-[4-(3,3-diphenyl-1-propyl)piperazin-1-yl]benzamide,
N-benzyl-N-cyclopropyl-3-[4-(3,3-diphenyl-1-propyl)piperazin-1-yl]benzamide,
N-(4-chlorobenzyl)-N-cyclohexyl-3-[4-(3,3-diphenyl-1-propyl)piperazin-1-yl]benzamide,
N-cyclohexyl-3-[4-(3,3-diphenyl-1-propyl)piperazin-1-yl]-N-(4-methylbenzyl)benzamide,
N-cyclohexyl-3-[4-(3,3-diphenyl-1-propyl)piperazin-1-yl]-N-isopropylbenzamide,
N-benzyl-N-(t-butyl)-3-[4-(3,3-diphenyl-1-propyl)piperazin-1-yl]benzamide,
N-benzyl-N-(n-butyl)-3-[4-(3,3-diphenyl-1-propyl)piperazin-1-yl]benzamide,
3-[4-(3,3-diphenyl-1-propyl)piperazin-1-yl]-N-methyl-N-(1-phenylethyl)benzamide,
3-[4-(3,3-diphenyl-1-propyl)piperazin-1-yl]-N-isopropyl-N-phenylbenzamide,
N-allyl-N-cyclohexyl-3-[4-(3,3-diphenyl-1-propyl)piperazin-1-yl]benzamide,
(2,6-dimethyl-piperidin-1-yl)-[3-[4-(3,3-diphenyl-1-propyl)piperazin-1-yl]phenyl]methanone,
N-cyclohexyl-3-[4-(3,3-diphenyl-1-propyl)piperazin-1-yl]-N-ethylbenzamide,
N-dimethylaminoethyl-3-[4-(3,3-diphenyl-1-propyl)piperazin-1-yl]-N-methylbenzamide,
N-allyl-N-cyclopentyl-3-[4-(3,3-diphenyl-1-propyl)piperazin-1-yl]benzamide,
N,N-diallyl-3-[4-(3,3-diphenyl-1-propyl)piperazin-1-yl]benzamide,
N-allyl-3-[4-(3,3-diphenyl-1-propyl)piperazin-1-yl]-N-phenylbenzamide,
N-allyl-N-cyclohexylmethyl-3-[4-(3,3-diphenyl-1-propyl)piperazin-1-yl]benzamide,
3-[4-(3,3-diphenyl-1-propyl)piperazin-1-yl]-N-methoxy-N-methylbenzamide,
N-benzyl-3-[4-(3,3-diphenyl-1-propyl)piperazin-1-yl]-N-ethylbenzamide,
N-allyl-N-benzyl-3-[4-(3,3-diphenyl-1-propyl)piperazin-1-yl]benzamide,
N-cyclohexylmethyl-3-[4-(3,3-diphenyl-1-propyl)piperazin-1-yl]-N-[(pyridin-2-yl)methyl]benzamide,
N-cyclohexylmethyl-3-[4-(3,3-diphenyl-1-propyl)piperazin-1-yl]-N-[(pyridin-4-yl)methyl]benzamide,
N-cyclohexylmethyl-3-[4-(3,3-diphenyl-1-propyl)piperazin-1-yl]-N-[(tetrahydropyran-2-yl)methyl]benzamide,
N-allyl-3-[4-(3,3-diphenyl-1-propyl)piperazin-1-yl]-N-(trans-4-hydroxy)cyclohexylbenzamide,
N-benzyl-N-(2,2,2-trifluoroethyl)-3-[4-(3,3-diphenyl-1-propyl)piperazin-1-yl]benzamide,
N-allyl-N-(2,2,2-trifluoroethyl)-3-[4-(3,3-diphenyl-1-propyl)piperazin-1-yl]benzamide,
N-cyclohexylmethyl-3-[4-(3,3-diphenyl-1-propyl)piperazin-1-yl]-N-[(4-trifluoromethylbiphenyl-2-yl)methyl]benzamide,
N-cinnamyl-N-cyclohexylmethyl-3-[4-(3,3-diphenyl-1-propyl)piperazin-1-yl]benzamide,
N-crotyl-N-cyclohexylmethyl-3-[4-(3,3-diphenyl-1-propyl)piperazin-1-yl]benzamide,
N-benzyl-N-cyclohexylmethyl-3-[4-(3,3-diphenyl-1-propyl)piperazin-1-yl]benzamide,
N-cyclohexylmethyl-3-[4-(3,3-diphenyl-1-propyl)piperazin-1-yl]-N-propargylbenzamide,
N-cyclohexylmethyl-3-[4-(3,3-diphenyl-1-propyl)piperazin-1-yl]-N-(2-trifluoromethylbenzyl)benzamide,
N-cyclohexylmethyl-3-[4-(3,3-diphenyl-1-propyl)piperazin-1-yl]-N-(3-trifluoromethylbenzyl)benzamide,
N-cyclohexylmethyl-3-[4-(3,3-diphenyl-1-propyl)piperazin-1-yl]-N-(4-trifluoromethylbenzyl)benzamide,
N-cyclohexylmethyl-3-[4-(3,3-diphenyl-1-propyl)piperazin-1-yl]-N-[(pyridin-3-yl)methyl]benzamide,
N-(1-benzylpiperidin-4-yl)-N-cyclohexylmethyl-3-[4-(3,3-diphenyl-1-propyl)piperazin-1-yl]benzamide,
N-cyclohexylmethyl-3-[4-(3,3-diphenyl-1-propyl)piperazin-1-yl]-N-(piperidin-4-yl)benzamide,
N-cyclohexyl-3-[4-(3,3-diphenyl-1-propyl)piperazin-1-yl]-N-isopropyl-4-methoxybenzamide,
N-benzyl-N-cyclohexyl-3-[4-(3,3-diphenyl-1-propyl)piperazin-1-yl]-4-methoxybenzamide,
N-benzyl-4-chloro-N-cyclohexyl-3-[4-(3,3-diphenyl-1-propyl)piperazin-1-yl]benzamide,
N-cyclohexyl-3-[4-(3,3-diphenyl-1-propyl)piperazin-1-yl]-N-isopropyl-4-methylbenzamide,
N-benzyl-N-cyclohexyl-3-[4-(3,3-diphenyl-1-propyl)piperazin-1-yl]-4-methylbenzamide,
3-[4-[3,3-bis(4-chlorophenyl)-1-propyl]piperazin-1-yl]-N-cyclohexyl-N-isopropylbenzamide,
N-allyl-3-[4-[3,3-bis(4-chlorophenyl)-1-propyl]piperazin-1-yl]-N-cyclohexylbenzamide,
N-cyclohexyl-3-[4-(3,3-diphenyl-1-propyl)piperazin-1-yl]-N-isopropyl-2-methylbenzamide,
N-benzyl-N-cyclohexyl-3-[4-(3,3-diphenyl-1-propyl)piperazin-1-yl]-2-methylbenzamide,
N-allyl-N-cyclohexyl-3-[4-(3,3-diphenyl-1-propyl)piperazin-1-yl]-2-methylbenzamide,
N-allyl-N-cyclohexyl-3-[4-(3,3-diphenyl-1-propyl)piperazin-1-yl]-2-methoxybenzamide,
N-benzyl-N-cyclohexyl-3-[4-(3,3-diphenyl-1-propyl)piperazin-1-yl]-2-methoxybenzamide,
N-allyl-2-chloro-N-cyclohexyl-3-[4-(3,3-diphenyl-1-propyl)piperazin-1-yl]benzamide,
N-allyl-N-cyclohexyl-5-[4-(3,3-diphenyl-1-propyl)piperazin-1-yl]-2-fluorobenzamide,
N-benzyl-N-cyclohexyl-5-[4-(3,3-diphenyl-1-propyl)piperazin-1-yl]-2-fluorobenzamide, N-cyclohexyl-5-[4-(3,3-diphenyl-1-propyl)piperazin-1-yl]-N-methyl-2-methylbenzamide,
N-benzyl-5-[4-(3,3-diphenyl-1-propyl)piperazin-1-yl]-N-isopropyl-2-methylbenzamide,
N-allyl-N-cyclohexyl-5-[4-(3,3-diphenyl-1-propyl)piperazin-1-yl]-2-methylbenzamide,
N-benzyl-N-cyclohexyl-5-[4-(3,3-diphenyl-1-propyl)piperazin-1-yl]-2-methylbenzamide,
N-cyclohexyl-5-[4-(3,3-diphenyl-1-propyl)piperazin-1-yl]-N-isopropyl-2-methylbenzamide,
N-benzyl-2-chloro-N-cyclohexyl-5-[4-(3,3-diphenyl-1-propyl)piperazin-1-yl]benzamide,
N-allyl-2-chloro-N-cyclohexyl-5-[4-(3,3-diphenyl-1-propyl)piperazin-1-yl]benzamide,
N-allyl-N-cyclohexyl-5-[4-(3,3-diphenyl-1-propyl)piperazin-1-yl]-2-isopropylbenzamide,
N-benzyl-N-cyclohexyl-5-[4-(3,3-diphenyl-1-propyl)piperazin-1-yl]-2-isopropylbenzamide,
N-benzyl-N-cyclohexyl-5-[4-(3,3-diphenyl-1-propyl)piperazin-1-yl]-2-methoxybenzamide,
N-cyclohexyl-5-[4-(3,3-diphenyl-1-propyl)piperazin-1-yl]-2-methoxy-N-methylbenzamide,
N-cyclohexyl-5-[4-(3,3-diphenyl-1-propyl)piperazin-1-yl]-N-isopropyl-2-methoxybenzamide,
N-benzyl-5-[4-(3,3-diphenyl-1-propyl)piperazin-1-yl]-N-isopropyl-2-methoxybenzamide,
N-benzyl-N-cyclohexyl-5-[4-(3,3-diphenyl-1-propyl)piperazin-1-yl]-2-isopropyloxybenzamide,
N-allyl-2-cyano-N-cyclohexyl-5-[4-(3,3-diphenyl-1-propyl)piperazin-1-yl]benzamide,
N-benzyl-2-cyano-N-cyclohexyl-5-[4-(3,3-diphenyl-1-propyl)piperazin-1-yl]benzamide,
N-benzyl-N-cyclohexyl-5-[4-(3,3-diphenyl-1-propyl)piperazin-1-yl]-2-hydroxybenzamide,
N-allyl-N-cyclohexyl-3-[1-(3,3-diphenyl-1-propyl)-1,2,3,6-tetrahydropyridin-4-yl]benzamide,
N-allyl-N-cyclohexyl-3-[1-(3,3-diphenyl-1-propyl)piperidin-4-yl]benzamide,
N-benzyl-N-cyclohexyl-4-[4-(3,3-diphenyl-1-propyl)piperazin-1-yl]benzamide,
N-allyl-N-cyclohexyl-4-[4-(3,3-diphenyl-1-propyl)piperazin-1-yl]-3-fluorobenzamide,
N-allyl-2-chloro-N-cyclohexyl-4-[4-(3,3-diphenyl-1-propyl)piperazin-1-yl]benzamide,
N-allyl-N-cyclohexyl-2-[4-(3,3-diphenyl-1-propyl)piperazin-1-yl]benzamide,
N-benzyl-N-cyclohexyl-5-[4-(2,2-diphenylethyl)piperazin-1-yl]-2-methylbenzamide,
N-allyl-N-cyclohexyl-3-[4-(3,3-diphenyl-1-propyl)piperazin-1-yl]-5-methoxybenzamide,
N-allyl-N-cyclohexyl-3-[4-(3,3-diphenyl-1-propyl)piperazin-1-yl]-5-hydroxybenzamide,
N-allyl-N-cyclohexyl-3-[4-[4-[9-(2,2,2-trifluoroethylcarbamoyl)-9H-fluoren-9-yl]butyl]piperazin-1-yl]benzamide,
N-benzyl-N-cyclohexyl-3-[4-[4-[9-(2,2,2-trifluoroethylcarbamoyl)-9H-fluoren-9-yl]butyl]piperazin-1-yl]benzamide,
N-allyl-N-cyclohexyl-4-[4-[4-[9-(2,2,2-trifluoroethylcarbamoyl)-9H-fluoren-9-yl]butyl]piperazin-1-yl]benzamide,
N-allyl-N-cyclohexyl-3-fluoro-4-[4-[4-[9-(2,2,2-trifluoroethylcarbamoyl)-9H-fluoren-9-yl]butyl]piperazin-1-yl]benzamide,
N-allyl-N-cyclohexyl-4-[4-[4,4-diphenyl-4-(2,2,2-trifluoroethylcarbamoyl)butyl]piperazin-1-yl]benzamide,
7-benzyl-2-[4-(3,3-diphenyl-1-propyl)piperazin-1-yl]-5,6-dihydro-7H-1,7-naphthyridin-8-one,
2-benzyl-7-[4-(3,3-diphenyl-1-propyl)piperazin-1-yl]-3,4-dihydro-2H-2,6-naphthyridin-1-one,
2-benzyl-5-[4-(3,3-diphenyl-1-propyl)piperazin-1-yl]-3,4-dihydro-2H-2,6-naphthyridin-1-one,
6-benzyl-3-[4-(3,3-diphenyl-1-propyl)piperazin-1-yl]-7,8-dihydro-6H-1,6-naphthyridin-5-one,
N-benzyl-N-cyclohexyl-3-[4-(3,3-diphenyl-1-propyl)piperazin-1-yl]-6-methylnicotinamide,
N-benzyl-N-cyclohexyl-2-[4-(3,3-diphenyl-1-propyl)piperazin-1-yl]-5-methylisonicotinamide,
N-benzyl-N-cyclohexyl-2-[4-(3,3-diphenyl-1-propyl)piperazin-1-yl]-3-methylisonicotinamide,
N-allyl-N-cyclohexyl-2-[4-(3,3-diphenyl-1-propyl)piperazin-1-yl]-5-methylisonicotinamide,
N-allyl-N-cyclohexyl-2-[4-(3,3-diphenyl-1-propyl)piperazin-1-yl]-3-methylisonicotinamide,
N-allyl-N-cyclohexyl-3-methyl-2-[4-[3-[9-(2,2,2-trifluoroethylcarbamoyl)-9H-fluoren-9-yl]propyl]piperazin-1-yl]isonicotinamide,
N-allyl-N-cyclohexyl-6-[4-[4-[9-(2,2,2-trifluoroethylcarbamoyl)-9H-fluoren-9-yl]butyl]piperazin-1-yl]nicotinamide,
N-allyl-N-cyclohexyl-3-methyl-2-[4-[3-[9-(2,2,2-trifluoroethylcarbamoyl)-9H-xanthen-9-yl]propyl]piperazin-1-yl]isonicotinamide,
N-cyclohexyl-N-propyl-6-[4-[4-[9-(2,2,2-trifluoroethylcarbamoyl)-9H-fluoren-9-yl]butyl]piperazin-1-yl]nicotinamide,
N-cyclohexyl-N-(pyridin-2-yl)methyl-6-[4-[4-[9-(2,2,2-trifluoroethylcarbamoyl)-9H-fluoren-9-yl]butyl]piperazin-1-yl]nicotinamide,
2-cyclohexyl-6-[4-[4-(9-carbamoyl-9H-fluoren-9-yl)butyl]piperazin-1-yl]-2,3-dihydro-1H-isoindol-1-one,
2-cyclohexyl-6-[4-[4-(9-ethylcarbamoyl-9H-fluoren-9-yl)butyl]piperazin-1-yl]-2,3-dihydro-1H-isoindol-1-one,
6-[4-[4-(9-benzylcarbamoyl-9H-fluoren-9-yl)butyl]piperazin-1-yl]-2-cyclohexyl-2,3-dihydro-1H-isoindol-1-one,
6-[4-[4-(9-allylcarbamoyl-9H-fluoren-9-yl)butyl]piperazin-1-yl]-2-cyclohexyl-2,3-dihydro-1H-isoindol-1-one,
2-cyclohexyl-6-[4-[4-[9-[allyl-(2,2,2-trifluoroethyl)]carbamoyl-9H-fluoren-9-yl]butyl]piperazin-1-yl]-2,3-dihydro-1H-isoindol-1-one,
2-cyclohexyl-6-[4-[4-[9-[benzyl-(2,2,2-trifluoroethyl)]carbamoyl-9H-fluoren-9-yl]butyl]piperazin-1-yl]-2,3-dihydro-1H-isoindol-1-one,
2-cyclohexyl-6-[4-[4-[9-[methyl-(2,2,2-trifluoroethyl)]carbamoyl-9H-fluoren-9-yl]butyl]piperazin-1-yl]-2,3-dihydro-1H-isoindol-1-one,
2-cyclohexyl-6-[4-[4-[5-(2,2,2-trifluoroethylcarbamoyl)-5H-dibenzosuberan-5-yl]butyl]piperazin-1-yl]-2,3-dihydro-1H-isoindol-1-one,
2-(pyridin-2-yl)methyl-7-[4-[4-[9-(2,2,2-trifluoroethylcarbamoyl)-9H-fluoren-9-yl]butyl]piperazin-1-yl]-3,4-dihydro-2H-isoquinolin-1-one,
2-(pyridin-2-yl)methyl-7-[4-[3-[9-(2,2,2-trifluoroethylcarbamoyl)-9H-fluoren-9-yl]propyl]piperazin-1-yl]-3,4-dihydro-2H-isoquinolin-1-one, 2-cyclohexyl-6-[4-[2-[9-(2,2,2-trifluoroethylcarbamoyl)-9H-fluoren-9-yl]ethyl]piperazin-1-yl]-2,3-dihydro-1H-isoindol-1-one, 8-chloro-2-(3-methoxybenzyl)-7-[4-[4-[9-(2,2,2-trifluoroethylcarbamoyl)-9H-fluoren-9-yl]butyl]piperazin-1-yl]-3,4-dihydro-2H-isoquinolin-1-one, 2-cyclohexyl-6-[4-[4-(9-ethoxycarbonyl-9H-fluoren-9-yl)butyl]piperazin-1-yl]-2,3-dihydro-1H-isoindol-1-one, 6-[4-[4-(9-carboxy-9H-fluoren-9-yl)butyl]piperazin-1-yl]-2-cyclohexyl-2,3-dihydro-1H-isoindol-1-one, 9H-fluorene-9-carboxylic acid [3-[4-(2-cyclohexyl-3-oxo-2,3-dihydro-1H-isoindol-5-yl)piperazin-1-yl]propyl]amide, 9-[2-[4-(2-cyclohexyl-3-oxo-2,3-dihydro-1H-isoindol-5-yl)piperazin-1-yl]ethoxy]-9H-fluorene-9-carboxylic acid (2,2,2-trifluoroethyl)amide, 2-cyclohexyl-6-[4-[4-[9-(2,2,2-trifluoroethylcarbamoyl)-9H-thioxanthen-9-yl]butyl]piperazin-1-yl]-2,3-dihydro-1H-isoindol-1-one, 2-benzyl-6-[4-[4-[9-(2,2,2-trifluoroethylcarbamoyl)-9H-fluoren-9-yl]butyl]piperazin-1-yl]-3,4-dihydro-2H-isoquinolin-1-one, 2-cyclohexyl-6-[4-[4-[10-oxo-9-(2,2,2-trifluoroethylcarbamoyl)-9,10-dihydro-10$\lambda^4$-thioxanthen-9-yl]butyl]piperazin-1-yl]-2,3-dihydro-1H-isoindol-1-one, 2-cyclohexyl-6-[4-[4-[10,10-dioxo-9-(2,2,2-trifluoroethylcarbamoyl)-9,10-dihydro-10$\lambda^6$-thioxanthen-9-yl]butyl]piperazin-1-yl]-2,3-dihydro-1H-isoindol-1-one, 2-benzyl-7-[4-[4-[9-(2,2,2-trifluoroethylcarbamoyl)-9H-fluoren-9-yl]butyl]piperazin-1-yl]-2H-phthalazin-1-one, 2-benzyl-7-[4-[4-[9-(2,2,2-trifluoroethylcarbamoyl)-9H-xanthen-9-yl]butyl]piperazin-1-yl]-2H-phthalazin-1-one, 2-benzyl-7-[4-[3-[9-(2,2,2-trifluoroethylcarbamoyl)-9H-fluoren-9-yl]propyl]piperazin-1-yl]-2H-phthalazin-1-one, 2-benzyl-7-[4-[3-[9-(2,2,2-trifluoroethylcarbamoyl)-9H-xanthen-9-yl]propyl]piperazin-1-yl]-2H-phthalazin-1-one, 2-(tetrahydropyran-2-yl)methyl-7-[4-[4-[9-(2,2,2-trifluoroethylcarbamoyl)-9H-fluoren-9-yl]butyl]piperazin-1-yl]-2H-phthalazin-1-one, 2-(tetrahydropyran-2-yl)methyl-7-[4-[4-[9-(2,2,2-trifluoroethylcarbamoyl)-9H-xanthen-9-yl]butyl]piperazin-1-yl]-2H-phthalazin-1-one, 2-(pyridin-2-yl)methyl-7-[4-[3-[9-(2,2,2-trifluoroethylcarbamoyl)-9H-fluoren-9-yl]propyl]piperazin-1-yl]-2H-phthalazin-1-one, 2-(pyridin-2-yl)methyl-7-[4-[3-[9-(2,2,2-trifluoroethylcarbamoyl)-9H-xanthen-9-yl]propyl]piperazin-1-yl]-2H-phthalazin-1-one, 2-(pyridin-3-yl)methyl-7-[4-[3-[9-(2,2,2-trifluoroethylcarbamoyl)-9H-fluoren-9-yl]propyl]piperazin-1-yl]-2H-phthalazin-1-one, 3-(4-bromo-2-methylphenyl)-6-[4-(3,3-diphenylpropyl)piperazin-1-yl]-2-methyl-3H-quinazolin-4-one, 3-benzyl-6-[4-(3,3-diphenylpropyl)piperazin-1-yl]-2-methyl-3H-quinazolin-4-one, 3-(4-bromo-2-methylphenyl)-6-[4-(3,3-diphenylpropyl)piperazin-1-yl]-3H-quinazolin-4-one, 2-benzyl-7-[4-(3,3-diphenylpropyl)piperazin-1-yl]-2H-phthalazin-1-one, N-allyl-N-cyclohexyl-4-[4-[3-[9-(2,2,2-trifluoroethylcarbamoyl)-9H-fluoren-9-yl]propyl]piperazin-1-yl]benzamide, N-allyl-N-cyclohexyl-4-[4-[4-[9-(2,2,2-trifluoroethylcarbamoyl)-9H-xanthen-9-yl]butyl]piperazin-1-yl]benzamide, N-allyl-2-chloro-N-cyclohexyl-4-[4-[4-[9-(2,2,2-trifluoroethylcarbamoyl)-9H-fluoren-9-yl]butyl]piperazin-1-yl]benzamide, N-benzyl-N-chloro-4-[4-[4-[9-(2,2,2-trifluoroethylcarbamoyl)-9H-fluoren-9-yl]butyl]piperazin-1-yl]benzamide, N-benzyl-N-isopropyl-4-[4-[4-[9-(2,2,2-trifluoroethylcarbamoyl)-9H-fluoren-9-yl]butyl]piperazin-1-yl]benzamide, N-allyl-N-cyclohexyl-2-methyl-3-[4-[3-[9-(2,2,2-trifluoroethylcarbamoyl)-9H-xanthen-9-yl]propyl]piperazin-1-yl]benzamide, N-allyl-N-cyclohexyl-4-[4-[5-[9-(2,2,2-trifluoroethylcarbamoyl)-9H-fluoren-9-yl]pentyl]piperazin-1-yl]benzamide, N-allyl-N-cyclohexyl-4-[4-[4-[9-(2,2,2-trifluoroethylcarbamoyl)-9H-fluoren-9-yl]butyl]piperazin-1-yl]-2-trifluoromethylbenzamide, N-allyl-N-cyclohexyl-2-fluoro-4-[4-[4-[9-(2,2,2-trifluoroethylcarbamoyl)-9H-fluoren-9-yl]butyl]piperazin-1-yl]-2-trifluoromethylbenzamide, N-benzyl-N-(2-tetrahydrofurfuryl)-4-[4-[4-[9-(2,2,2-trifluoroethylcarbamoyl)-9H-fluoren-9-yl]butyl]piperazin-1-yl]benzamide, N-cyclohexyl-N-(pyridin-2-yl)methyl-4-[4-[4-[9-(2,2,2-trifluoroethylcarbamoyl)-9H-fluoren-9-yl]butyl]piperazin-1-yl]benzamide, N-cyclohexyl-N-(2-furfuryl)-4-[4-[4-[9-(2,2,2-trifluoroethylcarbamoyl)-9H-fluoren-9-yl]butyl]piperazin-1-yl]benzamide, N-cyclohexyl-N-(2-thienyl)methyl-4-[4-[4-[9-(2,2,2-trifluoroethylcarbamoyl)-9H-fluoren-9-yl]butyl]piperazin-1-yl]benzamide, N-allyl-N-cyclohexyl-5-[4-[3-[9-(2,2,2-trifluoroethylcarbamoyl)-9H-fluoren-9-yl]propyl]piperazinyl]-2-methylbenzamide, N-allyl-N-cyclohexyl-3-[4-[3-[9-(2,2,2-trifluoroethylcarbamoyl)-9H-fluoren-9-yl]propyl]piperazin-1-yl]benzamide, N-cyclohexyl-3-[4-(3,3-diphenyl-1-propyl)piperazin-1-yl]-N-(pyridin-2-yl)methyl-2-methylbenzamide, N-allyl-4-[4-[4,4-bis(4-fluorophenyl)-1-butyl]piperazin-1-yl]-N-cyclohexylbenzamide, N-allyl-N-cyclohexyl-4-[4-[4-[9-(2,2,2-trifluoroethylcarbamoyl)-9H-thioxanthen-9-yl]butyl]piperazin-1-yl]benzamide, N-cyclohexyl-3-[4-(3,3-diphenyl-1-propyl)piperazin-1-yl]-N-[(pyridin-2-yl)methyl]benzamide, N-allyl-3-[4-[3,3-bis(4-fluorophenyl)-1-propyl]piperazin-1-yl]-N-cyclohexylbenzamide, 1-Methyl N-allyl-N-cyclohexyl-6-[4-(3,3-diphenylpropyl)piperazin-1-yl]phthalaminate, N-allyl-N-cyclohexyl-3-[4-[4-[9-[allyl-(2,2,2-trifluoroethylcarbamoyl)]-9H-fluoren-9-yl]butyl]piperazin-1-yl]benzamide, N-allyl-N-cyclohexyl-3-[4-[4-[9-(2,2,2-trifluoroethylcarbamoyl)-9H-fluoren-9-yl]butyl]piperazin-1-yl]-2-methylbenzamide, N-allyl-N-cyclohexyl-2-methyl-3-[4-[4-[9-(2,2,2-trifluoroethylcarbamoyl)-9H-xanthen-9-yl]butyl]piperazin-1-yl]benzamide, N-allyl-N-cyclohexyl-2-methyl-3-[4-[3-[9-(2,2,2-trifluoroethylcarbamoyl)-9H-fluoren-9-yl]propyl]piperazin-1-yl]benzamide, N-allyl-N-cyclohexyl-6-[4-(3,3-diphenylpropyl)piperazin-1-yl]-2-phthalamic acid, N-cyclohexyl-3-[4-(3,3-diphenyl-1-propyl)piperazin-1-yl]-N-(pyridin-3-yl)methyl-2-methylbenzamide, and N-cyclohexyl-3-[4-(3,3-diphenyl-1-propyl)piperazin-1-yl]-N-(pyridin-4-yl)methyl-2-methylbenzamide.

The compounds represented by formula (I) form salts with many bases or acids. This property is utilized for the production of pure materials and is utilized in forms provided as pharmaceuticals. Specifically, at the time of the production, for example, upon acidification, the compounds are solubilized in a polar solvent, such as water, are purified by extraction, and are isolated as a salt having preferable physicochemical properties. In pharmaceutical applications, the compounds can take as pharmaceutically acceptable salts. The compounds represented by formula (I) are present in a free form or as a salt thereof and, in addition, are sometimes present as a hydrate or a solvate. Any of the above forms may be adopted as the active component of the pharmaceuticals according to the present invention.

Forms of salts, which the compounds of the present invention can take, include, for example, lithium salt, sodium salt, potassium salt, magnesium salt, calcium salt, and ammonium salt and suitable nontoxic amine salts, for example, salts of alkyl amines having 1 to 6 carbon atoms, for example, triethylamine, salts of alkanolamines having 1 to 6 carbon atoms, for example, diethanolamine or triethanolamine, procaine salts, salts of cyclohexylamine, for example, dicyclohexylamine, salts of benzylamines, for example, N-methylbenzylamine, N-ethylbenzylamine, N-benzyl-p-phenethylamine, N,N-dibenzylethylenediamine, or dibenzylamine, and salts of heterocyclic amines, for example, morpholine and N-ethylpyridine, or salts of hydrohalogenic acids, such as hydrofluoric acid, hydrochloric acid, hydrobromic acid, and hydroiodic acid, salts of inorganic acids, such as sulfuric acid, nitric acid, phosphoric acid, perchloric acid, and carbonic acid, salts of carboxylic acids, such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid, and malic acid, salts of amino acids, such as alginic acid, aspartic acid, and glutamic acid, and salts of organic acids, such as methanesulfonic acid and p-toluenesulfonic acid. Preferred examples of salts include acid addition salts, such as salts of trifluoroacetic acid, hydrochloric acid, oxalic acid, methanesulfonic acid, and citric acid, and salts of amino acids, such as glutamic acid and aspartic acid.

Preferred solvates include hydrates and ethanolates.

On one hand, the above salts are important as pharmacologically acceptable pharmaceutical compositions, and are considered to have, as pharmaceutical compositions, an advantage in the preparation thereof and, when administered to human bodies, are considered useful, for example, from the viewpoints of dispersion and absorptioin.

The compounds represented by formula (I) sometimes have one or two or more asymmetric carbons and thus exist as stereoisomers (optical isomers or diastereomers) based on the asymmetric carbons. In addition to stereoisomers in pure forms, any mixture of stereoisomers, racemic forms and the like may be used as the active component of the pharmaceuticals according to the present invention. Further, when the compounds represented by formula (I) have an olefinic double bond, they sometimes exist as geometrical isomers in a Z or E form, or as a mixture of these geometrical isomers. Geometrical isomers in a pure form or mixtures of these geometrical isomers may be used as the active component of the pharmaceuticals according to the present invention.

Use of Compounds Represented by Formula (I)/
Pharmaceutical Composition

The compounds represented by formula (I) and pharmacologically acceptable salts or solvates thereof according to the present invention have triglyceride biosynthesis inhibitory activity and apolipoprotein B-containing lipoprotein secretion inhibitory activity in the liver. Therefore, the compounds according to the present invention can be used as prophylactic or therapeutic agents for hyperlipidemia, particularly hyper-VLDL-emia and/or arteriosclerotic diseases caused thereby, such as cardiac infarction, through the action of a lowering in the level of serum triglyceride and serum apolipoprotein B-containing lipoprotein. Among others, the compounds represented by formula (I) according to the present invention are considered to be advantageous in that they inhibit the biosynthesis of lipids in hepatic cells to prevent side effects such as the accumulation of hepatic lipids.

Thus, according to the present invention, there is provided a pharmaceutical composition comprising an effective amount of the compound according to the present invention or a pharmacologically acceptable salt or solvate thereof in combination with a pharmacologically acceptable carrier. This pharmaceutical composition is specifically used as apolipoprotein B-containing lipoprotein secretion inhibitors, triglyceride biosynthesis inhibitors, prophylactic or therapeutic agents for hyperlipidemia, prophylactic or therapeutic agents for arteriosclerotic diseases, or prophylactic or therapeutic agents for pancreatitis.

According to another aspect of the present invention, there are provided a method for inhibiting the secretion of an apolipoprotein B-containing lipoprotein, a method for inhibiting the biosynthesis of triglycerides, a method for preventing or treating hyperlipidemia, a method for preventing or treating arteriosclerotic diseases, and a method for preventing or treating pancreatitis, comprising the step of administering an effective amount of the compound according to the present invention or a pharmacologically acceptable salt or solvate thereof to animals including humans.

Further, according to still another aspect of the present invention, there are provided use of the compound according to the present invention or a pharmacologically acceptable salt or solvate thereof, for the manufacture of an apolipoprotein B-containing lipoprotein secretion inhibitor, use of the compound according to the present invention or a pharmacologically acceptable salt or solvate thereof, for the manufacture of a triglyceride biosynthesis inhibitor, use of the compound according to the present invention or a pharmacologically acceptable salt or solvate thereof, for the manufacture of a prophylatic or therapeutic agent for hyperlipidemia, use of the compound according to the present invention or a pharmacologically acceptable salt or solvate thereof, for the manufacture of a prophylactic or therapeutic agent for arteriosclerotic diseases, and use of the compound according to the present invention or a pharmacologically acceptable salt or solvate thereof, for the manufacture of a prophylactic or therapeutic agent for pancreatitis.

The compounds according to the present invention and pharmacologically acceptable salts and solvates thereof can be administered orally or parenterally by administration routes, for example, intravenous injection, intramuscular injection, subcutaneous administration, intraperitoneal administration, rectal administration, and percutaneous administration, to human and non-human animals.

Accordingly, the compounds according to the present invention and pharmacologically acceptable salts and solvates thereof may be formed into appropriate various dosage forms depending on administration routes, more specifically may be mainly formulated into, for example, injections such as intravenous injections or intramuscular injections; oral preparation such as capsules, tablets, granules, powders, pills, fine subtilaes, or troches; preparations for rectal administrations; oleaginous suppositories; and water-soluble suppositories.

These various preparations may be prepared by conventional methods with commonly used components, for example, excipients, extenders, binders, humidifiers, disintegrants, surface active agents, lubricants, dispersants, buffers, preservatives, dissolution aids, antiseptics, flavoring agents, analgesic agents, and stabilizers.

Excipients usable herein include, for example, lactose, fructose, glucose, corn starch, sorbit, and crystalline cellulosse. Disintegrants include, for example, starch, sodium alginate, gelatin, calcium carbonate, calcium citrate, dextrin, magnesium carbonate, and synthetic magnesium silicate. Binders include, for example, methylcellulose or salts thereof, ethylcellulose, gum arabic, gelatin, hydroxypropylcellulose, and polyvinyl pyrrolidone. Lubricants include, for example, talc, magnesium stearate, polyethylene glycol, and hydrogenated vegetable oils. Other additives include syrup, petrolatum, glycerin, ethanol, propylene glycol, citric acid, sodium chloride, sodium sulfite, and sodium phosphate.

The content of the compound according to the present invention in the pharmaceutical composition may vary according to the dosage form. In general, however, the content is about 1 to 70% by weight, preferably about 5 to 50% by weight, based on the whole composition.

The dose may be appropriately determined in consideration of, for example, the dosage route, the age and sex of patients, the type of diseases, and the severity of condition of patients, and, for the treatment of hyperlipidemia, the preparation may be administered usually in an amount of about 0.1 to 5000 mg, preferably 1 to 600 mg per day per adult. This dose may be administered at a time daily or divided doses of several times daily.

Compounds Represented by Formula

According to a further aspect of the present invention, there are provided compounds which are preferred for the production of the compounds represented by formula (I). The compounds are compounds represented by formula (III) and pharmacologically acceptable salts or solvates thereof:

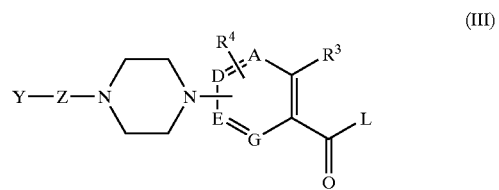

wherein
$R^3$ and $R^4$, which may be the same or different, represent a hydrogen atom,
optionally substituted alkyl having 1 to 6 carbon atoms,
a halogen atom,
hydroxyl,
nitrile,
alkoxycarbonyl having 2 to 5 carbon atoms,
alkoxy having 1 to 6 carbon atoms, or carboxyl,
A, D, E, and G each represent a carbon atom, or any one of A, D, E, and G represents a nitrogen atom with the other three each representing a carbon atom,
L represents group —O—$R^{11}$ wherein $R^{11}$ represents a hydrogen atom or optionally substituted alkyl having 1 to 6 carbon atoms,
Y represents a group represented by formula (II):

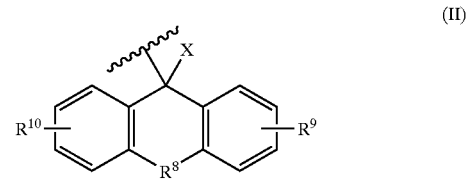

wherein
X represents a hydrogen atom; group —C(=O)N($R^5$)$R^6$ wherein $R^5$ and $R^6$, which may be the same or different, represent a hydrogen atom, optionally substituted alkyl having 1 to 6 carbon atoms, optionally substituted cycloalkyl having 3 to 8 carbon atoms, optionally substituted phenyl, optionally substituted alkenyl having 2 to 6 carbon atoms, or optionally substituted alkynyl having 2 to 6 carbon atoms; or group —C(=O)O$R^7$ wherein $R^7$ represents a hydrogen atom or optionally substituted alkyl having 1 to 6 carbon atoms, $R^8$ is absent or represents a bond, an oxygen atom, a sulfur atom, —$SO_2$—, —SO—, —$CH_2$—$CH_2$—, or —CH=CH—, and $R^9$ and $R^{10}$, which may be the same or different, represent a hydrogen atom, optionally substituted alkyl having 1 to 6 carbon atoms, alkoxy having 1 to 6 carbon atoms, a halogen atom, or hydroxyl, and
Z represents —$(CH_2)_n$—, wherein n is an integer of 0 to 6, —O—$(CH_2)_i$—, or —C(=O)NH—$(CH_2)_i$— wherein i is an integer of 1 to 6.

The compounds represented by formula (III) are intermediates useful for the synthesis of the compounds represented by formula (I). Therefore, substituents in formula (III) basically have the same meanings as described above in connection with formula (I), and preferred examples thereof are also the same as described above in connection with formula (I).

Synthesis of Compounds Represented by Formula
(I) (Part 1)

Among the compounds represented by formula (I), according to the present invention, compounds, wherein $R^1$, $R^4$, Y, and Z are as defined in formula (I), $R^2$ and $R^3$ represent group —$(CH_2)_m$— wherein m is 1 or 2, A, D, E, and G each represent a carbon atom, Q represents a nitrogen atom, and q represents a single bond, are preferably synthesized by the following synthesis processes 1 to 5.

In the following synthesis, a protective group or $C_{1-4}$ acyl on a substituent may if necessary be introduced and removed by conventional means.

[Synthesis Process 1]

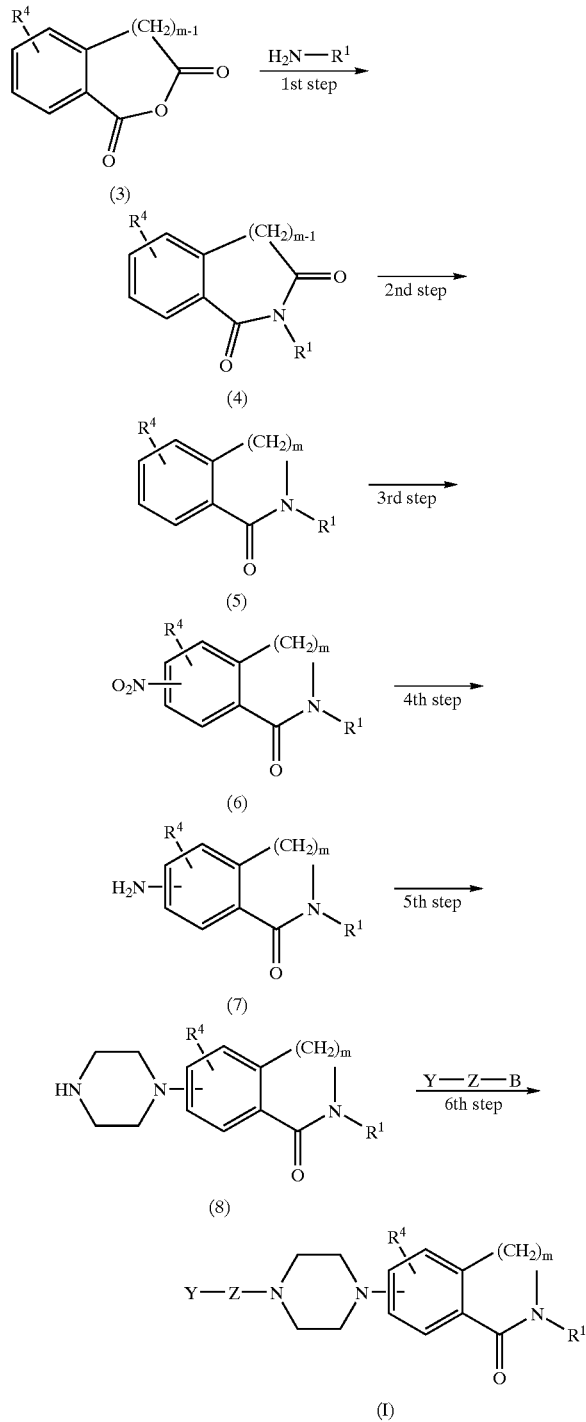

The first step is imidation of an acid anhydride. A compound represented by formula (3), wherein $R^4$ and m are as defined in formula (I), may be reacted with a compound $H_2N$—$R^1$, wherein $R^1$ is as defined in formula (I), in the presence or absence of a base in a solvent inert to the reaction, for example, tetrahydrofuran, benzene, toluene, or xylene or in the absence of a solvent for 0.5 to 48 hr, preferably 1 to 24 hr, at 50 to 200° C., preferably 100 to 180° C., to give a compound represented by formula (4) wherein $R^1$, $R^4$ and m are as defined in formula (I).

The second step is reduction of the imide to a lactam. The compound represented by formula (4) may be subjected to a reduction reaction in a solvent inert to the reaction, for example, acetic acid, N,N-dimethylformamide, dimethyl sulfoxide, tetrahydrofuran, benzene, or toluene, in the presence of a reducing agent, for example, zinc-acetic acid, tin, sodium boron hydride, or zinc boron hydride, for 0.5 to 48 hr, preferably 1 to 24 hr, at 50 to 200° C., preferably 80 to 150° C. to give a compound represented by formula (5) wherein $R^1$, $R^4$, and m are as defined in formula (I).

The third step is nitration. A conventional nitrating agent may be used in this nitration. The compound represented by formula (5) is reacted with a nitrating agent, preferably nitric acid or potassium nitrate, in concentrated sulfuric acid for 0.5 to 48 hr, preferably 0.5 to 24 hr, at −20 to 100° C., preferably −20 to 50° C. to give a compound represented by formula (6) wherein $R^1$, $R^4$, and m are as defined in formula (I).

In the fourth step, the compound represented by formula (6) is subjected to a reduction reaction to convert the nitro to amino. A reduction reaction by catalytic reduction in the presence of palladium-carbon, palladium-black, palladium hydroxide, platinum oxide, or Raney-nickel, reduction in the presence of tin, zinc, iron or the like in combination with an acid, such as acetic acid, or reduction with sodium boron hydride or hydrazine, preferably catalytic reduction in the presence of palladium-carbon or palladium-black or reduction in the presence of iron and acetic acid, is carried out in a solvent inert to the reaction, for example, methanol, ethanol, tetrahydrofuran, N,N-dimethylformamide, or benzene, for 0.5 to 48 hr, preferably 0.5 to 30 hr, at 0 to 100° C., preferably 0 to 50° C., to give a compound represented by formula (7) wherein $R^1$, $R^4$, and m are as defined in formula (I).

The fifth step is piperazination of the amine. The compound represented by formula (7) is reacted with 1 to 5 equivalents of bischloroethylamine in the presence of 1 to 3 equivalents of an acid, such as hydrochloric acid, or in the absence of the acid in a solvent inert to the reaction, for example, n-butanol, xylene, or toluene, for 0.5 hr to 7 days, preferably one hr to 5 days, at 50 to 200° C., preferably 60 to 180° C., to give a compound represented by formula (8) wherein $R^1$, $R^4$, and m are as defined in formula (I).

The sixth step is condensation of the compound represented by formula (8) with a compound Y—Z—B. This reaction may be carried out by the following process (i) or (ii).

Process (i): A compound Y—Z—B, wherein B represents a halogen atom, such as a chlorine, bromine, or iodine atom, $C_{1-4}$ alkylsulfonyl, such as methanesulfonyl, or arylsulfonyl, such as p-toluene sulfonyl, and Y and Z are as defined in formula (I), may be reacted with the compound represented by formula (8) in the presence or absence of a base in a solvent inert to the reaction, for example, dichloromethane, tetrahydrofuran, N,N-dimethylformamide, or dimethyl sulfoxide, for 10 min to 48 hr, preferably 10 min to 24 hr, at −20 to 150° C., preferably 0 to 100° C., to give a compound represented by formula (I) wherein $R^2$ and $R^3$ represent group —$(CH_2)_m$—, wherein m is 1 or 2, A, D, E, and G each represent a carbon atom, Q represents a nitrogen atom, q represents a single bond, $R^1$, $R^4$, and Y are as defined in formula (I), and Z represents —$(CH_2)_p$— wherein p is an integer of 1 to 6.

Process (ii): When the compound Y—Z—B is Y—$(CH_2)_{(p-1)}$—CHO wherein p is an integer of 1 to 6 and Y is as defined in formula (I), this compound and the compound represented by formula (8) may be reductively alkylated with 1 to 5 equivalents of a reducing agent, for example, a metal hydride reagent, such as sodium cyanoborohydride, lithium cyanoborohydride, sodium boron hydride, lithium borohydride, or sodium triacetoxyborohydride, in the presence or absence of 0.1 to 5 equivalents of an acid, such as acetic acid or hydrochloric acid, in a solvent inert to the reaction, for example, dichloroethane, dichloromethane, or tetrahydrofuran, for 0.5 to 48 hr, preferably 1 to 24 hr, at −20 to 100° C., preferably 0 to 70° C., to give a compound represented by formula (I) wherein $R^2$ and $R^3$ represent group —$(CH_2)_m$—, wherein m is 1 or 2, A, D, E, and G each represent a carbon atom, Q represents a nitrogen atom, q represents a single bond, $R^1$, $R^4$, and Y are as defined in formula (I), and Z represents —$(CH_2)_p$—wherein p is an integer of 1 to 6.

Compounds represented by formula (5), wherein $R^2$ and $R^3$ represent group —$CH_2CH_2$—, may also be synthesized by the process as described in Yakugaku Zasshi (Journal of the Pharmaceutical Society of Japan), 96, 176–179 (1976).

Bases usable in the reaction of synthesis process 1 include pyridine, triethylamine, N-methylmorpholine, and dimethylaminopyridine. The amount of the base used is preferably 0.1 to 5 equivalents.

[Synthesis Process 2]

Among the compounds represented by formula (I), compounds, wherein $R^4$ represents a halogen atom, may be produced as described below by halogenating a corresponding compound wherein $R^4$ represents a hydrogen atom.

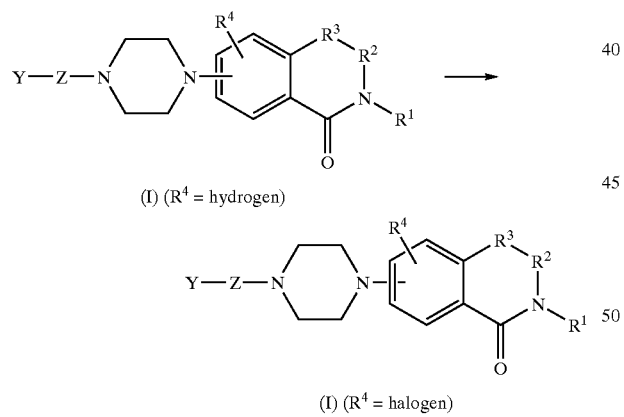

Specifically, a compound represented by formula wherein $R^1$, Y, and Z are as defined in formula (I), $R^2$ and $R^3$ are group —$(CH_2)_m$—, wherein m is 1 or 2, and $R^4$ represents a hydrogen atom, may be halogenated with a radical initiator, for example, N-halosuccinimide, preferably N-chlorosuccinimide or N-bromosuccinimide, preferably in the presence of 0.01 to 3 equivalents of 2,2'-azobisisobutyronitrile, in a solvent inert to the reaction, for example, carbon tetrachloride, tetrahydrofuran, or benzene, for 0.5 to 48 hr, preferably 1 to 24 hr, at −20 to 150° C., preferably 0 to 120° C., to give a compound represented by formula (I) wherein $R^4$ represents a halogen atom.

[Synthesis Process 3]

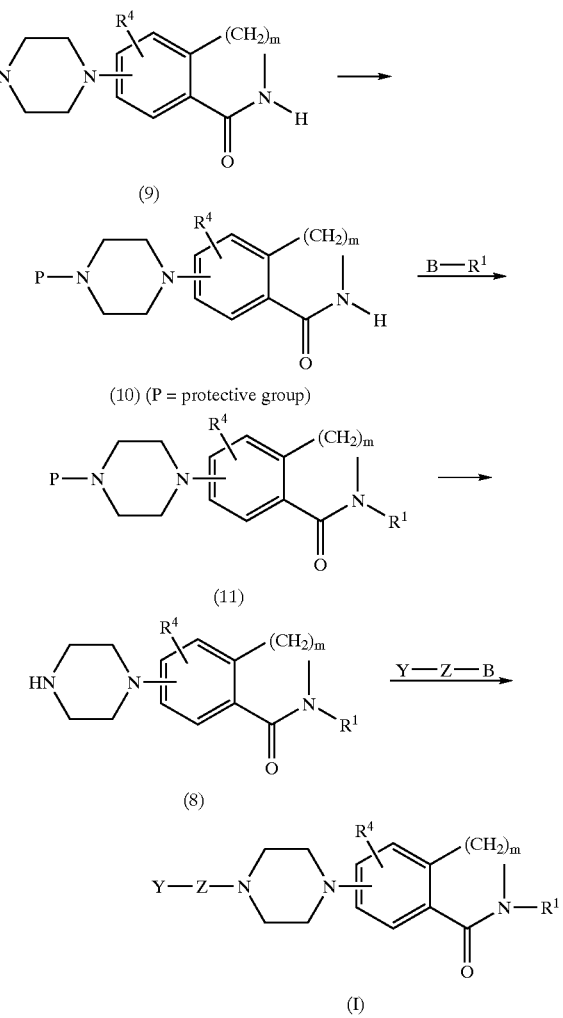

Specifically, the piperazine portion of a compound represented by formula (9), wherein $R^4$ and m are as defined in formula (I), is protected by a protective group, followed by a reaction according to the method as described in J. Med. Chem., 39, 4583–4591 (1996). Any conventional protective group used in the synthesis of peptides may be used as the protective group for piperazine, and preferred protective groups include t-butoxycarbonyl, benzyloxycarbonyl, p-methoxybenzyloxycarbonyl, 2,2,2-trichloroethoxycarbonyl, trifluoroacetyl, allyloxycarbonyl, and trityl. At the outset, the piperazine portion of the compound represented by formula (9) is protected by a conventional method to give a compound represented by formula (10) wherein $R^4$ and m are as defined in formula (I) and P represents a protective group for amino. Next, the compound represented by formula (10) is reacted with B—$R^1$, wherein B and $R^1$ are as defined above, according to the method as described in the above cited literature to give a compound represented by formula (II) wherein $R^1$, $R^4$, and m are as defined in formula (I) and P represents a protective group for amino. The protective group represented by formula (II) is removed by a conventional method to give a compound represented by formula (8). Further, the compound represented by formula (8) may be condensed with a compound Y—Z—B, wherein Y, Z, and B are as defined above, according to the method as described in the sixth step of synthesis process 1 to give a compound represented by formula (I) wherein $R^2$ and $R^3$ represent group —$(CH_2)_m$—, wherein m is 1 or 2, A, D, E, and G each represent a carbon atom, Q represents a nitrogen atom, q represents a single bond, $R^1$, $R^4$, Y, and Z are as defined in formula (I).

[Synthesis Process 4]

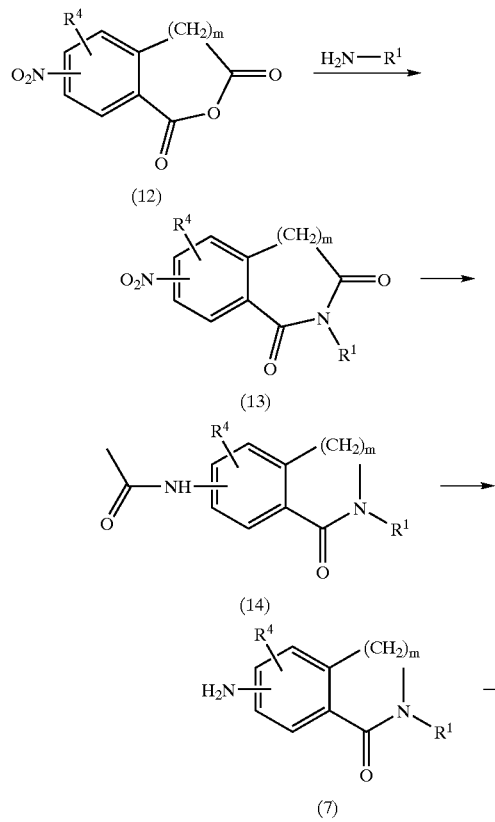

A compound represented by formula (12), wherein m is an integer of 1 or 2 and $R^4$ is as defined in formula (I), is reacted with the compound $H_2N$—$R^1$ in the same manner as described in the first step of synthesis process 1 to give a compound represented by formula (13). The compound represented by formula (13) is then subjected to a reduction reaction with zinc and acetic acid as described in the second step of synthesis process 1 to give a compound represented by formula (14). The acetamide is hydrolyzed under acidic conditions to give a compound represented by formula (7). Thereafter, the fifth step and later steps of synthesis process 1 may be repeated to give a compound represented by formula (I) wherein $R^2$ and $R^3$ represent group —$(CH_2)_m$—, wherein m is 1 or 2, A, D, E, and G each represent a carbon atom, Q represents a nitrogen atom, q represents a single bond, and $R^1$, $R^4$, Y, and Z are as defined in formula (I).

[Synthesis Process 5]

Among the compounds represented by formula (I), compounds, wherein $R^1$ represents optionally substituted phenyl or optionally substituted saturated or unsaturated five- or six-membered heterocyclic ring containing two or less hetero-atoms, are preferably produced by the following process.

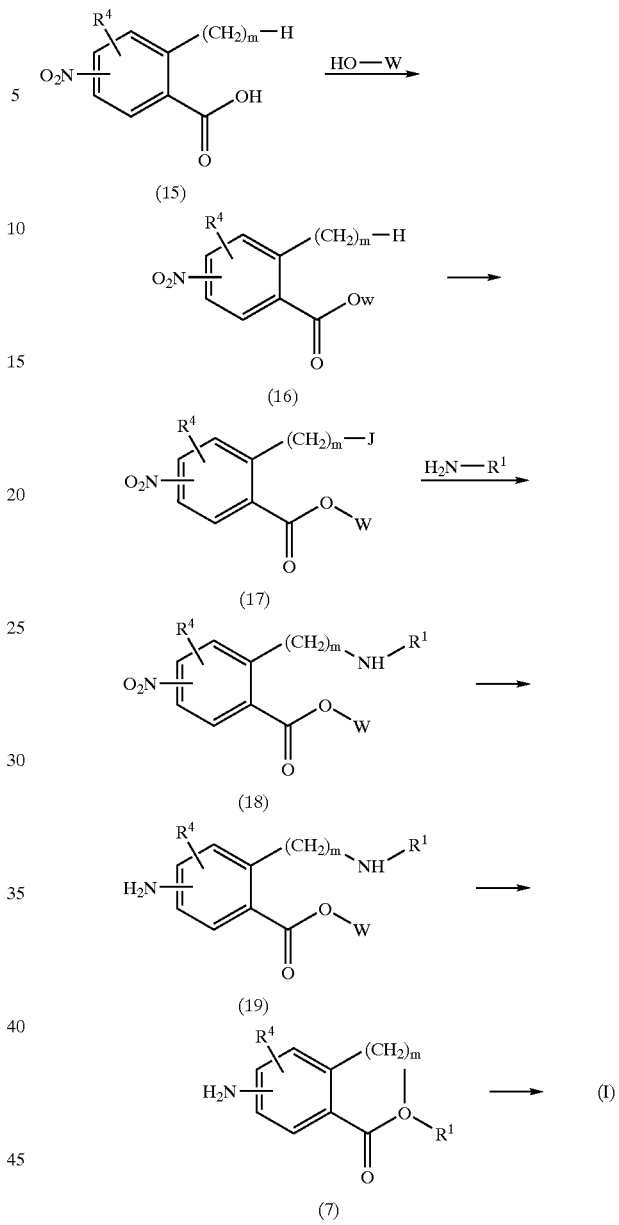

A compound represented by formula (15), wherein m and $R^4$ are as defined in formula (I), is esterified with a compound W—OH, wherein W represents $C_{1-6}$ alkyl, according to the method as described in "Jikken Kagaku Koza (Experimental Chemistry Series) 22," Vol. 4, pp. 43–47, edited by The Chemical Society of Japan and published by Maruzen Co., Ltd. to give a compound represented by formula (16) wherein m and $R^4$ are as defined in formula (I). Next, the compound represented by formula (16) is halogenated according to the method as described in "Jikken Kagaku Koza (Experimental Chemistry Series) 19," Vol. 4, pp. 422–438, edited by The Chemical Society of Japan and published by Maruzen Co., Ltd. to give a compound represented by formula (17) wherein J represents a halogen atom and m, $R^4$, and W are as defined above. The compound represented by formula (17) is then reacted with the above-described compound $H_2N$—$R^1$ in the presence or absence of a base in a solvent inert to the reaction, for example, methanol, ethanol, tetrahydrofuran, N,N- dimethylformamide, or dichloromethane, for 10 min to 48 hr, preferably 10 min to 24 hr, at −20 to 150° C., preferably 0 to 100° C., to give a compound represented by formula (18) wherein m, $R^1$, $R^4$, and W are as defined above. The compound represented by formula (18) is then subjected to a reduction reaction in the presence of palladium-carbon as described in the fourth step of synthesis process 1 to give a compound represented by formula (19) wherein m, $R^1$, $R^4$, and W are as defined above. The compound represented by formula (19) is reacted in the presence or absence of a base or an acid in a solvent inert to the reaction, for example, ethanol, tetrahydrofuran, N,N-dimethylformamide, dichloromethane, or toluene, for 10 min to 48 hr, preferably 10 min to 24 hr, at −20 to 150° C., preferably 0 to 100° C., to give a compound represented by formula (7) wherein m, $R^1$, and $R^4$ are as defined above. The compound represented by formula (7) thus obtained may be treated in the same manner as described in the fifth step and later steps of synthesis process 1 to give a compound represented by formula (I) wherein $R^1$ represents optionally substituted phenyl or an optionally substituted saturated or unsaturated five- or six-membered heterocyclic ring containing two or less hetero-atoms.

Synthesis of Compounds Represented by Formula (I) (Part 2)

Among the compounds represented by formula (I) according to the present invention, compounds, wherein $R^1$, $R^4$, Y, and Z are as defined in formula (I), $R^2$ and $R^3$ are as defined in formula (I) with the proviso that they are not attached to each other to form a ring, A, D, E, and G each represent a carbon atom, and Q represents a nitrogen atom or a carbon atom, are preferably synthesized by the following synthesis processes 6 to 14.

In the following synthesis, a protective group or $C_{1-4}$ acyl on a substituent may if necessary be introduced and removed by conventional means.

[Synthesis Process 6]

A compound represented by formula (I), wherein $R^1$, $R^4$, Y, and Z are as defined in formula (I), $R^2$ and $R^3$ are as defined in formula (I) with the proviso that they are not attached to each other to form a ring, A, D, E, and G each represent a carbon atom, Q represents a nitrogen atom, and q represents a single bond, is preferably produced by the following process.

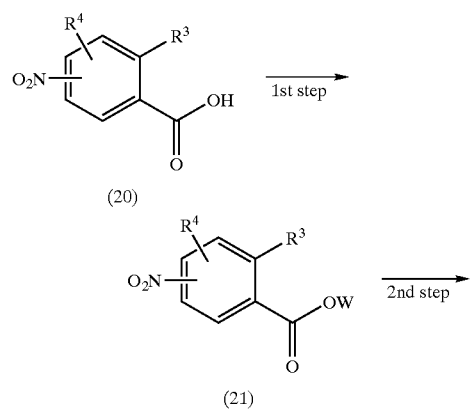

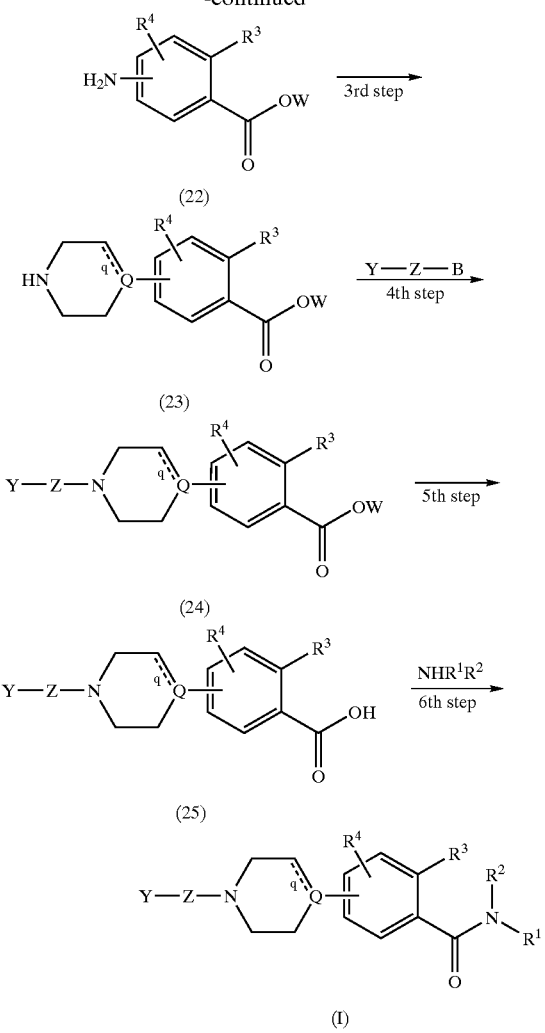

The first step is esterification of a carboxylic acid. A compound represented by formula (20), wherein $R^3$ and $R^4$ are as defined in formula (I), is heated in the presence of an acid, such as hydrochloric acid or sulfuric acid in an alcohol, such as methanol or ethanol, for one hr to one day. Alternatively, the above compound may be reacted, for example, with 1,3-dicyclohexylcarbodiimide or carbonylimidazole to convert the carboxylic acid to an active ester which is then reacted in an alcohol, such as methanol or ethanol, for one hr to one day at room temperature or with heating to give a compound represented by formula (21) wherein W represents alkyl having 1 to 6 carbon atoms and $R^3$ and $R^4$ are as defined in formula (I).

The second step is reduction of nitro to amino. The compound represented by formula (21) is subjected to catalytic reduction in the presence of palladium-carbon, palladium-black, palladium hydroxide, platinum oxide, or Raney-nickel, a reduction reaction with tin, zinc, iron or the like and an acid, such as acetic acid, or reduction with sodium boron hydride or hydrazine, preferably catalytic reduction in the presence of palladium-carbon or palladium-black or reduction with iron and acetic acid, in a solvent inert to the reaction, for example, methanol, ethanol, tetrahydrofuran, N,N-dimethylformamide, or benzene, for one hr to one day, at room temperature or with heating to give a compound represented by formula (22) wherein W, $R^3$, and $R^4$ are as defined above.

The third step is piperazination of the amine. The compound represented by formula (22) may be reacted with 1 to 5 equivalents of bischloroethylamine in the presence of 1 to 3 equivalents of an acid, such as hydrochloric acid, or in the absence of the acid in a solvent inert to the reaction, for example, n-butanol, xylene, or toluene, for 0.5 hr to 7 days at 50 to 200° C. to give a compound represented by formula (23) wherein Q represents a nitrogen atom, q represents a single bond, and W, $R^3$, and $R^4$ are as defined above.

The fourth step is condensation of the compound represented by formula (23) with a compound Y—Z—B. This reaction may be carried out by the following two processes.

Process (i): A compound Y—Z—B, wherein B represents a halogen atom, such as a chlorine, bromine, or iodine atom, $C_{1-4}$ alkylsulfonyl, such as methanesulfonyl, or arylsulfonyl, such as p-toluenesulfonyl, and Y and Z are as defined in formula (I), may be reacted with the compound represented by formula (23) in the presence or absence of a base, such as pyridine, triethylamine, N-methylmorpholine, dimethylaminopyridine, or potassium carbonate, in a solvent inert to the reaction, for example, dichloromethane, tetrahydrofuran, N,N-dimethylformamide, or dimethyl sulfoxide, for 10 min to 2 days at 0 to 100° C. to give a compound represented by formula (24) wherein Q, q, Y, Z, W, $R^3$, and $R^4$ are as defined above.

Process (ii): When the compound Y—Z—B is Y—$(CH_2)_{(p-1)}$—CHO wherein p is an integer of 1 to 6 and X and Y are as defined in formula (I), this compound and the compound represented by formula (23) may be reductively alkylated with 1 to 5 equivalents of a reducing agent, for example, a metal hydride reagent, such as sodium cyanoborohydride, lithium cyanoborohydride, sodium boron hydride, lithium borohydride, or sodium triacetoxyborohydride, in the presence or absence of 0.1 to 5 equivalents of an acid, such as acetic acid or hydrochloric acid, in a solvent inert to the reaction, for example, dichloromethane, dichloroethane, or tetrahydrofuran, for 10 min to 2 days at −20 to 100° C. to give a compound represented by formula (24) wherein Q, q, Y, Z, W, $R^3$, and $R^4$ are as defined above.

The fifth step is hydrolysis of the ester. The compound represented by formula (24) may be hydrolyzed with an aqueous alkali solution, such as an aqueous sodium hydroxide or potassium hydroxide solution, in a solvent inert to the reaction, for example, methanol, ethanol, or tetrahydrofuran, for 10 min to 2 days at room temperature to 100° C. to give a compound represented by formula (25) wherein Q, q, Y, Z, W, $R^3$, and $R^4$ are as defined above.

The sixth step is amidation of the carboxylic acid. This reaction can be carried out by the following two processes.

(i) The compound represented by formula (25) may be reacted with thionyl chloride, oxalyl chloride or the like in a solvent inert to the reaction, for example, dichloromethane, dichloroethane, or tetrahydrofuran, for 10 min to 5 hr at room temperature or with heating to convert the compound to an acid halide which is then reacted with 1 to 10 equivalents of $NHR^1R^2$, wherein $R^1$ and $R^2$ are as defined above, in the presence or absence of a base, such as pyridine, triethylamine, N-methylmorpholine, diisopropylethylamine, or dimethylaminopyridine, for 10 min to 2 days at room temperature or with heating to give a compound represented by formula (I) wherein $R^1$, $R^4$, Y, and Z are as defined in formula (I), $R^2$ and $R^3$ are as defined in formula (I) with the proviso that they are not attached to each other to form a ring, A, D, E, and G each represent a carbon atom, Q represents a nitrogen atom, and q represents a single bond.

(ii) The compound represented by formula (25) is reacted with 1,3-dicyclohexylcarbodiimide, N-ethyl-N'-(3-dimethylaminopropyl)carbodiimide, benzotriazol-1-yloxytris(dimethylamino)phosphonium hexafluorophosphate (BOP reagent) or the like in the presence or absence of a base, such as pyridine, triethylamine, N-methylmorpholine, diisopropylethylamine, or dimethylaminopyridine, in a solvent inert to the reaction, for example, dichloromethane, tetrahydrofuran, or N,N-dimethylformamide, for 10 min to one day at room temperature or with heating to activate the carboxylic acid. The activated carboxylic acid is then reacted with 1 to 10 equivalents of $NHR^1R^2$, wherein $R^1$ and $R^2$ are as defined above, for 10 min to 2 days at room temperature or with heating. Thus, a compound represented by formula (I) is prepared wherein Q represents a nitrogen atom, q represents a single bond, and Y, Z, $R^1$, $R^2$, $R^3$, and $R^4$ are as defined above.

The compound represented by formula (22), wherein W, $R^3$, and $R^4$ are as defined above, may also be synthesized by the following process. Specifically, a carboxylic acid compound represented by formula (26), wherein $R^3$ and $R^4$ are as defined in formula (I), may be heated in the presence of an acid, such as hydrochloric acid or sulfuric acid, in an alcohol, such as methanol or ethanol, for one hr to one day to esterify the carboxylic acid, thereby preparing the compound represented by formula (22).

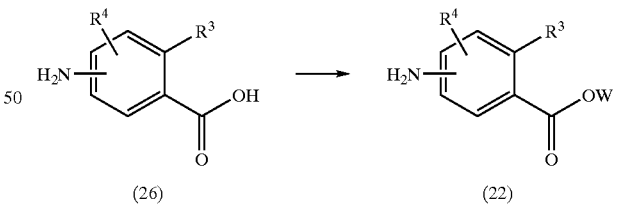

[Synthesis Process 7]

A compound represented by formula (I), wherein $R^1$, $R^4$, Y, and Z are as defined in formula (I), $R^2$ and $R^3$ are as defined in formula (I) with the proviso that they are not attached to each other to form a ring, A, D, E, and G each represent a carbon atom, Q represents a nitrogen atom, and q represents a single bond, is preferably produced by the following process.

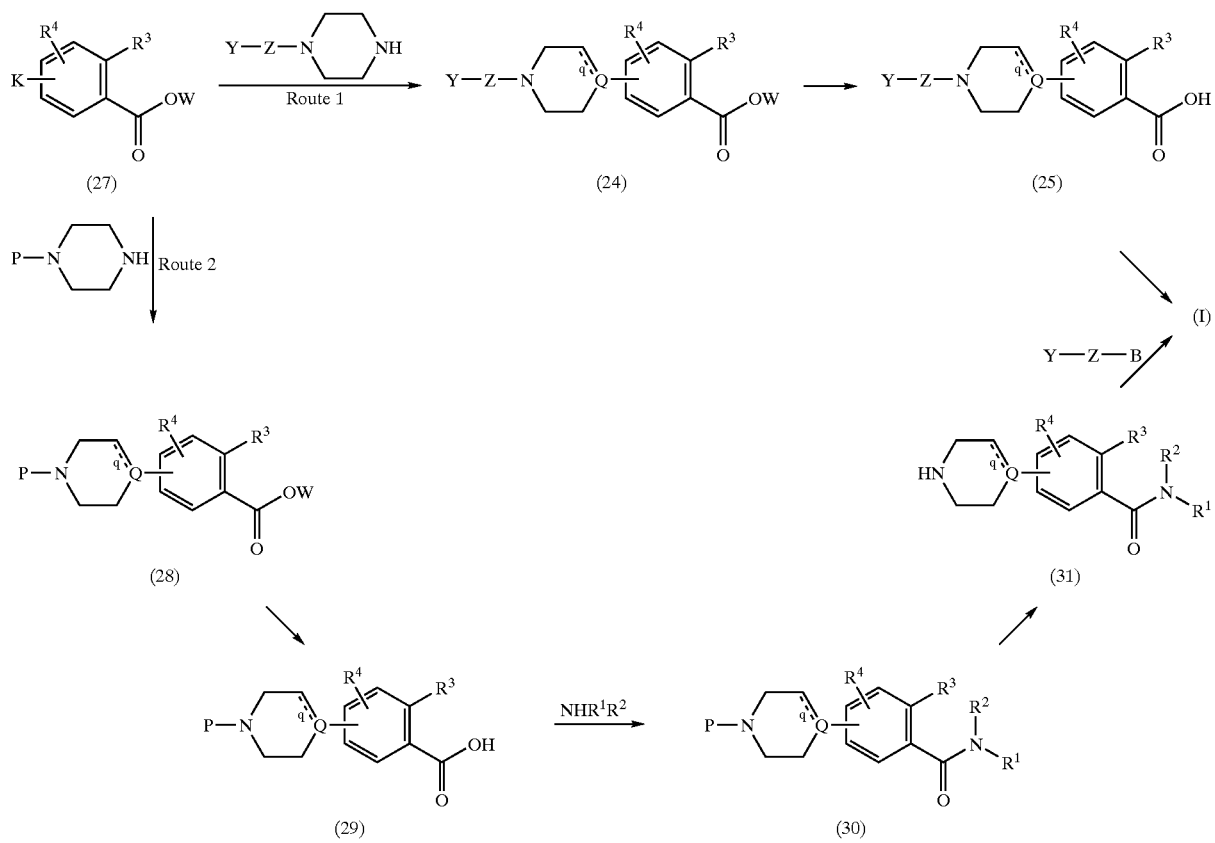

Specifically, as shown in route 1, a compound represented by formula (27), wherein K represents a halogen atom and W is as defined above, is reacted with a compound Y—Z—piperazine, wherein Y and Z are as defined in formula (I), in the absence of a solvent or in a solvent inert to the reaction, for example, dimethyl sulfoxide or xylene, for one hr to 2 days at 50 to 200° C. Alternatively, the compound represented by formula (27) is reacted with the compound Y—Z—piperazine, a metallic reagent, such as palladium acetate, and BINAP or cesium carbonate or the like in a solvent inert to the reaction, for example, toluene or xylene, for one hr to 2 days at 50 to 200° C. Thus, a compound represented by formula (24) is prepared wherein W, $R^3$, $R^4$, Y, Z, Q, and q are as defined above.

Further, the fifth and sixth steps as described in synthesis process 6 may then be carried out to give a compound represented by formula (I) wherein Y, Z, $R^1$, $R^2$, $R^3$, and $R^4$ are as defined above, A, D, E, and G each represent a carbon atom, Q represents a nitrogen atom, and q represents a single bond.

Further, as shown in route 2, a compound represented by formula (27), wherein K represents a halogen atom and W is as defined above, is reacted with a compound P-piperazine, wherein P represents a conventional protective group commonly used in the synthesis of peptides, preferably t-butoxycarbonyl, benzyloxycarbonyl, p-methoxybenzyloxycarbonyl, 2,2,2-trichloroethoxycarbonyl, trifluoroacetyl, allyloxycarbonyl, or trityl, in the absence of a solvent or in a solvent inert to the reaction, for example, dimethyl sulfoxide or xylene, for one hr to 2 days at 50 to 200° C. Alternatively, the compound represented by formula (27), wherein K represents a halogen atom and W is as defined above, is reacted with the compound P-piperazine, wherein P is as defined above, in the presence of a metallic reagent, such as palladium acetate, and BINAP or cesium carbonate or the like in a solvent inert to the reaction, for example, toluene or xylene, for one hr to 2 days at 50 to 200° C. Thus, a compound represented by formula (28) is prepared wherein Q, q, W, P, $R^3$, and $R^4$ are as defined above.

The compound represented by formula (28) may be treated in the same manner as described in the fifth step of synthesis process 6 to give a compound represented by formula (29) wherein Q, q, P, $R^3$, and $R^4$ are as defined above.

The compound represented by formula (29) may be treated in the same manner as described in the sixth step of synthesis process 6 to give a compound represented by formula (30) wherein Q, q, P, $R^1$, $R^2$, $R^3$, and $R^4$ are as defined above.

The protective group of the compound represented by formula (30) may be removed by a conventional method to give a compound represented by formula (31) wherein Q, q, P, $R^1$, $R^2$, $R^3$, and $R^4$ are as defined above.

The compound represented by formula (31) may be condensed with a compound Y—Z—B, wherein Y, Z, and B are as defined above, in the same manner as described in the fourth step of synthesis process 6 to give a compound represented by formula (I) wherein Y, Z, $R^1$, $R^2$, $R^3$, and $R^4$ are as defined above, A, D, E, and G each represent a carbon atom, Q represents a nitrogen atom, and q represents a single bond.

[Synthesis Process 8]

Among the compounds represented by formula (I), compounds, wherein $R^1$, $R^4$, Y, and Z are as defined in formula (I), $R^2$ and $R^3$ are as defined in formula (I) with the proviso that they are not attached to each other to form a ring, A, D, E, and G each represent a carbon atom, Q represents a nitrogen atom, and q represents a single bond, are also preferably produced by the following process.

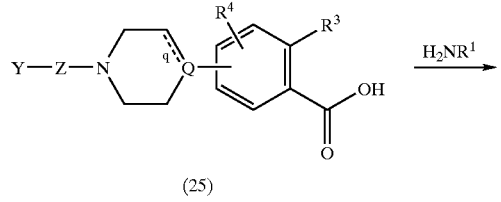

(25)

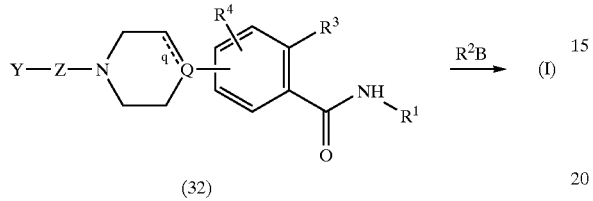

(32)

Specifically, a compound represented by formula (25), wherein Q, q, Y, Z, R$^3$, and R$^4$ are as defined in formula (I), may be amidated with a primary amine H$_2$NR$^1$, wherein R$^1$ is as defined in formula (I), in the same manner as described in the sixth step of synthesis process 6 to give a compound represented by formula (32), wherein Q, q, Y, Z, R$^1$, R$^3$, and R$^4$ are as defined above, which is then subjected to the alkylation of nitrogen in the amide with a compound R$^2$—B, wherein B and R$^2$ are as defined above, to give a compound represented by formula (I) wherein Q, q, Y, Z, R$^1$, R$^2$, R$^3$, and R$^4$ are as defined above.

[Synthesis Process 9]

Among the compounds represented by formula (I), compounds, wherein R$^1$, R$^4$, Y, and Z are as defined in formula (I), R$^2$ and R$^3$ are as defined in formula (I) with the proviso that they are not attached to each other to form a ring, A, D, E, and G each represent a carbon atom, Q represents a carbon atom, and q represents a single bond, are preferably produced by the following process.

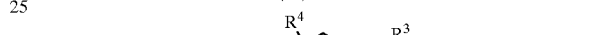

(33)

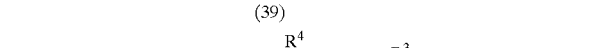

(34)

(35)

(36)

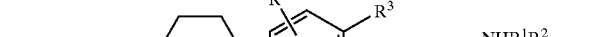

(37)

(38)

(39)

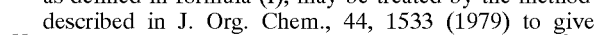

(40)

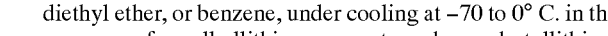

(41)

The first step is the protection of a carboxylic acid as an oxazole derivative. A compound represented by formula (33), wherein K represents a halogen atom and R$^3$ and R$^4$ are as defined in formula (I), may be treated by the method as described in J. Org. Chem., 44, 1533 (1979) to give a compound represented by formula (34) wherein K, R$^3$, and R$^4$ are as defined above.

The second step is the introduction of a piperidine side chain. The second step may be carried out as follows. A compound represented by formula (34) is reacted in a solvent inert to the reaction, for example, tetrahydrofuran, diethyl ether, or benzene, under cooling at −70 to 0° C. in the presence of an alkyllithium reagent, such as n-butyllithium or t-butyllithium, or an alkylmagnesium reagent for 5 min to 2 hr. Thereafter, 4-piperidone protected by a conventional protective group is added thereto, and a reaction is allowed to proceed at 0 to 100° C. for one hr to one day to give a compound represented by formula (35) wherein R$^3$ and R$^4$ are as defined above and P represents a conventional protective group commonly used in the synthesis of peptides, preferably t-butoxycarbonyl, benzyloxycarbonyl, p-methoxybenzyloxycarbonyl, 2,2,2-trichloroethoxycarbonyl, trifluoroacetyl, allyloxycarbonyl, or trityl.

The third step is the removal of the protective group of amine. The protective group of the compound represented by formula (35) may be removed by a conventional method to give a compound represented by formula (36) wherein $R^3$ and $R^4$ are as defined above.

The fourth step is condensation of the compound represented by formula (36) with a compound Y—Z—B wherein B represents a halogen atom, such as chlorine, bromine, or iodine, alkylsulfonyl having 1 to 4 carbon atoms, such as methanesulfonyl, or arylsulfonyl, such as p-toluene sulfonyl, and Y and Z are as defined in formula (I). A compound represented by formula (37), wherein Y, Z, $R^3$, and $R^4$ are as defined above, can be prepared from the compound represented by formula (36) in the same manner as described in the fourth step of synthesis process 6.

The fifth step involves the removal of the oxazoline ring as the protective group of the carboxylic acid and a dehydration reaction. The compound represented by formula (37) may be reacted in the presence of an acid, such as hydrochloric acid or sulfuric acid, in a solvent inert to the reaction, for example, tetrahydrofuran or dioxane, at 50 to 100° C. for one hr to 2 days to give a compound represented by formula (38) wherein Y, Z, $R^3$, and $R^4$ are as defined above.

The sixth step is esterification of carboxylic acid. The compound represented by formula (38) may be treated in the same manner as described in the first step of synthesis process 6 to give a compound represented by formula (39) wherein Y, Z, $R^3$, and $R^4$ are as defined above and W represents alkyl having 1 to 6 carbon atoms.

The seventh step is reduction of a double bond. The compound represented by formula (39) may be catalytically reduced, for example, in the presence of palladium-carbon or palladium-black, in a solvent inert to the reaction, for example, methanol, ethanol, or tetrahydrofuran, to give a compound represented by formula (40) wherein W, Y, Z, $R^3$, and $R^4$ are as defined above.

The eighth step is hydrolysis of the ester. The compound represented by formula (40) may be treated in the same manner as described in the fifth step of synthesis process 6 to give a compound represented by formula (41) wherein Y, Z, $R^3$, and $R^4$ are as defined above.

The ninth step is amidation of the carboxylic acid. The compound represented by formula (41) may be treated in the same manner as described in the sixth step of synthesis process 6 to give a compound represented by formula (I) wherein Q represents a carbon atom, q represents a single bond, and Y, Z, $R^1$, $R^2$, $R^3$, and $R^4$ are as defined above.

The compound represented by formula (I), wherein Q represents a carbon atom, q represents a double bond, and Y, Z, $R^1$, $R^2$, $R^3$, and $R^4$ are as defined above, may also be produced by reacting the compound represented by formula (38), wherein Y, Z, $R^3$, and $R^4$ are as defined above, in the same manner as described in the sixth step of synthesis process 6.

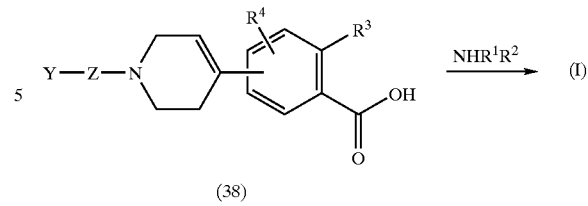

(38)

[Synthesis Process 10]

Among the compounds represented by formula (I), compounds, wherein $R^1$, $R^4$, Y, and Z are as defined in formula (I), $R^2$ and $R^3$ are as defined in formula (I) with the proviso that they are not attached to each other to form a ring, A, D, E, and G each represent a carbon atom, Q represents a nitrogen atom, and q represents a single bond, are also preferably produced by the following process.

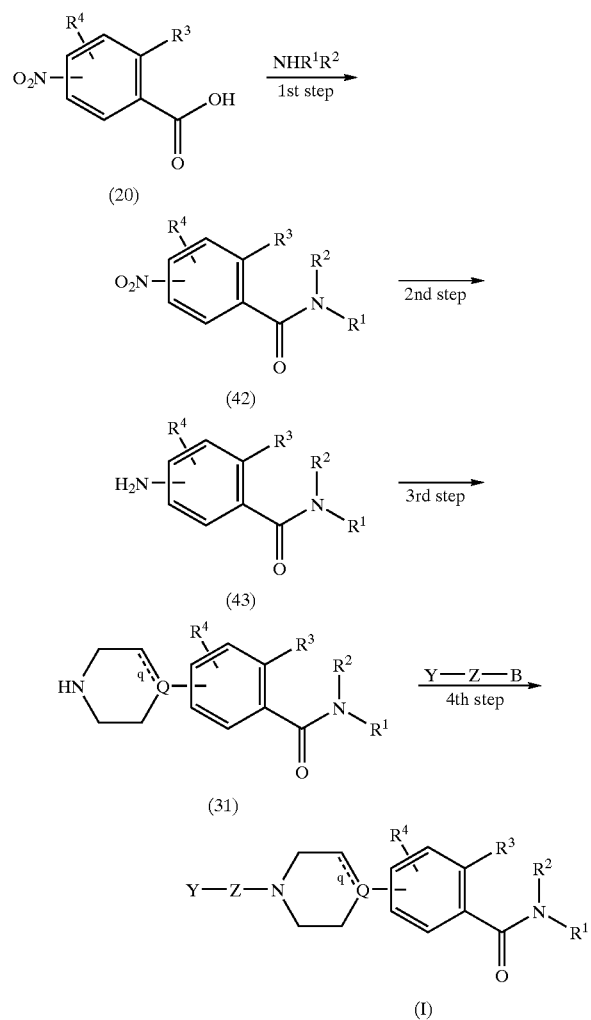

The first step is amidation of a carboxylic acid with a secondary amine. A compound represented by formula (20), wherein $R^3$ and $R^4$ are as defined in formula (I), may be reacted with a compound $NHR^1R^2$ wherein $R^1$ and $R^2$ are as defined in formula (I), in the same manner as described in the sixth step of synthesis process 6 to give a compound represented by formula (42) wherein $R^1$, $R^2$, $R^3$, and $R^4$ are as defined above.

The second step is reduction of nitro to amino. The compound represented by formula (42) may be treated in the same manner as described in the second step of synthesis process 6 to give a compound represented by formula (43) wherein $R^1$, $R^2$, $R^3$, and $R^4$ are as defined above.

The third step is piperazination of the amine. The compound represented by formula (43) may be treated in the same manner as described in the third step of synthesis process 6 to give a compound represented by formula (31) wherein Q represents a nitrogen atom, q represents a single bond, $R^1$, $R^2$, $R^3$, and $R^4$ are as defined above.

The fourth step is condensation of the compound represented by formula (31) with a compound Y—Z—B wherein B represents a halogen atom, such as chlorine, bromine, or iodine, alkylsulfonyl having 1 to 4 carbon atoms, such as methanesulfonyl, or arylsulfonyl, such as p-toluene sulfonyl, and Y and Z are as defined in formula (I). The compound represented by formula (31) may be treated in the same manner as described in the fourth step of synthesis process 6 to give a compound represented by formula (I) wherein Y, Z, $R^1$, $R^2$, $R^3$, and $R^4$ are as defined above, Q represents a nitrogen atom, and q represents a single bond.

[Synthesis Process 11]

Among the compounds represented by formula (I), compounds, wherein Q represents a nitrogen atom, q represents a single bond, A, D, E, and G each represent a carbon atom, Y, Z, $R^1$, and $R^4$ are as defined above, $R^2$ is as defined in formula (I) with the proviso that $R^2$ is not attached to $R^3$ to form a ring, and $R^3$ represents alkoxy, are also preferably produced by the following process.

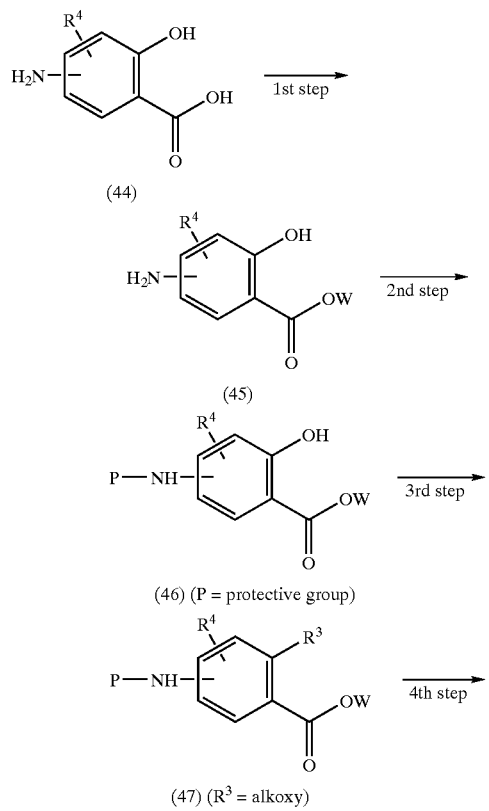

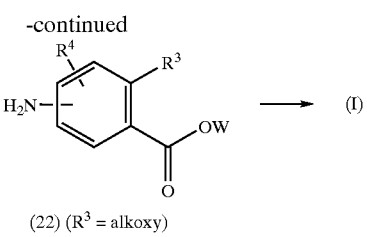

The first step is esterification of a carboxylic acid. A compound represented by formula (44) is heated in the presence of an acid, such as hydrochloric acid or sulfuric acid in an alcohol, such as methanol or ethanol, for one hr to one day. Alternatively, the above compound may be reacted, for example, with 1,3-dicyclohexylcarbodiimide or carbonylimidazole to convert the carboxylic acid to an active ester which is then reacted in an alcohol, such as methanol or ethanol, for one hr to one day at room temperature or with heating. Thus, a compound represented by formula (45) is prepared wherein W represents alkyl having 1 to 6 carbon atoms and $R^4$ is as defined in formula (I).

The second step is a reaction for the protection of amino. A conventional protective group commonly used in the synthesis of peptides may be used as the protective group for amine. Examples of preferred protective groups include t-butoxycarbonyl, benzyloxycarbonyl, p-methoxybenzyloxycarbonyl, 2,2,2-trichloroethoxycarbonyl, trifluoroacetyl, allyloxycarbonyl, and trityl. Specifically, amino in the compound represented by formula (45) is protected by a conventional method to give a compound represented by formula (46) wherein W and $R^4$ are as defined above and P represents a protective group for amino.

The third step is alkylation of hydroxyl. The compound represented by formula (46) may be reacted, for example, with alkyl halide, methanesulfonylated alkyl, or p-toluenesulfonylated alkyl in the presence or absence of a base in a solvent inert to the reaction, for example, dichloromethane, tetrahydrofuran, acetone, 1,4-dioxane, dimethylformamide, or dimethyl sulfoxide, for 1 to 72 hr, preferably 1 to 48 hr, at 0 to 200° C., preferably 50 to 150° C., to give a compound represented by formula (47) wherein W, P, and $R^4$ are as defined above and $R^3$ represents alkoxy.

The alkylation of hydroxyl in the third step may also be carried out using an alcohol. In this case, the compound represented by formula (46) and the alcohol are subjected to a Mitsunobu reaction using triphenylphosphine and an azodicarboxylic ester.

The fourth step is deprotection. The compound represented by formula (47) is deprotected by a conventional method to give a compound represented by formula (22) wherein W, $R^3$, and $R^4$ are as defined above.

Further, the compound represented by formula (22) may be treated in the same manner as described in the third step and later steps of synthesis process 6 to give a compound represented by formula (I) wherein Q, q, Y, Z, $R^1$, $R^2$, and $R^4$ are as defined above and $R^3$ represents alkoxy.

[Synthesis Process 12]

Among the compounds represented by formula (I), compounds, wherein $R^2$ is as defined in formula (I) with the proviso that $R^2$ and $R^3$ are not attached to each other to form a ring, A, D, E, and G each represent a carbon atom, Q, q, Y, Z, $R^1$, and $R^4$ are as defined in formula (I), and $R^3$ represents hydroxyl, are also preferably produced by the following process.

Specifically, among the compounds represented by formula (I), compounds, wherein Q, q, Y, Z, $R^1$, $R^2$, and $R^4$ are as defined above and R³ represents alkoxy, may also be dealkylated to give a compound represented by formula (I) wherein R³ represents hydroxyl.

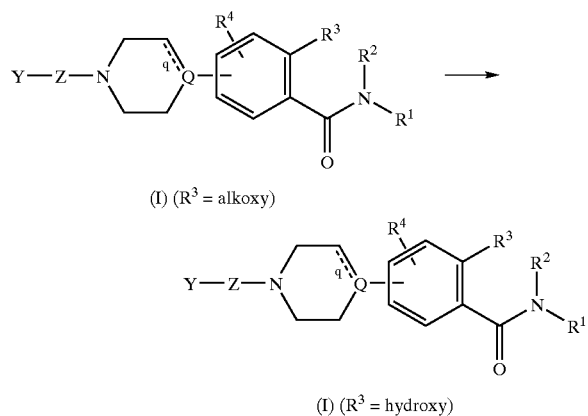

(I) (R³ = alkoxy)

(I) (R³ = hydroxy)

Specifically, a compound represented by formula (I), wherein Q, q, Y, Z, R¹, R², and R⁴ are as defined above and R³ represents alkoxy, may be dealkylated, for example, in the presence of boron tribromide, aluminum trichloride, hydrobromic acid, or hydroiodic acid, in a solvent inert to the reaction, for example, dichloromethane, dichloroethane, tetrahydrofuran, or benzene, for 10 min to 48 hr, preferably 0.5 to 24 hr, at −20 to 150° C., preferably 0 to 100° C., to give a compound represented by formula (I) wherein Q, q, Y, Z, R¹, R², and R⁴ are as defined above and R³ represents hydroxyl.

[Synthesis Process 13]

Among the compounds represented by formula (I), compounds, wherein R² is as defined in formula (I) with the proviso that R² and R³ are not attached to each other to form a ring, A, D, E, and G each represent a carbon atom, Q represents a nitrogen atom, q represents a single bond, Y, Z, R¹, R², and R⁴ are as defined in formula (I), and R³ represents isopropyl, are also preferably produced by the following process.

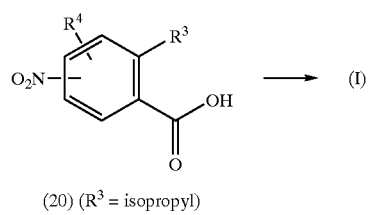

(20) (R³ = isopropyl)

Specifically, a compound represented by formula (20), wherein R³ represents isopropyl and R⁴ is as defined in formula (I), is synthesized according to the method as described in Roczniki Chemii, 31, 1207 (1957) and is then treated in the same manner as described in synthesis process 6 or synthesis process 10 to give a compound represented by formula (I) wherein R³ represents isopropyl and Q, q, Y, Z, R¹, R², and R⁴ are as defined above.

[Synthesis Process 14]

Among the compounds represented by formula (I), compounds, wherein R² is as defined in formula (I) with the proviso that R² and R³ are not attached to each other to form a ring, A, D, E, and G each represent a carbon atom, Q represents a nitrogen atom, q represents a single bond, Y, Z, R¹, R², and R⁴ are as defined in formula (I), and R³ represents cyano, are also preferably produced by the following process.

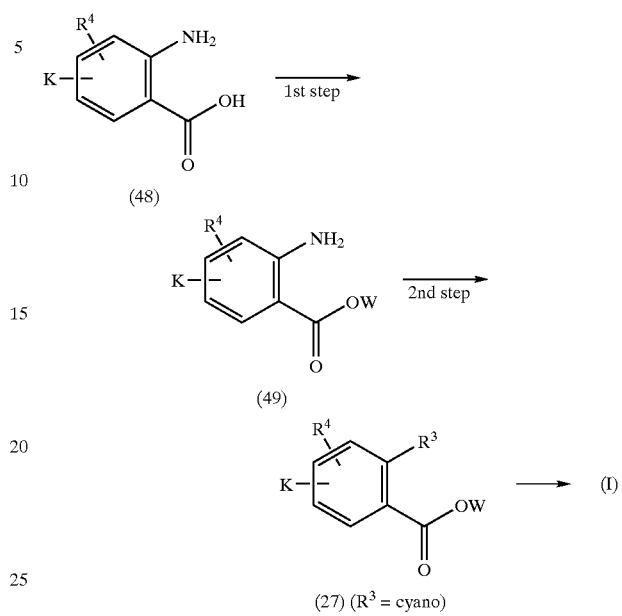

The first step is esterification of a carboxylic acid. A compound represented by formula (48), wherein K represents a halogen atom and R⁴ is as defined in formula (I), is heated in the presence of an acid, such as hydrochloric acid or sulfuric acid, in an alcohol, such as methanol or ethanol, for one hr to one day. Alternatively, the above compound may be reacted, for example, with 1,3-dicyclohexylcarbodiimide or carbonylimidazole to convert the carboxylic acid to an active ester which is then reacted in an alcohol, such as methanol or ethanol, for one hr to one day at room temperature or with heating. Thus, a compound represented by formula (49) is prepared wherein W represents alkyl having 1 to 6 carbon atoms and K and R⁴ are as defined above.

The second step is conversion of amino to cyano. The compound represented by formula (49) is treated according to the method as described in J. Med. Chem., 35, 4613 (1992) to synthesize a compound represented by formula (27) wherein R³ represents cyano and W, K, and R⁴ are as defined above.

Further, the compound represented by formula (27) may be treated in the same manner as described in synthesis process 7 to give a compound represented by formula (I) wherein R³ represents cyano and Q, q, Y, Z, R¹, R³, and R⁴ are as defined above.

Synthesis of Compounds Represented by Formula (I) (Part 3)

The compounds represented by formula (I) according to the present invention are also preferably synthesized by the following four processes.

In the following synthesis, a protective group or C₁₋₄ acyl on a substituent may if necessary be introduced and removed by conventional means.

[Synthesis Process 15]

Among the compounds represented by formula (I), compounds, wherein Q represents a nitrogen atom, q represents a single bond, any one of A, D, E, and G represents a nitrogen atom with the other three each representing a carbon atom, Y, Z, $R^3$, and $R^4$ are as defined in formula (I), $R^2$ and $R^3$ are as defined in formula (I) with the proviso that they are not attached to each other to form a ring, and the piperazine in the formula is attached to any one of the 2-, 4-, and 6-positions of pyridine, are preferably produced by the following process.

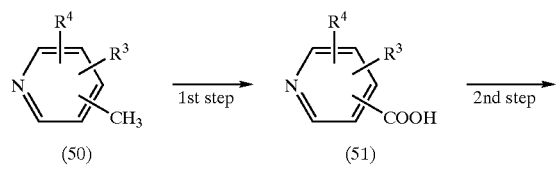

(50) → (51)

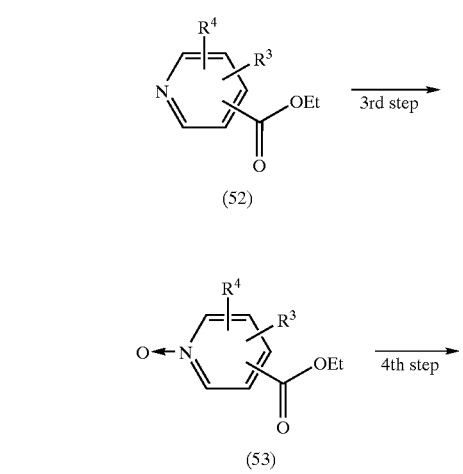

(52)

(53)

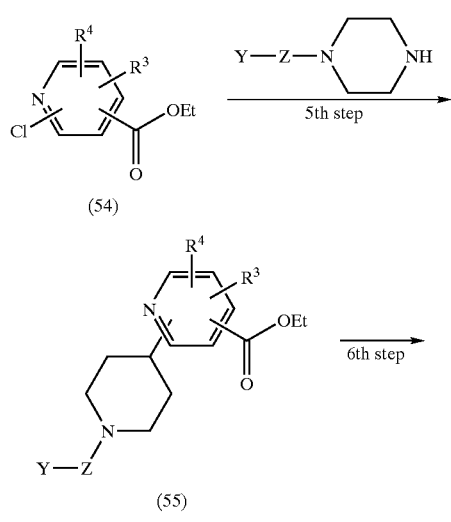

(54)

(55)

(56)

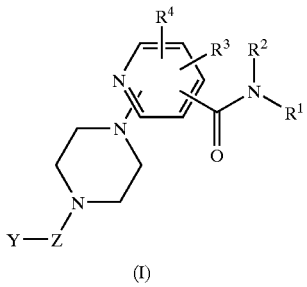

(I)

The first step is selective oxidation of methyl at the 2-, 4-, or 6-position of pyridine. A compound represented by formula (50), wherein $R^3$ and $R^4$ are defined in formula (I), is reacted with $SeO_2$ in a solvent inert to the reaction, for example, 1,4-dioxane, tetrahydrofuran, benzene, toluene, xylene, or diphenyl ether, for 0.5 to 48 hr, preferably 1 to 5 hr, at 50 to 250° C., preferably 100 to 200° C. When the oxidation reaction is stopped at the stage of aldehyde, a reaction is further carried out with silver(I) oxide and caustic soda in a solvent inert to the reaction, for example, water, 1,4-dioxane, toluene, xylene, or diphenyl ether, for 0.2 to 48 hr, preferably 0.2 to 5 hr, at −20 to 100° C., preferably −10 to 50° C., to give a compound represented by formula (51) wherein $R^3$ and $R^4$ are as defined above.

The second step is esterification of the carboxylic acid. The compound represented by formula (51) is reacted with a coupling agent, such as 1,3-dicyclohexylcarbodiimide (DCC), preferably in a hydrochloric acid-ethanol solvent in the presence of ethanol-pyridine for 0.5 to 56 hr, preferably 1 to 48 hr, at 50 to 200° C., preferably 80 to 150° C., to give a compound represented by formula (52) wherein $R^3$ and $R^4$ are as defined above.

The third step is conversion of the pyridine compound to N-oxide compound. The compound represented by formula (52) is reacted with m-chloroperbenzoic acid or hydrogen peroxide in a solvent inert to the reaction, for example, chloroform, dichloromethane, carbon tetrachloride, benzene, toluene, or xylene, for 1 to 48 hr, preferably 1 to 24 hr, at 0 to 200° C., preferably 0 to 100° C., to give a compound represented by formula (53) wherein $R^3$ and $R^4$ are as defined above.

The fourth step is chlorination of the pyridine compound. The compound represented by formula (53) is reacted with phosphorus oxychloride in a solvent inert to the reaction, for example, chloroform, dichloromethane, carbon tetrachloride, benzene, toluene, or xylene, or in the absence of any solvent for 1 to 48 hr, preferably 1 to 24 hr, at 0 to 250° C., preferably 30 to 200° C., to give a compound represented by formula (54) wherein $R^3$ and $R^4$ are as defined above.

The fifth step is replacement of the chlorine atom in the pyridine compound with piperazine. The compound represented by formula (54) is reacted with a compound Y—Z-piperazine, wherein Y and Z are as defined in formula (I), in a solvent inert to the reaction, for example, chloroform, dichloromethane, carbon tetrachloride, benzene, toluene, or xylene, or in the absence of any solvent for 1 to 48 hr, preferably 2 to 24 hr, at 0 to 250° C., preferably 30 to 200° C., to give a compound represented by formula (55) wherein $R^3$ and $R^4$ are as defined above, Y is as defined in formula (I), and Z represents —$(CH_2)_p$— wherein p is an integer of 1 to 6.

The sixth step is hydrolysis of the ester. The compound represented by formula (55) is reacted with caustic soda and water in a solvent, which is inert to the reaction and is miscible with water, for example, ethanol, dimethyl sulfoxide, or N,N-dimethylformamide, for 1 to 48 hr, preferably 2 to 24 hr, at 0 to 150° C., preferably 20 to 100° C., to give a compound represented by formula (56) wherein $R^3$, $R^4$, Y, and Z are as defined above.

The seventh step is amidation. In this case, synthesis is carried out by a conventional method commonly used in the synthesis of peptides. Specifically, the compound represented by formula (56) is reacted with an amide coupling reagent, such as 1,3-dicyclohexylcarbodiimide (DCC), a BOP reagent (benzotriazol-1-yloxytris(dimethylamino) phosphonium hexafluorophosphate), 1-(3-dimethylaminopropyl)-3-ethylcarbodiimide (WSCI), or 1-hydroxybenzotriazole (HOBt), in the presence of 0.1 to 5 equivalents of a base (pyridine, triethylamine, N-methylmorpholine, or dimethylaminopyridine) to give a compound represented by formula (I) wherein $R^1$, $R^2$, $R^3$, $R^4$, Y, and Z are as defined above. The amide bond can also be formed by an acid chloride method using thionyl chloride or the like.

[Synthesis Process 16]

Among the compounds represented by formula (I), compounds, wherein Q represents a nitrogen atom, q represents a single bond, any one of A, D, E, and G represents a nitrogen atom with the other three each representing a carbon atom, Y and Z are as defined in formula (I), $R^2$ and $R^3$ are as defined in formula (I) with the proviso that they are not attached to each other to form a ring, $R^3$ and $R^4$ do not represent a halogen, $R^1$ and $R^2$ are as defined in formula (I), and piperazine in the formula is attached to any one of the 3- and 5-positions of pyridine, are preferably produced by the following process.

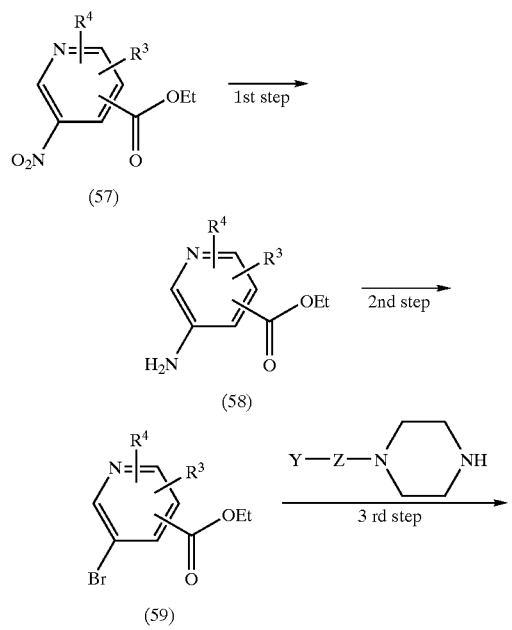

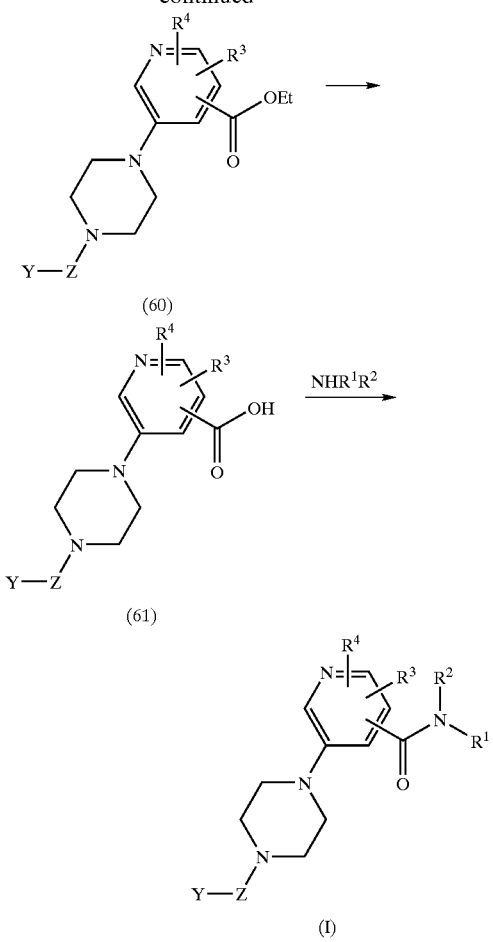

The first step is reduction of nitro to amino. A compound represented by formula (57), which has been synthesized in the same manner as described in J. Am. Chem. Soc., 75, 737–8 (1953), is subjected to catalytic reduction in the presence of palladium-carbon, palladium-black, palladium hydroxide, platinum oxide, or Raney-nickel, reduction with tin, zinc, iron or the like in combination with an acid, such as acetic acid, or reduction with sodium boron hydride or hydrazine, preferably catalytic reduction in the presence of palladium-carbon or palladium-black or reduction with iron and acetic acid. The reaction may be carried out in a solvent inert to the reaction, for example, methanol, ethanol, tetrahydrofuran, N,N-dimethylformamide, or benzene, for 0.5 to 48 hr, preferably 0.5 to 30 hr, at 0 to 100° C., preferably 0 to 50° C. Thus, a compound represented by formula (58), wherein $R^3$ and $R^4$ are as defined above, is prepared.

The second step is a Sandmyer reaction of the aniline compound. The compound represented by formula (58) may be treated in the same manner as described in Angew. Chem., 87, 143 (1975) to give a compound represented by formula (59) wherein $R^3$ and $R^4$ are as defined above.

The third step is a palladium coupling reaction. The compound represented by formula (59) may be reacted with a compound Y—Z-piperazine, wherein Y and Z are as defined in formula (I), in the same manner as described in Tetrahedron Lett., 38, 36, 6359–62 (1997) to give a compound represented by formula (60) wherein $R^3$, $R^4$, Y, and Z are as defined above.

The compound represented by formula (60) may be treated in the same manner as described in the fifth and sixth steps of synthesis process 6 to give a compound represented by formula (I) wherein $R^1$, $R^2$, $R^3$, $R^4$, Y, and Z are as defined above.
[Synthesis Process 17]

Among the compounds represented by formula (I), compounds, wherein Q represents a nitrogen atom, q represents a single bond, any one of A, D, E, and G represents a nitrogen atom with the other three each representing a carbon atom, Y, Z, $R^1$, and $R^4$ are as defined in formula (I), $R^2$ and $R^3$ represent group —$(CH_2)_m$—, wherein m is 1 or 2, and piperazine in the formula is attached to any one of the 2-, 4-, and 6-positions of pyridine, are preferably produced by the following process.

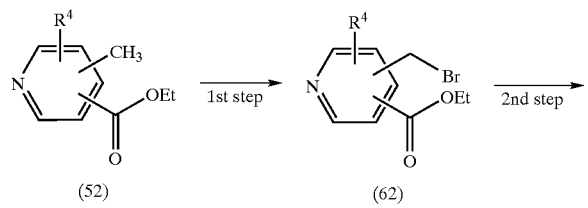

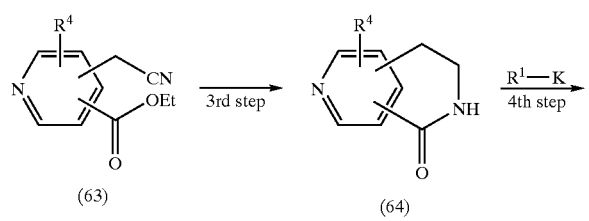

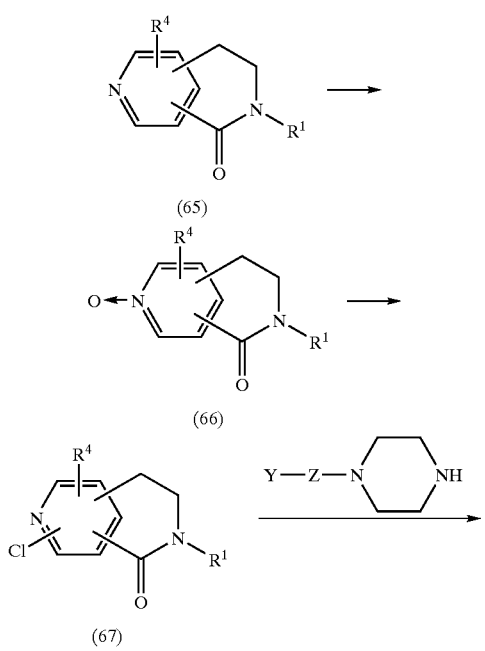

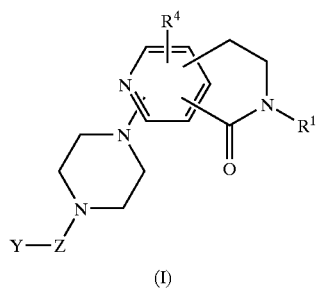

The first step is a halogenation at the position of benzyl. The compound obtained in the second step of synthesis process 15 (the compound represented by formula (52) wherein $R^3$ represents methyl) may be treated with N-bromosuccinimide or 2,2'-azobis(isobutyronitrile) by the method as described in Angew. Chem., 90, 360 (1978) to give a compound represented by formula (62) wherein $R^4$ is as defined above.

The second step is conversion of the compound represented by formula (62) to a nitrile compound. The compound represented by formula (62) is reacted with sodium prussiate, potassium prussiate, or silver(I) cyanide, in a solvent inert to the reaction, for example, dimethyl sulfoxide, N,N-dimethylformamide, 1,4-dioxane, tetrahydrofuran, or acetonitrile, for 0.5 to 24 hr, preferably 1 to 10 hr, at 0 to 100° C., preferably 10 to 80° C., to give a compound represented by formula (63) wherein $R^4$ is as defined above.

The third step is reductive lactam cyclization of the nitrile compound. The compound represented by formula (63) is subjected to a reduction reaction by catalytic reduction in the presence of palladium-carbon, palladium-black, palladium hydroxide, platinum oxide, or Raney-nickel, reduction with tin, zinc, iron or the like in combination with an acid, such as acetic acid, or reduction with sodium boron hydride or hydrazine, preferably catalytic reduction in the presence of palladium-carbon, palladium-black, or Raney-nickel. The reaction may be carried out in a solvent inert to the reaction, for example, methanol, ethanol, tetrahydrofuran, N,N-dimethylformamide, or benzene, for 0.5 to 48 hr, preferably 0.5 to 10 hr, at 0 to 200° C., preferably 0 to 100° C. Thus, a compound represented by formula (64), wherein $R^4$ is as defined above, is prepared.

The fourth step is alkylation of the amide compound. The compound represented by formula (64) as described in J. Med. Chem., 39, 4583–91 (1996) is reacted with a compound represented by $R^1$—K, wherein K represents a halogen atom and $R^1$ is as defined above, in a solvent inert to the reaction, for example, tetrahydrofuran or benzene, for example, in the presence of sodium hydride or trimethyldisilazane sodium. Alternatively, the compound represented by formula (65) is reacted with potassium carbonate, sodium hydroxide, or tetrabutylammonium hydrogen sulfate and a compound represented by $R^1$—K, wherein K represents a halogen atom and $R^1$ is as defined above, described in Synthesis, 526–9 (1979). Thus a compound represented by formula (65) is prepared wherein $R^1$ and $R^4$ are as defined above.

The compound represented by formula (65) may be treated in the same manner as described in the third, fourth, and fifth steps of synthesis process 15 to give a compound represented by formula (I) wherein $R^1$, $R^4$, Y, and Z are as defined above.
[Synthesis Process 18]

Among the compounds represented by formula (I), compounds, wherein Q represents a nitrogen atom, q represents a single bond, any one of A, D, E, and G represents a nitrogen atom with the other three each representing a carbon atom, Y, Z, $R^1$, and $R^4$ are as defined in formula (I), $R^2$ and $R^3$ represent group —$(CH_2)_m$—, wherein m is 1 or 2, and piperazine in the formula is attached to any one of the 3- and 5-positions of pyridine, are preferably produced by the following process.

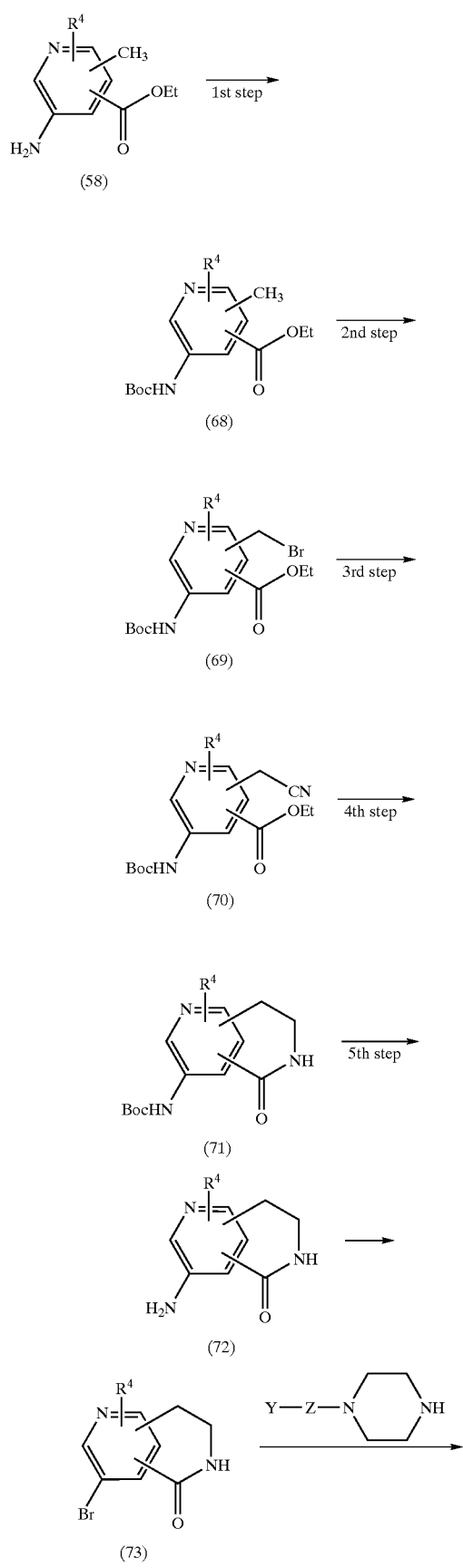

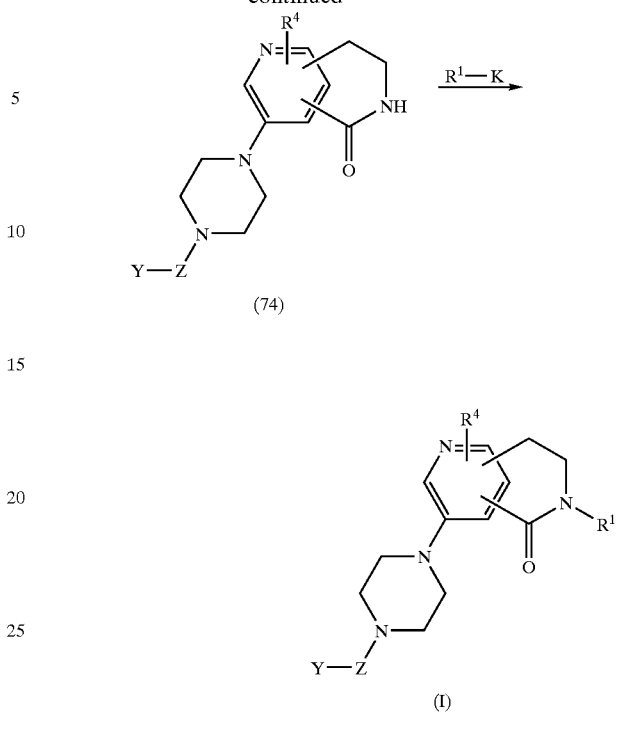

The first step is conversion of the aniline compound to a Boc compound. The compound, represented by formula (58) wherein $R^4$ is as defined above, prepared in the first step of synthesis process 16 is reacted with di-t-butyl dicarbonate in dichloromethane in the presence of triethylamine to give a compound represented by formula (68) wherein $R^4$ is as defined above.

The compound represented by formula (68) may be treated in the same manner as described in the first, second, and third steps of synthesis process 17 to give a compound represented by formula (71) wherein $R^4$ is as defined above.

The compound represented by formula (71) is reacted with concentrated hydrochloric acid or 3 N hydrochloric acid in a solvent inert to the reaction, for example, ethyl acetate or 1,4-dioxane, for 0.5 to 48 hr, preferably 0.5 to 10 hr, at 0 to 200° C., preferably 0 to 100° C., to give a compound represented by formula (72) wherein $R^4$ is as defined above.

The compound represented by formula (72) is treated in the same manner as described in the second and third steps of synthesis process 16 and in the fourth step of synthesis process 17 to give a compound represented by formula (I) wherein $R^1$, $R^4$, Y, and Z are as defined above.

[Synthesis Process 19

Among the compounds represented by formula (I), compounds, wherein $R^1$, Y, and Z are as defined in formula (I), $R^2$ and $R^3$ represent group —$(CH_2)_m$—, wherein m is 1 or 2, A, D, E, and G each represent a carbon atom, Q represents a nitrogen atom, q represents a single bond, and $R^4$ represents a halogen atom, may also be produced by halogenation of intermediates (10) and (11), wherein $R^4$ represents a hydrogen atom, in synthesis process 3.

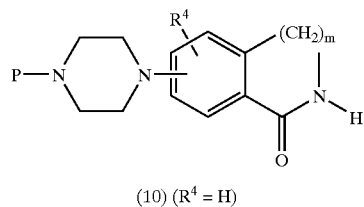 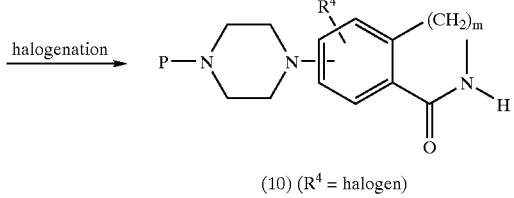

(10) ($R^4$ = H)    (10) ($R^4$ = halogen)

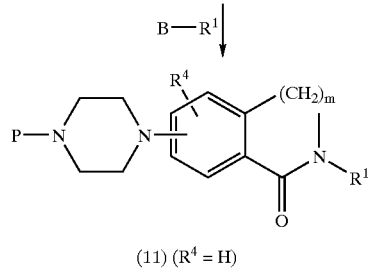 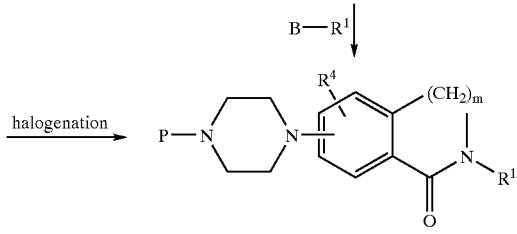

(11) ($R^4$ = H)    (11) ($R^4$ = halogen)

The compound represented by formula (10), wherein P represents a protective group and $R^4$ represents a hydrogen atom, and the compound represented by formula (11), wherein $R^1$ and P are as defined above and $R^4$ represents a hydrogen atom, may be halogenated by the method as described in synthesis process 2 to give a compound represented by formula (10), wherein $R^4$ represents a halogen atom, and a compound represented by formula (II) wherein $R^4$ represents a halogen atom, respectively. The compounds represented by formulae (10) and (11) thus obtained may be treated as described in the second and third steps and later steps of synthesis process 3 to give a compound represented by formula (I) wherein $R^1$, $R^2$, $R^3$, A, D, E, G, Q, q, Y, and Z are as defined above and $R^4$ represents a halogen atom.

[Synthesis Process 20]

Among the compounds represented by formula (I), compounds, wherein $R^1$, $R^4$, Y, and Z are as defined in formula (I), $R^2$ and $R^3$ represent group —N=CH—, A, D, E, and G each represent a carbon atom, Q represents a nitrogen atom, and q represents a single bond, are preferably produced by the following process.

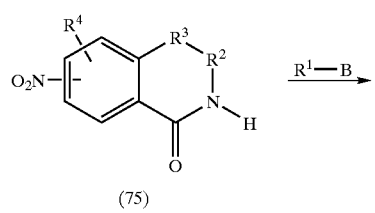

(75)

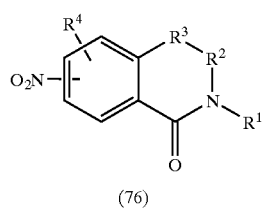

(76)

A compound represented by formula (75), wherein $R^2$ and $R^3$ represent —N=CH— and $R^4$ is as defined above, is synthesized according to the method as described in J. Chem. Soc., 5275 (1961).

The compound represented by formula (75) may be reacted with a compound $R^1$—B, wherein B represents a halogen atom, such as chlorine, bromine, or iodine, $C_1$-$C_4$ alkylsulfonyl, such as methanesulfonyl, or arylsulfonyl, such as p-toluene sulfonyl, and $R^1$ is as defined above, according to the method described in J. Med. Chem., 39, 4583–4591 (1996) or Synthesis, 79, 527–529 (1979) to give a compound represented by formula (76) wherein $R^1$, $R^2$, $R^3$, and $R^4$ are as defined above.

Next, the compound represented by formula (76) may be treated in the same manner as described in the fourth step and later steps of synthesis process 1 to give a compound represented by formula (I) wherein $R^3$ and $R^4$ represent group —N=CH—, $R^1$, $R^4$, A, D, E, G, Q, q, Y, and Z are as defined above.

[Synthesis Process 21]

Among the compounds represented by formula (I), compounds, wherein $R^1$, $R^4$, Y, and Z are as defined in formula (I), $R^2$ and $R^3$ represent group —CH=N—, A, D, E, and G each represent a carbon atom, Q represents a nitrogen atom, and q represents a single bond, are preferably produced by the following process.

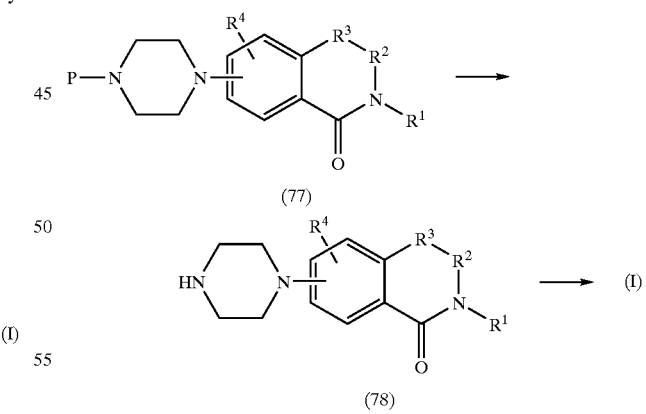

A compound represented by formula (77), wherein $R^2$ and $R^3$ represent group —CH=N—, P represents a conventional protective group used in the synthesis of peptides, preferably t-butoxycarbonyl, benzyloxycarbonyl, p-methoxybenzyloxycarbonyl, 2,2,2-trichloroethoxycarbonyl, trifluoroacetyl, allyloxycarbonyl, or trityl, and $R^1$ and $R^4$ are as defined above, is synthesized according to the method as described in J. Med. Chem., 39, 4583–4591 (1996).

The protective group of the compound represented by formula (77) may be removed by a conventional method to give a compound represented by formula (78) wherein $R^1$, $R^2$, $R^3$, and $R^4$ are as defined above.

Next, the compound represented by formula (78) may be treated as described in the sixth step of synthesis process 1 to give a compound represented by formula (I) wherein $R^2$ and $R^3$ represent group —CH=N— and $R^1$ and $R^4$ are as defined above.

[Synthesis Process 22]

Among the compounds represented by formula (I), compounds, wherein $R^1$, $R^4$, Y, and Z, are as defined in formula (I), $R^2$ and $R^3$ represent group —($C_{1-6}$ alkyl)C=N—, A, D, E, and G each represent a carbon atom, Q represents a nitrogen atom, and q represents a single bond, are preferably produced by the following process.

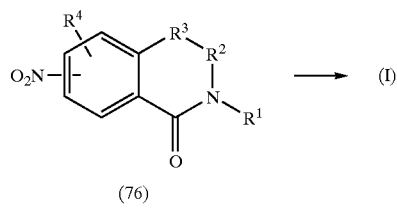

A compound represented by formula (76), wherein $R^2$ and $R^3$ represent group —($C_{1-6}$ alkyl)C=N— and $R^1$ and $R^4$ are as defined above, is synthesized according to the method as described in J. Med. Chem., 33, 161–166 (1990).

The compound represented by formula (76) may be treated as described in the fourth step and later steps of synthesis process 1 to give a compound represented by formula (I) wherein $R^2$ and $R^3$ represent group —($C_{1-6}$ alkyl)C=N— and $R^1$ and $R^4$ are as defined above.

[Synthesis Process 23]

Among the compounds represented by formula (I), compounds, wherein $R^1$, $R^2$, $R^3$, Y, and Z are as defined in formula (I), $R^4$ represents alkoxycarbonyl, A, D, E, and G each represent a carbon atom, Q represents a nitrogen atom, and q represents a single bond, are also preferably produced by the following process.

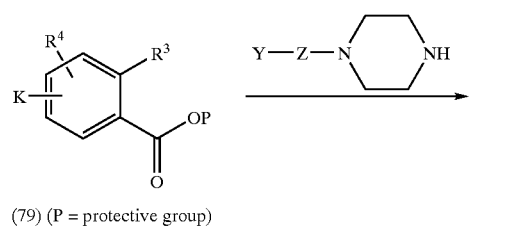

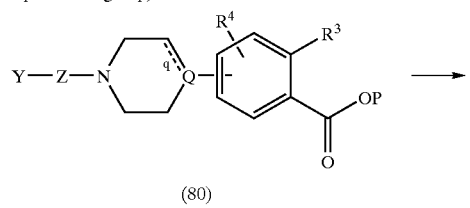

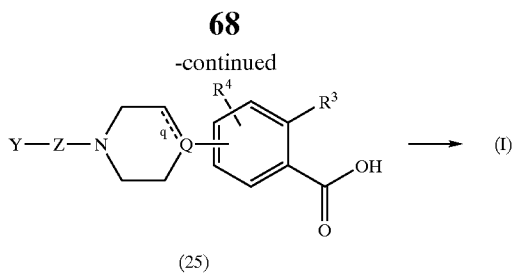

A compound represented by formula (79), wherein K represents a halogen atom, P represents a conventional protective group used in the synthesis of peptides, preferably benzyl, trimethylsilyl, trityl, or phenacyl, may be treated in the same manner as described in the first step of route 1 in synthesis process 7 to give a compound represented by formula (80) wherein P, Q, q, Y, Z, $R^3$, and $R^4$ are as defined above.

Next, the protective group of the compound represented by formula (80) may be removed by a conventional method to give a compound represented by formula (25) wherein Q, q, Y, Z, $R^3$, and $R^4$ are as defined above.

The compound represented by formula (25) may be then treated in the same manner as described in the sixth step of synthesis process 6 to give a compound represented by formula (I) wherein Q represents a nitrogen atom, q represents a single bond, Y, Z, $R^1$, $R^2$, and $R^3$ are as defined above, and $R^4$ represents alkoxycarbonyl.

[Synthesis Process 24]

Among the compounds represented by formula (I), compounds, wherein $R^1$, $R^2$, $R^3$, Y, and Z are as defined in formula (I), A, D, E, and G each represent a carbon atom, Q represents a nitrogen atom, q represents a single bond, and $R^4$ represents carboxyl, are also preferably produced by the following process.

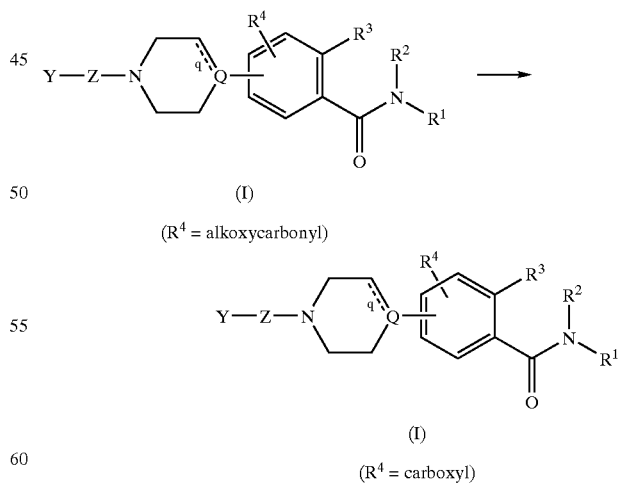

A compound represented by formula (I), wherein Q represents a nitrogen atom, q represents a single bond, Y, Z, $R^1$, $R^2$, and $R^3$ are as defined above, and $R^4$ represents alkoxycarbonyl, is hydrolyzed in the same manner as described in the fifth step of synthesis process 6 to give a compound represented by formula (I) wherein Q represents a nitrogen atom, q represents a single bond, Y, Z, R¹, R², and R³ are as defined above, and R⁴ represents carboxyl.

[Synthesis Process 25]

Among the compounds represented by formula (I), compounds, wherein Q represents a nitrogen atom, q represents a single bond, any one of A, D, E, and G represents a nitrogen atom with the other three each representing a carbon atom, Y, Z, R¹, and R⁴ are as defined in formula (I), R² and R³ are as defined in formula (I) with the proviso that they are not attached to each other to form a ring, and piperazine in the formula is attached to any one of the 2-, 4-, and 6-positions of pyridine, are also preferably produced by the following process.

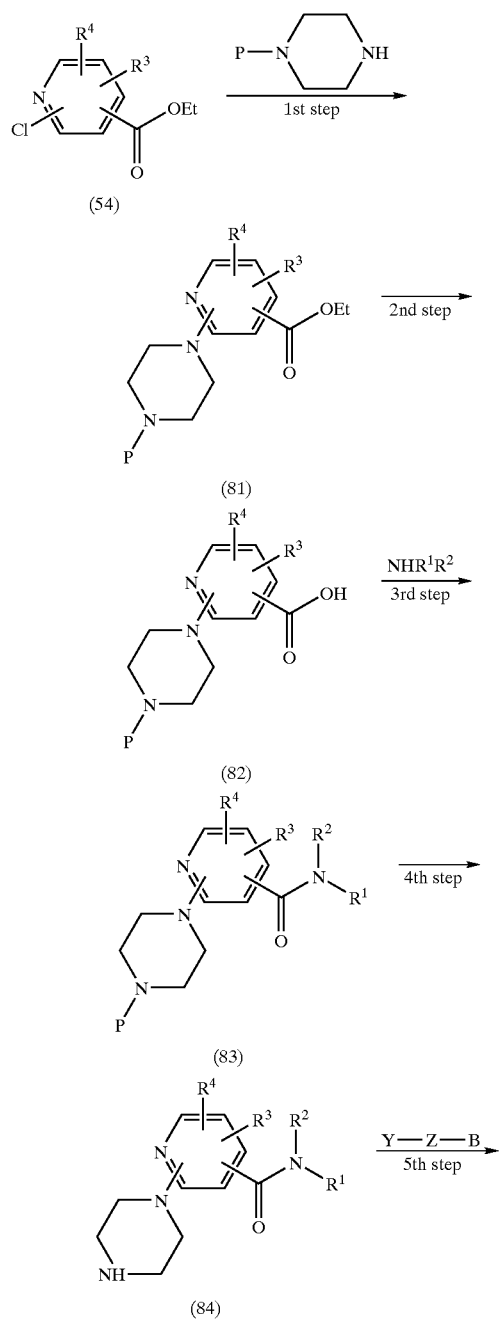

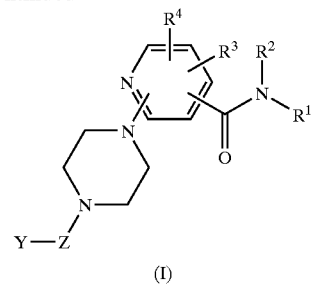

The first step is replacement of the chlorine atom in the pyridine compound with piperazine. Specifically, a compound represented by formula (54), wherein R³ and R⁴ are as defined above, is reacted with P-piperazine, wherein P represents a conventional protective group used in the synthesis of peptides, preferably t-butoxycarbonyl, benzyloxycarbonyl, p-methoxybenzyloxycarbonyl, 2,2,2-trichloroethoxycarbonyl, trifluoroacetyl, allyloxycarbonyl, or trityl, in a solvent inert to the reaction, for example, chloroform, dichloromethane, carbon tetrachloride, benzene, toluene, or xylene, or in the absence of any solvent, for 1 to 48 hr, preferably 2 to 24 hr, at 0 to 250° C., preferably 30 to 200° C., to give a compound represented by formula (81) wherein P, R³, and R⁴ are as defined above.

The second step is the hydrolysis of the ester. The compound represented by formula (81) is reacted with caustic soda and water in a solvent, which is inert to the reaction and is miscible with water, for example, ethanol, dimethyl sulfoxide, or N,N-dimethylformamide, for 1 to 48 hr, preferably 2 to 24 hr, 0 to 150° C., preferably 20 to 100° C., to give a compound represented by formula (82) wherein P, R³ and R⁴ are as defined above.

The third step is amidation. In this case, synthesis is carried out in the same manner as commonly used in the synthesis of peptides. Specifically, the compound represented by formula (82) is reacted with an amide coupling reagent, such as 1,3-dicyclohexylcarbodiimide(DCC), a BOP reagent (benzotriazol-1-yloxytris(dimethylamino) phosphonium hexafluorophosphate), 1-(3-dimethylaminopropyl)-3-ethylcarbodiimide (WSCI), or 1-hydroxybenzotriazole (HOBt), in the presence of 0.1 to 5 equivalents of a base (pyridine, triethylamine, N-methylmorpholine, or dimethylaminopyridine) to give a compound represented by formula (83) wherein R¹, R², R³, R³, and P are as defined above. This step of amidation may also be carried out by an acid chloride method, for example, using thionyl chloride.

The protective group of the compound represented by formula (83) thus obtained may be removed by a conventional method to give a compound represented by formula (84) wherein R¹, R², R³, and R⁴ are as defined above.

The compound represented by formula (84) may be condensed with a compound Y—Z—B, wherein Y, Z, and B are as defined above, in the same manner as described in the fourth step of synthesis process 6 to give a compound represented by formula (I) wherein Y, Z, R¹, R², R³, and R⁴ are as defined above.

[Synthesis Process 26]

Among the compounds represented by formula (I), compounds, wherein Q represents a nitrogen atom, q represents a single bond, any one of A, D, E, and G represents a nitrogen atom with the other three each representing a carbon atom, Y and Z are as defined in formula (I), R² and R³ are as defined in formula (I) with the proviso that they are not attached to each other to form a ring, $R^3$ and $R^4$ do not represent a halogen atom, $R^1$ and $R^2$ are as defined in formula (I), and piperazine in the formula is attached to any one of the 3- and 5-positions of pyridine, are also preferably produced by the following process.

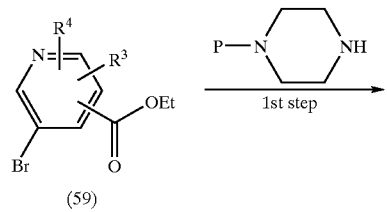

(59)

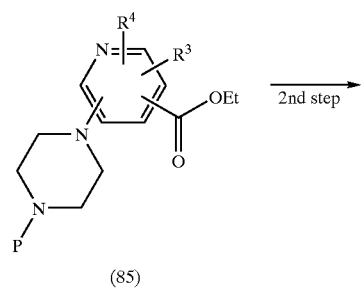

(85)

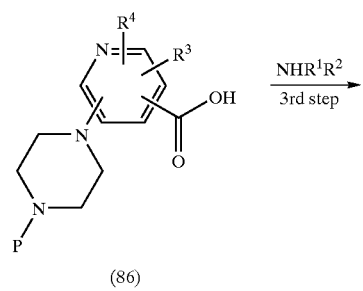

(86)

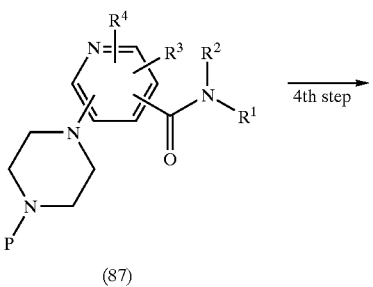

(87)

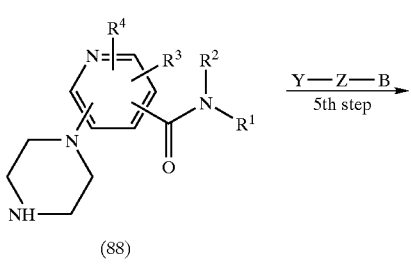

(88)

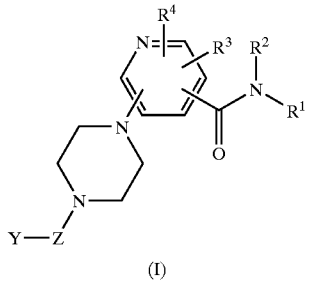

(I)

A compound represented by formula (59), wherein $R^3$ and $R^4$ are as defined above, is reacted with a compound P-piperazine wherein P represents a conventional protective group used in the synthesis of peptides, preferably t-butoxycarbonyl, benzyloxycarbonyl, p-methoxybenzyloxycarbonyl, 2,2,2-trichloroethoxycarbonyl, trifluoroacetyl, allyloxycarbonyl, or trityl, in the same manner as described in Tetrahedron Lett., 38, 36, 6359–62 (1997), in a solvent inert to the reaction, for example, chloroform, dichloromethane, carbon tetrachloride, benzene, toluene, or xylene, or in the absence of any solvent, for 1 to 48 hr, preferably 2 to 24 hr, at 0 to 250° C., preferably 30 to 200° C., to give a compound represented by formula (85) wherein P, $R^3$, and $R^4$ are as defined above.

The compound represented by formula (85) may be further treated in the same manner as described in the second step and later steps of synthesis process 25 to give a compound represented by formula (I) wherein $R^1$, $R^2$, $R^3$, $R^4$, Y, and Z are as defined above.

EXAMPLE 1

N-Benzyl-3-[4-(3,3-diphenyl-1-propyl)piperazin-1-yl]-N-methylbenzamide (a) Ethyl 3-aminobenzoate (1.65 g) was dissolved in xylene (20 ml), and bischloroethylamine hydrochloride (1.79 g) was added to the solution. The mixture was heated under reflux with stirring for two days. The solvent was removed from the reaction solution by distillation under the reduced pressure. Water and a saturated aqueous sodium hydrogencarbonate solution were added to the residue, followed by extraction with ethyl acetate. The organic layer was dried over anhydrous magnesium sulfate, and the solvent was then removed by distillation under the reduced pressure. The residue was purified by column chromatography on silica gel (chloroform:methanol=9:1–5:1) to give 1.60 g (70.0%) of ethyl 3-piperazin-1-yl-benzoate.

$^1$H-NMR (CDCl$_3$) δ: 1.38 (3H, t, J=7.0 Hz), 1.99 (1H, bs), 3.04 (4H, m), 3.19 (4H, m), 4.36 (2H, q, J=7.0 Hz), 7.08 (1H, m), 7.30 (1H, t, J=8.3 Hz), 7.51 (1H, m), 7.59 (1H, m).

(b) The compound (1.60 g) prepared in step (a) was dissolved in N,N-dimethylformamide (20 ml). Potassium carbonate (2.79 g) and 3,3-diphenylpropyl bromide (2.82 g) were added to the solution. The mixture was stirred at 70° C. for 8 hr. The reaction solution was extracted with ethyl acetate, followed by washing with water and saturated brine. The organic layer was dried over anhydrous magnesium sulfate, and the solvent was then removed by distillation under the reduced pressure. The residue was purified by column chromatography on silica gel (chloroform:ethyl acetate=5:1) to give 2.00 g (71.3%) of ethyl 3-[4-(3,3-diphenyl-1-propyl)piperazin-1-yl]benzoate.

¹H-NMR (CDCl₃) δ: 1.38 (3H, t, J=7.3 Hz), 2.31 (4H, m), 2.57 (4H, m), 3.25 (4H, m), 4.02 (1H, t, J=7.5 Hz), 4.35 (2H, q, J=7.3 Hz), 7.07 (1H, m), 7.14–7.30 (11H, m), 7.49 (1H, m), 7.57 (1H, m).

(c) The compound (2.00 g) prepared in step (b) was dissolved in a mixed solvent composed of tetrahydrofuran (20 ml) and methanol (10 ml), and a 1 mol/l aqueous sodium hydroxide solution (10 ml) was added to the solution. The mixture was then stirred at 65° C. for one hr. The solvent was removed from the reaction solution by distillation under the reduced pressure. Water (30 ml) was then added to the residue, and the mixture was adjusted to pH 4 by the addition of 1 mol/l hydrochloric acid. The resultant precipitate was collected by filtration, and was then dried to give 1.60 g (85.6%) of 3-[4-(3,3-diphenyl-1-propyl)piperazin-1-yl] benzoic acid.

¹H-NMR (CDCl₃) δ: 2.50 (2H, m), 2.66 (2H, m), 2.96 (4H, m), 3.41 (4H, m), 3.48 (1H, m), 3.96 (1H, t, J=7.5 Hz), 7.08 (1H, m), 7.17–7.32 (11H, m), 7.58 (2H, m).

(d) The compound (0.10 g) prepared in step (c) was dissolved in dichloromethane (2 ml). A BOP reagent (0.10 g) and diisopropylethylamine (0.052 ml) were added to the solution. The mixture was stirred at room temperature for 30 min. N-Methylbenzylamine (0.039 ml) was then added thereto, and the mixture was stirred at room temperature overnight. The reaction solution was extracted with ethyl acetate, followed by washing with water. The organic layer was dried over anhydrous magnesium sulfate, and the solvent was then removed by distillation under the reduced pressure. The residue was purified by preparative TLC (hexane:ethyl acetate=1:1) to give 0.072 g (57.3%) of the title compound.

¹H-NMR (CDCl₃) δ: 2.31 (4H, m), 2.54 (4H, m), 2.86–3.22 (7H, m), 4.02 (1H, m), 4.52–4.75 (2H, m), 6.92 (3H, m), 7.27 (16H, m).

EIMS (M/Z): 503 (M⁺).

Compounds of Examples 2 to 32 were synthesized in the same manner as in Example 1, except that the following amines were used instead of N-methylbenzylamine in step (d) of Example 1.

Example 2: N-Cyclohexylbenzylamine
Example 3: N-Isopropylbenzylamine
Example 4: 1,2,3,4-Tetrahydroisoquinoline
Example 5: Diisopropylamine
Example 6: 4-Benzylpiperidine
Example 7: N-Methylcyclohexylamine
Example 8: N-Phenylbenzylamine
Example 9: Dibenzylamine
Example 10: N-Cyclopropylbenzylamine
Example 11: N-Cyclohexyl-4-chlorobenzylamine
Example 12: N-Cyclohexyl-4-methylbenzylamine
Example 13: N-Isopropylcyclohexylamine
Example 14: N-t-Butylbenzylamine
Example 15: N-n-Butylbenzylamine
Example 16: N,α-Dimethylbenzylamine
Example 17: N-Isopropylaniline
Example 18: N-Allylcyclohexylamine
Example 19: 2,6-Dimethylpiperidine
Example 20: N-Ethylcyclohexylamine
Example 21: N-Methyl-2-dimethylamino-ethylamine
Example 22: N-Allylcyclopentylamine
Example 23: Diallylamine
Example 24: N-Allylaniline
Example 25: N-Allylcyclohexylmethylamine
Example 26: N-Methoxymethylamine
Example 27: N-Ethylbenzylamine
Example 28: N-Allylbenzylamine
Example 29: N-Cyclohexylmethyl-pyridin-2-ylmethylamine
Example 30: N-Cyclohexylmethyl-pyridin-4-ylmethylamine
Example 31: N-Cyclohexylmethyl-tetrahydropyran-2-ylmethylamine
Example 32: N-Allyl-trans-4-hydroxycyclohexylamine

EXAMPLE 2

N-Benzyl-N-cyclohexyl-3-[4-(3,3-diphenyl-1-propyl)piperazin-1-yl]benzamide

¹H-NMR (CDCl₃) δ: 1.02–1.76 (10H, m), 2.32 (4H, m), 2.57 (4H, m), 3.00–3.23 (4H, m), 3.69 (1H, m), 4.02 (1H, t, J=6.8 Hz), 4.48–4.68 (2H, m), 6.90 (3H, m), 7.24 (16H, m).

TSIMS (M/Z): 572 (M+H)⁺.

EXAMPLE 3

N-Benzyl-3-[4-(3,3-diphenyl-1-propyl)piperazin-1-yl]-N-isopropylbenzamide

¹H-NMR (CDCl₃) δ: 1.10 (6H, m), 2.32 (4H, m), 2.56 (4H, m), 2.98–3.23 (4H, m), 4.03 (1H, t, J=7.1 Hz), 4.19 (1H, m), 4.63 (2H, m), 6.90 (3H, m), 7.24 (16H, m).

TSIMS (M/Z): 532 (M+H)⁺.

EXAMPLE 4

(3,4-Dihydro-1H-isoquinolin-2-yl)-[3-[4-(3,3-diphenyl-1-propyl)piperazin-1-yl]phenyl]methanone ¹H-NMR (CDCl₃) δ: 2.28 (4H, m), 2.56 (4H, m), 2.91 (2H, m), 3.22 (4H, m), 3.63 (1H, m), 3.98 (1H, m), 4.02 (1H, t, J=7.2 Hz), 4.58 (1H, m), 4.89 (1H, m), 6.89 (3H, m), 7.23 (15H, m).

EIMS (M/Z): 515 (M⁺).

EXAMPLE 5

N,N-Diisopropyl-3-[4-(3,3-diphenyl-1-propyl)piperazin-1-yl]benzamide

¹H-NMR (CDCl₃) δ: 1.27 (12H, m), 2.23 (4H, m), 2.57 (4H, m), 3.22 (4H, m), 3.50–3.90 (2H, m), 4.02 (1H, t, J=7.4 Hz), 6.75 (1H, d, J=7.5 Hz), 6.85 (1H, s), 6.90 (1H, d, J=7.5 Hz), 7.21 (11H, m).

TSIMS (M/Z): 484 (M+H)⁺.

EXAMPLE 6

(4-Benzyl-piperidin-1-yl)-[3-[4-(3,3-diphenyl-1-propyl)piperazin-1-yl]phenyl]methanone ¹H-NMR (CDCl₃) δ: 1.61 (5H, m), 2.32 (4H, m), 2.56 (4H, m), 2.80 (4H, m), 3.21 (4H, m), 3.75 (1H, m), 4.02 (1H, t, J=7.2 Hz), 4.70 (1H, m), 6.80 (1H, d, J=7.3 Hz), 6.92 (2H, m), 7.22 (16H, m).

EIMS (M/Z): 557 (M⁺).

EXAMPLE 7

N-Cyclohexyl-3-[4-(3,3-diphenyl-1-propyl)piperazin-1-yl]-N-methylbenzamide

¹H-NMR (CDCl₃) δ: 1.06–1.72 (10H, m), 2.32 (4H, m), 2.57 (4H, m), 2.78+2.96 (3H, brs×2), 3.22 (4H, m), 3.51+

4.52 (1H, m), 4.03 (1H, t, J=7.0 Hz), 6.80 (1H, d, J=7.2 Hz), 6.93 (2H, m), 7.24 (11H, m).

TSIMS (M/Z): 496 (M+H)+.

EXAMPLE 8

N-Benzyl-3-[4-(3,3-diphenyl-1-propyl)piperazin-1-yl]-N-phenylbenzamide $^1$H-NMR (CDCl$_3$) δ: 2.27 (4H, m), 2.48 (4H, m), 3.00 (4H, m), 4.00 (1H, t, J=7.0 Hz), 5.13 (2H, s), 6.78–7.30 (24H, m).

TSIMS (M/Z): 566 (M+H)+.

EXAMPLE 9

N,N-Dibenzyl-3-[4-(3,3-diphenyl-1-propyl)piperazin-1-yl]benzamide $^1$H-NMR (CDCl$_3$) δ: 2.31 (4H, m), 2.51 (4H, m), 3.10 (4H, m), 4.02 (1H, t, J=7.2 Hz), 4.42 (2H, brs), 4.73 (2H, brs), 6.95 (3H, m), 7.27 (21H, m).

TSIMS (M/Z): 580 (M+H)+.

EXAMPLE 10

N-Benzyl-N-cyclopropyl-3-[4-(3,3-diphenyl-1-propyl)piperazin-1-yl]benzamide $^1$H-NMR (CDCl$_3$) δ: 0.53 (4H, brs), 2.33 (4H, m), 2.56 (4H, m), 3.19 (4H, m), 2.65–3.90 (1H, m), 4.02 (1H, t, J=7.1 Hz), 4.72 (2H, brs), 6.96 (3H, m), 7.27 (16H, m).

TSIMS (M/Z): 530 (M+H)+.

EXAMPLE 11

N-(4-Chlorobenzyl)-N-cyclohexyl-3-[4-(3,3-diphenyl-1-propyl)piperazin-1-yl]benzamide $^1$H-NMR (CDCl$_3$) δ: 1.02–1.67 (10H, m), 2.32 (4H, m), 2.57 (4H, m), 3.02–3.23 (4H, m), 3.68 (1H, m), 4.01 (1H, t, J=7.1 Hz), 4.45–4.65 (2H, m), 6.90 (3H, m), 7.28 (15H, m).

TSIMS (M/Z): 608 (M+H)+.

EXAMPLE 12

N-Cyclohexyl-3-[4-(3,3-diphenyl-1-propyl)piperazin-1-yl]-N-(4-methylbenzyl)benzamide $^1$H-NMR (CDCl$_3$) δ: 1.00–1.68 (10H, m), 2.32–2.57 (11H, m), 3.12 (4H, m), 3.68 (1H, m), 4.02 (1H, t, J=7.2 Hz), 4.43–4.66 (2H, m), 6.88 (2H, m), 7.21 (16H, m).

TSIMS (M/Z): 586 (M+H)+.

EXAMPLE 13

N-Cyclohexyl-3-[4-(3,3-diphenyl-1-propyl)piperazin-1-yl]-N-isopropylbenzamide $^1$H-NMR (CDCl$_3$) δ: 0.90–1.85 (16H, m), 2.30 (4H, m), 2.56 (4H, m), 3.00 (1H, m), 3.21 (4H, m), 3.50–3.70 (1H, m), 4.02 (1H, t, J=7.4 Hz), 6.75 (1H, d, J=7.2 Hz), 6.83 (1H, brs), 6.90 (1H, m), 7.25 (11H, m).

TSIMS (M/Z): 524 (M+H)+.

EXAMPLE 14

N-Benzyl-N-(t-butyl)-3-[4-(3,3-diphenyl-1-propyl)piperazin-1-yl]benzamide $^1$H-NMR (CDCl$_3$) δ: 1.20 (9H, brs), 2.26 (4H, m), 2.45 (4H, m), 3.00 (4H, m), 4.02 (1H, m), 4.67–4.70 (2H, brs×2), 6.85 (3H, m), 7.25 (16H, m).

TSIMS (M/Z): 546 (M+H)+.

EXAMPLE 15

N-Benzyl-N-(n-butyl)-3-[4-(3,3-diphenyl-1-propyl)piperazin-1-yl]benzamide $^1$H-NMR (CDCl$_3$) δ: 0.75–1.74 (7H, m), 2.31 (4H, m), 2.53 (4H, m), 3.07–3.46 (6H, m), 4.02 (1H, m), 4.67+4.70 (2H, brs×2), 6.89 (3H, m), 7.25 (16H, m).

TSIMS (M/Z): 546 (M+H)+.

EXAMPLE 16

3-[4-(3,3-Diphenyl-1-propyl)piperazin-1-yl]-N-methyl-N-(1-phenylethyl)benzamide $^1$H-NMR (CDCl$_3$) δ: 1.59 (3H, m), 2.52 (4H, m), 2.55–2.82 (7H, m), 3.18 (4H, m), 4.02 (1H, t, J=7.4 Hz), 5.10+6.10 (1H, m), 6.96 (3H, m), 7.26 (16H, m).

TSIMS (M/Z): 518 (M+H)+.

EXAMPLE 17

3-[4-(3,3-Diphenyl-1-propyl)piperazin-1-yl]-N-isopropyl-N-phenylbenzamide $^1$H-NMR (CDCl$_3$) δ: 1.20 (6H, d, J=6.8 Hz), 2.30 (4H, m), 2.50 (4H, m), 3.02 (4H, m), 4.01 (1H, t, J=7.0 Hz), 5.08 (1H, m), 6.75 (3H, m), 7.01 (3H, m), 7.24 (13H, m).

TSIMS (M/Z): 518 (M+H)+.

EXAMPLE 18

N-Allyl-N-cyclohexyl-3-[4-(3,3-diphenyl-1-propyl)piperazin-1-yl]benzamide $^1$H-NMR (CDCl$_3$) δ: 1.53–1.77 (10H, m), 2.33 (4H, m), 2.56 (4H, m), 3.21 (4H, m), 3.57 (1H, m), 3.70–4.20 (2H, m), 4.02 (1H, t, J=7.4 Hz), 5.14 (2H, m), 5.98 (1H, m), 6.80 (1H, d, J=7.5 Hz), 6.91 (2H, m), 7.24 (11H, m).

TSIMS (M/Z): 522 (M+H)+.

EXAMPLE 19

(2,6-Dimethyl-piperidin-1-yl)-[3-[4-(3,3-diphenyl-1-propyl)piperazin-1-yl]phenyl]methanone $^1$H-NMR (CDCl$_3$) δ: 1.26 (6H, m), 1.50–2.01 (6H, m), 2.31–2.36 (6H, m), 2.61 (4H, t, J=5.1 Hz), 4.61 (4H, t, J=5.1 Hz), 4.01 (1H, t, J=7.1 Hz), 4.70 (1H, m), 6.78–6.94 (3H, m), 7.18–7.30 (10H, m).

TSIMS (M/Z): 496 (M+H)+.

EXAMPLE 20

N-Cyclohexyl-3-[4-(3,3-diphenyl-1-propyl)piperazin-1-yl]-N-ethylbenzamide $^1$H-NMR (CDCl$_3$) δ: 1.03–1.74 (13H, m), 2.33 (4H, m), 2.57 (4H, m), 3.22 (4H, m), 3.42 (2H, m), 4.03 (1H, t, J=7.1 Hz), 4.31 (1H, m), 6.85 (3H, m), 7.26 (11H, m).

TSIMS (M/Z): 510 (M+H)$^+$.

EXAMPLE 21

N-Dimethylaminoethyl-3-[4-(3,3-diphenyl-1-propyl)piperazin-1-yl]-N-methylbenzamide $^1$H-NMR (CDCl$_3$) δ: 2.05–2.60 (9H, m), 2.56 (4H, m), 2.98–3.64 (4H, brs), 3.21 (4H, m), 4.01 (1H, t, J=7.3 Hz), 6.82 (1H, t, J=7.6 Hz), 6.92 (2H, m), 7.15–7.31 (11H, m).

FABMS (M/Z): 485 (M+H)$^+$.

EXAMPLE 22

N-Allyl-N-cyclopentyl-3-[4-(3,3-diphenyl-1-propyl)piperazin-1-yl]benzamide $^1$H-NMR (CDCl$_3$) δ: 1.46–2.00 (8H, m), 2.33 (4H, m), 2.56 (4H, m), 3.22 (4H, m), 3.97 (2H, m), 4.02 (1H, t, J=7.0 Hz), 4.15 (1H, m), 5.18 (2H, m), 5.95 (1H, m), 6.83 (1H, d, J=7.4 Hz), 6.93 (2H, m), 7.24 (11H, m).

TSIMS (M/Z): 508 (M+H)$^+$.

EXAMPLE 23

N,N-Diallyl-3-[4-(3,3-diphenyl-1-propyl)piperazin-1-yl]benzamide $^1$H-NMR (CDCl$_3$) δ: 2.33 (4H, m), 2.56 (4H, m), 3.21 (4H, m), 3.84 (2H, brs), 4.03 (1H, t, J=7.2 Hz), 4.13 (2H, brs), 5.23 (4H, m), 5.81 (2H, m), 6.88 (1H, d, J=7.2 Hz), 6.95 (2H, m), 7.26 (11H, m).

TSIMS (M/Z): 480 (M+H)$^+$.

EXAMPLE 24

N-Allyl-3-[4-(3,3-diphenyl-1-propyl)piperazin-1-yl]-N-phenylbenzamide $^1$H-NMR (CDCl$_3$) δ: 2.30 (4H, m), 2.50–2.59 (4H, m), 3.01–3.28 (4H, m), 4.00 (1H, t, J=7.2 Hz), 4.53 (2H, d, J=6.0 Hz), 5.19 (2H, m), 5.98 (1H, m), 6.76–7.70 (19H, m).

TSIMS (M/Z): 516 (M+H)$^+$.

EXAMPLE 25

N-Allyl-N-cyclohexylmethyl-3-[4-(3,3-diphenyl-1-propyl)piperazin-1-yl]benzamide $^1$H1-NMR (CDCl$_3$) δ: 0.88–1.76. (10H, m), 2.32 (4H, m), 2.56 (4H, m), 3.09+3.33 (2H, m), 3.19 (4H, m), 3.25 (11H, m), 3.84+4.15 (2H, m), 4.01 (1H, t, J=6.0 Hz), 5.16 (2H, m), 5.68–5.83 (1H, m), 6.86 (3H, m), 7.20 (11H, m).

TSIMS (M/Z): 536 (M+H)$^+$.

EXAMPLE 26

3-[4-(3,3-Diphenyl-1-propyl)piperazin-1-yl]-N-methoxy-N-methylbenzamide $^1$H-NMR (CDCl$_3$) δ: 2.32 (4H, m), 2.58 (4H, t, J=6.5 Hz), 3.23 (4H, t, J=6.5 Hz), 3.33 (3H, s), 3.57 (3H, s), 4.02 (1H, t, J=7.0 Hz), 6.98 (1H, dd, J=2.2, 8.1 Hz), 7.09 (1H, d, J=7.6 Hz), 7.16–7.30 (12H, m).

TSIMS (M/Z): 444 (M+H)$^+$.

EXAMPLE 27

N-Benzyl-3-[4-(3,3-diphenyl-1-propyl)piperazin-1-yl]-N-ethylbenzamide $^1$H-NMR (CDCl$_3$) δ: 1.08–1.22 (3H, m), 2.32 (4H, m), 2.54 (4H, m), 3.08–3.55 (6H, m), 4.01 (1H, t, J=6.9 Hz), 4.52 (1H, brs), 4.78 (1H, brs), 6.90 (3H, m), 7.18–7.36 (16H, m).

TSIMS (M/Z): 518 (M+H)$^+$.

EXAMPLE 28

N-Allyl-N-benzyl-3-[4-(3,3-diphenyl-1-propyl)piperazin-1-yl]benzamide $^1$H-NMR (CDCl$_3$) δ: 2.30 (4H, brs), 2.55 (4H, m), 3.07+3.20 (4H, brs), 3.76+4.10 (2H, m), 4.01 (1H, m), 4.50+4.74 (2H, s), 5.16 (1H, d, J=16.0 Hz), 5.23 (1H, d, J=10.0 Hz), 6.89–6.91 (2H, m), 7.16–7.34 (17H, m).

TSIMS (M/Z): 530 (M+H)$^+$.

EXAMPLE 29

N-Cyclohexylmethyl-3-[4-(3,3-diphenyl-1-propyl)piperazin-1-yl]-N-[(pyridin-2-yl)methyl]benzamide $^1$H-NMR (CDCl$_3$) δ: 0.66–1.95 (11H, m), 2.30–2.35 (4H, m), 2.58 (4H, brs), 3.07–3.22 (6H, m), 4.01 (1H, t, J=6.9 Hz), 4.53 (1H, brs), 4.75 (1H, brs), 6.87 (2H, m), 7.16–7.74 (14H, m), 8.39–8.54 (2H, m).

TSIMS (M/Z): 587 (M+H)$^+$.

EXAMPLE 30

N-Cyclohexylmethyl-3-[4-(3,3-diphenyl-1-propyl)piperazin-1-yl]-N-[(pyridin-4-yl)methyl]benzamide $^1$H-NMR (CDCl$_3$) δ: 0.66–1.73 (11H, m), 2.32–2.41 (4H, m), 2.59 (4H, brs), 3.18 (6H, m), 4.00 (1H, t, J=7.0 Hz), 4.50 (11H, brs), 4.73 (1H, brs), 6.79–7.30 (16H, m), 8.57 (2H, s).

TSIMS (M/Z): 587 (M+H)$^+$.

EXAMPLE 31

N-Cyclohexylmethyl-3-[4-(3,3-diphenyl-1-propyl)piperazin-1-yl]-N-[(tetrahydropyran-2-yl)methyl]benzamide $^1$H-NMR (CDCl$_3$) δ: 1.05–1.91 (17H, m), 2.44 (4H, m), 2.61 (4H, s), 3.22 (4H, s), 3.24–3.99 (7H, m), 4.00 (1H, t, J=7.6 Hz), 6.80–6.94 (4H, m), 7.16–7.30 (10H, m).

TSIMS (M/Z): 594 (M+H)$^+$.

EXAMPLE 32

N-Allyl-3-[4-(3,3-diphenyl-1-propyl)piperazin-1-yl]-N-(trans-4-hydroxy)cyclohexylbenzamide $^1$H-NMR (CDCl$_3$) δ: 1.12–1.96 (8H, m), 2.29 (4H, m), 2.56 (4H, s), 3.20 (4H, s), 3.58–3.84 (4H, m), 4.01 (1H, t, J=7.0 Hz), 4.22 (1H, brs), 5.13 (2H, m), 5.74–5.95 (1H, m), 6.78 (1H, d, J=7.6 Hz), 6.86 (1H, s), 6.93 (1H, d, J=7.6 Hz), 7.15–7.29 (11H, m).

TSIMS (M/Z): 538 (M+H)$^+$.

EXAMPLE 33

N-Benzyl-N-(2,2,2-trifluoroethyl)-3-[4-(3,3-diphenyl-1-propyl)piperazin-1-yl]benzamide (a) The procedure of step (d) of Example 1 was repeated using the compound prepared in step (c) of Example 1, except that 2,2,2-trifluoroethylamine hydrochloride was used instead of N-methylbenzylamine. Thus, 3-[4-(3,3-diphenyl-1-propyl)piperazin-1-yl]-N-(2,2,2-trifluoroethyl) benzamide was prepared.

¹H-NMR (CDCl₃) δ: 2.33–2.39 (2H, m), 2.70–2.74 (2H, m), 3.01 (4H, brs), 3.33 (4H, brs), 3.83 (1H, t, J=7.8), 4.09–4.18 (2H, m), 6.99 (1H, d, J=7.5 Hz), 7.07–7.52 (11H, m), 7.58–7.61 (1H, m), 7.79–7.81 (1H, m).

FABMS (M/Z): 482 (M+H)⁺.

(b) The compound (0.048 g) prepared in step (a) was dissolved in toluene (5 ml), and sodium hydroxide (0.014 g), potassium carbonate (0.028 g), tetrabutylammoniumhydrogen sulfate (0.003 g), and benzyl bromide (0.019 g) were added to the solution. The mixture was stirred at 60° C. for 3 hr. Water was added to the reaction solution, and the mixture was extracted with ethyl acetate, followed by washing with saturated brine. The organic layer was dried over anhydrous magnesium sulfate, and the solvent was then removed by distillation under the reduced pressure. The residue was purified by preparative TLC (hexane:ethyl acetate=1:2) to give 0.020 g (21.0%) of the title compound.

¹H-NMR (CDCl₃) δ: 2.28–2.32 (4H, m), 2.54 (4H, brs), 3.17 (4H, brs), 3.73+4.09 (2H, m), 4.02 (1H, t, J=7.3), 4.68+4.89 (2H, m), 6.94–6.96 (3H, m), 7.13–7.22 (4H, m), 7.25–7.36 (12H, m).

TSIMS (M/Z): 572 (M+H)⁺.

EXAMPLE 34

N-Allyl-N-(2,2,2-trifluoroethyl)-3-[4-(3,3-diphenyl-1-propyl)piperazin-1-yl]benzamide The procedure of step (b) of Example 33 was repeated using the compound prepared in step (a) of Example 33, except that allyl bromide was used instead of benzyl bromide. Thus, the title compound was prepared.

¹H-NMR (CDCl₃) δ: 2.26–2.36 (4H, m), 2.56 (4H, t, J=4.9 Hz), 3.21 (4H, t, J=4.9 Hz), 4.02 (1H, t, J=7.3 Hz), 4.15 (4H, m), 5.20 (1H, d, J=16.8 Hz), 5.28 (1H, d, J=9.8 Hz), 5.69 (1H, m), 6.83 (1H, d, J=7.3 Hz), 6.90 (1H, s), 6.96 (1H, dd, J=2.0, 8.2 Hz), 7.08–7.21 (2H, m), 7.24–7.30 (9H, m).

TSIMS (M/Z): 522 (M+H)⁺.

EXAMPLE 35

N-Cyclohexylmethyl-3-[4-(3,3-diphenyl-1-propyl) piperazin-1-yl]-N-[(4'-trifluoromethylbiphenyl-2-yl) methyl]benzamide (a) The compound (0.12 g) prepared in step (c) of Example 1 was dissolved in dichloromethane (5 ml), and a BOP reagent (0.16 g) and diisopropylethylamine (0.078 ml) were added to the solution. The mixture was stirred at room temperature for 30 min. Cyclohexanemethylamine (0.057 ml) was then added thereto, and the mixture was stirred at room temperature overnight. The reaction solution was extracted with ethyl acetate, followed by washing with water. The organic layer was dried over anhydrous magnesium sulfate, and the solvent was then removed by distillation under the reduced pressure. The residue was purified by preparative TLC (hexane:ethyl acetate=1:1) to give 0.13 g (91.6%) of N-cyclohexylmethyl-3-[4-(3,3-diphenyl-1-propyl)piperazin-1-yl]benzamide.

¹H-NMR (CDCl₃) δ: 0.90–1.76 (10H, m), 2.32 (4H, m), 2.57 (4H, m), 3.26 (6H, m), 4.02 (1H, t, J=7.0 Hz), 6.13 (1H, m), 7.05 (2H, m), 7.25 (11H, m), 7.39 (1H, brs).

TSIMS (M/Z): 496 (M+H)⁺.

(b) The compound (0.030 g) prepared just above in step (a) was dissolved in toluene (3 ml). Sodium hydroxide (0.008 g), potassium carbonate (0.017 g), tetrabutylammonium hydrogen sulfate (0.002 g), and 4'-trifluoromethyl-biphenyl-2-ylmethyl bromide (0.021 g) were added to the solution, and the mixture was stirred at 60° C. for 5.5 hr. Water was added to the reaction solution, and the mixture was extracted with ethyl acetate, followed by washing with saturated brine. The organic layer was dried over anhydrous magnesium sulfate, and the solvent was then removed by distillation under the reduced pressure. The residue was purified by preparative TLC (hexane:ethyl acetate=1:2) to give 0.015 g (34.0%) of the title compound.

¹H-NMR (CDCl₃) δ: 0.89 (3H, m), 1.12 (2H, brs), 1.22–1.27 (2H, m), 1.51–1.66 (4H, m), 2.30 (4H, brs), 2.49+2.55 (4H, brs), 2.78 (1H, d, J=7.3 Hz), 3.05+3.18 (4H, brs), 3.28 (1H, d, J=6.1 Hz), 4.01 (1H, t, J=7.2 Hz), 4.35 (1H, s), 4.76 (1H, s), 6.61–6.90 (2H, m), 6.99–7.30 (15H, m), 7.37–7.70 (5H, m).

TSIMS (M/Z): 730 (M+H)⁺.

Compounds of Examples 36 to 44 were synthesized in the same manner as in step (b) of Example 35, except that the following halides were used instead of 4'-trifluoromethyl-biphenyl-2-ylmethyl bromide in step (b) of Example 35.

Example 36: Cinnamyl bromide
Example 37: Crotyl bromide
Example 38: Benzyl bromide
Example 39: Propargyl bromide
Example 40: 2-(Trifluoromethyl)benzyl bromide
Example 41: 3-(Trifluoromethyl)benzyl bromide
Example 42: 4-(Trifluoromethyl)benzyl bromide
Example 43: 3-Pyridylmethyl bromide
Example 44: 4-Bromo-1-benzylpiperidine

EXAMPLE 36

N-Cinnamyl-N-cyclohexylmethyl-3-[4-(3,3-diphenyl-1-propyl)piperazin-1-yl]benzamide ¹H-NMR (CDCl₃) δ: 1.05–1.78 (10H, m), 2.30 (4H, m), 2.54 (4H, m), 3.18 (5H, m), 3.41–4.32 (2H, m), 4.02 (3H, m), 6.01–6.58 (2H, m), 6.94–7.34 (19H, m).

TSIMS (M/Z): 612 (M+H)⁺.

EXAMPLE 37

N-Crotyl-N-cyclohexylmethyl-3-[4-(3,3-diphenyl-1-propyl)piperazin-1-yl]benzamide ¹H-NMR (CDCl₃) δ: 1.05–1.78 (16H, m), 2.33 (4H, m), 2.57 (4H, m), 3.08+3.32 (2H, m), 3.21 (5H, m), 3.82+4.14 (2H, m), 4.03 (1H, t, J=7.0 Hz), 5.10+5.29 (1H, brs×2), 6.78–6.93 (3H, m), 7.24 (11H, m).

TSIMS (M/Z): 564 (M+H)⁺.

EXAMPLE 38

N-Benzyl-N-cyclohexylmethyl-3-[4-(3,3-diphenyl-1-propyl)piperazin-1-yl]benzamide $^{1}$H-NMR (CDCl$_{3}$) δ: 0.90–1.86 (10H, m), 2.31 (4H, m), 2.54 (4H, m), 3.09 (4H, m), 3.22–3.35 (3H, m), 4.02 (1H, t, J=6.6 Hz), 4.53–4.79 (2H, brs×2), 6.89 (3H, m), 7.28 (16H, m).

TSIMS (M/Z): 586 (M+H)$^{+}$.

EXAMPLE 39

N-Cyclohexylmethyl-3-[4-(3,3-diphenyl-1-propyl)piperazin-1-yl]-N-propargylbenzamide $^{1}$H-NMR (CDCl$_{3}$) δ: 0.80–1.78 (10H, m), 2.32 (5H, m), 2.56 (5H, m), 3.22 (4H, m), 3.30 (1H, m), 3.60 (2H, m), 4.02 (1H, m), 4.30 (1H, m), 6.95 (3H, m), 7.30 (11H, m).

FABMS (M/Z): 534 (M+H)$^{+}$.

EXAMPLE 40

N-Cyclohexylmethyl-3-[4-(3,3-diphenyl-1-propyl)piperazin-1-yl]-N-(2-trifluoromethylbenzyl)benzamide $^{1}$H-NMR (CDCl$_{3}$) δ: 0.89–1.74 (10H, m), 2.29 (4H, m), 2.48+2.58 (4H, brs), 3.05+3.24 (4H, brs), 2.98–3.34 (3H, m), 4.00 (1H, m), 4.71+4.98 (2H, s), 6.80–7.00 (3H, m), 7.16–7.20 (2H, m), 7.27–7.30 (10H, m), 7.37–7.67 (3H, m).

FABMS (M/Z): 654 (M+H)$^{+}$.

EXAMPLE 41

N-Cyclohexylmethyl-3-[4-(3,3-diphenyl-1-propyl)piperazin-1-yl]-N-(3-trifluoromethylbenzyl)benzamide $^{1}$H-NMR (CDCl$_{3}$) δ: 0.88–1.74 (10H, m), 2.29 (4H, m), 2.51 (4H, m), 3.09+3.21 (4H, brs), 3.09–3.32 (3H, m), 4.01 (1H, t, J=7.2 Hz), 4.56+4.80 (2H, s), 6.80–6.88 (3H, m), 7.15–7.20 (2H, m), 7.25–7.53 (13H, m).

TSIMS (M/Z): 654 (M+H)$^{+}$.

EXAMPLE 42

N-Cyclohexylmethyl-3-[4-(3,3-diphenyl-1-propyl)piperazin-1-yl]-N-(4-trifluoromethylbenzyl)benzamide $^{1}$H-NMR (CDCl$_{3}$) δ: 0.88–1.74 (10H, m), 2.30 (4H, m), 2.50+2.57 (4H, brs), 3.07+3.22 (4H, brs), 3.07–3.32 (3H, m), 4.01 (1H, t, J=7.2 Hz), 4.57+4.80 (2H, s), 6.80–6.89 (3H, m), 7.15–7.30 (12H, m), 7.47–7.49 (1H, m), 7.61–7.63 (2H, m).

FABMS (M/Z): 654 (M+H)$^{+}$.

EXAMPLE 43

N-Cyclohexylmethyl-3-[4-(3,3-diphenyl-1-propyl)piperazin-1-yl]-N-[(pyridin-3-yl)methyl]benzamide $^{1}$H-NMR (CDCl$_{3}$) δ: 0.66–1.95 (11H, m), 2.30–2.35 (4H, m), 2.58 (4H, m), 3.07–3.32 (6H, m), 4.01 (1H, t, J=7.0 Hz), 4.53 (1H, brs), 4.75 (1H, brs), 6.87 (2H, m), 7.16–7.74 (13H, m), 8.54 (2H, m).

FABMS (M/Z): 587 (M+H)$^{+}$.

EXAMPLE 44

N-(1-Benzylpiperidin-4-yl)-N-cyclohexylmethyl-3-[4-(3,3-diphenyl-1-propyl)piperazin-1-yl]benzamide $^{1}$H-NMR (CDCl$_{3}$) δ: 1.05–2.00 (18H, m), 2.10 (1H, m), 2.32 (4H, m), 2.56 (4H, brs), 2.61 (1H, brs), 2.86 (2H, brs), 3.20 (4H, brs), 3.40 (2H, s), 4.02 (1H, t, J=7.0 Hz), 6.79 (1H, brs), 4.53 (1H, brs), 6.92 (2H, m), 7.17 (2H, m), 7.20–7.35 (14H, m).

TSIMS (M/Z): 669 (M+H)$^{+}$.

EXAMPLE 45

N-Cyclohexylmethyl-3-[4-(3,3-diphenyl-1-propyl)piperazin-1-yl]-N-(piperidin-4-yl)benzamide The compound (7.9 mg) prepared in Example 44 was dissolved in methanol (1 ml), and Pd—C (8.0 mg) was added to the solution, followed by catalytic reduction at room temperature overnight. The reaction solution was filtered through Celite, and was washed with methanol. The solvent was then removed by distillation under the reduced pressure to give 6.8 mg (99.5%) of the title compound.

$^{1}$H-NMR (CDCl$_{3}$) δ: 1.10–2.00 (18H, m), 2.08 (4H, m), 2.63 (4H, brs), 3.13 (2H, brs), 3.21 (4H, brs), 3.49 (1H, brs), 3.68 (1H, brs), 3.87 (1H, brs), 4.06 (1H, t, J=7.5 Hz), 6.85–7.38 (14H, m).

TSIMS (M/Z): 579 (M+H)$^{+}$.

EXAMPLE 46

N-Cyclohexyl-3-[4-(3,3-diphenyl-1-propyl)piperazin-1-yl]-N-isopropyl-4-methoxybenzamide (a) 3-Amino-4-methoxybenzoic acid (3.34 g) was dissolved in ethanol (100 ml). Concentrated sulfuric acid (3 ml) was added to the solution, and the mixture was stirred at 65° C. overnight. The solvent was removed from the reaction solution by distillation under the reduced pressure, and the residue was adjusted to pH 7 by the addition of a saturated aqueous sodium carbonate solution, followed by extraction with ethyl acetate. The organic layer was dried over anhydrous magnesium sulfate, and the solvent was then removed by distillation under the reduced pressure. The residue was purified by column chromatography on silica gel (hexane:ethyl acetate=1:1) to give 3.50 g (89.4%) of ethyl 3-amino-4-methoxybenzoate.

$^{1}$H-NMR (CDCl$_{3}$) δ: 1.37 (3H, t, J=7.1 Hz), 3.86 (2H, brs), 3.91 (3H, s), 4.33 (2H, q, J=7.1 Hz), 6.79 (1H, d, J=8.5 Hz), 7.40 (1H, d, J=1.4 Hz), 7.49 (1H, dd, J=1.4, 8.5 Hz).

EIMS (M/Z): 195 (M$^{+}$).

(b) Steps (a) to (c) of Example 1 were repeated, except that the compound prepared just above in step (a) was used. Step (d) of Example 1 was then repeated, except that N-isopropylcyclohexylamine was used instead of N-methylbenzylamine. Thus, the title compound was prepared.

$^{1}$H-NMR (CDCl$_{3}$) δ: 1.15–1.83 (16H, m), 2.34 (4H, m), 2.62 (4H, m), 3.09 (5H, m), 3.70 (1H, m), 3.87 (3H, s), 4.02 (1H, t, J=7.0 Hz), 6.82 (1H, d, J=8.1 Hz), 6.90 (1H, d, J=1.7 Hz), 6.97 (1H, dd, J=1.7, 8.1 Hz), 7.27 (10H, m).

TSIMS (M/Z): 554 (M+H)$^{+}$.

EXAMPLE 47

N-Benzyl-N-cyclohexyl-3-[4-(3,3-diphenyl-1-propyl)piperazin-1-yl]-4-methoxybenzamide The procedure of Example 46 was repeated, except that N-cyclohexylbenzylamine was used instead of N-isopropylcyclohexylamine. Thus, the title compound was prepared.

$^{1}$H-NMR (CDCl$_{3}$) δ: 1.02–1.75 (10H, m), 2.32 (4H, m), 2.59 (4H, m), 3.00 (4H, m), 3.86 (4H, m), 4.01 (1H, t, J=7.2

Hz), 4.62 (2H, m), 6.82–7.27 (18H, m).
TSIMS (M/Z): 602 (M+H)+.

EXAMPLE 48

N-Benzyl-4-chloro-N-cyclohexyl-3-[4-(3,3-diphenyl-1-propyl)piperazin-1-yl]benzamide Step (a) of Example 46 was repeated, except that 3-amino-4-chlorobenzoic acid was used instead of 3-amino-4-methoxybenzoic acid. Step (b) of Example 46 was then repeated, except that N-cyclohexylbenzylamine was used instead of N-isopropylcyclohexylamine. Thus, the title compound was prepared.

$^1$H-NMR (CDCl$_3$) δ: 0.90–1.90 (10H, m), 2.25–2.85 (9H, m), 3.09+3.61 (4H, brs×2), 4.01 (1H, t, J=7.5 Hz), 4.44+4.68 (2H, brs×2), 6.80–7.45 (18H, m).
FABMS (M/Z): 606 (M+H)+.

EXAMPLE 49

N-Cyclohexyl-3-[4-(3,3-diphenyl-1-propyl)piperazin-1-yl]-N-isopropyl-4-methylbenzamide Steps (a) to (c) of Example 1 were repeated, except that methyl 3-amino-4-methylbenzoate was used instead of ethyl 3-aminobenzoate. Step (d) of Example 1 was then repeated, except that N-isopropylcyclohexylamine was used instead of N-methylbenzylamine. Thus, the title compound was prepared.

$^1$H-NMR (CDCl$_3$) δ: 1.10–1.70 (16H, m), 2.31 (7H, m), 2.58 (4H, m), 2.93 (4H, m), 3.50–3.80 (2H, m), 4.02 (1H, t, J=7.3 Hz), 6.93 (2H, m), 7.23 (11H, m).
FABMS (M/Z): 538 (M+H)+.

EXAMPLE 50

N-Benzyl-N-cyclohexyl-3-[4-(3,3-diphenyl-1-propyl)piperazin-1-yl]-4-methylbenzamide The procedure of Example 49 was repeated, except that N-cyclohexylbenzylamine was used instead of N-isopropylcyclohexylamine. Thus, the title compound was prepared.

$^1$H-NMR (CDCl$_3$) δ: 1.00–2.94 (10H, m), 2.32 (7H, m), 2.56 (4H, m), 2.93 (4H, m), 3.80 (1H, m), 4.02 (1H, t, J=7.2 Hz), 4.69 (2H, m), 7.25 (18H, m).
FABMS (M/Z): 586 (M+H)+.

EXAMPLE 51

3-[4-[3,3-Bis(4-chlorophenyl)-1-propyl]piperazin-1-yl]-N-cyclohexyl-N-isopropylbenzamide (a) The compound (0.23 g) prepared in step (a) of Example 1 was dissolved in dichloromethane (2 ml). 3,3-Bis(4-chlorophenyl)propylaldehyde (0.33 g), sodium boron triacetoxyhydride (0.25 g), and acetic acid (1 ml) were added to the solution. The mixture was stirred at room temperature overnight. The reaction solution was neutralized with a saturated aqueous sodium hydrogencarbonate solution, followed by extraction with ethyl acetate. The organic layer was dried over anhydrous magnesium sulfate, and the solvent was removed by distillation under the reduced pressure. The residue was purified by column chromatography on silica gel (hexane:ethyl acetate=1:1) to give 0.12 g (23.1%) of ethyl 3-[4-[3,3-bis(4-chlorophenyl)-1-propyl]piperazin-1-yl]benzoate.

$^1$H-NMR (CDCl$_3$) δ: 1.39 (3H, t, J=7.2 Hz), 2.20–2.34 (4H, m), 2.57 (4H, m), 3.25 (4H, m), 4.01 (1H, t, J=7.7 Hz), 4.37 (2H, q, J=7.2 Hz), 6.79–7.34 (10H, m), 7.53 (1H, d, J=6.7 Hz), 7.60 (1H, brs).
TSIMS (M/Z): 499 (M+H)+.

(b) Steps (c) and (d) of Example 1 were repeated, except that the compound prepared just above in step (a) was used and N-isopropylcyclohexylamine was used instead of N-methylbenzylamine. Thus, the title compound was prepared.

$^1$H-NMR (CDCl$_3$) δ: 1.05–1.67 (16H, m), 2.26 (4H, m), 2.55 (4H, m), 3.21 (4H, m), 3.00–3.50 (2H, m), 4.00 (1H, t, J=7.1 Hz), 6.75 (1H, d, J=7.4 Hz), 6.84 (1H, brs), 6.90 (1H, m), 7.21 (9H, m).
TSIMS (M/Z): 594 (M+H)+.

EXAMPLE 52

N-Allyl-3-[4-[3,3-bis(4-chlorophenyl)-1-propyl]piperazin-1-yl]-N-cyclohexylbenzamide The procedure of Example 51 was repeated, except that N-allylcyclohexylamine was used instead of N-isopropylcyclohexylamine. Thus, the title compound was prepared.

$^1$H-NMR (CDCl$_3$) δ: 1.00–1.78 (10H, m), 2.25 (4H, m), 2.55 (4H, m), 3.20 (4H, m), 3.55–3.80 (1H, m), 4.00 (3H, m), 4.11 (2H, m), 5.97 (1H, m), 6.80 (1H, d, J=7.4 Hz), 6.89 (2H, m), 7.15 (4H, d, J=8.4 Hz), 7.24 (1H, m), 7.26 (4H, d, J=8.4 Hz).
TSIMS (M/Z): 592 (M+H)+.

EXAMPLE 53

N-Cyclohexyl-3-[4-(3,3-diphenyl-1-propyl)piperazin-1-yl]-N-isopropyl-2-methylbenzamide (a) Step (a) of Example 1 was repeated, except that ethyl 3-amino-2-methylbenzoate was used instead of ethyl 3-aminobenzoate to give ethyl 2-methyl-3-piperazin-1-ylbenzoate.

$^1$H-NMR (CDCl$_3$) δ: 1.39 (3H, t, J=7.1 Hz), 2.50 (3H, s), 2.89 (4H, m), 3.07 (4H, m), 4.36 (2H, q, J=7.1 Hz), 7.21 (2H, m), 7.51 (1H, m).
EIMS (M/Z): 248 (M+).

(b) Step (b) of Example 1 was repeated, except that the compound prepared just above in step (a) was used instead of ethyl 3-piperazin-1-ylbenzoate to give ethyl 3-[4-(3,3-diphenyl-1-propyl)piperazin-1-yl]-2-methylbenzoate.

$^1$H-NMR (CDCl$_3$) δ: 1.38 (3H, t, J=7.1 Hz), 2.32 (4H, m), 2.48 (3H, s), 2.59 (4H, m), 2.92 (4H, m), 4.03 (1H, t, J=7.6 Hz), 4.35 (2H, q, J=7.1 Hz), 7.18–7.30 (12H, m), 7.52 (1H, m).

(c) The hydrolysis of an ester was carried out in the same manner as in step (c) of Example 1, except that the compound prepared just above in step (b) was used. Thus, 3-[4-(3,3-diphenyl-1-propyl)piperazin-1-yl]-2-methylbenzoic acid was prepared.

$^1$H-NMR (CDCl$_3$) δ: 2.50 (3H, s), 2.77 (4H, m), 3.00 (4H, m), 3.62 (4H, m), 4.00 (1H, t, J=7.9 Hz), 7.28 (12H, m), 7.74 (1H, dd, J=1.1, 7.5 Hz).
TSIMS (M/Z): 415 (M+H)+.

(d) Step (d) of Example 1 was repeated, except that the compound prepared just above in step (c) was used instead of 3-[4-(3,3-diphenyl-1-propyl)piperazin-1-yl]-2-methylbenzoic acid and N-isopropylcyclohexylamine was used instead of N-methylbenzylamine. Thus, the title compound was prepared.

¹H-NMR (CDCl₃) δ: 0.96–1.68 (16H, m), 2.23 (3H, brs), 2.30–3.20 (13H, m), 3.49–3.72 (1H, m), 4.02 (1H, t, J=7.7 Hz), 6.81 (1H, dd, J=1.1, 7.8 Hz), 7.00 (1H, d, J=7.8 Hz), 7.21 (11H, m).

FABMS (M/Z): 538 (M+H)⁺.

EXAMPLE 54

N-Benzyl-N-cyclohexyl-3-[4-(3,3-diphenyl-1-propyl)piperazin-1-yl]-2-methylbenzamide The procedure of Example 53 was repeated, except that N-cyclohexylbenzylamine was used instead o N-isopropylcyclohexylamine. Thus, the title compound was prepared.

¹H-NMR (CDCl₃) δ: 0.96–1.90 (10H, m), 2.30 (3H, brs), 2.35 (4H, m), 2.59 (4H, m), 2.92 (4H, m), 3.37+4.45 (1H, m), 4.03 (1H, t, J=7.4 Hz), 4.32–4.82 (2H, m), 6.90–7.42 (18H, m).

TSIMS (M/Z): 586 (M+H)⁺.

EXAMPLE 55

N-Allyl-N-cyclohexyl-3-[4-(3,3-diphenyl-1-propyl)piperazin-1-yl]-2-methylbenzamide The procedure of Example 53 was repeated, except that N-allylcyclohexylamine was used instead of N-isopropylcyclohexylamine. Thus, the title compound was prepared.

¹H-NMR (CDCl₃) δ: 1.00–1.85 (10H, m), 2.17+2.22 (3H, brs×2), 2.36 (4H, m), 2.59 (4H, m), 2.93 (4H, m), 3.27+4.47 (1H, m), 3.62–4.20 (3H, m), 4.83–5.29 (2H, m), 5.56–6.07 (1H, m), 6.85 (1H, d, J=7.5 Hz), 7.02 (1H, m), 7.12–7.19 (11H, m).

TSIMS (M/Z): 536 (M+H)⁺.

EXAMPLE 56

N-Allyl-N-cyclohexyl-3-[4-(3,3-diphenyl-1-propyl)piperazin-1-yl]-2-methoxybenzamide Step (a) of Example 46 was repeated, except that 3-aminosalicylic acid was used instead of 3-amino-4-methoxybenzoic acid. Step (b) of Example 46 was then repeated, except that N-allylcyclohexylamine was used instead of N-isopropylcyclohexylamine. Thus, the title compound was prepared.

¹H-NMR (CDCl₃) δ: 1.15–1.50 (10H, m), 2.25–2.35 (4H, m), 2.58 (4H, brs), 3.32 (4H, brs), 3.72 (1H, brs), 3.83 (3H, s), 3.92 (1H, brs), 4.03 (1H, m), 4.85–6.00 (4H, m), 6.80 (1H, m), 6.90 (1H, m), 7.18 (1H, m), 7.23–7.33 (10H, m).

TSIMS (M/Z): 552 (M+H)⁺.

EXAMPLE 57

N-Benzyl-N-cyclohexyl-3-[4-(3,3-diphenyl-1-propyl)piperazin-1-yl]-2-methoxybenzamide The procedure of Example 56 was repeated, except that N-cyclohexylbenzylamine was used instead of N-allylcyclohexylamine. Thus, the title compound was prepared.

¹H-NMR (CDCl₃) δ: 1.15–1.60 (10H, m), 2.25–2.42 (4H, m), 2.54 (4H, brs), 3.32 (2H, t, J=6.6 Hz), 3.45 (2H, t, J=6.6 Hz), 3.64 (1H, brs), 3.87 (3H, s), 4.05 (1H, t, J=6.6 Hz), 4.50 (2H, m), 7.15–7.45 (18H, m).

TSIMS (M/Z): 602 (M+H)⁺.

EXAMPLE 58

N-Allyl-2-chloro-N-cyclohexyl-3-[4-(3, 3-diphenyl-1-propyl)piperazin-1-yl]benzamide Step (a) of Example 46 was repeated, except that 3-amino-2-chlorobenzoic acid was used instead of 3-amino-4-methoxybenzoic acid. Step (b) of Example 46 was then repeated, except that N-allylcyclohexylamine was used instead of N-isopropylcyclohexylamine. Thus, the title compound was prepared.

¹H-NMR (CDCl₃) δ: 0.90–1.86 (10H, m), 2.29 (4H, m), 2.58 (4H, m), 2.96–3.19 (4H, m), 3.70+4.20 (2H, m), 4.02 (1H, t, J=7.4 Hz), 4.40 (1H, m), 4.87–5.33 (2H, m), 5.65–6.04 (1H, m), 6.90 (1H, m), 7.04 (1H, m), 7.20 (11H, m).

TSIMS (M/Z): 558 (M+H)⁺.

EXAMPLE 59

N-Allyl-N-cyclohexyl-5-[4-(3,3-diphenyl-1-propyl)piperazin-1-yl]-2-fluorobenzamide (a) 2-Fluoro-5-nitrobenzoic acid (1.85 g) was dissolved in ethanol (30 ml). Concentrated sulfuric acid (1.0 ml) was added to the solution, and the mixture was stirred at 65° C. overnight. The solvent was removed from the reaction solution by distillation under the reduced pressure, and the residue was adjusted to pH 7 by the addition of a saturated aqueous sodium hydrogencarbonate solution, followed by extraction with ethyl acetate. The organic layer was dried over anhydrous magnesium sulfate, and the solvent was then removed by distillation under the reduced pressure to give 1.79 g (84.3%) of ethyl 2-fluoro-5-nitrobenzoate.

¹H-NMR (CDCl₃) δ: 1.44 (3H, t, J=7.2 Hz), 4.45 (2H, q, J=7.2 Hz), 7.33 (1H, t, J=9.1 Hz), 8.41 (1H, ddd, J=2.9, 3.9, 9.1 Hz), 8.85 (1H, dd, J=2.9, 6.2 Hz).

TSIMS (M/Z): 213 (M⁺).

(b) Ethyl 2-fluoro-5-nitrobenzoate (0.63 g) was dissolved in ethanol (10 ml), and 10% Pd—C (0.064 g) was added to the solution. The mixture was subjected to catalytic reduction at room temperature for 7 hr. The reaction solution was filtered through Celite, and was washed with ethanol. The solvent was then removed by distillation under the reduced pressure to give 0.55 g (100%) of ethyl 5-amino-2-fluorobenzoate.

¹H-NMR (CDCl₃) δ: 1.39 (3H, t, J=7.1 Hz), 3.65 (2H, brs), 4.37 (2H, q, J=7.1 Hz), 6.80 (1H, m), 6.93 (1H, m), 7.20 (1H, m).

EIMS (M/Z): 183 (M⁺).

(c) Steps (a) to (c) of Example 1 were repeated, except that the compound prepared just above in step (b) was used instead of ethyl 3-aminobenzoate. Step (d) of Example 1 was then repeated, except that N-allylcyclohexylamine was used instead of N-methylbenzylamine. Thus, the title compound was prepared.

¹H-NMR (CDCl₃) δ: 1.05 (10H, m), 2.32 (4H, m), 2.57 (4H, m), 3.14 (4H, m), 3.40+4.42 (1H, m), 3.79+4.13 (2H, m), 4.02 (1H, m), 4.91–5.29 (2H, m), 5.63–6.00 (1H, m), 6.80–6.99 (3H, m), 7.24 (10H, m).

TSIMS (M/Z): 540 (M+H)⁺.

EXAMPLE 60

N-Benzyl-N-cyclohexyl-5-[4-(3,3-diphenyl-1-propyl)piperazin-1-yl]-2-fluorobenzamide Step (c) of Example 59 was repeated, except that N-cyclohexylbenzylamine was used instead of N-allylcyclohexylamine. Thus, the title compound was prepared.

¹H-NMR (CDCl₃) δ: 1.00–1.80 (10H, m), 2.31 (4H, m), 2.53 (4H, m), 2.93–3.16 (4H, m), 3.50 (1H, m), 4.00 (1H, m), 4.41–4.95 (2H, m), 6.80–7.41 (18H, m).

TSIMS (M/Z): 590 (M+H)⁺.

EXAMPLE 61

N-Cyclohexyl-5-[4-(3,3-diphenyl-1-propyl) piperazin-1-yl]-N-methyl-2-methylbenzamide Steps (a) and (b) of Example 59 were repeated, except that 2-methyl-5-nitrobenzoic acid was used instead of 2-fluoro-5-nitrobenzoic acid. Step (c) of Example 59 was then repeated, except that N-methylcyclohexylamine was used instead of N-allylcyclohexylamine. Thus, the title compound was prepared.

¹H-NMR (CDCl₃) δ: 1.00–1.09 (1H, m), 1.44–1.83 (9H, m), 2.16+2.18 (3H, s), 2.28–2.33 (4H, m), 2.56 (4H, brs), 2.65+2.98 (3H, s), 3.15 (4H, brs), 3.25+4.61 (1H, m), 3.99–4.03 (1H, m), 6.64+6.69 (1H, d, J=2.7 Hz), 6.81+6.84 (1H, dd, J=2.7, 8.5 Hz), 7.05–7.09 (1H, m), 7.15–7.21 (2H, m), 7.24–7.30 (8H, m).

EIMS (M/Z): 509 (M⁺).

EXAMPLE 62

N-Benzyl-5-[4-(3,3-diphenyl-1-propyl)piperazin-1-yl]-N-isopropyl-2-methylbenzamide The procedure of Example 61 was repeated, except that N-benzyl-N-isopropylamine was used instead of N-methylcyclohexylamine. Thus, the title compound was prepared.

¹H-NMR (CDCl₃) δ: 1.04 (4H, d, J=6.8 Hz), 1.25 (2H, brs), 2.19+2.27 (3H, s), 2.28–2.35 (4H, m), 2.47+2.57 (4H, brs), 2.93+3.16 (4H, brs), 3.89+4.74 (1H, m), 3.97–4.03 (1H, m), 4.30+4.57+4.84 (2H, s+d, J=15.5 Hz), 6.60+6.74 (1H, d, J=2.6 Hz), 6.73+6.85 (1H, dd, J=2.6, 8.5 Hz), 7.00+7.10 (1H, d, J=8.5 Hz), 7.12+7.42 (2H, d, J=7.3 Hz), 7.15–7.34 (13H, m).

EIMS (M/Z): 545 (M⁺).

EXAMPLE 63

N-Allyl-N-cyclohexyl-5-[4-(3,3-diphenyl-1-propyl) piperazin-1-yl]-2-methylbenzamide The procedure of Example 61 was repeated, except that N-allylcyclohexylamine was used instead of N-methylcyclohexylamine. Thus, the title compound was prepared.

¹H-NMR (CDCl₃) δ: 0.99–1.84 (10H, m), 2.16+2.20 (3H, 9), 2.29–2.33 (4H, m), 2.57 (4H, brs), 3.13 (4H, brs), 3.14+3.70 (1H, m), 3.29+4.45 (1H, m), 3.95+4.18 (1H, dd, J=5.7, 15.4 Hz), 4.00 (1H, t, J=7.4 Hz), 4.90+5.25 (1H, d, J=17.3 Hz), 4.99+5.14 (1H, d, J=10.2 Hz), 5.63+5.99 (1H, m), 6.66 (1H, d, J=2.4 Hz), 6.80+6.84 (1H, dd , J=2.4, 8.4 Hz), 7.03+7.07 (1H, d, J=8.4 Hz), 7.15–7.19 (2H, m), 7.24–7.30 (8H, m).

TSIMS (M/Z): 536 (M+H)⁺.

EXAMPLE 64

N-Benzyl-N-cyclohexyl-5-[4-(3,3-diphenyl-1-propyl)piperazin-1-yl]-2-methylbenzamide The procedure of Example 61 was repeated, except that N-cyclohexylbenzylamine was used instead of N-methylcyclohexylamine. Thus, the title compound was prepared.

¹H-NMR (CDCl₃) δ: 0.88–1.85 (10H, m), 2.18+2.27 (3H, s), 2.32–2.33 (4H, m), 2.45+2.58 (4H, brs), 2.90+3.16 (4H, brs), 3.97–4.03 (1H, m), 3.39+4.50 (1H, m), 4.32+4.58+4.88 (2H, m), 6.58+6.73 (1H, d, J=2.5 Hz), 6.72+6.86 (1H, dd, J=2.5, 8.5 Hz), 6.99+7.10 (1H, d, J=8.5 Hz), 7.15–7.33 (13H, m), 7.11+7.40 (2H, d, J=7.0 Hz).

TSIMS (M/Z): 586 (M+H)⁺.

EXAMPLE 65

N-Cyclohexyl-5-[4-(3,3-diphenyl-1-propyl) piperazin-1-yl]-N-isopropyl-2-methylbenzamide The procedure of Example 61 was repeated, except that N-isopropylcyclohexylamine was used instead of N-methylcyclohexylamine. Thus, the title compound was prepared.

¹H-NMR (CDCl₃) δ: 0.88–0.99 (1H, m), 1.05 (1H, d, J=6.6 Hz), 1.10 (1H, d, J=6.6 Hz), 1.24–1.28 (2H, m), 1.45–1.85 (7H, m), 1.55 (4H, t, J=6.6 Hz), 2.20 (3H, s), 2.30–2.34 (4H, m), 2.58 (4H, brs), 2.69 (1H, m), 2.99+3.15 (1H, m), 3.15 (4H, brs), 3.52+3.69 (1H, m), 4.00 (1H, t, J=7.5 Hz), 6.59+6.61 (1H, d, J=2.5 Hz), 6.79–6.82 (1H, d, J=8.5 Hz), 7.15–7.23 (2H, m), 7.24–7.30 (8H, m).

TSIMS (M/Z): 538 (M+H)⁺.

EXAMPLE 66

N-Benzyl-2-chloro-N-cyclohexyl-5-[4-(3,3-diphenyl-1-propyl)piperazin-1-yl]benzamide Steps (a) to (c) of Example 1 were repeated, except that ethyl 5-amino-2-chlorobenzoate was used instead of ethyl 3-aminobenzoate. Step (d) of Example 1 was then repeated, except that N-cyclohexylbenzylamine was used instead of N-methylbenzylamine. Thus, the title compound was prepared.

¹H-NMR (CDCl₃) δ: 0.92–1.05 (2H, m), 1.25–1.99 (8H, m), 2.26–2.35 (4H, m), 2.43+2.56 (4H, brs), 2.87+2.94+3.18 (4H, brs), 3.37+4.52 (1H, m), 3.99–4.03 (1H, m), 4.35+4.50+4.98 (2H, d, J=15.8 Hz), 6.50+6.78 (1H, d, J=3.0 Hz), 6.70+6.86 (1H, dd, J=3.0, 8.9 Hz), 7.09+7.43 (2H, d, J=7.3 Hz), 7.10–7.33 (14H, m).

TSIMS (M/Z): 606 (M+H)⁺.

EXAMPLE 67

N-Allyl-2-chloro-N-cyclohexyl-5-[4-(3,3-diphenyl-1-propyl)piperazin-1-yl]benzamide The procedure of Example 66 was repeated, except that N-allylcyclohexylamine was used instead of N-cyclohexylbenzylamine. Thus, the title compound was prepared.

¹H-NMR (CDCl₃) δ: 0.98–1.13 (2H, m), 1.26–1.57 (3H, m), 1.66–1.91 (5H, m), 2.29–2.33 (4H, m), 2.26 (4H, brs), 3.17 (4H, brs), 3.27+4.45 (1H, m), 3.63–3.84 (1H, m), 3.94+4.20 (1H, dd, J=5.6, 15.7 Hz), 4.01 (1H, t, J=7.3 Hz), 4.92+5.30 (1H, d, J=17.2 Hz), 4.99+5.15 (1H, d, J=10.4 Hz), 5.67+5.98 (1H, m), 6.71 (1H, d, J=2.9 Hz), 6.80+6.84 (1H, dd, J=2.9, 8.8 Hz), 7.15–7.30 (11H, m).

FABMS (M/Z); 556 (M+H)⁺.

EXAMPLE 68

N-Allyl-N-cyclohexyl-5-[4-(3,3-diphenyl-1-propyl) piperazin-1-yl]-2-isopropylbenzamide (a) 2-Isopropyl-5-nitrobenzoic acid was synthesized using 4-nitrocumene by the method described in Roczniki Chemii, vol. 31, 1207 (1957).

¹H-NMR (CD₃OD) δ: 1.30 (6H, d, J=6.8 Hz), 3.87–3.96 (1H, m), 7.72 (1H, d, J=8.6 Hz), 8.31 (1H, dd, J=2.5, 8.6 Hz), 8.56 (1H, d, J=2.5 Hz).

EIMS (M/Z): 209 (M⁺).

(b) Steps (a) and (b) of Example 59 were repeated, except that the compound prepared just above in step (a) was used instead of 2-fluoro-5-nitrobenzoic acid. Step (d) of Example 1 was then repeated, except that N-allylcyclohexylamine was used instead of N-methylbenzylamine. Thus, the title compound was prepared.

¹H-NMR (CDCl₃) δ: 1.00–1.84 (10H, m), 1.18 (3H, d, J=7.1 Hz), 1.20 (3H, d, J=7.1 Hz), 2.27–2.36 (4H, m), 2.58 (4H, brs), 2.77–2.91 (1H, m), 3.15 (4H, brs), 3.16+3.71 (1H, m), 3.31+4.42 (1H, m), 3.97+4.15 (1H, dd, J=5.7, 15.5 Hz), 3.99 (1H, t, J=7.2 Hz), 4.95+5.24 (1H, dd, J=1.4, 17.2 Hz), 5.00+5.14 (1H, dd, J=1.4, 10.3 Hz), 5.65+5.99 (1H, m), 6.59+6.60 (1H, d, J=2.8 Hz), 6.88+6.92 (1H, dd, J=2.8, 8.7 Hz), 7.15–7.30 (11H, m).

FABMS (M/Z): 564 (M+H)⁺.

EXAMPLE 69

N-Benzyl-N-cyclohexyl-5-[4-(3,3-diphenyl-1-propyl)piperazin-1-yl]-2-isopropylbenzamide The procedure of Example 68 was repeated, except that N-cyclohexylbenzylamine was used instead of N-allylcyclohexylamine. Thus, the title compound was prepared.

¹H-NMR (CDCl₃) δ: 0.94–1.90 (10H, m), 1.19 (3H, d, J=6.8 Hz), 1.24 (3H, d, J=6.8 Hz), 2.28–2.33 (4H, m), 2.47+2.60 (4H, brs), 2.86+3.18 (4H, brs), 2.90+2.99 (1H, m), 3.41+4.48 (1H, m), 4.00 (1H, t, J=7.6 Hz), 4.33+4.64+4.80 (2H, s+d, J=15.4 Hz), 6.53+6.67 (1H, d, J=2.6 Hz), 6.80+6.94 (1H, dd, J=2.6, 8.8 Hz), 7.13–7.40 (16H, m).

FABMS (M/Z): 614 (M+H)⁺.

EXAMPLE 70

N-Benzyl-N-cyclohexyl-5-[4-(3,3-diphenyl-1-propyl)piperazin-1-yl]-2-methoxybenzamide (a) Step (a) of Example 46 was repeated, except that 3-aminosalicylic acid was used instead of 3-amino-4-methoxybenzoic acid. Thus, ethyl 3-aminosalicylate was prepared.

¹H-NMR (CDCl₃) δ: 1.41 (3H, t, J=7.2 Hz), 2.98 (2H, brs), 4.39 (2H, q, J=7.2 Hz), 6.83 (1H, d, J=8.8 Hz), 6.90 (1H, dd, J=2.9, 8.8 Hz), 7.20 (1H, dd, J=2.9 Hz), 10.30 (1H, brs).

EIMS (M/Z): 181 (M⁺).

(b) The compound (7.25 g) prepared just above in step (a) was dissolved in dichloromethane (200 ml). Sodium hydrogencarbonate (10.08 g) and benzyloxycarbonyl chloride (6.28 ml) was added at 0° C. to the solution. The mixture was stirred for 30 min. A 0.1 mol/liter aqueous citric acid solution was added to the reaction solution. The mixture was extracted with dichloromethane, followed by washing with saturated brine. The organic layer was dried over anhydrous magnesium sulfate, and the solvent was then removed by distillation under the reduced pressure. The precipitated crystal was collected by filtration, was washed with hexane, and was then dried under the reduced pressure to give 10.12 g (80.0%) of ethyl 3-(N-benzyloxycarbonyl)aminosalicylate.

¹H-NMR (CDCl₃) δ: 1.41 (3H, t, J=7.1 Hz), 4.41 (2H, q, J=7.1 Hz), 5.20 (2H, s), 6.55 (1H, brs), 6.94 (1H, d, J=8.8 Hz), 7.32–7.45 (6H, m), 7.87 (1H, brs), 10.66 (1H, s).

TSIMS (M/Z): 316 (M+H)⁺.

(c) The compound (3.15 g) prepared just above in step (b) was dissolved in acetone (40 ml), and potassium carbonate (6.91 g) and methyl iodide (6.23 ml) were added to the solution. The mixture was heated under reflux for 8 hr. The reaction solution was cooled to room temperature, and the cooled solution was filtered. The filtrate was then concentrated under the reduced pressure. The residue was extracted with ethyl acetate, followed by washing with water and saturated brine. The organic layer was dried over anhydrous magnesium sulfate, and the solvent was then removed by distillation under the reduced pressure. The precipitated crystal was collected by filtration, was washed with hexane, and was then dried under the reduced pressure to give 2.54 g (77.0%) of ethyl 3-(N-benzyloxycarbonyl)amino-6-methoxybenzoate.

¹H-NMR (CDCl₃) δ: 1.36 (3H, t, J=7.1 Hz), 3.88 (3H, s), 4.34 (2H, q, J=7.1 Hz), 5.20 (2H, s), 6.61 (1H, brs), 6.94 (1H, d, J=9.0 Hz), 7.32–7.41 (5H, m), 7.61 (1H, brs), 7.69 (1H, d, J=2.6 Hz).

TSIMS (M/Z): 330 (M+H)⁺.

(d) The compound (2.31 g) prepared just above in step (c) was dissolved in anhydrous ethanol (70 ml), and 10% Pd—C (0.23 g) was added to the solution. The mixture was subjected to catalytic reduction at room temperature overnight. The reaction solution was filtered through Celite, and was then washed with ethanol. The filtrate was concentrated under the reduced pressure. The residue was purified by column chromatography on silica gel (hexane:ethyl acetate= 1:1) to give 1.31 g (96.0%) of ethyl 3-amino-6-methoxybenzoate.

¹H-NMR (CDCl₃) δ: 1.37 (3H, t, J=7.1 Hz), 3.83 (3H, s), 4.34 (2H, q, J=7.1 Hz), 6.81–6.82 (2H, m), 7.15 (1H, dd, J=1.0, 2.5 Hz).

EIMS (M/Z): 195 (M⁺).

(e) Steps (a) to (d) of Example 1 were repeated, except that the compound prepared just above in step (d) was used and N-cyclohexylbenzylamine was used instead of N-methylbenzylamine. Thus, the title compound was prepared.

¹H-NMR (CDCl₃) δ: 0.95–1.83 (10H, m), 2.17–2.34 (4H, m), 2.49+2.59 (4H, brs), 2.91+3.12 (4H, brs), 2.43+4.36 (1H, m), 3.75+3.82 (3H, s), 3.98–4.03 (1H, m), 4.50+4.97 (2H, d, J=15.9 Hz), 6.64+6.87 (1H, d, J=2.8 Hz), 6.73+6.86 (1H, d, J=9.0 Hz), 6.78+6.93 (1H, dd, J=2.8, 9.0 Hz), 7.11+7.40 (2H, d, J=6.8 Hz), 7.15–7.32 (13H, m).

TSIMS (M/Z): 602 (M+H)⁺.

EXAMPLE 71

N-Cyclohexyl-5-[4-(3,3-diphenyl-1-propyl) piperazin-1-yl]-2-methoxy-N-methylbenzamide Step (e) of Example 70 was repeated, except that N-methylcyclohexylamine was used instead of N-cyclohexylbenzylamine. Thus, the title compound was prepared.

¹H-NMR (CDCl₃) δ: 0.98–1.11 (2H, m), 1.33–1.51 (4H, m), 1.67–1.81 (4H, m), 2.28–2.32 (4H, m), 2.57 (4H, brs), 2.67+2.96 (3H, s), 3.10 (4H, brs), 3.27+4.58 (1H, m), 3.75+3.76 (3H, s), 4.01 (1H, t, J=7.2 Hz), 6.77–6.83 (2H, m), 6.86–6.91 (1H, m), 7.15–7.21 (2H, m), 7.24–7.52 (8H, m).

TSIMS (M/Z): 526 (M+H)⁺.

EXAMPLE 72

N-Cyclohexyl-5-[4-(3,3-diphenyl-1-propyl)piperazin-1-yl]-N-isopropyl-2-methoxybenzamide Step (e) of Example 70 was repeated, except that N-isopropylcyclohexylamine was used instead of N-cyclohexylbenzylamine. Thus, the title compound was prepared.

$^1$H-NMR (CDCl$_3$) δ: 0.88–1.02 (2H, m), 1.12 (1H, d, J=6.7 Hz), 1.25–1.27 (2H, m), 1.42–1.47 (1H, m), 1.52 (3H, dd, J=2.2, 6.7 Hz), 1.63–1.68 (5H, m), 1.83 (1H, m), 2.31–2.35 (4H, m), 2.59 (5H, brs), 2.95–3.22 (1H, m), 3.11 (4H, brs), 3.50+3.70 (1H, m), 3.75 (3H, s), 4.01 (1H, t, J=7.3 Hz), 6.74 (1H, d, J=2.9 Hz), 6.79 (1H, d, J=9.0 Hz), 6.83–6.88 (1H, m), 7.15–7.20 (2H, m), 7.25–7.30 (8H, m).

TSIMS (M/Z): 554 (M+H)$^+$.

EXAMPLE 73

N-Benzyl-5-[4-(3,3-diphenyl-1-propyl)piperazin-1-yl]-N-isopropyl-2-methoxybenzamide Step (e) of Example 70 was repeated, except that N-isopropylbenzylamine was used instead of N-cyclohexylbenzylamine. Thus, the title compound was prepared.

$^1$H-NMR (CDCl$_3$) δ: 1.01+1.04 (4H, d, J=6.9 Hz), 1.22–1.25 (2H, m), 2.29–2.34 (4H, m), 2.50+2.58 (4H, brs), 2.94+3.11 (4H, brs), 3.76+3.82 (3H, s), 3.92+4.76 (1H, m), 4.00–4.03 (1H, m), 4.33+4.50+4.92 (2H, m), 6.67+6.87 (1H, d, J=3.0 Hz), 6.74+6.85 (1H, d, J=8.9 Hz), 6.79+6.92 (1H, dd, J=3.0, 8.9 Hz), 7.13+7.41 (2H, d, J=6.9 Hz), 7.14–7.33 (13H, m).

TSIMS (M/Z): 562 (M+H)$^+$.

EXAMPLE 74

N-Benzyl-N-cyclohexyl-5-[4-(3,3-diphenyl-1-propyl)piperazin-1-yl]-2-isopropyloxybenzamide (a) Ethyl 3-(N-benzyloxycarbonyl)amino-6-isopropyloxybenzoate was prepared using the compound prepared in step (b) of Example 70 and isopropanol according to the method described in Japanese Patent Laid-Open No. 48663/1996.

$^1$H-NMR (CDCl$_3$) δ: 1.34 (6H, d, J=6.1 Hz), 1.36 (3H, t, J=7.1 Hz), 4.33 (2H, q, J=7.1 Hz), 4.51 (2H, dq, J=6.1 Hz), 4.94 (1H, m), 5.19 (2H, s), 6.66 (1H, brs), 6.94 (1H, d, J=9.0 Hz), 7.32–7.41 (5H, m), 7.62–7.63 (1H, m).

TSIMS (M/Z): 358 (M+H)$^+$.

(b) The compound (1.72 g) prepared just above in step (a) was dissolved in anhydrous ethanol (48 ml), and 10% Pd—C (0.17 g) was added to the solution. The mixture was subjected to catalytic reduction at room temperature for 4 hr. The reaction solution was filtered through Celite, followed by washing with ethanol. The filtrate was concentrated under the reduced pressure. The residue was purified by column chromatography on silica gel (hexane:ethyl acetate=1:1) to give 0.92 g (86.0%) of ethyl 3-amino-6-isopropyloxybenzoate.

$^1$H-NMR (CDCl$_3$) δ: 1.30 (6H, d, J=6.1 Hz), 1.38 (3H, t, J=7.2 Hz), 4.34 (2H, q, J=7.2 Hz), 4.37 (1H, dq, J=6.1 Hz), 6.77 (1H, dd, J=2.9, 8.6 Hz), 6.84 (1H, d, J=8.6 Hz), 7.10 (1H, d, J=2.9 Hz).

EIMS (M/Z): 223 (M$^+$).

(c) Steps (a) to (d) of Example 1 were repeated, except that the compound prepared just above in step (b) was used and N-benzylcyclohexylamine was used instead of N-methylbenzylamine. Thus, the title compound was prepared.

$^1$H-NMR (CDCl$_3$) δ: 0.87–0.96 (2H, m), 1.19–1.86 (8H, m), 1.32+1.35 (6H, d, J=6.1 Hz), 2.25–2.34 (4H, m), 2.49+2.59 (4H, brs), 2.89+3.12 (4H, brs), 3.44+4.51 (1H, m), 4.01 (1H, t, J=7.6 Hz), 4.26+4.33+4.39+5.20 (2H, s+d, J=16.1 Hz), 6.61–6.92 (3H, m), 7.10+7.43 (2H, d, J=7.1 Hz), 7.14–7.31 (13H, m).

TSIMS (M/Z): 630 (M+H)$^+$.

EXAMPLE 75

N-Allyl-2-cyano-N-cyclohexyl-5-[4-(3,3-diphenyl-1-propyl)piperazin-1-yl]benzamide (a) Ethyl 2-amino-5-bromobenzoate was prepared in the same manner as in step (a) of Example 59, except that 2-amino-5-bromobenzoic acid was used as the starting compound.

$^1$H-NMR (CDCl$_3$) δ: 1.39 (3H, t, J=7.1 Hz), 4.33 (2H, q, J=7.1 Hz), 6.56 (1H, d, J=8.8 Hz), 7.32 (1H, dd, J=2.4, 8.8 Hz), 7.97 (1H, d, J=2.4 Hz).

EIMS (M/Z): 243 (M)$^-$.

(b) Ethyl 2-cyano-5-bromobenzoate was prepared using the compound prepared just above in step (a) according to the method described in J. Med. Chem, vol. 35, 4613 (1992).

$^1$H-NMR (CDCl$_3$) δ: 1.47 (3H, t, J=7.2 Hz), 4.48 (2H, q, J=7.2 Hz), 7.66 (1H, d, J=8.5 Hz), 7.80 (1H, dd, J=2.1, 8.5 Hz), 8.29 (1H, d, J=2.1 Hz).

TSIMS (M/Z): 253 (M)$^-$.

(c) Ethyl 2-cyano-5-[4-(3,3-diphenyl-1-propyl)piperazin-1-yl]benzoate was prepared using the compound prepared just above in step (b) and 4-(3,3-diphenyl-1-propyl)piperazine according to the method described in Tetrahedron Lett., Vol. 38, 6359 (1997).

$^1$H-NMR (CDCl$_3$) δ: 1.44 (3H, t, J=7.2 Hz), 2.25–2.30 (2H, m), 2.32–2.36 (2H, m), 2.54 (4H, t, J=5.1 Hz), 3.37 (4H, t, J=5.1 Hz), 4.03 (1H, t, J=7.3 Hz), 4.45 (2H, q, J=7.2 Hz), 6.96 (1H, dd, J=2.8, 8.8 Hz), 7.16–7.22 (2H, m), 7.25–7.31 (8H, m), 7.52 (1H, d, J=2.8 Hz), 7.59 (1H, d, J=8.8 Hz).

TSIMS (M/Z): 454 (M+H)$^+$.

(d) Steps (c) and (d) of Example 1 were repeated, except that the compound prepared in step (a) of this example was used and N-allylcyclohexylamine was used instead of N-methylbenzylamine. Thus, the title compound was prepared.

$^1$H-NMR (CDCl$_3$) δ: 1.04–1.73 (8H, m), 1.81–1.92 (2H, m), 2.26–2.33 (4H, m), 2.52 (4H, brs), 3.30+4.07 (1H, m), 3.32 (4H, brs), 3.78+3.95 (1H, m), 3.83+4.40 (1H, m), 4.02 (1H, t, J=7.3 Hz), 4.96+5.32 (1H, d, J=17.2 Hz), 5.04+5.18 (1H, d, J=10.5 Hz), 5.72+5.98 (1H, m), 6.72 (1H, d, J=2.6 Hz), 6.79+6.84 (1H, dd, J=2.6, 8.9 Hz), 7.15–7.30 (10H, m), 7.46+7.50 (1H, d, J=8.9 Hz).

TSIMS (M/Z): 547 (M+H)$^+$.

EXAMPLE 76

N-Benzyl-2-cyano-N-cyclohexyl-5-[4-(3,3-diphenyl-1-propyl)piperazin-1-yl]benzamide (a) Step (d) of Example 75 was repeated, except that N-cyclohexylbenzylamine was used instead of N-allylcyclohexylamine. Thus, the title compound was prepared.

$^1$H-NMR (CDCl$_3$) δ: 0.97–1.97 (10H, m), 2.25–2.34 (4H, m), 2.39+2.54 (4H, t, J=4.9 Hz), 3.07+3.35 (4H, t, J=4.9), 3.40+4.50 (1H, m), 3.98–4.04 (1H, m), 4.42+4.75 (2H, s+m), 6.48+6.77 (1H, d, J=2.5 Hz), 6.69+6.86 (1H, dd, J=2.5, 8.8 Hz), 7.06–7.45 (15H, m), 7.41+7.54 (1H, d, J=8.9 Hz).

TSIMS (M/Z): 597 (M+H)$^+$.

EXAMPLE 77

N-Benzyl-N-cyclohexyl-5-[4-(3,3-diphenyl-1-propyl)piperazin-1-yl]-2-hydroxybenzamide The compound (46 mg) prepared in Example 70 was dissolved in dichloromethane (3.8 ml). A 1 M solution (0.23 ml) of boron tribromide in dichloromethane was added to the solution at 0° C. The mixture was stirred at 0° C. for 20 min, and was then stirred at room temperature for 30 min. Water and a saturated aqueous sodium hydrogencarbonate solution were added to the reaction solution, and the mixture was extracted with dichloromethane, followed by washing with saturated brine. The organic layer was dried over anhydrous magnesium sulfate. The solvent was then removed by distillation under the reduced pressure. The residue was developed by preparative TLC (chloroform:methanol=20:1) to give the title compound (35 mg).

$^1$H-NMR (CDCl$_3$) δ: 1.03–1.12 (1H, m), 1.26 (2H, q, J=13.1 Hz), 1.56–1.62 (3H, m), 1.78 (2H, d, J=13.1 Hz), 1.86 (2H, d, J=11.0 Hz), 2.26–2.28 (4H, m), 2.44 (4H, brs), 2.78 (4H, brs), 3.99 (1H, t, J=7.3 Hz), 4.10–4.16 (1H, m), 4.68 (2H, s), 6.81 (1H, d, J=2.7 Hz), 6.90 (1H, d, J=9.0 Hz), 6.95 (1H, dd, J=2.7, 9.0 Hz), 7.16–7.20 (2H, m), 7.23–7.52 (13H, m), 9.23 (1H, brs).

TSIMS (M/Z): 588 (M+H)$^+$.

EXAMPLE 78

N-Allyl-N-cyclohexyl-3-[1-(3,3-diphenyl-1-propyl)-1,2,3,6-tetrahydropyridin-4-yl]-benzamide (a) 3-Bromobenzoic acid (6.03 g) was dissolved in dichloromethane (30 ml), and thionyl chloride (10.7 ml) and N,N-dimethylformamide (1 ml) were added to the solution. The mixture was stirred at room temperature for 30 min. The solvent was removed by distillation under the reduced pressure to dryness. 2-Amino-2-methyl-1-propanol (5.7 ml) was then added thereto, and the mixture was stirred at room temperature for 1.5 hr. Water was added to the reaction solution, and the mixture was extracted with dichloromethane. The organic layer was dried over anhydrous magnesium sulfate. The solvent was removed by distillation under the reduced pressure to give 7.03 g (86.2%) of 3-bromo-N-(2-hydroxy-1,1-dimethylethyl)benzamide.

$^1$H-NMR (CDCl$_3$) δ: 1.42 (6H, s), 3.70 (2H, s), 6.15 (1H, brs), 7.30 (1H, t, J=8.1 Hz), 7.63 (2H, m), 7.85 (1H, t, J=1.7 Hz).

FABMS (M/Z): 274 (M$^+$).

(b) The compound (7.0 g) prepared just above in step (a) was dissolved in dichloromethane (20 ml), and thionyl chloride (5.5 ml) was added to the solution. The mixture was stirred at room temperature for one hr. The solvent was removed by distillation under the reduced pressure. A saturated aqueous sodium hydrogencarbonate solution was then added to the residue, and the mixture was extracted with dichloromethane. The organic layer was dried over anhydrous magnesium sulfate. The solvent was then removed by distillation under the reduced pressure to give 5.0 g (76.9%) of 2-(3-bromophenyl-4,4-dimethyl-4,5-dihydroxazole.

$^1$H-NMR (CDCl$_3$) δ: 1.38 (6H, s), 4.08 (2H, s), 7.25 (1H, dd, J=7.8, 8.0 Hz), 7.58 (1H, ddd, J=1.2, 2.0, 8.0 Hz), 7.84 (1H, ddd, J=1.2, 1.6, 7.8 Hz), 8.11 (1H, dd, J=1.6, 2.0 Hz).

EIMS (M/Z): 255 (M$^+$).

(c) The compound (2.1 g) prepared just above in step (b) was dissolved in tetrahydrofuran (40 ml). A 1.6 M solution of n-butyl lithium (6.4 ml) was added dropwise to the solution under cooling at −78° C. The mixture was stirred at −78° C. for 30 min. N-t-Butoxycarbonyl-4-piperidone (2.0 g) was then added thereto, and the mixture was stirred at −78° C. for 30 min, and was then stirred at room temperature for 5 hr. Water was added to the reaction solution, and the mixture was extracted with ethyl acetate. The organic layer was dried over anhydrous magnesium sulfate. The solvent was then removed by distillation under the reduced pressure. The residue was purified by column chromatography on silica gel (hexane:ethyl acetate 1:1) to give 0.13 g (34.8%) of t-butyl 4-[3-(4,4-dimethyl-4,5-dihydroxazol-2-yl)phenyl]-4-hydroxypiperidine-1-carboxylate.

$^1$H-NMR (CDCl$_3$) δ: 1.39 (6H, s), 1.49 (9H, s), 1.72 (2H, m), 2.05 (2H, m), 3.23 (2H, m), 4.06 (2H, m), 4.12 (2H, s), 7.41 (1H, dd, J=7.6, 7.9 Hz), 7.60 (1H, ddd, J=1.2, 2.0, 7.9 Hz), 7.85 (1H, ddd, J=1.2, 1.6, 7.6 Hz), 8.04 (1H, dd, J=1.6, 2.0 Hz).

TSIMS (M/Z): 375 (M+H)$^+$.

(d) The compound (0.05 g) prepared just above in step (c) was dissolved in dichloromethane (2 ml), and trifluoroacetic acid (2 ml) was added dropwise to the solution. The mixture was stirred at room temperature for 5 hr. A saturated aqueous sodium carbonate solution was added to the reaction solution, and the mixture was extracted with dichloromethane. The organic layer was dried over anhydrous magnesium sulfate. The solvent was then removed by distillation under the reduced pressure to give 0.034 g (88.5%) of 4-[3-(4,4-dimethyl-4,5-dihydroxazol-2-yl)phenyl]-4-hydroxypiperidine.

$^1$H-NMR (CD$_3$OD) δ: 1.38 (6H, s), 1.93 (2H, m), 2.25 (2H, m), 3.32 (2H, m), 3.46 (2H, m), 4.20 (2H, S), 7.48 (1H, m), 7.71 (1H, m), 7.80 (1H, m), 8.07 (1H, m).

EIMS (M/Z): 275 (M+H)$^+$.

(e) The compound (0.46 g) prepared just above in step (d) was dissolved in N,N-dimethylformamide (5 ml), and potassium carbonate (0.46 g) and 3,3-diphenylpropyl bromide (0.50 g) were added to the solution. The mixture was stirred at room temperature overnight. Water was added to the reaction solution, and the mixture was extracted with ethyl acetate. The organic layer was then dried over anhydrous magnesium sulfate. The solvent was then removed by distillation under the reduced pressure. The residue was purified by column chromatography on silica gel (hexane:ethyl acetate=1:1) to give 0.59 g (75.6%) of 4-[3-(4,4-dimethyl-4,5-dihydroxazol-2-yl)phenyl]-1-(3,3-diphenyl-1-propyl)-4-hydroxypiperidine.

$^1$H-NMR (CDCl$_3$) δ: 1.39 (6H, s), 1.76 (2H, m), 2.18–2.44 (6H, m), 2.80 (2H, m), 4.01 (1H, t, J=7.2 Hz), 4.11 (2H, s), 7.17–7.29 (10H, m), 7.39 (1H, dd, J=7.7, 7.9 Hz), 7.63 (1H, d, J=7.9 Hz), 7.84 (1H, d, J=7.7 Hz), 8.10 (1H, brs).

TSIMS (M/Z): 275 (M+H)$^+$.

(f) The compound (0.46 g) prepared just above in step (e) was dissolved in 1,4-dioxane (10 ml) and concentrated hydrochloric acid (15 ml), and the solution was heated under reflux for one day. Water was added to the reaction solution. The precipitated crystal was collected by filtration, and was then dried. The crystal thus obtained as such was used in the next reaction without any purification.

(g) Step (d) of Example 1 was repeated, except that the compound prepared just above in step (f) was used and N-allylcyclohexylamine was used instead of N-methylbenzylamine. Thus, the title compound was prepared.

$^1$H-NMR (CDCl$_3$) δ: 0.80–1.90 (10H, m), 1.79 (4H, m), 2.54 (2H, m), 2.69 (2H, m), 3.15 (2H, m), 4.02 (1H, t, J=7.2 Hz), 5.12 (2H, m), 5.90–6.09 (1H, m), 7.18–7.80 (14H, m).

TSIMS (M/Z): 519 (M+H)$^+$.

EXAMPLE 79

N-Allyl-N-cyclohexyl-3-[1-(3,3-diphenyl-1-propyl) piperidin-4-yl]benzamide (a) Ethanol (5 ml) and concentrated sulfuric acid (0.2 ml) were added to the crystal (0.10 g) prepared in step (f) of Example 78, and the mixture was stirred at 100° C. overnight. A saturated aqueous sodium hydrogencarbonate solution was added to the reaction solution, and the mixture was extracted with ethyl acetate. The organic layer was dried over anhydrous magnesium sulfate. The solvent was then removed by distillation under the reduced pressure to give 0.13 g (100%) of ethyl 3-[1-(3,3-diphenyl-1-propyl)-1,2,3, 6-tetrahydropyridin-4-yl]benzoate.

$^1$H-NMR (CDCl$_3$) δ: 1.40 (3H, t, J=7.1 Hz), 2.33–2.43 (4H, m), 2.60 (2H, brs), 2.69 (2H, m), 4.03 (1H, t, J=7.3 Hz), 4.39 (2H, q, J=7.1 Hz), 6.14 (1H, brs), 7.10–7.30 (10H, m), 7.38 (1H, dd, J=7.7 Hz), 7.57 (1H, d, J=7.7 Hz), 7.91 (1H, d, J=7.7 Hz), 8.07 (1H, brs).

TSIMS (M/Z): 426 (M+H)$^+$.

(b) The crystal (0.13 g) prepared just above in step (a) was dissolved in ethanol (10 ml). 10% Pd—C (0.013 g) was added to the solution, and the mixture was subjected to catalytic reduction overnight. The reaction solution was filtered through Celite, followed by washing with ethanol. The solvent was then removed from the filtrate by distillation under the reduced pressure to give 0.08 g (74.9%) of ethyl 3-[1-(3,3-diphenyl-1-propyl)piperidin-4-yl]benzoate.

$^1$H-NMR (CDCl$_3$) δ: 1.40 (3H, t, J=7.1 Hz), 1.84 (4H, m), 2.03 (2H, m), 2.34 (4H, m), 3.04 (2H, m), 4.00 (1H, m), 4.38 (1H, m), 7.29 (12H, m), 7.91 (2H, m).

TSIMS (M/Z): 428 (M+H)$^+$.

(c) Steps (c) and (d) of Example 1 were repeated, except that the compound prepared just above in step (b) was used and N-allylcyclohexylamine was used instead of N-methylbenzylamine. Thus, the title compound was prepared.

$^1$H-NMR (CDCl$_3$) δ: 1.00–2.04 (14H, m), 2.32–2.80 (6H, m), 3.04 (2H, m), 3.49+3.80 (1H, m), 4.02 (3H, m), 4.30 (1H, m), 5.13 (2H, m), 5.96 (1H, m), 7.25 (14H, m).

TSIMS (M/Z): 521 (M+H)$^+$.

EXAMPLE 80

N-Benzyl-N-cyclohexyl-4-[4-(3,3-diphenyl-1-propyl)piperazin-1-yl]benzamide (a) Ethyl 4-fluorobenzoate (20.1 g) was dissolved in dimethyl sulfoxide (50 ml). Piperazine (31.1 g) was added to the solution, and the mixture was stirred at 120° C. for 2 hr. The reaction solution was poured into 1.2 liters of ice water. The precipitated crystal was washed with a mixed solution composed of hexane (500 ml) and diethyl ether (50 ml), was collected by filtration, and was dried under the reduced pressure to give 24.3 g (86.8%) of ethyl 4-(piperazin-1-yl) benzoate.

$^1$H-NMR (CDCl$_3$) δ: 1.37 (3H, t, J=7.0 Hz), 3.02 (4H, m), 4.32 (2H, q, J=7.0 Hz), 6.86 (2H, d, J=9.0 Hz), 7.92 (2H, d, J=9.0 Hz).

TSIMS (M/Z): 235 (M+H)$^+$.

(b) Steps (b) and (c) of Example 1 were repeated, except that the compound prepared just above in step (a) was used. Step (d) of Example 1 was then repeated, except that N-benzylcyclohexylamine was used instead of N-methylbenzylamine. Thus, the title compound was prepared.

$^1$H-NMR (CDCl$_3$) δ: 0.96–1.16 (2H, m), 1.60 (4H, m), 1.66–1.76 (4H, m), 2.24–2.38 (5H, m), 2.53–2.60 (4H, m), 3.20–3.28 (4H, m), 4.02 (1H, t, J=7.1 Hz), 4.64 (2H, brs), 6.87 (2H, brs), 7.15–7.40 (17H, m).

TSIMS (M/Z): 572 (M+H)$^+$.

EXAMPLE 81

N-Allyl-N-cyclohexyl-4-[4-(3,3-diphenyl-1-propyl) piperazin-1-yl]-3-fluorobenzamide (a) Step (a) of Example 59 was repeated, except that 3,4-difluorobenzoic acid was used instead of 2-fluoro-5-nitrobenzoic acid. Thus, ethyl 3,4-difluorobenzoate was prepared.

$^1$H-NMR (CDCl$_3$) δ: 1.40 (3H, t, J=7.1 Hz), 4.38 (2H, q, J=7.1 Hz), 7.21 (1H, m), 7.85 (2H, m).

EIMS (M/Z): 186 (M$^+$).

(b) Step (c) of Example 75 was repeated, except that the compound prepared just above in step (a) was used. Thus, ethyl 4-[4-(3,3-diphenyl-1-propyl)piperazin-1-yl]-3-fluorobenzoate was prepared.

$^1$H-NMR (CDCl$_3$) δ: 1.38 (3H, t, J=7.1 Hz), 2.35 (4H, m), 2.60 (4H, m), 3.23 (4H, m), 4.04 (1H, t, J=7.6 Hz), 4.35 (2H, q, J=7.1 Hz), 6.91 (1H, t, J=8.6 Hz), 7.25 (10H, m), 7.68 (1H, dd, J=2.0, 13.5 Hz), 7.77 (1H, dd, J=2.7, 8.6 Hz).

EIMS (M/Z): 446 (M$^+$).

(c) Steps (c) and (d) of Example 1 were repeated, except that the compound prepared just above in step (b) was used. Thus, the title compound was prepared.

$^1$H-NMR (CDCl$_3$) δ: 1.00–1.80 (10H, m), 2.33 (4H, m), 2.62 (4H, m), 3.15 (4H, m), 3.40–3.70 (1H, m), 3.90 (2H, brs), 4.03 (1H, t, J=7.7 Hz), 5.14 (2H, m), 6.85 (2H, m), 6.85 (1H, m), 6.92 (1H, t, J=8.3 Hz), 7.05–7.32 (12H, m).

FABMS (M/Z): 540 (M+H)$^+$.

EXAMPLE 82

N-Allyl-2-chloro-N-cyclohexyl-4-[4-(3,3-diphenyl-1-propyl)piperazin-1-yl]benzamide The procedure of Example 1 was repeated, except that ethyl 4-amino-2-chlorobenzoate was used instead of ethyl 3-aminobenzoate and N-cyclohexylallylamine was used instead of N-benzylmethylamine. Thus, the title compound was prepared.

$^1$H-NMR (CDCl$_3$) δ: 0.93–1.84 (10H, m), 0.93 (4H, m), 2.56 (4H, m), 3.23 (4H, m), 3.70+4.47 (1H, m), 3.74–4.24 (3H, m), 4.90–5.32 (2H, m), 5.62–6.02 (1H, m), 6.70–6.89 (3H, m), 7.08–7.32 (10H, m).

TSIMS (M/Z): 558 (M+H)$^+$.

EXAMPLE 83

N-Allyl-N-cyclohexyl-2-[4-(3,3-diphenyl-1-propyl)piperazin-1-yl]benzamide (a) Step (c) of Example 75 was repeated, except that ethyl 2-bromobenzoate and 4-(3,3-diphenyl-1-propyl)piperazine were used. Thus, ethyl 2-[4-(3,3-diphenyl-1-propyl)piperazin-1-yl]benzoate was prepared.

$^1$H-NMR (CDCl$_3$) δ: 2.23–2.38 (4H, m), 2.58 (4H, brs), 3.07 (4H, brs), 3.86 (3H, s), 4.01 (1H, t, J=7.5 Hz), 6.98–7.04 (1H, m), 7.15–7.30 (10H, m), 7.40 (1H, m), 7.71 (1H, dd, J=1.6, 7.7 Hz).

TSIMS (M/Z): 415 (M+H)$^+$.

(b) Steps (c) and (d) of Example 1 were repeated, except that the compound prepared just above in step (a) was used and N-allylcyclohexylamine was used instead of N-methylbenzylamine. Thus, the title compound was prepared.

$^1$H-NMR (CDCl$_3$) δ: 1.31–1.87 (10H, m), 2.38–2.54 (4H, m), 2.81 (4H, brs), 3.31 (4H, brs), 3.76–3.82 (1H, m), 4.01 (1H, t, J=6.8 Hz), 4.17–4.24 (1H, m), 4.42 (1H, m), 4.75+5.27 (1H, dd, J=1.5, 17.0 Hz), 4.84+5.12. (1H, dd, J=1.5, 10.5 Hz), 5.57+5.96 (1H, m), 7.16–7.29 (14H, m).

TSIMS (M/Z): 522 (M+H)$^+$.

EXAMPLE 84

N-Benzyl-N-cyclohexyl-5-[4-(2,2-diphenylethyl)piperazin-1-yl]-2-methylbenzamide (a) Step (a) of Example 1 was repeated, except that methyl 5-amino-2-methylbenzoate was used instead of ethyl 3-aminobenzoate. The compound (0.248 g) thus obtained and diphenylacetaldehyde (0.196 g) were dissolved in dichloromethane (10 ml), and sodium boron triacetoxyhydride (0.318 g) and acetic acid (3 ml) were added to the solution. The mixture was stirred at room temperature for one hr. A saturated aqueous sodium hydrogencarbonate solution was added to the reaction solution, and the mixture was extracted with chloroform, followed by washing with saturated brine. The organic layer was dried over anhydrous magnesium sulfate, and the solvent was then removed by distillation under the reduced pressure. The residue was purified by column chromatography on silica gel (hexane:ethyl acetate=8:1) to give 0.364 g of ethyl 5-[4-(2,2-diphenylethyl)piperazin-1-yl]-2-methylbenzoate.

$^1$H-NMR (CDCl$_3$) δ: 1.37 (3H, t, J=7.2 Hz), 2.47 (3H, s), 2.63 (4H, t, J=5.0 Hz), 3.04 (2H, d, J=7.4 Hz), 3.09 (4H, t, J=5.0 Hz), 4.25 (1H, t, J=7.4 Hz), 4.33 (2H, q, J=7.2 Hz), 6.93 (1H, dd, J=2.7, 8.3 Hz), 7.09 (1H, d, J=8.3 Hz), 7.16–7.22 (2H, m), 7.25–7.30 (8H, m), 7.42 (1H, d, J=2.7 Hz).

TSIMS (M/Z): 428 (M+H)$^+$.

(b) Steps (c) and (d) of Example 1 were repeated, except that the compound prepared just above in step (a) was used as the starting compound. Thus, the title compound was prepared.

$^1$H-NMR (CDCl$_3$) δ: 0.95–1.84 (10H, m), 2.17+2.25 (3H, s), 2.51+2.63 (4H, brs), 2.81+3.06 (4H, brs), 2.98–3.08 (2H, m), 3.38+4.48 (1H, m), 4.23–4.25 (1H, m), 4.30+4.59+4.84 (2H, m), 6.53+6.69 (1H, d, J=2.6 Hz), 6.68+6.82 (1H, dd, J=2.6, 8.5 Hz), 6.96+7.07 (1H, d, J=8.5 Hz), 7.09+7.39 (2H, d, J=7.5 Hz), 7.12–7.33 (13H, m).

TSIMS (M/Z): 572 (M+H)$^+$.

EXAMPLE 85

N-Allyl-N-cyclohexyl-3-[4-(3,3-diphenyl-1-propyl)piperazin-1-yl]-5-methoxybenzamide The procedure of Example 83 was repeated, except that 3-bromo-5-methoxybenzoic acid was used as the starting compound. Thus, the title compound was prepared.

$^1$H-NMR (CDCl$_3$) δ: 1.05–1.71 (10H, m), 2.30 (4H, m), 2.55 (4H, m), 3.47 (4H, m), 3.59 (1H, m), 3.78 (3H, m), 3.98 (1H, brs), 4.01 (1H, t, J=6.8 Hz), 4.27–5.94 (4H, m), 6.36 (1H, s), 6.47 (1H, s), 7.14–7.29 (11H, m).

FABMS (M/Z): 552 (M+H)$^+$.

EXAMPLE 86

N-Allyl-N-cyclohexyl-3-[4-(3,3-diphenyl-1-propyl)piperazin-1-yl]-5-hydroxybenzamide The procedure of Example 77 was repeated, except that the compound prepared in Example 85 was used as the starting compound. Thus, the title compound was prepared.

$^1$H-NMR (CDCl$_3$) δ: 1.05–1.71 (10H, m), 2.30 (4H, m), 2.55 (4H, m), 3.16 (4H, m), 3.59–3.98 (2H, m), 4.00 (1H, t, J=7.0 Hz), 4.27–5.94 (4H, m), 6.30 (1H, s), 6.47 (1H, s), 7.14–7.29 (11H, m).

FABMS (M/Z): 538 (M+H)$^+$.

EXAMPLE 87

N-Allyl-N-cyclohexyl-3-[4-[4-[9-(2,2,2-trifluoroethylcarbamoyl)-9H-fluoren-9-yl]butyl]piperazin-1-yl]benzamide (a) 4-[9-(2,2,2-Trifluoroethylcarbamoyl)-9H-fluoren-9-yl]butyl bromide was synthesized according to the method described in U.S. Pat. No. 5,712,279.

$^1$H-NMR (CDCl$_3$) δ: 0.79–0.87 (2H, m), 1.70 (2H, qu, J=7.1 Hz), 2.41–2.46 (2H, m), 3.21 (2H, t, J=7.1 Hz), 3.69 (2H, dq, J=9.0, 2.4 Hz), 5.35 (1H, brs), 7.38 (2H, dt, J=7.5, 1.2 Hz), 7.46 (2H, dt, J=7.5, 1.2 Hz), 7.55 (2H, d, J=7.5 Hz), 7.78 (2H, d, J=7.5 Hz).

EIMS (M/Z): 426 (M+H)$^+$.

(b) Step (b) of Example 1 was repeated, except that the compound prepared just above in step (a) was used instead of 3,3-diphenylpropyl bromide. Thus, ethyl 3-[4-[4-[9-(2,2,2-trifluoroethylcarbamoyl)-9H-fluoren-9-yl]butyl]piperazin-1-yl]benzoate was prepared.

$^1$H-NMR (CDCl$_3$) δ: 0.68–0.76 (2H, m), 1.34–1.40 (2H, m), 1.38 (3H, t, J=7.1 Hz), 2.16–2.20 (2H, m), 2.44–2.48 (2H, m), 2.47 (4H, t, J=4.6 Hz), 3.16 (4H, t, J=4.6 Hz), 3.65–3.74 (2H, m), 4.36 (2H, q, J=7.1 Hz), 5.11–5.24 (2H, m), 5.37 (1H, t, J=6.4 Hz), 5.37 (1H, t, J=6.1 Hz), 7.06 (1H, d, J=8.3 Hz), 7.29–7.57 (9H, m), 7.78 (2H, d, J=7.5 Hz).

TSIMS (M/Z): 580 (M+H)$^+$.

(c) Steps (c) and (d) of Example 1 were repeated, except that the compound prepared just above in step (b) was used and N-allylcyclohexylamine was used instead of N-methylbenzylamine. Thus, the title compound was prepared.

$^1$H-NMR (CDCl$_3$) δ: 0.68–0.76 (2H, m), 1.03–1.77 (10H, m), 1.33–1.41 (2H, m), 2.18 (2H, t, J=7.6), 2.43 (2H, m), 2.45 (4H, brs), 3.13 (4H, brs), 3.55+4.31 (1H, m), 3.65–3.73 (2H, m), 3.80+4.03 (2H, m), 5.11–5.24 (2H, m), 5.37 (1H, t, J=6.4 Hz), 5.71+5.95 (1H, m), 6.78 (1H, d, J=7.4 Hz), 6.85–6.89 (2H, m), 7.23–7.26 (1H, m), 7.37 (2H, t, J=7.4 Hz), 7.45 (2H, t, J=7.4 Hz), 7.55 (2H, d, J=7.4 Hz), 7.77 (2H, d, J=7.4 Hz).

TSIMS (M/Z): 673 (M+H)$^+$.

EXAMPLE 88

N-Benzyl-N-cyclohexyl-3-[4-[4-[9-(2,2,2-trifluoroethylcarbamoyl)-9H-fluoren-9-yl]butyl]piperazin-1-yl)benzamide Steps (c) and (d) of Example 1 were repeated, except that the compound prepared in step (b) of Example 87 was used and N-cyclohexylbenzylamine was used instead of N-methylbenzylamine. Thus, the title compound was prepared.

¹H-NMR (CDCl₃) δ: 0.70–0.76 (2H, m), 1.00–1.66 (10H, m), 1.24 (2H, m), 2.17 (2H, m), 2.43 (2H, m), 2.46 (4H, m), 2.92+3.15 (4H, brs), 3.65–3.74 (3H, m), 4.47+4.69 (2H, m), 5.36 (1H, t, J=6.5 Hz), 6.86–6.92 (2H, m), 7.21–7.29 (7H, m), 7.37 (2H, dt, J=1.2, 7.4 Hz), 7.46 (2H, dt, J=1.2, 7.4 Hz), 7.56 (2H, d, J=7.4 Hz), 7.77 (2H, d, J=7.4 Hz).

TSIMS (M/Z): 723 (M+H)⁺.

EXAMPLE 89

N-Allyl-N-cyclohexyl-4-[4-[4-[9-(2,2,2-trifluoroethylcarbamoyl)-9H-fluoren-9-yl]butyl]piperazin-1-yl]benzamide (a) Step (b) of Example 1 was repeated, except that the compound prepared in step (a) of Example 80 and the compound prepared in step (a) of Example 87 were used. Thus, ethyl 4-[4-[4-[9-(2,2,2-trifluoroethylcarbamoyl)-9H-fluoren-9-yl]butyl]piperazin-1-yl]benzoate was prepared.

¹H-NMR (CDCl₃) δ: 0.69–0.77 (2H, m), 1.32–1.40 (2H, m), 1.36 (3H, t, J=7.1 Hz), 2.15–2.19 (2H, m), 2.42–2.47 (2H, m), 2.43 (4H, t, J=5.1 Hz), 3.24 (4H, t, J=5.1 Hz), 3.69 (2H, dq, J=9.0, 2.5 Hz), 4.32 (2H, q, J=7.1.Hz), 5.36 (1H, t, J=6.4 Hz), 6.82 (2H, d, J=9.2 Hz), 7.37 (2H, dt, J=7.4, 1.2 Hz), 7.45 (2H, dt, J=7.4, 1.2 Hz), 7.55 (2H, d, J=7.4 Hz), 7.77 (2H, d, J=7.4 Hz), 7.90 (2H, d, J=9.2 Hz).

EIMS (M/Z): 579 (M⁺).

(b) Step (c) of Example 87 was repeated, except that the compound prepared just above in step (a) was used as the starting compound. Thus, the title compound was prepared.

¹H-NMR (CDCl₃) δ: 0.69–0.77 (2H, m), 1.04–1.28 (4H, m), 1.33–1.40 (2H, m), 1.49–1.58 (2H, m), 1.74–1.77 (4H, m), 2.15–2.19 (2H, m), 2.43–2.47 (6H, m), 3.16 (4H, t, J=4.9 Hz), 3.65–3.73 (2H, m), 3.97 (3H, m), 5.09 (1H, dd, J=1.4, 10.4 Hz), 5.15 (1H, d, J=17.0 Hz), 5.36 (1H, t, J=6.4 Hz), 5.88 (1H, brs), 6.84 (2H, d, J=8.8 Hz), 7.29 (2H, d, J=8.8 Hz), 7.37 (2H, dt, J=1.1, 7.5 Hz), 7.45 (2H, dt, J=1.1, 7.5 Hz), 7.56 (2H, d, J=7.5 Hz), 7.78 (2H, d, J=7.5 Hz).

TSIMS (M/Z): 673 (M+H)⁺.

EXAMPLE 90

N-Allyl-N-cyclohexyl-3-fluoro-4-[4-[4-[9-(2,2,2-trifluoroethylcarbamoyl)-9H-fluoren-9-yl]butyl]piperazin-1-yl]benzamide (a) Step (c) of Example 75 was repeated, except that the compound prepared in step (a) of Example 81 was used and 4-(t-butoxycarbonyl)piperazine was used instead of 4-(3,3-diphenyl-1-propyl)piperazine. Thus, ethyl 3-fluoro-[4-[4-(t-butoxycarbonyl)piperazin-1-yl]butyl]benzoate was prepared.

¹H-NMR (CDCl₃) δ: 1.39 (3H, t, J=7.2 Hz), 1.49 (9H, s), 3.14 (4H, m), 3.60 (4H, m), 4.35 (2H, q, J=7.2 Hz), 6.90 (1H, t, J=8.5 Hz), 7.69 (1H, dd, J=2.0, 13.5 Hz), 7.77 (1H, dd, J=2.0, 8.5 Hz).

TSIMS (M/Z): 353 (M+H)⁺.

(b) Steps (c) and (d) of Example 1 were repeated, except that the compound prepared just above in step (a) was used as the starting compound. Thus, N-allyl-N-cyclohexyl-3-fluoro-4-[4-(t-butoxycarbonyl)piperazin-1-yl]benzamide was prepared.

¹H-NMR (CDCl₃) δ: 0.86–1.74 (10H, m), 1.47 (9H, s), 3.04 (4H, m), 3.59 (4H, m), 3.94 (2H, brs), 5.12 (2H, m), 5.85 (1H, m), 6.89 (1H, t, J=8.5 Hz), 7.05 (2H, m).

TSIMS (M/Z): 446 (M+H)⁺.

(c) The compound (0.22 g) prepared just above in step (b) was dissolved in dichloromethane (5 ml), and trifluoroacetic acid (1 ml) was added to the solution. The mixture was stirred at room temperature for one hr. A saturated aqueous sodium hydrogencarbonate solution was added to the reaction solution, and the mixture was extracted with dichloromethane. The organic layer was dried over anhydrous magnesium sulfate. The solvent was removed by distillation under the reduced pressure. Step (b) of Example 87 was repeated, except that the compound thus obtained was used. Thus, the title compound was prepared.

¹H-NMR (CDCl₃) δ: 0.85 (2H, m), 1.30 (2H, m), 1.40–1.90 (10H, m), 2.48 (2H, m), 2.98 (4H, m), 3.64 (4H, m), 3.70 (2H, m), 3.91 (4H, m), 5.16 (2H, m), 5.37 (1H, t, J=7.0 Hz), 5.85 (1H, m), 6.87 (1H, t, J=8.2 Hz), 7.10 (1H, d, J=3.4 Hz), 7.26–7.38 (10H, m).

EXAMPLE 91

N-Allyl-N-cyclohexyl-4-[4-[4,4-diphenyl-4-(2,2,2-trifluoroethylcarbamoyl)butyl]piperazin-1-yl]benzamide (a) 4,4-Diphenyl-4-(2,2,2-trifluoroethylcarbamoyl)butyl bromide was synthesized using diphenylacetic acid as a starting compound according to the method described in U.S. Pat. No. 5,712,279.

¹H-NMR (CDCl₃) δ: 1.28–1.36 (2H, m), 1.85 (2H, dt, J=7.3 Hz), 2.39–2.43 (2H, m), 3.32 (2H, t, J=7.1 Hz), 3.86 (2H, dq, J=9.0 Hz), 5.67 (1H, brs), 7.24–7.38 (10H, m).

TSIMS (M/Z): 428 (M+H)⁺.

(b) Step (b) of Example 1 was repeated, except that the compound prepared just above in step (a) was used instead of 3,3-diphenylpropyl bromide. Thus, ethyl 4-[4-(4,4-diphenyl-4-(2,2,2-trifluoroethylcarbamoyl)butyl]piperazin-1-yl]benzoate was prepared.

¹H-NMR (CDCl₃) δ: 1.18–1.28 (2H, m), 1.36 (3H, d, J=7.1 Hz), 1.48–1.55 (2H, m), 2.30–2.34 (2H, m), 2.41–2.46 (2H, m), 2.52 (4H, t, J=5.0 Hz), 3.29 (4H, t, J=5.0 Hz), 3.86 (2H, dq, J=2.5, 9.0 Hz), 4.32 (2H, q, J=7.1 Hz), 5.72 (1H, t, J=6.3 Hz), 8.85 (2H, d, J=8.8 Hz), 7.26–7.36 (10H, m), 7.91 (2H, d, J=8.8 Hz).

TSIMS (M/Z): 582 (M+H)⁺.

(c) Steps (c) and (d) of Example 1 were repeated, except that the compound prepared just above in step (b) was used and N-allylcyclohexylamine was used instead of N-methylbenzylamine. Thus, the title compound was prepared.

¹H-NMR (CDCl₃) δ: 1.04–1.25 (6H, m), 1.49–1.57 (4H, m), 1.74–1.77 (4H, m), 2.32–2.36 (2H, m), 2.41–2.46 (2H, m), 2.56 (4H, t, J=4.8 Hz), 3.23 (4H, t, J=4.8Hz), 3.82–3.90 (3H, m), 3.97 (2H, brs), 5.10 (1H, dd, J=1.5, 10.3 Hz), 5.15 (1H, d, J=17.8 Hz), 5.74 (1H, t, J=6.3 Hz), 5.87 (1H, brs), 6.86 (2H, d, J=8.8 Hz), 7.26–7.36 (12H, m).

FABMS (M/Z): 675 (M+H)⁺.

EXAMPLE 92

2-Cyclohexyl-6-[4-[4-[9-(2,2,2-trifluoroethylcarbamoyl)-9H-fluoren-9-yl]butyl]piperazin-1-yl]-2,3-dihydro-1H-isoindol-1-one (a) 2-Cyclohexyl-6-(piperazin-1-yl)-2,3-dihydro-1H-isoindol-1-one was synthesized according to the method described in WO 9854135.

¹H-NMR (CDCl₃) δ: 1.13–1.26 (1H, m), 1.43–1.54 (4H, m), 1.69–1.76 (1H, m), 1.80–1.90 (4H, m), 3.04–3.08 (4H, m), 3.19–3.22 (4H, m), 4.25 (1H, m), 4.27 (2H, s), 7.11 (1H, dd, J=2.4, 8.4 Hz), 7.31 (1H, d, J=8.4 Hz), 7.36 (1H, d, J=2.4 Hz).

EIMS (M/Z): 299 (M⁺).

(b) The compound (1.50 g) prepared just above in step (a) was dissolved in DMF, and potassium carbonate (1.38 g) and the compound (2.34 g) prepared in step (a) of Example 87 were added to the solution. The mixture was stirred at 50° C. for 4 hr. The reaction solution was concentrated, and 0.1N aqueous citric acid solution was then added to the concentrate. The mixture was extracted with chloroform, followed by washing with saturated brine. The extract was dried over anhydrous MgSO₄, and the solvent was then removed by distillation under the reduced pressure. The residue was purified by column chromatography on silica gel (CHCl₃:MeOH=30:1) to give the title compound (2.12 g).

¹H-NMR (CDCl₃) δ: 0.70–0.76 (2H, m), 1.07–1.23 (1H, m), 1.35–1.43 (2H, m), 1.45–1.48 (4H, m), 1.70–1.73 (1H, m), 1.83–1.85 (4H, m), 2.16–2.19 (2H, m), 2.44–2.48 (6H, m), 3.16 (4H, t, J=5.0 Hz), 3.69 (2H, dq, J=9.0, 2.5 Hz), 4.22–4.23 (1H, m), 4.25 (2H, s), 5.36 (1H, t, 6.5 Hz), 7.07 (1H, dd, J=8.3, 2.4 Hz), 7.28 (1H, d, J=8.3 Hz), 7.3i (1H, d, J=2.4 Hz), 7.37 (2H, dt, J=7.7, 1.2 Hz), 7.45 (2H, dt, J=7.7, 1.2 Hz), 7.56 (2H, dt, J=7.3, 0.9 Hz), 7.77 (2H, dt, J=7.3, 0.9 Hz).

FABMS (M/Z): 645 (M+H)⁺.

EXAMPLE 93

2-Cyclohexyl-6-[4-[3-[9-(2,2,2-trifluoroethylcarbamoyl)-9H-fluoren-9-yl]propyl]piperazin-1-yl]-2,3-dihydro-1H-isoindol-1-one (a) 3-[9-(2,2,2-Trifluoroethylcarbamoyl)-9H-fluoren-9-yl]propyl bromide was synthesized using 1,3-dibromopropane as a starting compound according to the method described in U.S. Pat. No. 5,712,279.

¹H-NMR (CDCl₃) δ: 1.18–1.26 (2H, m), 2.57–2.61 (2H, m), 3.17 (2H, t, J=6.7 Hz), 3.69 (2H, dq, J=9.0, 2.4 Hz), 5.31 (1H, brs), 7.39 (2H, dt, J=7.4, 1.2 Hz), 7.46 (2H, dt, J=7.4, 1.2 Hz), 7.55 (2H, d, J=7.4 Hz), 7.78 (2H, d, J=7.4 Hz).

TSIMS (M/Z): 412 (M+H)⁺.

(b) Step (b) of Example 92 was repeated, except that the compound prepared just above in step (a) was used as the starting compound. Thus, the title compound was prepared.

¹H-NMR (CDCl₃) δ: 0.86–0.94 (2H, m), 1.13–1.17 (1H, m), 1.40–1.50 (4H, m), 1.71 (1H, d, J=12.2 Hz), 1.83–1.85 (4H, m), 2.21 (2H, t, J=7.5 Hz), 2.36 (4H, t, J=4.8 Hz), 2.46–2.51 (2H, m), 3.13 (4H, t, J=4.8 Hz), 3.69 (2H, dq, J=9.0, 2.4 Hz), 4.22–4.24 (1H, m), 4.42 (2H, s), 5.36 (1H, t, J=6.5 Hz), 7.04 (1H, dd, J=8.4, 2.3 Hz), 7.29 (2H, d, J=2.7 Hz), 7.38 (2H, t, J=7.7 Hz), 7.45 (2H, t, J=7.7 Hz), 7.56 (2H, d, J=7.5 Hz), 7.78 (2H, d, J=7.5 Hz).

TSIMS (M/Z): 631 (M+H)⁺.

EXAMPLE 94

2-Cyclohexyl-6-[4-[5-[9-(2,2,2-trifluoroethylcarbamoyl)-9H-fluoren-9-yl]pentyl]piperazin-1-yl]-2,3-dihydro-1H-isoindol-1-one (a) 5-[9-(2,2,2-Trifluoroethylcarbamoyl)-9H-fluoren-9-yl]pentyl bromide was synthesized using 1,5-dibromopentane as a starting compound according to the method described in U.S. Pat. No. 5,712,279.

¹H-NMR (CDCl₃) δ: 0.68–0.76 (2H, m), 1.27 (2H, qu, J=7.6 Hz), 1.63–1.70 (2H, m), 2.40–2.44 (2H, m), 3.22 (2H, t, J=7.0 Hz), 3.69 (2H, dq, J=9.0, 2.5 Hz), 5.35 (1H, brs), 7.38 (2H, dt, J=7.4, 1.2 Hz), 7.45 (2H, dt, J=7.4, 1.2 Hz), 7.55 (2H, d, J=7.4 Hz), 7.75 (2H, d, J=7.4 Hz).

APCIMS (M/Z): 440 (M+H)⁺.

(b) Step (b) of Example 92 was repeated, except that the compound prepared just above in step (a) was used as the starting compound. Thus, the title compound was prepared.

¹H-NMR (CDCl₃) δ: 0.70–0.78 (2H, m), 1.14–1.21 (3H, m), 1.30–1.38 (2H, m), 1.40–1.51 (4H, m), 1.72 (1H, d, J=12.4 Hz), 1.85 (4H, brs), 2.22 (2H, t, J=7.6 Hz), 2.40–2.44 (2H, m), 2.51 (4H, brs), 3.19 (4H, t, J=4.9 Hz), 3.69 (2H, dq, J=8.9, 2.3 Hz), 4.22–4.23 (1H, m), 4.25 (2H, s), 5.39 (1H, t, J=6.5 Hz), 7.08 (1H, dd, J=8.3, 2.3 Hz), 7.29 (1H, d, J=8.3 Hz), 7.32 (1H, d, J=2.3 Hz), 7.38 (2H, t, J=7.3 Hz), 7.45 (2H, t, J=7.3 Hz), 7.56 (2H, d, J=7.6 Hz), 7.74 (2H, d, J=7.6 Hz).

ESIMS (M/Z): 659 (M+H)⁺.

EXAMPLE 95

2-Cyclohexyl-6-[4-[4,4-diphenyl-4-(2,2,2-trifluoroethylcarbamoyl)butyl]piperazin-1-yl]-2,3-dihydro-1H-isoindol-1-one (a) 4,4-Diphenyl-4-(2,2,2-trifluoroethylcarbamoyl)butyl bromide was synthesized using diphenylacetic acid as a starting compound according to the method described in U.S. Pat. No. 5,712,279.

¹H-NMR (CDCl₃) δ: 1.28–1.36 (2H, m), 1.85 (2H, dt, J=7.3 Hz), 2.39–2.43 (2H, m), 3.32 (2H, t, J=7.1 Hz), 3.86 (2H, dq, J=9.0 Hz), 5.67 (1H, brs), 7.24–7.38 (10H, m).

TSIMS (M/Z): 428 (M+H)⁺.

(b) Step (b) of Example 92 was repeated, except that the compound prepared just above in step (a) was used as the starting compound. Thus, the title compound was prepared.

¹H-NMR (CDCl₃) δ: 1.14–1.26 (3H, m), 1.44–1.57 (6H, m), 1.70–1.74 (1H, m), 1.83–1.86 (4H, m), 2.33 (2H, t, J=7.6 Hz), 2.42–2.46 (2H, m), 2.56 (4H, brs), 3.22 (4H, t, J=4.9 Hz), 3.87 (2H, dq, J=9.1, 2.4 Hz), 4.23–4.24 (1H, m), 4.26 (2H, s), 5.74 (1H, t, J=6.5 Hz), 7.09 (1H, dd, J=8.3, 2.4 Hz), 7.26–7.37 (12H, m).

TSIMS (M/Z): 647 (M+H)⁺.

EXAMPLE 96

2-Cyclohexyl-6-[4-[4-[9-(2,2,2-trifluoroethylcarbamoyl)-9H-xanthen-9-yl]butyl]piperazin-1-yl]-2,3-dihydro-1H-isoindol-1-one (a) 4-[9-(2,2,2-Trifluoroethylcarbamoyl)-9H-xanthen-9-yl]butyl bromide was synthesized using xanthene-9-carboxylic acid as a starting compound according to the method described in U.S. Pat. No. 5,712,279.

¹H-NMR (CDCl₃) δ: 0.90–0.98 (2H, m), 1.65–1.72 (2H, m), 2.25–2.30 (2H, m), 3.19 (2H, t, J=7.0 Hz), 3.77–3.85 (2H, m), 5.43 (1H, t, J=6.1 Hz), 7.09–7.16 (4H, m), 7.23–7.25 (2H, m), 7.29–7.33 (2H, m).

FABMS (M/Z): 442 (M+H)⁺.

(b) Step (b) of Example 92 was repeated, except that the compound prepared just above in step (a) was used as the starting compound. Thus, the title compound was prepared.

¹H-NMR (CDCl₃) δ: 0.82–0.88 (2H, m), 1.16–1.17 (1H, m), 1.34–1.40 (2H, m), 1.43–1.48 (4H, m), 1.70–1.73 (1H, m), 1.84–1.85 (4H, m), 2.16–2.19 (2H, m), 2.28–2.32 (2H, m), 2.45–2.46 (4H, m), 3.13–3.16 (4H, m), 3.81 (2H, dq, J=8.9, 2.3 Hz), 4.22–4.23 (1H, m), 4.25 (2H, 9), 5.47 (1H, t, J=6.6 Hz), 7.05–7.12 (5H, m), 7.24–7.32 (6H, m).

FABMS (M/Z): 661 (M+H)$^+$.

EXAMPLE 97

2-Benzyl-7-[4-[4-[9-(2,2,2-trifluoroethylcarbamoyl)-9H-fluoren-9-yl]butyl]piperazin-1-yl]-3,4-dihydro-2H-isoquinolin-1-one (a) 2-Benzyl-7-(4-t-butoxycarbonyl-piperazin-1-yl)-3,4-dihydro-2H-isoquinolin-1-one was synthesized according to the method described in WO 9854135.

$^1$H-NMR (CDCl$_3$) δ: 1.49 (9H, s), 2.86 (2H, t, J=6.7 Hz), 3.18 (4H, t, J=5.0 Hz), 3.47 (2H, t, J=6.7 Hz), 3.59 (4H, t, J=5.0 Hz), 4.80 (1H, s), 7.01 (1H, dd, J=8.3, 2.2 Hz), 7.08 (1H, d, J=8.3 Hz), 7.32 (5H, m), 7.72 (1H, d, J=2.2 Hz).

ESIMS (M/Z): 422 (M+H)$^+$.

(b) The compound (2.25 g) prepared just above in step (a) was dissolved in dichloromethane (20 ml), and trifluoroacetic acid (10 ml) was added to the solution. The mixture was stirred at room temperature overnight. A saturated aqueous NaHCO$_3$ solution was added to the reaction solution, and the mixture was extracted with dichloromethane. The extract was dried over anhydrous MgSO$_4$, and the solvent was then removed by distillation under the reduced pressure. The residue was dissolved in DMF (20 ml). Potassium carbonate (1.33 g) and the compound (2.26 g) prepared in step (a) of Example 87 were then added to the solution, and the mixture was stirred at 50° C. for 3 hr. Water was added to the reaction solution, and the mixture was extracted with dichloromethane. The extract was dried over anhydrous MgSO$_4$, and the solvent was then removed by distillation under the reduced pressure. The residue was purified by column chromatography on silica gel (hexane:ethyl acetate=1:1) to give the title compound (2.40 g).

$^1$H-NMR (CDCl$_3$) δ: 0.70–0.75 (2H, m), 1.35–1.39 (2H, m), 2.18 (2H, t, J=7.6 Hz), 2.44–2.48 (6H, m), 2.83 (2H, t, J=6.7 Hz), 3.16 (4H, t, J=4.5 Hz), 3.44 (2H, t, J=6.7 Hz), 3.65–3.74 (2H, m), 4.78 (2H, s), 5.36 (1H, t, J=6.4 Hz), 6.95 (1H, dd, J=8.4, 2.7 Hz), 7.03 (1H, d, J=8.4 Hz), 7.26–7.29 (5H, m), 7.36 (2H, dt, J=7.5, 1.2 Hz), 7.44 (2H, dt, J=7.5, 1.2 Hz), 7.55 (2H, d, J=7.5 Hz), 7.62 (1H, d, J=2.7 Hz), 7.76 (2H, d, J=7.5 Hz).

TSIMS (M/Z): 667 (M+H)$^+$.

EXAMPLE 98

2-Benzyl-7-[4-[4-[9-(2,2,2-trifluoroethylcarbamoyl)-9H-xanthen-9-yl]butyl]piperazin-1-yl]-3,4-dihydro-2H-isoquinolin-1-one Step (b) of Example 97 was repeated, except that the compound prepared in step (a) of Example 97 and the compound prepared in step (a) of Example 96 were used. Thus, the title compound was prepared.

$^1$H-NMR (CDCl$_3$) δ: 0.79–0.85 (2H, m), 1.37–1.39 (2H, m), 2.16–2.17 (2H, m), 2.28–2.32 (2H, m), 2.45 (4H, brs), 2.83 (2H, t, J=6.6 Hz), 3.15 (4H, brs), 3.44 (2H, t, J=6.6 Hz), 3.81 (2H, dq, J=8.9, 2.4 Hz), 4.78 (2H, s), 5.46 (1H, t, J=6.5 Hz), 6.96 (1H, dd, J=8.4, 2.7 Hz), 7.03 (1H, d, J=8.4 Hz), 7.08–7.12 (4H, m), 7.24–7.32 (9H, m), 7.67 (1H, d, J=2.4 Hz).

TSIMS (M/Z): 683 (M+H)$^+$.

EXAMPLE 99

2-(Tetrahydropyran-2-yl)methyl-7-[4-[4-[9-(2,2,2-trifluoroethylcarbamoyl)-9H-fluoren-9-yl]butyl]piperazin-1-yl]-3,4-dihydro-2H-isoquinolin-1-one (a) Step (a) of Example 97 was repeated, except that 2-(tetrahydropyran-2-yl)methyl bromide was used as the starting compound. Thus, 2-(tetrahydropyran-2-yl)methyl-7-(4-t-butoxycarbonyl-piperazin-1-yl)-3,4-dihydro-2H-isoquinolin-1-one was synthesized.

$^1$H-NMR (CDCl$_3$) δ: 1.26–1.35 (1H, m), 1.45–1.64 (12H, m), 1.68 (1H, d, J=12.9 Hz), 1.83–1.84 (1H, m), 2.88 (2H, t, J=6.6 Hz), 3.15 (4H, t, J=5.1 Hz), 3.29 (1H, dd, J=13.9, 7.6 Hz), 3.38 (1H, dt, J=11.3, 2.7 Hz), 3.56–3.66 (6H, m), 3.69–3.75 (1H, m), 3.85 (1H, dd, J=13.9, 3.5 Hz), 3.93–3.96 (1H, m), 6.99 (1H, dd, J=8.3, 2.7 Hz), 7.08 (1H, d, J=8.3 Hz), 7.64 (1H, d, J=2.7 Hz).

TSIMS (M/Z): 430(M+H)$^+$.

(b) Step (b) of Example 97 was repeated, except that the compound prepared just above in step (a) and the compound prepared in step (a) of Example 87 were used as the starting compounds. Thus, the title compound was prepared.

$^1$H-NMR (CDCl$_3$) δ: 0.72–0.74 (2H, m), 1.22–1.34 (3H, m), 1.36–1.50 (2H, m), 1.65 (1H, d, J=12.7 Hz), 1.79–1.86 (1H, m), 2.17 (2H, t, J=7.7 Hz), 2.43–2.47 (6H, m), 2.86 (2H, t, J=6.6 Hz), 3.14 (4H, t, J=4.8 Hz), 3.27 (1H, dd, J=13.7, 7.4 Hz), 3.37 (1H, dt, J=11.4, 2.6 Hz), 3.57–3.73 (5H, m), 3.85 (1H, dd, J=13.7, 3.4 Hz), 3.94 (1H, d, J=11.4 Hz), 5.36 (1H, t, J=6.5 Hz), 6.94 (1H, dd, J=8.4, 2.8 Hz), 7.04 (1H, d, J=7.3 Hz), 7.37 (2H, dt, J=7.5, 1.2 Hz), 7.45 (2H, dt, J=7.5, 1.2 Hz), 7.55 (2H, d, J=7.3 Hz), 7.60 (1H, d, J=2.7 Hz), 7.77 (2H, d, J=7.3 Hz).

TSIMS (M/Z): 675 (M+H)$^+$.

EXAMPLE 100

2-(Tetrahydropyran-2-yl)methyl-7-[4-[3-[9-(2,2,2-trifluoroethylcarbamoyl)-9H-fluoren-9-yl]propyl]piperazin-1-yl]-3,4-dihydro-2H-isoquinolin-1-one Step (b) of Example 97 was repeated, except that the compound prepared in step (a) of Example 99 and the compound prepared in step (a) of Example 93 were used as the starting compounds. Thus, the title compound was prepared.

$^1$H-NMR (CDCl$_3$) δ: 0.88–0.91 (2H, m), 1.25–1.31 (1H, m), 1.47–1.52 (3H, m), 1.65–1.68 (1H, m), 1.79–1.86 (1H, m), 2.21 (2H, brs), 2.35 (4H, brs), 2.46–2.50 (2H, m), 2.85 (2H, t, J=6.6 Hz), 3.11 (4H, brs), 3.26 (1H, dd, J=13.8, 7.5 Hz), 3.37 (1H, dt, J=11.3, 2.8 Hz), 3.56–3.62 (2H, m), 3.65–3.73 (3H, m), 3.84 (1H, dd, J=13.8, 3.6 Hz), 3.93 (1H, d, J=11.3 Hz), 5.36 (1H, t, J=6.5 Hz), 6.92 (1H, dd, J=8.3, 2.7 Hz), 7.03 (1H, d, J=8.3 Hz), 7.38 (2H, dt, J=7.5, 1.2 Hz), 7.45 (2H, dt, J=7.5, 1.2 Hz), 7.55–7.57 (3H, m), 7.78 (2H, d, J=7.1 Hz).

TSIMS (M/Z): 661 (M+H)$^+$.

EXAMPLE 101

2-(Tetrahydropyran-2-yl)methyl-7-[4-[4-[9-(2,2,2-trifluoroethylcarbamoyl)-9H-xanthen-9-yl]butyl]piperazin-1-yl]-3,4-dihydro-2H-isoquinolin-1-one Step (b) of Example 97 was repeated, except that the compound prepared in step (a) of Example 99 and the compound prepared in step (a) of Example 96 were used as the starting compounds. Thus, the title compound was prepared.

$^1$H-NMR (CDCl$_3$) δ: 0.81–0.85 (2H, m), 1.31–1.38 (3H, m), 1.47–1.52 (3H, m), 1.67 (1H, d, J=12.9 Hz), 1.79–1.86 (1H, m), 2.17 (2H, t, J=7.1 Hz), 2.27–2.32 (2H, m), 2.44 (4H, brs), 2.85 (2H, t, J=6.6 Hz), 3.13 (4H, brs), 3.27 (1H, dd, J=13.7, 7.4 Hz), 3.38 (1H, dt, J=11.4, 2.5 Hz), 3.55–3.62 (2H, m), 3.69–3.70 (1H, m), 3.78–3.86 (3H, m), 3.94 (1H, d, J=11.4 Hz), 5.44 (1H, t, J=6.5 Hz), 6.94 (1H, dd, J=8.3, 2.7 Hz), 7.04 (1H, d, J=8.3 Hz), 7.08–7.12 (4H, m), 7.24–7.32 (4H, m), 7.59 (1H, d, J=2.7 Hz).

FABMS (M/Z): 691 (M+H)$^+$.

EXAMPLE 102

7-[4-[4-[9-[Allyl-(2,2,2-trifluoroethyl)carbamoyl]-9H-fluoren-9-yl]butyl]piperazin-1-yl]-2-benzyl-3,4-dihydro-2H-isoquinolin-1-one The compound (67 mg) prepared in Example 97 was dissolved in toluene (5 ml), and sodium hydroxide (12 mg), potassium carbonate (28 mg), tetrabutylammonium hydrogensulfate (8 mg), and allyl bromide (0.010 ml) were added to the solution, and the mixture was stirred at 60° C. overnight. Water was added to the reaction solution, and the mixture was extracted with ethyl acetate. The extract was dried over anhydrous MgSO$_4$, and the solvent was then removed by distillation under the reduced pressure. The residue was purified by preparative TLC (hexane:ethyl acetate=1:1) to give the title compound (17 mg).

$^1$H-NMR (CDCl$_3$) δ: 0.49 (2H, m), 1.27 (2H, m), 2.12 (2H, m), 2.32 (2H, m), 2.43 (4H, m), 2.83 (2H, t, J=6.6 Hz), 2.88 (2H, brs), 3.15 (4H, m), 3.44 (2H, t, J=6.6 Hz), 3.95 (2H, m), 4.57–4.81 (3H, m), 4.78 (2H, s), 6.96 (1H, dd, J=2.4, 8.3 Hz), 7.03 (1H, d, J=8.3 Hz), 7.27–7.44 (11H, m), 7.67 (1H, d, J=2.4 Hz), 7.79 (2H, dd, J=0.8, 7.4 Hz).

TSIMS (M/Z): 707 (M+H)$^+$.

EXAMPLE 103

7-Benzyl-2-[4-(3,3-diphenyl-1-propyl)piperazin-1-yl]-5,6-dihydro-7H-1,7-naphthyridin-8-one (a) 2,3-Lutidine (1.0 g, 9.33 mmol) was refluxed in a 1,4-dioxane (20 ml) solution in the presence of selenium dioxide (1.24 g, 11.2 mmol) in an argon atmosphere for one hr. The temperature of the reaction solution was then returned to room temperature, and the reaction solution was filtered. The solvent was removed from the filtrate by distillation under the reduced pressure. The residue was purified by column chromatography on silica gel (hexane:ethyl acetate=5:2) to give 422 mg (37.3%) of 3-methylpyridine-2-carbaldehyde as a colorless liquid.

$^1$H-NMR (CDCl$_3$) δ: 2.44 (3H, s), 7.26 (1H, dd, J=4.9, 7.6 Hz), 7.66 (1H, d, J=7.6 Hz), 8.26 (1H, d, J=4.9 Hz).

TSIMS (M/Z): 122 (M+H)$^+$.

(b) Silver(I) oxide (650 mg, 2.81 mmol) was added to the compound (170 mg, 1.4 mmol) prepared just above in step (a) in water (5 ml) as a solvent at 0° C., and the mixture was stirred for 30 min. Next, caustic soda (56 mg, 1.4 mmol) was slowly added thereto, and the mixture was stirred for 5 min. The reaction solution was filtered, and the residue was washed with 5 N hydrochloric acid. The filtrates were combined, and the combined filtrates were neutralized, followed by the removal of water as the solvent by distillation under the reduced pressure. The residue was washed with ethanol, and ethanol was removed by distillation under the reduced pressure. Thus, 142 mg (73.5%) of 3-methylpyridine-2-carboxylic acid was obtained as the residual white crystal.

$^1$H-NMR (CDCl$_3$) δ: 2.67 (3H, s), 7.39 (1H, dd, J=4.7, 7.8 Hz), 7.63 (1H, d, J=7.8 Hz), 8.66 (1H, d, J=4.7 Hz), 10.20 (1H, s).

TSIMS (M/Z): 138 (M+H)$^+$.

(c) The compound (1.2 g) prepared just above in step (b) was refluxed in the presence of 1 N hydrochloric acid-ethanol for 2 hr. The solution was removed by distillation under the reduced pressure. A saturated sodium hydrogencarbonate solution and ethyl acetate were added to the residue to perform extraction. The solvent was removed from the organic layer by distillation. Thus, 1.1 g (76.1%) of ethyl 3-methylpyridine-2-carboxylate as a colorless liquid was obtained.

$^1$H-NMR (CDCl$_3$) δ: 1.14 (3H, t, J=7.2 Hz), 2.57 (3H, s), 4.39 (2H, q, J=7.2 Hz), 7.69 (1H, d, J=5.1 Hz), 8.55 (1H, d, J=5.1 Hz), 8.57 (1H, s).

TSIMS (M/Z): 166 (M+H)$^+$.

(d) N-Bromosuccinimide (215 mg) and 2,2'-azobis(isobutyronitrile) (198 mg) were added to a carbon tetrachloride solution (4 ml) of the compound (200 mg) prepared just above in step (c), and the mixture was refluxed for 3 hr. The reaction mixture was cooled to room temperature, and the cooled reaction mixture was filtered. The filtrate was then removed by distillation under the reduced pressure in an ice bath. The residue was purified by column chromatography on silica gel (hexane:ethyl acetate=1:1) to give ethyl 3-bromomethylpyridine-2-carboxylate (183 mg) as a red solid.

$^1$H-NMR (CDCl$_3$) δ: 1.45 (3H, t, J=7.2 Hz), 4.90 (2H, s), 7.76 (1H, d, J=5.1 Hz), 8.68 (1H, d, J=5.1 Hz), 8.74 (1H, s).

TSIMS (M/Z): 244 (M+H)$^+$.

(e) Sodium prussiate (36.7 mg) was slowly added to a dimethyl sulfoxide solution (4 ml) of the compound prepared just above in step (d) (183 mg) at room temperature, and the mixture was stirred at room temperature for 2 hr. A saturated aqueous sodium hydrogencarbonate solution (20 ml) and ethyl acetate (50 ml) were added to the reaction solution, followed by separation. The organic layer was washed with a saturated aqueous sodium chloride solution and was dried over anhydrous magnesium sulfate. The solvent was then removed by distillation under the reduced pressure. The residue was purified by column chromatography on silica gel (hexane:ethyl acetate=2:1) to give ethyl 3-cyanomethylpyridine-2-carboxylate (92.7 mg) as a white crystal.

$^1$H-NMR (CDCl$_3$) δ: 1.47 (3H, t, J=7.0 Hz), 4.28 (3H, s), 4.50 (2H, q, J=7.0 Hz), 7.55 (1H, dd, J=4.6, 8.0 Hz), 8.01 (1H, d, J=8.0 Hz), 8.75 (1H, d, J=4.6 Hz).

TSIMS (M/Z): 190 (M+H)$^+$.

(f) Raney nickel (19 mg) was added to a solution of the compound (190 mg, 1.0 mmol), prepared just above in step (e), in EtOH (8 ml), and the mixture was heated in a hydrogen atmosphere at 50° C. for 2 hr. The reaction solution was filtered through Celite, followed by purification by column chromatography on silica gel (hexane:ethyl acetate=1:1) to give 110 mg (74.3%) of 5,6-dihydro-7H-1,7-naphthyridin-8-one as a colorless solid.

$^1$H-NMR (CDCl$_3$) δ: 3.07 (2H, t, J=6.6 Hz), 3.63 (2H, dt, J=2.9, 6.6 Hz), 7.38 (1H, dd, J=4.6, 7.7 Hz), 7.61 (1H, d, J=7.7 Hz), 7.78 (1H, brs), 8.71 (1H, d, J=4.6 Hz).

TSIMS (M/Z): 149 (M+H)$^+$.

(g) Potassium carbonate (149 mg), sodium hydroxide (75.6 mg), tetrabutylammonium hydrogen sulfate (18.3 mg), and benzyl bromide (134 mg) were added to a toluene solution (2 ml) of the compound prepared just above in step (f) (80 mg, 0.54 mmol), and the mixture was stirred at 80° C. overnight. The reaction solution was cooled to room temperature. A saturated aqueous ammonium chloride solution (5 ml) was then added to the cooled reaction solution, followed by separation with ethyl acetate and water. The ethyl acetate layer was washed with an aqueous sodium chloride solution, was dried over magnesium sulfate, and was then concentrated under the reduced pressure. The residue was purified by column chromatography on silica gel (ethyl acetate:hexane=1:1) to give 62 mg of 7-benzyl-5,6-dihydro-7H-1,7-naphthyridin-8-one as a white crystal.

$^1$H-NMR (CDCl$_3$) δ: 2.97 (2H, t, J=6.7 Hz), 3.50 (2H, t, J=6.7 Hz), 4.84 (2H, s), 7.28–7.38 (6H, m), 7.55 (1H, d, J=7.5 Hz), 8.71 (1H, d, J=4.4 Hz).

TSIMS (M/Z): 239 (M+H)$^+$.

(h) The compound prepared just above in step (g) (73 mg) was slowly added to a chloroform solution (3 ml) of m-chloroperbenzoic acid (52.9 g) at 0° C. The temperature of the mixture was slowly raised to room temperature, and the mixture was then stirred for 3 hr. A saturated aqueous sodium hydrogencarbonate solution (10 ml) was added to the reaction solution, followed by separation with chloroform and water. The chloroform layer was washed with an aqueous sodium chloride solution, was dried over anhydrous sodium sulfate, and was then concentrated under the reduced pressure. The residue was purified by column chromatography on silica gel (chloroform:methanol=40:1) to give 7-benzyl-1-oxo-5,6-dihydro-7H-1,7-naphthyridin-8-one (33 mg) as a white crystal.

$^1$H-NMR (CDCl$_3$) δ: 2.85 (2H, t, J=6.1 Hz), 3.44 (2H, t, J=6.1 Hz), 4.78 (2H, s), 7.00 (1H, d, J=7.6 Hz), 7.20 (1H, t, J=7.2 Hz), 7.27–7.38 (5H, m), 8.20 (1H, d, J=7.6 Hz).

TSIMS (M/Z): 255 (M+H)$^+$.

(i) A phosphorus oxychloride (5 ml) solution of the compound (135 mg) prepared just above in step (h) was stirred at 50° C. for 7 hr. The reaction solution was cooled to 0° C. The cooled reaction solution was neutralized by the addition of a saturated aqueous sodium hydrogencarbonate solution, and ethyl acetate was further added thereto, followed by separation. The ethyl acetate layer was washed with an aqueous sodium chloride solution, was dried over magnesium sulfate, and was then concentrated under the reduced pressure. The residue was purified by column chromatography on silica gel (chloroform:methanol=10:1) to give 7-benzyl-2-chloro-5,6-dihydro-7H-1,7-naphthyridin-8-one (72 mg) as a white crystal.

$^1$H-NMR (CDCl$_3$) δ: 2.96 (2H, t, J=6.6 Hz), 3.51 (2H, t, J=6.6 Hz), 4.83 (2H, s), 7.28–7.39 (10H, m), 7.51 (1H, d, J=8.1 Hz).

TSIMS (M/Z): 273 (M+H)$^+$.

(j) The compound (36 mg) prepared just above in step (i) was stirred together with 3,3-diphenyl-1-propylpiperazine (40 mg) at 50° C. for 4 hr and then at 120° C. for 3 hr. The reaction mixture was purified by column chromatography on silica gel (chloroform:methanol=30:1) to give the title compound (22 mg) as a white crystal.

$^1$H-NMR (CDCl$_3$) δ: 2.35 (4H, m), 2.60 (4H, brs), 2.79 (2H, t, J=6.8 Hz), 3.45 (2H, t, J=6.8 Hz), 3.68 (4H, brs), 4.00 (1H, t, J=7.5 Hz), 4.79 (2H, s), 6.70 (1H, d, J=6.8 Hz), 7.18–7.34 (16H, m).

TSIMS (M/Z): 517 (M+H)$^+$.

EXAMPLE 104

2-Benzyl-7-[4-(3,3-diphenyl-1-propyl)piperazin-1-yl]-3,4-dihydro-2H-2,6-naphthyridin-1-one (a) Selenium dioxide (36 g) was added to a solution of 3,4-lutidine (21.4 g) in diphenyl ether (200 ml), and the mixture was heated at 155° C. for 4 hr, and was then heated at 185° C. for one hr. The reaction solution was cooled to room temperature, and was filtered. The residue was washed with boiling water. The aqueous layer was washed with chloroform. The solvent was removed from the aqueous layer by distillation under the reduced pressure. Thus, 3-methylisonicotinic acid (26 g) was obtained as a white crystal.

$^1$H-NMR (CDCl$_3$) δ: 2.67 (3H, s), 7.39 (1H, dd, J=4.7, 7.8 Hz), 7.63 (1H, d, J=7.8 Hz), 8.66 (1H, d, J=4.7 Hz), 10.20 (1H, s).

TSIMS (M/Z): 138 (M+H)$^+$.

(b) Step (c) of Example 103 was repeated, except that the compound (26 g) prepared just above in step (a) was used as the starting compound. Thus, ethyl 3-methylisonicotinate (20.6 g) was obtained as a colorless liquid.

$^1$H-NMR (CDCl$_3$) δ: 1.14 (3H, t, J=7.2 Hz), 2.57 (3H, s), 4.39 (2H, q, J=7.2 Hz), 7.69 (1H, d, J=5.1 Hz), 8.55 (1H, d, J=5.1 Hz), 8.57 (1H, s).

TSIMS (M/Z): 166 (M+H)$^+$.

(c) Step (d) of Example 103 was repeated, except that the compound (1.65 g) prepared just above in step (b) was used as the starting compound. Thus, ethyl 3-bromomethylisonicotinate (1.7 g) was obtained as a red crystal.

$^1$H-NMR (CDCl$_3$) δ: 1.45 (3H, t, J=7.2 Hz), 4.90 (2H, s), 7.76 (1H, d, J=5.1 Hz), 8.68 (1H, d, J=5.1 Hz), 8.74 (1H, s).

TSIMS (M/Z): 244 (M+H)$^+$.

(d) Step (e) of Example 103 was repeated, except that the compound (1.7 g) prepared just above in step (c) was used as the starting compound. Thus, ethyl 3-cyanomethylisonicotinate (185 mg) was obtained as a white crystal.

$^1$H-NMR (CDCl$_3$) δ: 1.47 (3H, t, J=7.0 Hz), 4.28 (3H, s), 4.50 (2H, q, J=7.0 Hz), 7.55 (1H, dd, J=4.6, 8.0 Hz), 8.01 (1H, d, J=8.0 Hz), 8.75 (1H, d, J=4.6 Hz).

TSIMS (M/Z): 191 (M+H)$^+$.

(e) Step (f) of Example 103 was repeated, except that the compound (180 mg) prepared just above in step (d) was used as the starting compound. Thus, 3,4-dihydro-2H-2,6-naphthyridin-1-one was obtained as a white crystal.

$^1$H-NMR (CDCl$_3$) δ: 3.04 (2H, t, J=6.7 Hz), 3.64 (2H, dt, J=3.0, 6.7 Hz), 6.22 (1H, brs), 7.87 (1H, d, J=4.9 Hz), 8.61 (1H, s), 8.68 (1H, d, J=4.9 Hz)

TSIMS (M/Z): 149 (M+H)$^+$.

(f) Step (g) of Example 103 was repeated, except that the compound (75 mg) prepared just above in step (e) was used as the starting compound. Thus, 2-benzyl-3,4-dihydro-2H-2,6-naphthyridin-1-one (95 mg) was obtained as a white crystal.

$^1$H-NMR (CDCl$_3$) δ: 2.96 (2H, t, J=6.9 Hz), 3.55 (2H, t, J=6.9 Hz), 4.80 (2H, s), 7.27–7.37 (5H, m), 7.95 (1H, d, J=4.8 Hz), 8.54 (1H, s), 8.68 (1H, d, J=4.8 Hz).

TSIMS (M/Z): 239 (M+H)$^+$.

(g) Step (h) of Example 103 was repeated, except that the compound (83 mg) prepared just above in step (f) was used as the starting compound. Thus, 2-benzyl-6-oxo-3,4-dihydro-2H-2,6-naphthyridin-1-one (75 mg) was obtained as a white crystal.

$^1$H-NMR (CDCl$_3$) δ: 2.91 (2H, t, J=6.7 Hz), 3.55 (2H, t, J=6.7 Hz), 4.78 (2H, s), 7.31–7.35 (5H, m), 7.98 (1H, d, J=6.6 Hz), 8.09 (1H, s), 8.18 (1H, d, J=6.6 Hz).

TSIMS (M/Z): 255 (M+H)$^+$.

(h) Step (i) of Example 103 was repeated, except that the compound (66 mg) prepared just above in step (g) was used as the starting compound. Thus, 2-benzyl-7-chloro-3,4- dihydro-2H-2,6-naphthyridin-1-one (5 mg) was obtained as a white crystal.

¹H-NMR (CDCl₃) δ: 2.94 (2H, t, J=6.7 Hz), 3.53 (2H, t, J=6.7 Hz), 4.79 (2H, s), 7.31–7.35 (5H, m), 7.99 (1H, s), 8.31 (1H, s).

TSIMS (M/Z): 273 (M+H)⁺.

(i) Step (j) of Example 103 was repeated, except that the compound (5 mg) prepared just above in step (h) was used as the starting compound. Thus, the title compound (4 mg) was obtained as a white crystal.

¹H-NMR (CDCl₃) δ: 2.25 (4H, m), 2.49 (4H, brs), 2.74 (2H, t, J=6.6 Hz), 3.39 (2H, t, J=6.6 Hz), 3.53 (4H, brs), 3.93 (1H, t, J=7.3 Hz), 4.71 (2H, s), 7.12–7.27 (16H, m), 7.99 (1H, s).

TSIMS (M/Z): 517 (M+H)⁺.

EXAMPLE 105

2-Benzyl-5-[4-(3,3-diphenyl-1-propyl)piperazin-1-yl]-3,4-dihydro-2H-2,6-naphthyridin-1-one (a) Step (i) of Example 103 was repeated, except that the compound (66 mg) prepared in step (g) of Example 104 was used as the starting compound. Thus, 2-benzyl-5-chloro-3,4-dihydro-2H-2,6-naphthyridin-1-one (35 mg) was obtained as a white crystal.

¹H-NMR (CDCl₃) δ: 3.05 (2H, t, J=7.2 Hz), 3.55 (2H, t, J=7.2 Hz), 4.79 (2H, s), 7.31–7.36 (5H, m), 7.94 (1H, d, J=5.1 Hz), 8.45 (1H, d, J=5.1 Hz).

TSIMS (M/Z): 273 (M+H)⁺.

(b) Step (h) of Example 103 was repeated, except that the compound (25 mg) prepared just above in step (a) was used as the starting compound. Thus, the title compound (6 mg) was obtained as a white crystal.

¹H-NMR (CDCl₃) δ: 2.29–2.41 (4H, m), 2.54 (4H, brs), 2.79 (2H, t, J=6.5 Hz), 3.17 (4H, brs), 3.42 (2H, t, J=6.5 Hz), 4.02 (1H, t, J=7.2 Hz), 4.76 (2H, s), 7.15–7.33 (15H, m), 7.55 (1H, d, J=5.0 Hz), 8.33 (1H, d, J=5.0 Hz).

FABMS (M/Z): 517 (M+H)⁺.

EXAMPLE 106

6-Benzyl-3-[4-(3,3-diphenyl-1-propyl)piperazin-1-yl]-7,8-dihydro-6H-1,6-naphthyridin-5-one (a) Nitromalonaldehyde sodium monohydrate was synthesized using mucobromic acid as a starting compound according to the method described in Org. Syntheses, Vol. 32, 95 (1952). Ethyl 2-methyl-5-nitronicotinate was prepared using the nitromalonaldehyde sodium monohydrate as a starting compound according to the method described in J. Am. Chem. Soc., Vol. 75, 737–8 (1953).

¹H-NMR (CDCl₃) δ: 1.54 (3H, t, J=7.0 Hz), 2.98 (3H, s), 4.43 (2H, q, J=7.0 Hz), 8.94 (1H, d, J=2.5 Hz), 9.41 (1H, d, J=2.5 Hz).

TSIMS (M/Z): 211 (M+H)⁺.

(b) 10% palladium-carbon (40 mg) was added to an ethanol solution (15 ml) of the compound (562 mg) prepared just above in step (a) in an argon atmosphere. The atmosphere in the system was replaced by hydrogen, followed by stirring for 3 hr. The reaction solution was filtered through Celite, and the filtrate was removed by distillation under the reduced pressure. The residue was purified by column chromatography on silica gel (chloroform:methanol=20:1) to give ethyl 5-amino-2-methylnicotinate (480 mg) as a colorless crystal.

¹H-NMR (CDCl₃) δ: 1.39 (3H, t, J=7.2 Hz), 2.70 (3H, s), 3.68 (2H, brs), 4.36 (2H, q, J=7.2 Hz), 7.52 (1H, d, J=2.9 Hz), 8.11 (1H, d, J=2.9 Hz).

TSIMS (M/Z): 181 (M+H)⁺.

(c) Di-t-butyl dicarbonate (5.99 g) was added to a methylene chloride solution (90 ml) of the compound (4.5 g) prepared just above in step (b). The mixture was cooled to 0° C., and triethylamine (4.18 ml) was slowly added thereto. Further, the mixture was gradually heated and was refluxed for 2 hr. The reaction solution was cooled to room temperature, and a saturated aqueous ammonium chloride solution (100 ml) and chloroform (200 ml) were then added to the cooled reaction solution, followed by separation. The chloroform layer was washed with a saturated aqueous ammonium chloride solution, and was dried over sodium sulfate. The solvent was removed from the solution by distillation under the reduced pressure. The residue was purified by column chromatography on silica gel (hexane:ethyl acetate=2:1) to give ethyl 5-tert-butoxycarbonylamino-2-methylnicotinate (3.36 g) as a yellow crystal.

¹H-NMR (CDCl₃) δ: 1.40 (3H, t, J=7.2 Hz), 1.53 (9H, s), 2.73 (3H, s), 4.38 (2H, q, J=7.2 Hz), 6.56 (1H, brs), 8.36 (1H, s), 8.51 (1H, s).

TSIMS (M/Z): 166 (M+H)⁺.

(d) Step (d) of Example 103 was repeated, except that the compound (56 mg) prepared just above in step (c) was used as the starting compound. Thus, ethyl 5-tert-butoxycarbonylamino-2-bromomethylnicotinate (43 mg) was obtained.

¹H-NMR (CDCl₃) δ: 1.43 (3H, t, J=7.1 Hz), 1.54 (9H, s), 4.43 (2H, q, J=7.1 Hz), 5.00 (2H, s), 6.69 (1H, brs), 8.46 (1H, s), 8.58 (1H, d, J=2.7 Hz).

TSIMS (M/Z): 359 (M+H)⁺, FABMS (M/Z): 359 (M+H)⁺.

(e) Step (e) of Example 103 was repeated, except that the compound (450 mg) prepared just above in step (d) was used as the starting compound. Thus, ethyl 5-tert-butoxycarbonylamino-2-cyanomethylnicotinate (130 mg) was obtained as a white crystal.

¹H-NMR (CDCl₃) δ: 1.43 (3H, t, J=7.0 Hz), 1.54 (9H, s), 4.34 (2H, s), 4.42 (2H, q, J=7.0 Hz), 6.73 (1H, s), 8.59 (1H, s), 8.61 (1H, s).

EIMS (M/Z): 305(M)⁺.

(f) Step (f) of Example 103 was repeated, except that the compound (130 mg) prepared just above in step (e) was used as the starting compound. Thus, 3-tert-butoxycarbonylamino-7,8-dihydro-6H-1,6-naphthyridin-5-one (45 mg) was obtained as a white crystal.

¹H-NMR (CDCl₃) δ: 1.53 (9H, s), 3.16 (2H, t, J=5.0 Hz), 3.63 (2H, t, J=5.0 Hz), 6.54 (1H, brs), 8.27 (1H, s), 8.74 (1H, s).

TSIMS (M/Z): 264 (M+H)⁺.

(g) Concentrated hydrochloric acid (2 ml) was added to a 1,4-dioxane solution (5 ml) of the compound (260 mg) prepared just above in step (f). The mixture was stirred at room temperature for one hr. The reaction solution was cooled to 0° C., and ethyl acetate (80 ml) was added to the cooled reaction solution. Subsequently, a saturated aqueous sodium carbonate solution was added thereto, followed by separation. The ethyl acetate layer was washed with a saturated aqueous sodium chloride solution, and was then dried over sodium sulfate. The solvent was then removed by distillation under the reduced pressure. The residue was purified by column chromatography on silica gel (dichloromethane:methanol=10:1) to give 3-amino-7,8-dihydro-6H-1,6-naphthyridin-5-one (140 mg) as a white solid.

$^1$H-NMR (CDCl$_3$) δ: 3.07 (2H, t, J=6.7 Hz), 3.61 (2H, dt, J=2.9, 6.7 Hz), 6.37 (2H, brs), 7.62 (1H, d, J=2.9 Hz), 8.12 (1H, d, J=2.9 Hz).

EIMS (M/Z): 163 (M)$^+$.

(h) The compound (40 mg) prepared just above in step (g) was dissolved in 40% hydrobromic acid (1.5 ml). Water (1.0 ml) was added thereto, followed by stirring. This aqueous solution was cooled to 0° C. A solution of sodium nitrite (28 mg) in water (1 ml) was slowly added dropwise to the aqueous solution. The mixture was stirred at 0° C. until foaming ceased. The aqueous solution was slowly added dropwise to an aqueous mixed solution composed of copper (II) bromide (35 mg), 40% hydrobromic acid (1.5 ml), and water (1.0 ml) at room temperature. The reaction solution was stirred at 80° C. for one hr. The stirred reaction solution was then cooled to 0° C., and a saturated aqueous sodium hydrogencarbonate solution and chloroform were added to the cooled reaction solution, followed by separation. The chloroform layer was washed with a saturated aqueous sodium chloride solution and was dried over sodium sulfate. The solvent was then removed by distillation under the reduced pressure. The residue was purified by column chromatography on silica gel (dichloromethane 3 methanol=10:1) to give 3-bromo-7,8-dihydro-6H-1,6-naphthyridin-5-one (12 mg) as a white solid.

$^1$H-NMR (CDCl$_3$) δ: 3.17 (2H, t, J=4.5 Hz), 3.67 (2H, dt, J=2.9, 4.5 Hz), 6.45 (1H, brs), 8.46 (1H, d, J=2.4 Hz), 8.70 (1H, d, J=2.4 Hz).

EIMS (M/Z): 228 (M)$^+$.

(i) The compound (60 mg) prepared just above in step (h), together with 3-diphenyl-1-propyl-piperazine (89 mg), palladium(II) acetate (0.9 mg), R-(+)-2,2'-bis(diphenylphosphino)-1,1'-binaphthyl (2.5 mg), and cesium carbonate (121 mg), was stirred in toluene as a solvent in an argon atmosphere at 100° C. for 5 hr. The reaction solution was cooled to room temperature. A saturated aqueous ammonium chloride solution (100 ml) and chloroform (200 ml) were then added to the cooled reaction solution, followed by separation. The chloroform layer was washed with a saturated aqueous ammonium chloride solution and was dried over sodium sulfate. The solvent was removed from the solution by distillation under the reduced pressure. The residue was purified by column chromatography on silica gel (chloroform:methanol=10:1) to give 3-[4-(3,3-diphenyl-1-propyl)piperazin-1-yl]-7,8-dihydro-6H-1,6-naphthyridin-5-one (50 mg) as a white solid.

$^1$H-NMR (CDCl$_3$) δ: 2.30 (4H, m), 2.58 (4H, t, J=5.0 Hz), 3.20 (2H, t, J=6.9 Hz), 3.26 (4H, t, J=5.0 Hz), 3.62 (2H, td, J=6.9, 20.3 Hz), 4.02 (1H, t, J=7.1 Hz), 7.15–7.33 (10H, m), 7.80 (1H, d, J=2.9 Hz), 8.31 (1H, d, J=2.9 Hz).

TSIMS (M/Z): 427 (M+H)$^+$.

(j) Step (g) of Example 103 was repeated, except that the compound (41 mg) prepared just above in step (i) was used as the starting compound. Thus, the title compound (36 mg) was obtained as a white solid.

$^1$H-NMR (CDCl$_3$) δ: 2.29–2.34 (4H, m), 2.58 (4H, brs), 3.04 (2H, t, J=6.8 Hz), 3.27 (4H, brs), 3.53 (2H, t, J=6.8 Hz), 4.02 (1H, t, J=6.9 Hz), 4.79 (2H, s), 7.16–7.38 (15H, m), 7.89 (1H, d, J=2.9 Hz), 8.27 (1H, d, J=2.9 Hz).

FABMS (M/Z): 517 (M+H)$^+$.

EXAMPLE 107

N-Benzyl-N-cyclohexyl-3-[4-(3,3-diphenyl-1-propyl)piperazin-1-yl]-6-methylnicotinamide (a) Step (h) of Example 106 was repeated, except that the compound (1.3 g) prepared in step (b) of Example 106 was used as the starting compound. Thus, ethyl 2-methyl-5-bromonicotinate (913 mg) was obtained.

$^1$H-NMR (CDCl$_3$) δ: 1.41 (3H, t, J=7.0 Hz), 2.79 (3H, s), 4.39 (2H, q, J=7.0 Hz), 8.31 (1H, d, J=2.4 Hz), 8.66 (1H, d, J=2.4 Hz).

TSIMS (M/Z): 292 (M+H)$^+$.

(b) Step (i) of Example 106 was repeated, except that the compound (50 mg) prepared just above in step (a) was used as the starting compound. Thus, ethyl 3-[4-(3,3-diphenyl-1-propyl)piperazin-1-yl]-6-methylnicotinate (72 mg) was obtained.

$^1$H-NMR (CDCl$_3$) δ: 1.40 (3H, t, J=7.0 Hz), 2.32 (4H, m), 2.58 (4H, brs), 2.71 (3H, s), 3.21 (4H, brs), 4.02 (1H, t, J=6.9 Hz), 4.37 (2H, q, J=7.0 Hz), 7.17–7.30 (10H, m), 7.67 (1H, d, J=3.0 Hz), 8.28 (1H, d, J=3.0 Hz).

FABMS (M/Z): 444 (M+H)$^+$.

(c) A 5 N aqueous sodium hydroxide solution (0.5 ml) was added to an ethanol solution (2 ml) of the compound (72 mg) prepared just above in step (b), and the mixture was stirred at room temperature overnight. The solvent was removed from the reaction solution by distillation under the reduced pressure. Ethanol (10 ml) was added to the residue, and the mixture was stirred. The stirred mixture was filtered, and the solvent was removed from the filtrate by distillation under the reduced pressure. A saturated aqueous ammonium chloride solution and ethyl acetate were added to the residue, followed by separation. The ethyl acetate layer was dried over sodium sulfate, and the solvent was removed by distillation under the reduced pressure to give 3-[4-(3,3-diphenyl-1-propyl)piperazin-1-yl]-6-methylnicotinic acid (60 mg) as a white crystal.

$^1$H-NMR (CD$_3$OD) δ: 2.40–2.44 (4H, m), 2.45 (3H, s), 2.94 (4H, brs), 3.15 (4H, brs), 4.00 (1H, t, J=7.0 Hz), 7.02–7.11 (10H, m), 7.65 (1H, s), 7.94 (1H, s).

TSIMS (M/Z): 416 (M+H)$^+$.

(d) Benzylcyclohexylamine (55 mg) was added to a methylene chloride solution (2 ml) of the compound (60 mg) prepared just above in step (c). The mixture was cooled to 0° C. 1-Hydroxybenzotriazole (36 mg), 1-(3-dimethylaminopropyl)-3-ethylcarbodiimide hydrochloride (23.4 mg), and triethylamine (24 μl) were added thereto. The temperature of the mixture was raised to room temperature, and the mixture was then stirred overnight. A saturated aqueous ammonium chloride solution (20 ml) and chloroform (50 ml) were added to the reaction solution, followed by separation. The chloroform layer was washed with a saturated aqueous sodium chloride solution and was dried over magnesium sulfate. The solvent was removed by distillation under the reduced pressure. The residue was purified by column chromatography on silica gel (chloroform:methanol=10:1) to give the title compound (55 mg).

$^1$H-NMR (CDCl$_3$) δ: 0.89–1.92 (10H, m), 2.26–2.38 (4H, m), 2.40 (3/2H, s), 2.49 (3/2H, s), 2.59 (4H, brs), 3.20 (4H, brs), 3.31 (1/2H, brs), 4.01 (3/2H, m), 4.30–4.90 (2H, m), 6.70 (1/2H, d, J=3.0 Hz), 7.00 (1/2H, d, J=3.0 Hz), 7.05 (1H, d, J=2.8 Hz), 7.19–7.38 (14H, m), 8.07 (1/2H, d, J=2.8 Hz), 8.23 (1/2H, d, J=2.8 Hz).

TSIMS (M/Z): 587 (M+H)$^+$.

EXAMPLE 108

N-Benzyl-N-cyclohexyl-2-[4-(3,3-diphenyl-1-propyl)piperazin-1-yl]-5-methylisonicotinamide (a) Step (h) of Example 103 was repeated, except that the compound (15.0 g) prepared in step (b) of Example 104 was used as the starting compound. Thus, ethyl 3-methyl-1-oxoisonicotinate (15.5 g) was obtained.

$^1$H-NMR (CDCl$_3$) δ: 1.40 (3H, t, J=7.1 Hz), 2.56 (3H, s), 4.38 (2H, q, J=7.1 Hz), 7.83 (1H, d, J=6.8 Hz), 8.09 (1H, d, J=6.8 Hz), 8.11 (1H, s).

TSIMS (M/Z): 182 (M+H)$^+$.

(b) Step (i) of Example 103 was repeated, except that the compound (2.1 g) prepared just above in step (a) was used as the starting compound. Thus, ethyl 6-chloro-3-methylisonicotinate (609 mg) was obtained.

$^1$H-NMR (CDCl$_3$) δ: 1.41 (3H, t, J=7.0 Hz), 2.53 (3H, s), 4.40 (2H, q, J=7.0 Hz), 7.73 (1H, s), 8.33 (1H, s).

TSIMS (M/Z): 199 (M+H)$^+$.

(c) Step (b) of Example 107 was repeated, except that the compound (186 mg) prepared just above in step (b) was used as the starting compound. Thus, ethyl 2-[4-(3,3-diphenyl-1-propyl)piperazin-1-yl]-5-methylisonicotinate (89 mg) was obtained.

$^1$H-NMR (CDCl$_3$) δ: 1.39 (3H, t, J=7.1 Hz), 2.37 (4H, m), 2.40 (3H, s), 2.58 (4H, brs), 3.57 (4H, brs), 4.00 (1H, t, J=7.0 Hz), 4.38 (2H, q, J=7.1 Hz), 7.06 (1H, s), 7.15–7.30 (10H, m), 8.09 (1H, s).

TSIMS (M/Z): 444 (M+H)$^+$.

(d) Step (c) of Example 107 was repeated, except that the compound (72 mg) prepared just above in step (c) was used as the starting compound. Thus, 2-[4-(3,3-diphenyl-1-propyl)piperazin-1-yl]-5-methylisonicotinic acid (60 mg) was obtained.

$^1$H-NMR (CD$_3$OD) δ: 2.15 (3H, s), 2.42–2.43 (4H, m), 2.97 (4H, brs), 3.15 (4H, brs), 3.99 (1H, t, J=7.0 Hz), 6.82 (1H, s), 7.02–7.11 (10H, m), 8.02 (1H, s).

TSIMS (M/Z): 416 (M+H)$^+$.

(e) Step (d) of Example 107 was repeated, except that the compound (60 mg) prepared just above in step (d) and benzylcyclohexylamine (60 mg) were used as the starting compounds. Thus, the title compound (55 mg) was obtained.

$^1$H-NMR (CDCl$_3$) δ: 0.88–1.86 (10H, m), 2.11 (3/2H, s), 2.20 (3/2H, s), 2.26–2.37 (4H, m), 2.52 (4H, m), 3.49 (4H, m), 4.01 (1H, t, J=7.0 Hz), 4.30–4.89 (3H, m), 6.23 (1/2H, brs), 6.46 (1/2H, brs), 7.10–7.39 (15H, m), 7.95 (1/2H, brs), 8.06 (1/2H, brs).

TSIMS (M/Z): 587 (M+H)$^+$.

EXAMPLE 109

N-Benzyl-N-cyclohexyl-2-[4-(3,3-diphenyl-1-propyl)piperazin-1-yl]-3-methylisonicotinamide (a) Step (i) of Example 103 was repeated, except that the compound (12.8 g) prepared in step (a) of Example 108 was used as the starting compound. Thus, ethyl 2-chloro-3-methylisonicotinate (11.4 g) was obtained.

$^1$H-NMR (CDCl$_3$) δ: 1.41 (3H, t, J=7.0 Hz), 2.59 (3H, s), 4.41 (2H, g, J=7.0 Hz), 7.52 (1H, d, J=5.1 Hz), 8.33 (1H, d, J=5.1 Hz).

TSIMS (M/Z): 199 (M+H)$^+$.

(b) Step (b) of Example 107 was repeated, except that the compound (11.4 g) prepared just above in step (a) was used as the starting compound. Thus, ethyl 2-[4-(3,3-diphenyl-1-propyl)piperazin-1-yl]-3-methylisonicotinate (7.8 g) was obtained.

$^1$H-NMR (CDCl$_3$) δ: 1.38 (3H, t, J=7.1 Hz), 2.21–2.58 (4H, m), 2.41 (3H, s), 2.58 (4H, brs), 3.21 (4H, brs), 4.03 (1H, t, J=7.3 Hz), 4.37 (2H, q, J=7.1 Hz), 7.14–7.28 (11H, m), 8.22 (1H, d, J=4.9 Hz).

TSIMS (M/Z): 444 (M+H)$^+$.

(c) Step (C) of Example 107 was repeated, except that the compound (1.4 g) prepared just above in step (b) was used as the starting compound. Thus, 2-[4-(3,3-diphenyl-1-propyl)piperazin-1-yl]-3-methylisonicotinic acid (1.12 g) was obtained.

$^1$H-NMR (CD$_3$OD) δ: 2.20 (3H, s), 2.40–2.44 (4H, m), 2.97 (4H, brs), 3.15 (4H, brs), 3.97 (1H, t, J=7.0 Hz), 6.88 (1H, d, J=4.9 Hz), 7.02–7.11 (10H, m), 7.94 (1H, d, J=4.9 Hz).

TSIMS (M/Z): 416 (M+H)$^+$.

(d) Step (d) of Example 107 was repeated, except that the compound (670 mg) prepared just above in step (C) and benzylcyclohexylamine (610 mg) were used as the starting compounds. Thus, the title compound (750 mg) was obtained.

$^1$H-NMR (CDCl$_3$) δ: 0.86–1.86 (10H, m), 2.09 (3/2H, s), 2.56 (3/2H, s), 2.30–2.35 (4H, m), 2.58 (4H, m), 3.07–3.31 (4H, m), 4.04 (1H, t, J=7.0 Hz), 4.30 (1/2, brs), 4.45 (1/2H, brs), 4.65 (1/2H, d, J=5.9 Hz), 4.79 (1/2H, d, J=5.9 Hz), 6.70 (1/2H, d, J=4.9 Hz), 6.79 (1/2H, d, J=4.9 Hz), 7.06–7.28 (15H, m), 8.04 (1/2H, d, J=4.8 Hz), 8.20 (1/2H, d, J=4.8 Hz).

TSIMS (M/Z): 587 (M+H)$^+$.

EXAMPLE 110

N-Allyl-N-cyclohexyl-2-[4-(3,3-diphenyl-1-propyl)piperazin-1-yl]-5-methylisonicotinamide Step (d) of Example 107 was repeated, except that the compound (50 mg) prepared in step (d) of Example 108 and allylcyclohexylamine (34 mg) were used as the starting compounds. Thus, the title compound (47 mg) was obtained.

$^1$H-NMR (CDCl$_3$) δ: 0.88–1.85 (10H, m), 2.09 (3/2H, s), 2.14 (3/2H, s), 2.33 (4H, m), 2.52 (4H, brs), 3.49 (4H, brs), 3.95–4.02 (2H, m), 4.14 (1H, m), 4.40 (1H, m), 4.95 (1/2H, d, J=17.6 Hz), 5.04 (1/2H, d, J=9.7 Hz), 5.16 (1/2H, d, J=9.7 Hz), 5.26 (1/2H, d, J=17.6 Hz), 5.65 (1/2H, m), 5.95 (1/2H, m), 6.40 (1H, s), 7.18–7.30 (10H, m), 8.02 (1H, d, J=17.3 Hz).

TSIMS (M/Z): 537 (M+H)$^+$.

EXAMPLE 111

N-Allyl-N-cyclohexyl-2-[4-(3,3-diphenyl-1-propyl)piperazin-1-yl]-3-methylisonicotinamide Step (d) of Example 107 was repeated, except that the compound (50 mg) prepared in step (c) of Example 109 and allylcyclohexylamine (34 mg) were used as the starting compounds. Thus, the title compound (44 mg) was obtained.

$^1$H-NMR (CDCl$_3$) δ: 1.00–1.85 (10H, m), 2.15 (3/2H, s), 2.20 (3/2H, s), 2.30–2.35 (4H, m), 2.58 (4H, brs), 3.16 (4H, brs), 3.71 (1H, m), 3.99–4.14 (2H, m), 4.41 (1H, m), 4.90 (1/2H, dd, J=1.8, 12.0 Hz), 5.02 (1/2H, dd, J=1.8, 9.4 Hz), 5.16 (1/2H, dd, J=1.8, 9.4 Hz), 5.26 (1/2H, dd, J=1.8, 12.0), 5.62 (1/2H, m), 5.96 (1/2H, m), 6.71 (1H, d, J=4.9 Hz), 7.15–7.30 (10H, m), 8.17 (1H, dd, J=4.9, 9.7 Hz).

TSIMS (M/Z): 537. (M+H)$^+$.

EXAMPLE 112

N-Allyl-N-cyclohexyl-3-methyl-2-[4-[3-[9-(2,2,2-trifluoroethylcarbamoyl)-9H-fluoren-9-yl]propyl]piperazin-1-yl]isonicotinamide (a) Step (i) of Example 106 was repeated, except that the compound prepared in step (a) of Example 109 was used instead of 3-bromo-7,8-dihydro-6H-1,6-naphthyridin-5-one and 1-tert-butoxycarbonylpiperazine was used instead of 3,3-diphenyl-1-propylpiperazine. Thus, ethyl 3-methyl-2-[4-(tert-butoxycarbonyl)piperazin-1-yl]isonicotinate was obtained.

$^1$H-NMR (CDCl$_3$) δ: 1.42 (3H, t, J=7.0 Hz), 1.49 (9H, s), 2.54 (3H, s), 3.12 (4H, brs), 3.52 (4H, m), 4.38 (2H, q, J=7.0 Hz), 7.2–7.25 (2H, m), 8.23 (1H, d, J=4.9 Hz).

TSIMS (M/Z): 349 (M+H)$^+$.

(b) The compound prepared just above in step (a) was subjected to ester hydrolysis in the same manner as in step (c) of Example 1. Thus, 3-methyl-2-[4-(tert-butoxycarbonyl)piperazin-1-yl]isonicotinic acid was obtained.

$^1$H-NMR (CDCl$_3$) δ: 1.46 (9H, s), 2.46 (3H, s), 2.63 (4H, brs), 3.10 (4H, brs), 7.16 (2H, d, J=4.8 Hz), 8.23 (1H, d, J=4.8 Hz).

FABMS (M/Z): 322 (M+H)$^+$.

(c) Step (c) of Example 87 was repeated, except that the compound prepared just above in step (b) was used instead of 3-[4-[4-[9-(2,2,2-trifluoroethylcarbamoyl)-9H-fluoren-9-yl]butyl]piperazin-1-yl]benzoic acid. Thus, N-allyl-N-cyclohexyl-3-methyl-2-[4-(tert-butoxycarbonyl)piperazin-1-yl]isonicotinamide was obtained.

$^1$H-NMR (CDCl$_3$) δ: 1.48 (9H, s), 1.62–2.08 (10H, m), 2.23 (3/2H, s), 2.36 (3/2H, s), 2.98 (4H, s), 5.36–5.47 (4H, m), 5.89–6.00 (2H, m), 6.98 (1H, d, J=4.8 Hz), 8.13 (1H, d, J=4.8 Hz).

TSIMS (M/Z): 443 (M+H)$^+$.

(d) The compound prepared just above in step (c) was deprotected in the same manner as in step (b) of Example 97 to give N-allyl-N-cyclohexyl-3-methyl-2-piperazin-1-yl-isonicotinamide.

$^1$H-NMR (CDCl$_3$) δ: 1.50–2.08 (10H, m), 2.18 (3/2H, s), 2.23 (3/2H, s), 3.02–3.24 (8H, m), 4.80–5.34 (4H, m), 5.62 (1H, m), 6.73 (1H, d, J=5.2 Hz), 8.19 (1H, d, J=5.2 Hz).

(e) Step (b) of Example 1 was repeated, except that the compound prepared just above in step (d) was used instead of 3-piperazin-1-ylbenzoic acid and the compound prepared in step (a) of Example 93 was used instead of 3,3-diphenylpropyl bromide. Thus, the title compound was prepared.

$^1$H-NMR (CDCl$_3$) δ: 0.89–1.83 (12H, m), 2.10 (3/2H, s), 2.15 (3/2H, s), 2.55 (4/2H, m), 2.39 (4/2H, m), 2.49 (2H, m), 3.07 (4H, m), 3.62 (2H, m), 3.70 (2H, m), 3.94 (1H, d, J=5.4 Hz), 3.97 (1H, d, J=5.8 Hz), 4.12 (1H, d, J=5.4 Hz), 4.16 (1H, d, J=5.8 Hz), 4.41 (1H, m), 4.88 (1/2H, dd, J=1.5, 16.1 Hz), 5.02 (1/2H, dd, J=1.5, 10.3 Hz), 5.16 (1/2H, dd, J=1.5, 10.3 Hz), 5.25 (1/2H, dd, J=1.5, 16.1 Hz), 5.83 (2H, t, J=6.0 Hz), 5.61 (1/2H, m), 5.95 (1/3H, m), 6.77 (1H, d, J=5.1 Hz), 7.38 (2H, dd, J=6.4, 6.3 Hz), 7.45 (2H, dd, J=6.3, 6.5 Hz), 7.56 (2H, d, J=6.5 Hz), 7.76 (2H, d, J=6.4 Hz), 8.12 (1/2H, d, J=4.9 Hz), 8.14 (1/2H, d, J=4.9 Hz).

FABMS (M/Z): 674 (M+H)$^+$.

EXAMPLE 113

N-Allyl-N-cyclohexyl-6-[4-[4-[9-(2,2,2-trifluoroethylcarbamoyl)-9H-fluoren-9-yl]butyl]piperazin-1-yl]nicotinamide (a) 6-Chloronicotinic acid (1.6 g, 10.0 mmol) was dissolved in ethanol. Concentrated sulfuric acid (0.5 ml) was added to the solution, and the mixture was refluxed overnight. The reaction solution was concentrated under the reduced pressure. The residue was diluted with methylene chloride and was then washed with water, followed by drying over anhydrous magnesium sulfate. The solvent was removed by distillation under the reduced pressure. The residue was purified by column chromatography on silica gel (development system, n-hexane:ethyl acetate=5:1) to give ethyl 6-chloronicotinate 1.6 g (yield 84%) as a colorless oil.

$^1$H-NMR (CDCl$_3$) δ: 1.42 (3H, t, J=7.2 Hz), 4.42 (2H, q, J=7.2 Hz), 7.42 (1H, d, J=8.4 Hz), 8.25 (1H, dd, J=2.4, 8.4 Hz), 9.00 (1H, d, J=2.4 Hz).

TSIMS (M/Z): 186 (M+H)$^+$.

(b) Piperazine anhydride (130 mg) and anhydrous DMF (0.5 ml) were added to the compound (60 mg, 0.32 mmol) prepared just above in step (a), and the mixture was stirred at 80° C. for 50 min. The temperature of the reaction solution was returned to room temperature, and the reaction solution was diluted with ethyl acetate and was washed twice with water, followed by drying over anhydrous magnesium sulfate. The solvent was removed by distillation under the reduced pressure to give ethyl 6-piperazin-1-ylnicotinate (51 mg, yield 68%) as a white solid.

$^1$H-NMR (CDCl$_3$) δ: 1.37 (3H, t, J=7.2 Hz), 2.97 (4H, t, J=5.1 Hz), 3.65 (4H, t, J=5.1 Hz), 4.33 (2H, q, J=7.2 Hz), 6.58 (1H, d, J=9.0 Hz), 8.02 (1H, dd, J=2.3, 9.0 Hz), 8.80 (1H, d, J=2.3 Hz).

TSIMS (M/Z): 236 (M+H)$^+$.

(c) The compound (494 mg, 2.1 mmol) prepared just above in step (b) was dissolved in 8 ml of anhydrous DMF. Potassium carbonate (580 mg) and the compound (892 mg, 2.1 mmol) prepared in step (b) of Example 92 were added to the solution, and the mixture was stirred at 50° C. overnight. The reaction solution was diluted with ethyl acetate, and the dilution was washed twice with water and was then dried over anhydrous magnesium sulfate. The solvent was removed by distillation under the reduced pressure. The residue was purified by column chromatography (development system, n-hexane:ethyl acetate=1:1) to give ethyl 6-[4-[4-[9-(2,2,2-trifluoroethylcarbamoyl)-9H-fluoren-9-yl]butyl]piperazin-1-yl]nicotinate (742 mg, yield 62%) as a pale yellow oil.

$^1$H-NMR (CDCl$_3$) δ: 0.68–0.77 (2H, m), 1.32–1.40 (2H, m), 1.36 (3H, t, J=7.2 Hz), 2.16 (2H, t, J=7.7 Hz), 2.38 (4H, t, J=5.1 Hz), 2.42–2.48 (2H, m), 3.59 (4H, t, J=5.1 Hz), 3.65–3.74 (2H, m), 4.32 (2H, q, J=7.2 Hz), 5.38 (1H, t, J=6.5 Hz), 6.54 (1H, d, J=9.1 Hz), 7.37 (2H, dt, J=1.2, 7.5 Hz), 7.45 (2H, dt, J=1.2 Hz, 7.5 Hz), 7.56 (2H, d, J=7.5 Hz), 7.78 (2H, d, J=7.5 Hz), 8.00 (1H, dd, J=2.4, 9.1 Hz), 8.77 (1H, d, J=2.4 Hz).

TSIMS (M/Z): 581 (M+H)$^+$.

(d) The compound (300 mg, 0.52 mmol) prepared just above in step (c) was dissolved in a mixed solution composed of 2.5 ml of methanol and 2.5 ml of THF. A 1 N aqueous sodium hydroxide solution (2.6 ml) was added to the solution, and the mixture was stirred at 70° C. for 5 hr. The reaction solution was concentrated to about 10 ml, and the residue was diluted with methylene chloride. Water was added thereto, and the mixture was rendered acidic by the addition of a 1 N aqueous hydrochloric acid solution, followed by extraction twice with methylene chloride. The organic layer was dried over anhydrous magnesium sulfate. The solvent was removed by distillation under the reduced pressure to give 6-[4-[4-[9-(2,2,2-trifluoroethylcarbamoyl)-9H-fluoren-9-yl]butyl]piperazin-1-yl]nicotinic acid (295 mg, yield 100%) as a pink m.

$^1$H-NMR (CDCl$_3$) δ: 0.75–0.85 (2H, m), 1.70–1.79 (2H, m), 2.40–2.47 (2H, m), 2.72–2.79 (2H, m), 3.07 (4H, brs), 3.64–3.74 (2H, m), 4.10 (4H, brs), 5.40 (1H, t, J=6.5 Hz), 6.59 (1H, d, J=8.9 Hz), 7.37 (2H, t, J=7.4 Hz), 7.46 (2H, t, J=7.4 Hz), 7.52 (2H, d, J=7.4 Hz), 7.77 (2H, d, J=7.4 Hz), 8.04 (1H, dd, J=2.3, 8.9 Hz), 8.76 (1H, d, J=2.3 Hz).

TSIMS (M/Z): 553 (M+).

(e) The compound (290 mg, 0.52 ml) prepared just above in step (d) was dissolved in 3 ml of anhydrous DMF. BOP reagent (276 mg) and 0.27 ml of diisopropylethylamine were added to the solution. The mixture was stirred at room temperature for one hr. Allylcyclohexylamine (0.11 ml) was then added thereto, and the mixture was stirred at room temperature overnight. The reaction solution was diluted with ethyl acetate, and the dilution was washed with water and was then dried over anhydrous magnesium sulfate. The solvent was removed by distillation under the reduced pressure. The residue was purified by column chromatography (development system, methylene chloride methanol= 50:1–25:1). The resultant yellow oil was further purified by column chromatography on silica gel (development system, ethyl acetate) to give the title compound 300 mg (yield 86%).

$^1$H-NMR (CDCl$_3$) δ: 0.71–0.80 (2H, m), 1.00–2.02 (13H, m), 2.25 (2H, t, J=7.8 Hz), 2.41–2.51 (6H, m), 3.51–3.58 (4H, m), 3.65–3.74 (2H, m), 3.97 (2H, brs), 5.10–5.20 (2H, m), 5.39 (1H, t, J=6.6 Hz), 5.79–5.91 (1H, m), 6.59 (1H, d, J=9.2 Hz), 7.38 (2H, dd, J=1.2, 7.6 Hz), 7.45 (2H, dd, J=1.2, 7.6 Hz), 7.52–7.57 (3H, m), 7.78 (2H, d, J=7.6 Hz), 8.22 (1H, d, J=2.0 Hz).

TSIMS (M/Z): 674 (M+H)$^+$.

EXAMPLE 114

N-Allyl-N-cyclohexyl-3-methyl-2-[4-[3-[9-(2,2,2-trifluoroethylcarbamoyl)-9H-xanthen-9-yl]propyl] piperazin-1-yl]isonicotinamide (a) 9-(3-Bromopropyl)-9-xanthenecarboxylic acid was synthesized using xanthene-9-carboxylic acid as a starting compound according to the method described in U.S. Pat. No. 5,712,279.

$^1$H-NMR (CD$_3$OD) δ: 1.29–1.37 (2H, m), 2.40–2.44 (2H, m), 3.23 (2H, t, J=6.6 Hz), 7.05–7.12 (4H, m), 7.24–7.31 (4H, m).

TSIMS (M/Z): 346 (M+H)$^+$.

(b) 3-[9-(2,2,2-Trifluoroethylcarbamoyl)-9H-xanthen-9-yl]propyl bromide was synthesized using the compound prepared just above in step (a) as a starting compound according to the method described in U.S. Pat. No. 5,712,279.

$^1$H-NMR (CDCl$_3$) δ: 1.35–1.42 (2H, m), 2.38–2.42 (2H, m), 3.19 (2H, t, J=6.8 Hz), 3.81 (2H, dq, J=9.0, 2.4 Hz), 5.44 (1H, t, J=6.4 Hz), 7.01–7.14 (4H, m), 7.25–7.27 (2H, m), 7.29–7.34 (2H, m).

FABMS (M/Z): 428 (M+H)$^+$.

(c) Step (e) of Example 112 was repeated, except that the compound prepared just above in step (b) was used instead of the compound prepared in step (a) of Example 93. Thus, the title compound was obtained.

$^1$H-NMR (CDCl$_3$) δ: 0.89–1.83 (12H, m), 2.10 (3/2H, s), 2.15 (3/2H, s), 2.33 (2H, m), 2.38 (4H, brs), 3.12 (4H, brs), 3.57 (2H, m), 3.81 (2H, m), 3.94 (2/2H, d, J=5.4 Hz), 3.98 (2/2H, d, J=5.9 Hz), 4.13 (2/2H, d, J=.5.4 Hz), 4.16 (1H, d, J=5.9 Hz), 4.39 (1H, m), 4.88 (1/2H, dd, J=0.8, 17.2 Hz), 5.02 (1/2H, dd, J=0.8, 10.4 Hz), 5.16 (1/2H, dd, J=1.4, 10.4 Hz), 5.25 (1/2H, dd, J=1.4, 17.2 Hz), 5.49 (1H, t, J=6.5 Hz), 5.60 (1/2H, m), 5.93 (1/2H, m), 6.69 (1H, d, J=5.1 Hz), 7.12 (4H, d, J=7.8 Hz), 7.25–7.30 (4H, m), 8.12 (1/2H, d, J=4.8 Hz), 8.15 (1/2H, d, J=4.8 Hz).

FABMS (M/Z): 690 (M+H)$^+$.

EXAMPLE 115

N-Cyclohexyl-N-propyl-6-[4-[4-[9-(2,2,2-trifluoroethylcarbamoyl)-9H-fluoren-9-yl]butyl] piperazin-1-yl]nicotinamide The compound (50 mg, 0.07 mmol) prepared in Example 113 was dissolved in 1 ml of methanol and 0.5 ml of methylene chloride. 10% Pd—C (5 mg) was added to the solution. The mixture was subjected to catalytic reduction under the atmospheric pressure at room temperature for 4 hr. The reaction solution was filtered, and the solution was concentrated under the reduced pressure to give the title compound (40 mg, yield 80%) as a white foam.

$^1$H-NMR (CDCl$_3$) δ: 0.71–3.28 (26H, m), 2.57 (4H, brs), 3.59 (4H, brs), 3.65–3.74 (2H, m), 5.41 (1H, t, J=6.5 Hz), 6.61 (1H, d, J=8.8 Hz), 7.38 (2H, dt, J=1.2, 7.6 Hz), 7.45 (2H, dt, J=1.2, 7.6 Hz), 7.51 (1H, dd, J=2.3, 8.8 Hz), 7.55 (2H, d, J=7.6 Hz), 7.78 (2H, d, J=7.6 Hz), 8.18 (1H, d, J=2.3 Hz).

TSIMS (M/Z): 676 (M+H)$^+$.

EXAMPLE 116

N-Cyclohexyl-N-[(pyridin-2-yl)methyl]-6-[4-[4-[9-(2,2,2-trifluoroethylcarbamoyl)-9H-fluoren-9-yl] butyl]piperazin-1-yl]nicotinamide The compound (110 mg, 0.20 mmol) prepared in step (d) of Example 113 was dissolved in 2 ml of anhydrous DMF. BOP reagent (106 mg) and 0.11 ml of diisopropylethylamine were added to the solution, and the mixture was stirred at room temperature for one hr. Cyclohexyl(2-pyridylmethyl) amine (0.11 ml) was then added thereto, and the mixture was stirred at room temperature overnight. The reaction solution was diluted with ethyl acetate. The dilution was washed with water and was then dried over anhydrous magnesium sulfate. The solvent was removed by distillation under the reduced pressure. The residue was purified by column chromatography (development system, methylene chloride:methanol=50:1–25:1) to give the title compound (88 mg, yield 61%) as a pale yellow foam.

$^1$H-NMR (CDCl$_3$) δ: 0.70–2.48 (23H, m), 3.53 (4H, brs), 3.64–3.72 (2H, m), 4.77 (2H, brs), 5.40 (1H, t, J=6.6 Hz), 6.58 (1H, brs), 7.11–7.16 (1H, m), 7.30 (1H, d, J=7.8 Hz), 7.37 (2H, dt, J=1.1, 7.6 Hz), 7.45 (2H, dt, J=1.1, 7.6 Hz), 7.55 (2H, d, J=7.6 Hz), 7.60–7.65 (2H, m), 7.77 (2H, d, J=7.6 Hz), 8.31 (1H, d, J=2.3 Hz), 8.50 (1H, d, J=4.1 Hz).

TSIMS (M/Z): 725 (M+H)$^+$.

EXAMPLE 117

2-Cyclohexyl-6-[4-[4-(9-carbamoyl-9H-fluoren-9-yl)butyl]piperazin-1-yl]-2,3-dihydro-1H-isoindol-1-one (a) 9-(4-Bromobutyl)-9H-fluorenecarboxylic acid (50 mg, 0.15 mmol) synthesized according to the method described in U.S. Pat. No. 5,712,279 was dissolved in 0.25 ml of thionyl chloride. The solution was stirred at 55° C. for 2 hr. The reaction solution was concentrated under the reduced pressure, followed by azeotropic distillation with toluene and drying by means of a vacuum pump. The residue was dissolved in 1.5 ml of methylene chloride, and the solution was added to 1 ml of 28% aqueous ammonia under ice cooling. The mixture was stirred under ice cooling for 30 min. Water was then added thereto, followed by extraction with methylene chloride. The solvent was removed by distillation under the reduced pressure to give 43 mg (yield 86%) of 9-(4-bromobutyl)-9H-fluorene-9-carboxamide as a white solid as a crude product.

$^1$H-NMR (CDCl$_3$) δ: 0.79–0.87 (2H, m), 1.66–1.73 (2H, m), 2.42–2.46 (2H, m), 3.21 (2H, t, J=6.9 Hz), 4.95 (1H, brs), 5.04 (1H, brs), 7.37 (2H, dt, J=1.2, 7.6 Hz), 7.44 (2H, dt, J=1.2, 7.6 Hz), 7.59 (2H, d, J=7.6 Hz), 7.77 (2H, d, J=7.6 Hz).

EIMS (M/Z): 343 (M$^+$).

(b) 2-Cyclohexyl-2,3-dihydro-6-piperazinyl-1H-isoindol-1-one (37 mg, 0.12 mmol) synthesized according to the method described in WO 9854135 was dissolved in 0.5 ml of anhydrous DMF. Potassium carbonate (33 mg) and the compound (43 mg, 0.12 mmol) prepared just above in step (a) were added to the solution. The mixture was stirred at room temperature for one hr and was then stirred at 55° C. for 5.5 hr. The reaction solution was diluted with ethyl acetate. The dilution was washed twice with water and was then dried over anhydrous magnesium sulfate. The solvent was removed by distillation under the reduced pressure. The residue was purified by column chromatography (development system, methylene chloride:methanol=30:1–15:1) to give the title compound (49 mg, yield 71%) as a pale yellow foam.

$^1$H-NMR (CDCl$_3$) δ: 0.68–0.76 (2H, m), 1.11–1.89 (12H, m), 2.18 (2H, t, J=7.8 Hz), 2.43–2.48 (6H, m), 3.16 (4H, t, J=4.9 Hz), 4.19–4.24 (1H, m), 4.25 (2H, s), 4.95 (1H, brs), 5.05 (1H, brs), 7.07 (1H, dd, J=2.3, 8.4 Hz), 7.28 (1H, d, J=8.4 Hz), 7.31 (1H, d, J=2.3 Hz), 7.37 (2H, dt, J=1.2, 7.6 Hz), 7.43 (2H, dt, J=1.2, 7.6 Hz), 7.59 (2H, d, J=7.6 Hz), 7.76 (2H, d, J=7.6 Hz)

FABMS (M/Z): 563 (M+H)$^+$.

EXAMPLE 118

2-Cyclohexyl-6-[4-[4-(9-ethylcarbamoyl-9H-fluoren-9-yl)butyl]piperazin-1-yl]-2,3-dihydro-1H-isoindol-1-one (a) Step (b) of Example 92 was repeated, except that ethylamine was used instead of 2,2,2-trifluoroethylamine. Thus, 4-(9-ethylcarbamoyl-9H-fluoren-9-yl)butyl bromide was obtained.

$^1$H-NMR (CDCl$_3$) δ: 0.80 (2H, m), 0.90 (3H, t, J=7.2 Hz), 1.69 (2H, m), 2.43 (2H, m), 3.08 (2H, m), 3.21 (2H, t, J=7.0 Hz), 5.13 (1H, brs), 7.37 (2H, dt, J=1.2, 7.4 Hz), 7.44 (2H, dt, J=1.2, 7.4 Hz), 7.59 (2H, d, J=7.4 Hz), 7.77 (2H, d, J=7.4 Hz).

TSIMS (M/Z): 374 (M+H)$^+$.

(b) Step (c) of Example 92 was repeated, except that the compound prepared just above in step (a) was used instead of 4-[9-(2,2,2-trifluoroethylcarbamoyl)-9H-fluoren-9-yl] butyl bromide. Thus, the title compound was prepared.

$^1$H-NMR (CDCl$_3$) δ: 0.80 (2H, m), 0.89 (4H, m), 1.21–1.87 (11H, m), 2.18 (2H, m), 2.48 (6H, m), 3.09 (2H, m), 3.18 (4H, m), 4.26 (3H, m), 5.14 (1H, m), 7.08 (1H, dd, J=2.1, 8.5 Hz), 7.39 (6H, m), 7.59 (2H, d, J=7.4 Hz), 7.76 (2H, d, J=7.4 Hz).

FABMS (M/Z): 591 (M+H)$^+$.

EXAMPLE 119

6-[4-[4-(9-Benzylcarbamoyl-9H-fluoren-9-yl)butyl] piperazin-1-yl]-2-cyclohexyl-2,3-dihydro-1H-isoindol-1-one (a) Step (a) of Example 118 was repeated, except that benzylamine was used instead of ethylamine. Thus, 4-(9-benzylcarbamoyl-9H-fluoren-9-yl)butyl bromide was obtained.

$^1$H-NMR (CDCl$_3$) δ: 0.80–0.89 (2H, m), 1.71 (2H, tt, J=7.1 Hz), 2.49 (2H, m), 3.21 (2H, t, J=7.1 Hz), 4.26 (2H, d, J=5.9 Hz), 5.45 (1H, brt, J=5.9 Hz), 6.92–6.96 (2H, m), 7.16–7.19 (3H, m), 7.36 (2H, dt, J=0.9, 7.6 Hz), 7.43 (2H, dt, J=0.9, 7.6 Hz), 7.59 (2H, d, J=7.6 Hz), 7.76 (2H, d, J=7.6 Hz).

TSIMS (M/Z): 434, 436 (M+H)$^+$.

(b) Step (b) of Example 92 was repeated, except that the compound prepared just above in step (a) was used instead of 4-[9-(2,2,2-trifluoroethylcarbamoyl)-9H-fluoren-9-yl] butyl bromide. Thus, the title compound was obtained.

$^1$H-NMR (CDCl$_3$) δ: 0.70–2.16 (12H, m), 2.48–2.63 (8H, m), 3.02 (4H, brs), 3.16 (2H, brs), 4.23–4.27 (5H, m), 5.47 (1H, brs), 6.94 (2H, d, J=6.4 Hz), 7.14–7.33 (6H, m), 7.36 (2H, d, J=7.2 Hz), 7.42 (2H, d, J=7.2 Hz), 7.60 (2H, d, J=7.3 Hz), 7.75 (2H, d, J=7.6 Hz).

TSIMS (M/Z): 653 (M+H)$^+$.

EXAMPLE 120

6-[4-[4-(9-Allylcarbamoyl-9H-fluoren-9-yl)butyl] piperazin-1-yl]-2-cyclohexyl-2,3-dihydro-1H-isoindol-1-one (a) Step (a) of Example 118 was repeated, except that allylamine was used instead of ethylamine. Thus, 4-(9-allylcarbamoyl-9H-fluoren-9-yl)butyl bromide was obtained.

$^1$H-NMR (CDCl$_3$) δ: 0.77–0.84 (2H, m), 1.69 (2H, tt, J=7.3 Hz), 2.49 (2H, m), 3.21 (2H, t, J=7.3 Hz), 3.67 (2H, m), 4.79 (1H, dd, J=1.4, 17.3 Hz), 4.92 (1H, dd, J=1.4, 10.5 Hz), 5.20 (1H, brs), 5.56–5.66 (1H, m), 7.37 (2H, dt, J=1.1, 7.6 Hz), 7.44 (2H, dt, J=1.1, J=1.1, 7.6 Hz), 7.59 (2H, d, J=7.6 Hz), 7.76 (2H, J=7.6 Hz).

TSIMS (M/Z): 384, 386 (M+H)$^+$.

(b) Step (c) of Example 92 was repeated, except that the compound prepared just above in step (a) was used instead of 4-[9-(2,2,2-trifluoroethylcarbamoyl)-9H-fluoren-9-yl] butyl bromide. Thus, the title compound was obtained.

$^1$H-NMR (CDCl$_3$) δ: 0.72 (2H, brs), 1.17–1.73 (10H, m), 1.85 (4H, brs), 2.17 (2H, brs), 2.48 (4H, brs), 2.54 (2H, m), 3.01 (2H, brs), 3.73 (2H, m), 4.25 (3H, m), 4.79 (1H, dd, J=1.4, 17.3 Hz), 4.92 (1H, dd, J=1.4, 10.5 Hz), 5.20 (1H, brs), 5.56–5.66 (1H, m), 7.14–7.48 (7H, m), 7.59 (2H, d, J=7.6 Hz), 7.76 (2H, J=7.6 Hz).

TSIMS (M/Z): 603 (M+H)$^+$.

EXAMPLE 121

2-Cyclohexyl-6-[4-[9-[allyl-(2,2,2-trifluoroethyl)] carbamoyl-9H-fluoren-9-yl]butyl]piperazin-1-yl]-2,3-dihydro-1H-isoindol-1-one The compound (0.100 g) prepared in Example 92 was dissolved in toluene (5 ml). Sodium hydroxide (0.019 g), potassium carbonate (0.041 g), tetrabutylammonium hydrogen sulfate (0.012 g), and allyl bromide (0.015 ml) were added to the solution, and the mixture was stirred at 60° C. overnight. Water was added to the reaction solution, and the mixture was extracted with ethyl acetate. The organic layer was dried over anhydrous magnesium sulfate, and the solvent was then removed by distillation under the reduced pressure. The residue was purified by preparative TLC (hexane:ethyl acetate=1:3) to give the title compound (0.017 g, 16.5%).

$^1$H-NMR (CDCl$_3$) δ: 0.49 (2H, m), 1.27–1.84 (10H, m), 2.12 (2H, m), 2.31 (2H, m), 2.44 (4H, m), 2.87 (2H, m), 3.15 (4H, m), 3.93 (2H, m), 4.25 (3H, m), 4.78 (5H, m), 7.06 (1H, dd, J=2.2, 8.5 Hz), 7.37 (8H, m), 7.79 (2H, d, J=7.4 Hz).

TSIMS (M/Z): 685 (M+H)$^+$.

EXAMPLE 122

2-Cyclohexyl-6-[4-[4-[9-[benzyl-(2,2,2-trifluoroethyl)]carbamoyl-9H-fluoren-9-yl]butyl] piperazin-1-yl]-2,3-dihydro-1H-isoindol-1-one The procedure of Example 121 was repeated, except that benzyl bromide was used instead of allyl bromide. Thus, the title compound was obtained.

$^1$H-NMR (CDCl$_3$) δ: 0.55 (2H, m), 0.90 (2H, m), 1.27 (8H, m), 1.86 (4H, m), 2.08 (2H, m), 2.46 (6H, m), 3.15 (4H, m), 3.41 (1H, m), 3.85 (1H, m), 4.26 (3H, m), 6.42 (1H, m), 7.09 (3H, m), 7.38 (10H, m), 7.73 (2H, d, J=7.2 Hz).

TSIMS (M/Z): 735 (M+H)$^+$.

EXAMPLE 123

2-Cyclohexyl-6-[4-[4-[9-[methyl-(2,2,2-trifluoroethyl)]carbamoyl-9H-fluoren-9-yl]butyl] piperazin-1-yl]-2,3-dihydro-1H-isoindol-1-one The procedure of Example 121 was repeated, except that methyl iodide was used instead of allyl bromide. Thus, the title compound was obtained.

$^1$H-NMR (CDCl$_3$) δ: 0.52 (2H, m), 0.89 (2H, m), 1.33 (2H, m), 1.46 (4H, m), 1.59–1.89 (7H, m), 2.09 (2H, m), 2.30 (2H, m), 2.42 (4H, m), 3.17 (4H, m), 3.97 (2H, m), 4.25 (3H, m), 7.07 (1H, dd, J=2.1, 8.3 Hz), 7.37 (8H, m), 7.78 (2H, d, J=7.4 Hz).

TSIMS (M/Z): 659 (M+H)$^+$.

EXAMPLE 124

2-Cyclohexyl-6-[4-[4-[5-(2,2,2-trifluoroethylcarbamoyl)-5H-dibenzosuberan-5-yl]-butyl]piperazin-1-yl]-2,3-dihydro-1H-isoindol-1-one (a) 5-Dibenzosuberanecarboxylic acid was synthesized using dibenzosuberane as a starting compound according to the method described in Tetrahedron., Vol. 54, 2251–2256 (1998).

$^1$H-NMR (CD$_3$OD) δ: 2.80–2.89 (2H, m), 3.32–3.40 (2H, m), 4.84 (1H, s), 7.10–7.19 (6H, m), 7.24–7.26 (2H, m).

FABMS (M/Z): 239 (M+H)$^+$.

(b) The compound (0.72 g) prepared just above in step (a) was dissolved in dichloromethane (60 ml). BOP reagent (1.59 g) and diisopropylethylamine (2.55 ml) were added to the solution. The mixture was stirred at room temperature for 30 min. 2,2,2-Trifluoroethylamine hydrochloride (0.81 g) was then added thereto, and the mixture was stirred at room temperature overnight. Water was added to the reaction solution, and the mixture was extracted with chloroform, followed by washing with saturated brine. The extract was dried over anhydrous MgSO$_4$, and the solvent was then removed by distillation under the reduced pressure. The residue was purified by column chromatography on silica gel (hexane:ethyl acetate=4:1) to give 5-dibenzosuberanecarboxylic acid (2,2,2-trifluoroethyl) amide (0.82 g).

$^1$H-NMR (CDCl$_3$) δ: 2.85–2.93 (2H, m), 3.23–3.32 (2H, m), 3.87 (2H, dq, J=9.0, 2.4 Hz), 4.65 (1H, s), 5.68 (1H, m), 7.17–7.27 (8H, m).

FABMS (M/Z): 320 (M+H)$^+$.

(c) The compound (0.42 g) prepared just above in step (b) was dissolved in anhydrous THF (13 ml). A 1.6 M n-butyllithiumhexane solution (0.89 ml) was added to the solution at −20° C., and the mixture was stirred for one hr. 1,4-Dibromobutane (0.47 ml) was added thereto, and the mixture was stirred at −20° C. for 2 hr. 1,4-Dibromobutane (0.17 ml) was then additionally added, and the mixture was stirred at 0° C. for one hr. Water was added to the reaction solution, and the mixture was extracted with chloroform, followed by washing with saturated brine. The extract was dried over anhydrous MgSO$_4$, and the solvent was then removed by distillation under the reduced pressure. The residue was purified by column chromatography on silica gel (hexane:ethyl acetate=9:1–2:1) to give 4-[5-(2,2,2-trifluoroethylcarbamoyl)-5H-dibenzo-suberan-5-yl]butyl bromide (76 mg).

$^1$H-NMR (CDCl$_3$) δ: 1.24–1.32 (2H, m), 1.79–1.86 (2H, m), 2.42–2.46 (2H, m), 3.07–3.23 (4H, m), 3.31 (2H, t, J=7.0 Hz), 3.85 (2H, dq, J=9.1, 2.5 Hz), 5.31 (1H, m), 7.11–7.21 (6H, m), 7.29–7.33 (2H, m).

TSIMS (M/Z): 454 (M+H)$^+$.

(d) Step (c) of Example 92 was repeated, except that the compound prepared just above in step (c) was used as the starting compound. Thus, the title compound was obtained.

$^1$H-NMR (CDCl$_3$) δ: 1.14–1.24 (3H, m), 1.38–1.48 (4H, m), 1.52–1.53 (2H, m), 1.70–1.73 (1H, m), 1.85 (4H, m), 2.33 (2H, t, J=7.0 Hz), 2.46–2.50 (2H, m), 2.56 (4H, m), 3.05–3.12 (2H, m), 3.19–3.23 (6H, m), 3.81–3.90 (2H, m), 4.23 (1H, m), 4.26 (2H, s), 5.38 (1H, m), 7.08–7.20 (7H, m), 7.28–7.35 (4H, m).

TSIMS (M/Z): 673 (M+H)$^+$.

EXAMPLE 125

2-[(Pyridin-2-yl)methyl]-7-[4-[4-[9-(2,2,2-trifluoroethylcarbamoyl)-9H-fluoren-9-yl]butyl] piperazin-1-yl]-3,4-dihydro-2H-isoquinolin-1-one (a) 7-(4-Tert-butoxycarbonyl-piperazin-1-yl)-3,4-dihydro-2H-isoquinolin-1-one was synthesized according to the method described in J. Med. Chem., Vol. 39, 4583 (1996).

$^1$H-NMR (CDCl$_3$) δ: 1.49 (9H, s), 2.29 (2H, t, J=6.6 Hz), 3.19 (4H, m), 3.60 (6H, m), 6.15 (1H, brs), 7.02 (1H, dd, J=8.3, 2.7 Hz), 7.13 (1H, d, J=8.3 Hz), 7.62 (1H, d, J=2.7 Hz).

(b) The compound (331 mg, 1 mmol) prepared just above in step (a) was dissolved in 10 ml of toluene. Sodium hydroxide (140 mg), 276 mg of potassium carbonate, 34 mg of tetrabutylammonium hydrogen sulfate, and 246 mg of 2-(chloromethyl)pyridine hydrochloride were added to the solution. The mixture was stirred at 75° C. for 20 hr. The reaction solution was diluted with ethyl acetate. The dilution was washed twice with water and was then dried over anhydrous magnesium sulfate. The solvent was removed by distillation under the reduced pressure. The residue was purified by column chromatography (development system, methylene chloride:methanol=50:1) to give 364 mg (yield 86%) of 2-[(pyridin-2-yl)methyl]-7-(4-tert-butoxycarbonyl-piperazin-1-yl)-3,4-dihydro-2H-isoquinolin-1-one as a white foam.

$^1$H-NMR (CDCl$_3$) δ: 1.60 (9H, s), 2.91 (2H, t, J=6.6 Hz), 3.16 (4H, t, J=5.1 Hz), 3.58 (4H, t, J=5.1 Hz), 3.63 (2H, t, J=6.6 Hz), 4.91 (2H, s), 7.01 (1H, dd, J=2.8, 8.4 Hz), 7.09 (1H, d, J=8.4 Hz), 7.17–7.21 (1H, m), 7.38 (1H, d, J=7.8 Hz), 7.65 (1H, dt, J=1.7, 7.8 Hz), 7.69 (1H, d, J=2.8 Hz), 8.54 (1H, d, J=4.1 Hz).

TSIMS (M/Z): 423 (M+H)$^+$.

(c) The compound (1.14 g, 3.4 mmol) prepared just above in step (b) was dissolved in 15 ml of methylene chloride. Trifluoroacetic acid (2.7 ml) was added to the solution, and the mixture was stirred at room temperature for 5 hr. The reaction solution was diluted with methylene chloride, and a saturated aqueous sodium hydrogencarbonate solution was added thereto, followed by extraction three times with methylene chloride. The organic layer was dried over anhydrous magnesium sulfate, and the solvent was removed by distillation under the reduced pressure to give 7-piperazin-1-yl-2-[(pyridin-2-yl)methyl]-3,4-dihydro-2H-isoquinolin-1-one (934 mg, yield 85%) as an orange oil.

$^1$H-NMR (CDCl$_3$) δ: 2.91 (2H, t, J=6.6 Hz), 3.04–3.08 (4H, m), 3.18–3.22 (4H, m), 3.63 (2H, t, J=6.6 Hz), 4.91 (2H, s), 7.01 (1H, dd, J=2.7, 8.3 Hz), 7.08 (1H, d, J=8.3 Hz), 7.17–7.21 (1H, m), 7.39 (1H, d, J=7.8 Hz), 7.65 (1H, dt, J=2.0, 7.8 Hz), 7.69 (1H, d, J=2.7 Hz), 8.54 (1H, d, J=4.9 Hz).

TSIMS (M/Z): 323 (M+H)$^+$.

(d) The compound (50 mg, 0.16 mmol) prepared just above in step (c) was dissolved in anhydrous DMF. Potassium carbonate (44 mg) and 66 mg of the compound prepared in step (a) of Example 87 were added to the solution, and the mixture was stirred at 50° C. for 20 hr and further at 80° C. for 4.5 hr. The reaction solution was diluted with ethyl acetate, and the dilution was washed twice with water, followed by drying over anhydrous magnesium sulfate. The solvent was removed by distillation under the reduced pressure, and the residue was purified by column chromatography (development system, methylene chloride:methanol=30:1) to give the title compound (57 mg, yield 85%) as a white foam.

$^1$H-NMR (CDCl$_3$) δ: 0.68–0.76 (2H, m), 1.32–1.41 (2H, m), 2.17 (2H, t, J=7.7 Hz), 2.42–2.49 (6H, m), 2.89 (2H, t, J=6.7 Hz), 3.15 (4H, t, J=4.9 Hz), 3.61 (2H, t, J=6.7 Hz), 3.65–3.74 (2H, m), 4.89 (2H, s), 5.39 (1H, t, J=6.5 Hz), 6.97 (1H, dd, J=2.7, 8.3 Hz), 7.05 (1H, d, J=8.3 Hz), 7.16–7.20 (1H, m), 7.35–7.40 (3H, m), 7.42–7.48 (2H, m), 7.56 (2H, d, J=7.6 Hz), 7.61–7.67 (2H, m), 7.76 (2H, d, J=7.6 Hz), 8.53 (1H, d, J=4.9 Hz).

TSIMS (M/Z): 668 (M+H)$^+$.

EXAMPLE 126

2-[(Pyridin-2-yl)methyl]-7-[4-[3-[9-(2,2,2-trifluoroethylcarbamoyl)-9H-fluoren-9-yl]propyl]piperazin-1-yl]-3,4-dihydro-2H-isoquinolin-1-one The compound (50 mg, 0.16 mmol) prepared in step (b) of Example 125 was dissolved in anhydrous DMF. Potassium carbonate (44 mg) and 66 mg of the compound prepared in step (a) of Example 93 were added to the solution. The mixture was stirred at 50° C. for 20 hr and further at 80° C. for 4.5 hr. The reaction solution was diluted with ethyl acetate, and the dilution was washed twice with water, followed by drying over anhydrous magnesium sulfate. The solvent was removed by distillation under the reduced pressure. The residue was purified by column chromatography (development system, methylene chloride:methanol=30:1) to give the title compound (46 mg, yield 71%) as a white foam.

$^1$H-NMR (CDCl$_3$) δ: 0.86–0.94 (2H, m), 2.20 (2H, t, J=7.4 Hz), 2.35 (4H, t, J=4.6 Hz), 2.46–2.51 (2H, m), 2.88 (2H, t, J=6.6 Hz), 3.12 (4H, t, J=4.6 Hz), 3.60 (2H, t, J=6.6 Hz), 3.65–3.72 (2H, m), 4.89 (2H, s), 5.29 (1H, t, J=6.6 Hz), 6.94 (1H, dd, J=2.7, 8.3 Hz), 7.04 (1H, d, J=8.3 Hz), 7.15–7.20 (1H, m), 7.34–7.40 (3H, m), 7.42–7.48 (2H, m), 7.56 (2H, d, J=7.6 Hz), 7.61–7.67 (2H, m), 7.78 (2H, d, J=7.6 Hz), 8.53 (1H, d, J=4.9 Hz).

TSIMS (M/Z): 654 (M+H)$^+$.

EXAMPLE 127

2-Cyclohexyl-6-[4-[2-[9-(2,2,2-trifluoroethylcarbamoyl)-9H-fluoren-9-yl]ethyl]piperazin-1-yl]-2,3-dihydro-1H-isoindol-1-one (a) n-Butyllithium (1.50 mol/l, n-hexane solution) was slowly added dropwise to a solution of fluorene-9-carboxylic acid (3.0 g) in THF in an argon atmosphere at −78° C. The mixture was stirred at −78° C. for 30 min and then at 0° C. for 30 min. The stirred mixture was again cooled to −78° C. Allyl bromide (2.5 ml) was slowly added dropwise thereto at −78° C., and the mixture was stirred at −78° C. for 30 min and then at room temperature overnight. After the disappearance of fluorene-9-carboxylic acid was confirmed by TLC, a saturated aqueous ammonium chloride solution was slowly added to the reaction solution. Ethyl acetate was then added thereto to perform extraction. The organic layer was washed with a saturated aqueous sodium chloride solution and was then dried over anhydrous magnesium sulfate. The solvent was removed by distillation under the reduced pressure. The residue was purified by column chromatography on silica gel (dichloromethane:methanol=20:1) to give 9-allyl-9H-fluorene-9-carboxylic acid (3.58 g) as a white solid.

$^1$H-NMR (CDCl$_3$) δ: 3.52 (2H, m), 4.18 (2H, m), 5.00 (1H, m), 7.34 (2H, t, J=7.6 Hz), 7.38 (2H, t, J=7.6 Hz), 7.59 (2H, d, J=7.6 Hz), 7.73 (2H, d, J=7.6 Hz).

TSIMS (M/Z): 251 (M+H)$^+$.

(b) A hydrochloric acid-ethanol solution of the compound (3.58 g) prepared just above in step (a) was refluxed for 4 hr, and the solvent was removed by distillation under the reduced pressure to give ethyl 9-allyl-9H-fluorene-9-carboxylate (3.99 g) as a white solid.

$^1$H-NMR (CDCl$_3$) δ: 1.13 (3H, t, J=7.0 Hz), 3.49 (2H, d, J=5.6 Hz), 4.11 (2H, q, J=7.0 Hz), 4.14 (2H, m), 5.09 (1H, m), 7.34 (2H, dt, J=1.2, 7.6 Hz), 7.38 (2H, dt, J=1.2, 7.6 Hz), 7.62 (2H, d, J=7.6 Hz), 7.74 (2H, d, J=7.6 Hz).

TSIMS (M/Z): 279 (M+H)$^+$.

(c) Water (5 ml) was added to a 1,4-dioxane solution (10 ml) of the compound (500 mg) prepared just above in step (b), and 4-methylmorpholine-N-oxide (631 mg) was added thereto. While stirring the mixture at room temperature, 4% osmium(VIII) oxide (1.1 ml) was slowly added to the mixture, followed by stirring at room temperature for 2 hr. After the disappearance of the starting compound was confirmed, the reaction solution was cooled to 0° C., and a saturated aqueous sodium chloride solution was slowly added to the cooled reaction solution. Ethyl acetate was then added thereto to perform extraction. The organic layer was dried over anhydrous magnesium sulfate, and the solvent was removed by distillation under the reduced pressure. The residue (532 mg) as such was added to and was dissolved in 1,4-dioxane (8 ml) and water (8 ml). Sodium periodate (886 mg) was added to the solution at room temperature, and the mixture was stirred at room temperature for one hr. After the disappearance of the diol as the starting compound was confirmed by TLC, a saturated aqueous sodium chloride solution and dichloroethane were added thereto to extract an organic layer. The organic layer was washed with an aqueous sodium thiosulfate solution and a saturated aqueous sodium chloride solution and was dried over anhydrous magnesium sulfate. The solvent was removed by distillation under the reduced pressure. The residue was purified by column chromatography on silica gel (ethyl acetate:n-hexane=1:4) to give ethyl 9-(2-oxo-ethyl)-9H-fluorene-9-carboxylate (400 mg) as a white oil.

$^1$H-NMR (CDCl$_3$) δ: 1.13 (3H, t, J=7.0 Hz), 3.28 (2H, d, J=1.7 Hz), 4.11 (2H, q, J=7.0 Hz), 7.34 (2H, dt, J=1.2, 7.6 Hz), 7.43 (2H, dt, J=1.2, 7.6 Hz), 7.60 (2H, d, J=7.6 Hz), 7.75 (2H, d, J=7.6 Hz), 9.39 (1H, t, J=1.7 Hz).

EIMS (M/Z): 280 (M$^+$).

(d) Step (a) of Example 51 was repeated, except that the compound (75 mg) prepared just above in step (c) and the compound prepared in step (a) of Example 92 were used to perform reductive amination. Thus, ethyl 9-[2-[4-(2-cyclohexyl-3-oxo-2,3-dihydro-1H-isoindol-5-yl)piperazin-1-yl]ethyl]-9H-fluorene-9-carboxylate (150 mg) was obtained as a white solid.

$^1$H-NMR (CDCl$_3$) δ: 1.13 (3H, t, J=7.0 Hz), 1.42–1.91 (12H, m), 2.41 (4H, brs), 2.60 (2H, t, J=7.5 Hz), 3.12 (4H, brs), 4.08 (2H, q, J=7.0 Hz), 4.21 (1H, brs), 4.24 (2H, s), 7.03 (1H, dd, J=2.4, 8.3 Hz), 7.28–7.30 (2H, m), 7.34 (2H, dt, J=1.2, 7.6 Hz), 7.41 (2H, dt, J=1.2, 7.6 Hz), 7.58 (2H, d, J=6.8 Hz), 7.73 (2H, d, J=7.6 Hz).

TSIMS (M/Z): 564 (M+H)$^+$.

(e) The compound (145 mg) prepared just above in step (d) was subjected to ester hydrolysis in the same manner as in step (c) of Example 1. Thus, 9-[2-[4-(2-cyclohexyl-3-oxo-2,3-dihydro-1H-isoindol-5-yl)piperazin-1-yl]-ethyl]-9H-fluorene-9-carboxylic acid (90 mg) was obtained as a white solid.

$^1$H-NMR (CDCl$_3$) δ: 1.38–1.93 (12H, m), 2.41 (4H, brs), 2.61 (2H, t, J=7.0 Hz), 3.12 (4H, brs), 4.21 (1H, brs), 4.24 (2H, 5), 7.03 (1H, d, J=7.5 Hz), 7.27–7.31 (2H, m), 7.34 (2H, dt, J=2.4, 7.6 Hz), 7.41 (2H, dt, J=2.4, 7.6 Hz), 7.60 (2H, d, J=7.6 Hz), 7.72 (2H, d, J=7.6 Hz).

(f) Step (b) of Example 124 was repeated, except that the compound (90 mg) prepared just above in step (e) was used as the starting compound. Thus, the title compound (55 mg) was obtained as a white solid.

$^1$H-NMR (CDCl$_3$) δ: 1.15–1.84 (12H, m), 2.38 (4H, brs), 2.69 (2H, t, J=7.4 Hz), 3.07 (4H, brs), 3.69 (2H, m), 4.21 (1H, brs), 4.23 (2H, s), 5.41 (1H, brs), 7.02 (1H, J=8.3 Hz), 7.25–7.28 (2H, m), 7.38 (2H, dt, J=3.7, 7.5 Hz), 7.45 (2H, dt, J=3.7, 7.5 Hz), 7.58 (2H, dd, J=3.2, 7.5), 7.77 (2H, dd, J=3.2, 7.5).

TSIMS (M/Z): 617 (M+H)$^+$.

EXAMPLE 128

8-Chloro-2-(3-methoxybenzyl)-7-[4-[4-[9-(2,2,2-trifluoroethylcarbamoyl)-9H-fluoren-9-yl]butyl]piperazin-1-yl]-3,4-dihydro-2H-isoquinolin-1-one (a) The compound (6.63 g) prepared in step (a) of Example 125 was dissolved in carbon tetrachloride (200 ml). N-Chlorosuccinimide (3.47 g) and AIBN (0.66 g) were added to the solution, and the mixture was heated at 90° C. with stirring for one hr. The temperature of the reaction solution was returned to room temperature. Chloroform was then added to the reaction solution, and the mixture was washed with water, followed by drying over anhydrous MgSO$_4$. The solvent was then removed by distillation under the reduced pressure. The residue was crudely purified by column chromatography on silica gel (ethyl acetate). The solvent was removed by distillation under the reduced pressure. Chloroform was added to the residue, and the precipitated crystal was collected by filtration (and washed with diethyl ether) to give 7-(4-tert-butoxycarbonyl-piperazin-1-yl)-8-chloro-3,4-dihydro-2H-isoquinolin-1-one (0.89 g).

$^1$H-NMR (CD$_3$OD) δ: 1.48 (9H, s), 2.89 (2H, t, J=6.2 Hz), 2.96 (4H, t, J=4.8 Hz), 3.37 (2H, t, J=6.2 Hz), 3.59 (4H, brs), 7.20–7.26 (2H, m).

TSIMS (M/Z): 366 (M+H)$^+$.

(b) Step (b) of Example 125 was repeated, except that the compound prepared just above in step (a) and 3-methoxybenzyl chloride were used as the starting compounds. Thus, 7-(4-tert-butoxycarbonyl-piperazin-1-yl)-8-chloro-2-(3-methoxybenzyl)-3,4-dihydro-2H-isoquinolin-1-one was obtained.

$^1$H-NMR (CDCl$_3$) δ: 1.49 (9H, s), 2.79 (2H, t, J=6.2 Hz), 2.98 (4H, m), 3.43 (2H, t, J,=6.2 Hz), 3.62 (4H, brs), 3.79 (3H, s), 4.77 (2H, s), 6.81–6.84 (1H, m), 6.90–6.93 (2H, m), 7.01–7.07 (2H, m), 7.23 (1H, d, J=7.8 Hz).

TSIMS (M/Z): 486 (M+H)$^+$.

(c) The compound prepared just above in step (b) was deprotected in the same manner as in step (c) of Example 125. Thus, 8-chloro-2-(3-methoxybenzyl)-7-piperazinyl-3,4-dihydro-2H-isoquinolin-1-one was obtained.

$^1$H-NMR (CDCl$_3$) δ: 2.79 (2H, t, J=6.2 Hz), 3.01–3.02 (4H, m), 3.07–3.09 (4H, m), 3.42 (2H, t, J=6.2 Hz), 3.79 (3H, s), 4.77 (2H, s), 6.82 (1H, dd, J=8.2, 2.4 Hz), 6.90 (1H, m), 6.92 (1H, d, J=7.8 Hz), 7.02 (1H, d, J=8.0 Hz), 7.09 (1H, d, J=8.0 Hz), 7.23 (1H, d, J=7.8 Hz).

TSIMS (M/Z): 386 (M+H)$^+$.

(d) Step (c) of Example 92 was repeated, except that the compound prepared just above in step (c) was used as the starting compound. Thus, the title compound was obtained.

$^1$H-NMR (CDCl$_3$) δ: 0.68–0.76 (2H, m), 1.34–1.41 (2H, m), 2.20 (2H, t, J=7.6 Hz), 2.44–2.48 (2H, m), 2.52 (4H, brs), 2.77 (2H, t, J=6.2 Hz), 2.99 (4H, brs), 3.41 (2H, t, J=6.2 Hz), 3.64–3.74 (2H, m), 3.78 (3H, s), 4.76 (2H, s), 5.36 (1H, t, J=6.5 Hz), 6.81 (1H, dd, J=8.3, 2.4 Hz), 6.89–6.92 (2H, m), 6.99 (1H, d, J=8.2 Hz), 7.06 (1H, d, J=8.2 Hz), 7.21–7.25 (1H, m), 7.38 (2H, t, J=7.4 Hz), 7.45 (2H, t, J=7.4 Hz), 7.56 (2H, d, J=7.4 Hz), 7.78 (2H, d, J=7.4 Hz).

TSIMS (M/Z): 731 (M+H)$^+$.

EXAMPLE 129

2-Cyclohexyl-6-[4-[4-(9-ethoxycarbonyl-9H-fluoren-9-yl)-butyl]piperazin-1-yl]-2,3-dihydro-1H-isoindol-1-one (a) 9-(4-Bromobutyl)-9-fluorenecarboxylic acid was synthesized using 9-fluorenecarboxylic acid as a starting compound according to the method described in U.S. Pat. No. 5,712,279.

$^1$H-NMR (CDCl$_3$) δ: 0.87–0.95 (2H, m), 1.67 (2H, qu, J=7.1 Hz), 2.31–2.36 (2H, m), 3.19 (2H, t, J=7.1 Hz), 7.33

(2H, dt, J=7.3, 1.2 Hz), 7.41 (2H, dt, J=7.3, 1.2 Hz), 7.54 (2H, d, J=7.3 Hz), 7.73 (2H, d, J=7.3 Hz).

FABMS (M/Z): 345 (M+H)+.

(b) The compound (0.17 g) prepared just above in step (a) was dissolved in ethanol (0.5 ml). Concentrated sulfuric acid (0.1 ml) was added to the solution, and the mixture was heated under reflux for 2 hr. After the temperature of the reaction solution was returned to room temperature, a saturated aqueous NaHCO$_3$ solution was added thereto and the mixture was extracted with ethyl acetate, followed by washing with saturated brine. The extract was dried over anhydrous MgSO$_4$, and the solvent was then removed by distillation under the reduced pressure. The residue was purified by column chromatography on silica gel (n-hexane:ethyl acetate=9:1) to give 4-(9-ethoxycarbonyl-9H-fluoren-9-yl) butyl bromide (0.18 g).

$^1$H-NMR (CDCl$_3$) δ: 0.88–0.96. (2H, m), 1.13 (3H, t, J=7.1 Hz), 1.65–1.72 (2H, m), 2.31–2.36 (2H, m), 3.20 (2H, t, J=6.9 Hz), 4.08 (2H, q, J=7.1 Hz), 7.33 (2H, dt, J=7.5, 1.2 Hz), 7.40 (2H, dt, J=7.5, 1.2 Hz), 7.54 (2H, d, J=7.5 Hz), 7.72 (2H, d, J=7.5 Hz).

TSIMS (M/Z): 373 (M+H)+.

(c) Step (c) of Example 92 was repeated, except that the compound prepared just above in step (b) was used as the starting compound. Thus, the title compound was obtained.

$^1$H-NMR (CDCl$_3$) δ: 0.76–0.84 (2H, m), 1.13 (3H, t, J=7.1 Hz), 1.11–1.17 (1H, m), 1.32–1.40 (2H, m), 1.43–1.48 (4H, m), 1.70–1.73 (1H, m), 1.84 (4H, m), 2.18 (2H, t, J=7.7 Hz), 2.34–2.38 (2H, m), 2.47 (4H, t, J=4.6 Hz), 3.17 (4H, t, J=4.9 Hz), 4.08 (2H, q, J=7.1 Hz), 4.22–4.23 (1H, m), 4.25 (2H, s), 7.07 (1H, dd, J=8.3, 2.5 Hz), 7.27–7.34 (4H, m), 7.39 (2H, dt, J=7.5, 1.2 Hz), 7.55 (2H, d, J=7.5 Hz), 7.72 (2H, d, J=7.5 Hz).

TSIMS (M/Z): 592 (M+H)+.

EXAMPLE 130

6-(4-[4-(9-Carboxy-9H-fluoren-9-yl)butyl]piperazin-1-yl]-2-cyclohexyl-2,3-dihydro-1H-isoindol-1-one The compound (50 mg) prepared in Example 129 was dissolved in a mixed solvent composed of THF (0.3 ml) and methanol (0.3 ml). 1 N NaOH (0.3 ml) was added to the solution, and the mixture was heated at 65° C. with stirring for 3 hr. The temperature of the reaction solution was returned to room temperature, and 1 N HCl was then added thereto, followed by extraction with chloroform. The extract was dried over anhydrous MgSO$_4$. The solvent was then removed by distillation under the reduced pressure. The residue was purified by preparative TLC (chloroform:methanol=5:1) to give the title compound (29 mg).

$^1$H-NMR (CDCl$_3$) δ: 1.01 (2H, m), 1.13–1.17 (1H, m), 1.39–1.47 (6H, m), 1.70–1.73 (1H, m), 1.84–1.85 (4H, m), 2.34 (2H, m), 2.43 (2H, t, J=7.6 Hz), 2.71 (4H, m), 3.13 (4H, m), 4.21 (1H, m), 4.24 (2H, s) 5.18 (1H, brs), 6.92 (1H, dd, J=8.3, 2.4 Hz), 7.23–7.35 (6H, m), 7.65–7.69 (4H, m).

FABMS (M/Z): 564 (M+H)+.

EXAMPLE 131

9H-Fluorene-9-carboxylic acid [3-[4-(2-cyclohexyl-3-oxo-2,3-dihydro-1H-isoindol-6-yl)piperazin-1-yl] propyl]amide (a) Bop reagent (253 mg) was added to a dichloromethane solution (5 ml) of fluorene-9-carboxylic acid (100 mg), and the mixture was stirred at room temperature for 30 min. Diisopropylethylamine (184 mg) was added thereto, and the mixture was stirred at room temperature for 30 min. 3-Aminopropanol (71 mg) was then added thereto, and the mixture was stirred at room temperature overnight. After the disappearance of the starting compound was confirmed by TLC, a saturated aqueous ammonium chloride solution was slowly added to the reaction solution and the mixture was then extracted with chloroform. The organic layer was washed with a saturated aqueous sodium chloride solution and was dried over anhydrous sodium sulfate. The solvent was removed by distillation under the reduced pressure. The residue was purified by column chromatography on silica gel (dichloromethane:methanol=20:1) to give 9H-fluorene-9-carboxylic acid [3-[4-(2-cyclohexyl-3-oxo-2,3-dihydro-1H-isoindol-5-yl)-piperazin-1-yl]propyl]amide as a white oil.

$^1$H-NMR (CDCl$_3$) δ: 1.82 (2H, tt, J=5.0, 6.5 Hz), 3.29 (2H, t, J=6.5 Hz), 3.60 (2H, t, J=5.0 Hz), 7.37 (2H, t, J=7.5 Hz), 7.46 (2H, d, J=7.5 Hz), 7.68 (2H, d, J=7.5 Hz), 7.80 (2H, d, J=7.5 Hz).

EIMS (M/Z): 267 (M+H)+.

(b) A dichloromethane solution (1 ml) of the compound (80 mg) prepared just above in step (a) was cooled to 0° C. Subsequently, methanesulfonic acid chloride (26 μl) and triethylamine (46 μl) were added dropwise to the cooled solution, and the mixture was stirred at 0° C. for 2 hr. After the disappearance of the starting compound was confirmed by TLC, a saturated aqueous ammonium chloride solution was slowly added to the reaction solution, and chloroform was then added thereto to extract an organic layer. The organic layer was washed with a saturated aqueous sodium chloride solution and was dried over anhydrous sodium sulfate. The solvent was removed by distillation under the reduced pressure to give 3-[(9H-fluorene-9-carbonyl) amino]propyl methanesulfonate (96 mg) as a yellow solid.

$^1$H-NMR (CDCl$_3$) δ: 1.84 (2H, tt, J=5.0, 6.9 Hz), 2.89 (3H, s), 3.26 (2H, t, J=6.9 Hz), 4.08 (2H, t, J=5.0 Hz), 7.37 (2H, dt, J=0.9, 7.5 Hz), 7.46 (2H, d, J=7.5 Hz), 7.68 (2H, dd, J=0.9, 7.5 Hz), 7.80 (2H, d, J=7.5 Hz).

FABMS (M/Z): 346 (M+H)+.

(c) 2-Cyclohexyl-6-(piperazin-1-yl)-2,3-dihydro-1H-isoindol-1-one (90 mg) synthesized according to the method described in WO 9854135 and potassium carbonate (82 mg) were added to a DMF solution (1 ml) of the compound (96 mg) prepared just above in step (b), and the mixture was stirred at room temperature overnight. A saturated aqueous ammonium chloride solution was added to the reaction solution, and ethyl acetate was then added thereto to perform extraction. The organic layer was washed with a saturated aqueous sodium chloride solution and was dried over anhydrous magnesium sulfate. The solvent was then removed by distillation under the reduced pressure. The residue was purified by column chromatography on silica gel (dichloromethane:methanol=20:1) to give the title compound (35 mg) as a white solid.

$^1$H-NMR (CDCl$_3$) δ: 1.42–1.91(12H, m), 2.26 (4H, t, J=6.3 Hz), 2.31 (4H, brs), 2.82 (4H, brs), 3.30 (2H, dt, J=3.9, 6.3 Hz), 4.28 (1H, brs), 4.30 (2H, s), 4.79 (1H, s), 6.21 (1H, brs), 7.03 (1H, dd, J=2.4, 8.3 Hz), 7.28–7.38 (6H, m), 7.67 (4H, d, J=6.8 Hz).

TSIMS (M/Z): 549 (M+H)+.

EXAMPLE 132

9-[2-[4-(2-Cyclohexyl-3-oxo-2,3-dihydro-1H-isoindol-5-yl)piperazin-1-yl]ethoxy]-9H-fluorene-9-carboxylic acid (2,2,2-trifluoroethyl)amide (a) Sodium hydride (1.33 g) was slowly added to a THF solution (100 ml) of 9-hydroxy-9-fluorene-9-carboxylic acid (5.0 g) at 0° C. with stirring. The temperature of the reaction solution was then slowly raised to room temperature, and the reaction solution was stirred for 2 hr. Allyl bromide (7.56 ml) was added thereto, and the mixture was further stirred overnight. The reaction solution was cooled to 0° C., and a 1 N aqueous hydrochloric acid solution was slowly added to render the cooled reaction solution neutral, followed by the addition of ethyl acetate to perform extraction. The organic layer was washed with a saturated aqueous sodium chloride solution and was dried over anhydrous magnesium sulfate. The solvent was removed by distillation under the reduced pressure. The residue was purified by column chromatography on silica gel (dichloromethane:methanol=15:1) to give 9-allyloxy-9H-fluorene-9-carboxylic acid (6.6 g) as a white solid.

$^1$H-NMR (CDCl$_3$) δ: 3.48 (2H, d, J=5.4 Hz), 5.03 (2H, m), 5.71 (1H, m), 7.27 (2H, t, J=7.3 Hz), 7.41 (2H, t, J=7.5 Hz), 7.47 (2H, d, J=7.3 Hz), 7.64 (2H, d, J=7.5 Hz).

TSIMS (M/Z): 267 (M+H)$^+$.

(b) Step (b) of Example 124 was repeated, except that the compound (5.5 g) prepared just above in step (a) was used as the starting compound. Thus, 9-allyloxy-9H-fluorene-9-carboxylic acid (2,2,2-trifluoroethyl)amide (1.54 g) was obtained as a white oil.

$^1$H-NMR (CDCl$_3$) δ: 3.49 (2H, d, J=5.6 Hz), 4.00 (2H, m), 5.10 (1H, m), 5.77 (2H, m), 7.31 (2H, t, J=7.3 Hz), 7.38–7.44 (4H, m), 7.67 (2H, d, J=7.3 Hz).

TSIMS (M/Z): 348 (M+H)$^+$.

(c) Water (5 ml) was added to a 1,4-dioxane solution (10 ml) of the compound (500 mg) prepared just above in step (b), and 4-methylmorpholine-N-oxide (631 mg) was then added thereto. 4% osmium(VIII) oxide (1.1 ml) was slowly added to the mixture at room temperature with stirring, and the mixture was stirred at room temperature for 2 hr. After the disappearance of the starting compound was confirmed, the reaction solution was cooled to 0° C. A saturated aqueous sodium chloride solution was slowly added to the cooled reaction solution, and ethyl acetate was then added thereto to perform extraction. The organic layer was dried over anhydrous magnesium sulfate. The solvent was removed by distillation under the reduced pressure. The residue (532 mg) as such was added to and dissolved in 1,4-dioxane (8 ml) and water (8 ml). Sodium periodate (886 mg) was added to the solution at room temperature, and the mixture was stirred at room temperature for one hr. After the disappearance of the diol as the starting compound was confirmed by TLC, a saturated aqueous sodium chloride solution and dichloroethane were added to perform extraction. The organic layer was washed with an aqueous sodium thiosulfate solution and a saturated aqueous sodium chloride solution and was dried over anhydrous magnesium sulfate. The solvent was then removed by distillation under the reduced pressure. The residue was purified by column chromatography on silica gel (ethyl acetate:n-hexane=1:4) to give 9-(2-oxo-ethoxy)-9H-fluorene-9-carboxylic acid (2,2,2-trifluoroethyl)amide (400 mg) as a white oil.

$^1$H-NMR (CDCl$_3$) δ: 3.67 (2H, m), 4.45 (2H, d, J=1.6 Hz), 7.42 (2H, dt, J=1.2, 7.6 Hz), 7.45 (2H, dt, J=1.2, 7.6 Hz), 7.62 (2H, d, J=7.6 Hz), 7.75 (2H, d, J=7.6 Hz), 9.41 (1H, t, J=1.6 Hz).

TSIMS (M/Z): 350 (M+H)$^+$.

(d) The compound (80 mg) prepared in step (a) of Example 92 was added to a dichloroethane solution (2 ml) of the compound (100 mg) prepared just above in step (c). Acetic acid (19 mg) and sodium triacetoxyboron hydride (80 mg) were then added thereto, and the mixture was heated at 80° C. for 5 hr. After the disappearance of substantially the whole starting compound by TLC was confirmed, a saturated aqueous sodium chloride solution and dichloroethane were added to perform extraction. The organic layer was dried over anhydrous magnesium sulfate, and the solvent was then removed by distillation under the reduced pressure. The residue was purified by column chromatography on silica gel (dichloromethane:methanol=20:1) to give the title compound (52 mg) as a white solid.

$^1$H-NMR (CDCl$_3$) δ: 1.14–1.85 (10H, m), 2.55 (4H, brs), 3.10 (2H, t, J=5.2 Hz), 3.27 (4H, brs), 3.46 (2H, t, J=5.2 Hz), 3.93–4.02 (2H, m), 4.20 (1H, m), 4.21 (2H, s), 7.10 (1H, dd, J=2.4, 8.3 Hz), 7.27–7.45 (6H, m), 7.68 (4H, d, J=6.8 Hz).

TSIMS (M/Z): 633 (M+H)$^+$.

EXAMPLE 133

2-Cyclohexyl-6-[4-[4-[9-(2,2,2-trifluoroethylcarbamoyl)-9H-thioxanthen-9-yl]butyl] piperazin-1-yl]-2,3-dihydro-1H-isoindol-1-one (a) Thioxanthone (0.21 g) was dissolved in ethylene glycol (1.5 ml). Potassium hydroxide (0.19 g) and hydrazine monohydrate (0.15 ml) were added to the solution. The mixture was heated at 140° C. with stirring for 2 hr and then at 200° C. for 4 hr. The temperature of the reaction solution was returned to room temperature. Water was then added to the reaction solution, and the mixture was extracted with ethyl acetate. The extract was dried over anhydrous MgSO$_4$. The solvent was then removed by distillation under the reduced pressure. The residue was purified by column chromatography on silica gel (chloroform) to give thioxanthene (0.12 g).

$^1$H-NMR (CDCl$_3$) δ: 3.86 (2H, s), 7.16–7.23 (4H, m), 7.31–7.33 (2H, m), 7.43–7.45 (2H, m).

ESIMS (M/Z): 198 (M+H)$^+$.

(b) 9-Thioxanthenecarboxylic acid was synthesized using the compound prepared just above in step (a) as a starting compound according to the method described in Tetrahedron., Vol. 54, 2251–2256 (1998).

$^1$H-NMR (CDCl$_3$) δ: 5.02 (1H, s), 7.22–7.28 (4H, m), 7.34–7.39 (2H, m), 7.40–7.44 (2H, m).

ESIMS (M/Z): 242 (M+H)$^+$.

(c) 9-(4-Bromobutyl)-9-thioxanthenecarboxylic acid was synthesized using the compound prepared just above in step (b) as a starting compound according to the method described in U.S. Pat. No. 5,712,279.

$^1$H-NMR (CDCl$_3$) δ: 1.18–1.26 (2H, m), 1.65–1.73 (2H, m), 2.12–2.16 (2H, m), 3.23 (2H, t, J=7.0 Hz), 7.20–7.27 (6H, m), 7.31–7.34 (2H, m).

FABMS (M/Z): 378 (M+H)$^+$.

(d) 4-[9-(2,2,2-Trifluoroethylcarbamoyl)-9H-thioxanthen-9-yl]butyl bromide was synthesized using the compound prepared just above in step (c) as a starting compound according to the method described in U.S. Pat. No. 5,712,279.

$^1$H-NMR (CDCl$_3$) δ: 1.14–1.22 (2H, m), 1.65–1.72 (2H, m), 2.14–2.18 (2H, m), 3.29 (2H, t, J=7.1 Hz), 3.89 (2H, dq, J=9.1, 2.4 Hz), 5.39 (1H, t, J=6.5 Hz), 7.18–7.31 (8H, m).

FABMS (M/Z): 458 (M+H)$^+$.

(e) Step (c) of Example 92 was repeated, except that the compound prepared just above in step (d) was used as the starting compound. Thus, the title compound was obtained.

$^1$H-NMR (CDCl$_3$) δ: 1.05–1.17 (3H, m), 1.34–1.41 (2H, m), 1.43–1.48 (4H, m), 1.70–1.73 (1H, m), 1.84–1.86 (4H, m), 2.19–2.25 (4H1 m), 2.49 (4H, t, J=4.8 Hz), 3.17 (4H, t, J=4.8 Hz), 3.88 (2H, dq, J=9.0, 2.5 Hz), 4.22–4.23 (1H, m), 4.25 (2H, s), 5.42 (1H, t, J=6.6 Hz), 7.07 (1H, dd, J=8.5, 2.4 Hz), 7.17–7.30 (9H, m), 7.31 (1H, d, J=2.4 Hz).

FABMS (M/Z): 677 (M+H)$^+$.

EXAMPLE 134

2-Benzyl-6-[4-[4-[9-(2,2,2-trifluoroethylcarbamoyl)-9H-fluoren-9-yl]butyl]piperazin-1-yl]-3,4-dihydro-2H-isoquinolin-1-one (a) 6-Fluoro-3,4-dihydro-2H-isoquinolin-1-one (0.99 g) prepared according to the method described in J. Med. Chem., Vol. 39, 4583–4591 (1996) was dissolved in dimethyl sulfoxide (2.5 ml). N-t-Butoxycarbonylpiperazine (3.4 g) was added to the solution, and the mixture was stirred at 120° C. overnight. Water was added to the reaction solution, and the mixture was extracted with ethyl acetate. The organic layer was dried over anhydrous magnesium sulfate, and the solvent was then removed by distillation under the reduced pressure. The residue was purified by column chromatography on silica gel (n-hexane:ethyl acetate=1:3) to give 6-[4-(t-butoxycarbonyl)piperazin-1-yl]-3,4-dihydro-2H-isoquinolin-1-one (0.495 g, 24.9%).

$^1$H-NMR (CDCl$_3$) δ: 1.48 (9H, s), 2.93 (2H, t, J=6.6 Hz), 3.28 (4H, m), 3.53 (2H, dt, J=2.9, 6.6 Hz), 3.57 (4H, m), 5.84 (1H, brs), 6.62 (1H, dt, J=2.5 Hz), 6.81 (1H, dd, J=2.5, 8.5 Hz), 7.94 (1H, d, J=8.5 Hz).

TSIMS (M/Z): 332 (M+H)$^+$.

(b) Step (b) of Example 125 was repeated, except that the compound prepared just above in step (a) was used instead of the compound prepared in Example 92. Thus, 2-benzyl-6-[4-(t-butoxycarbonyl)piperazin-1-yl]3,4-dihydro-2H-isoquinolin-1-one was obtained.

$^1$H-NMR (CDCl$_3$) δ: 1.48 (9H, s), 2.87 (2H, t, J=6.5 Hz), 3.26 (4H, m), 3.44 (2H, t, J=6.5 Hz), 3.57 (4H, m), 4.76 (2H, s), 6.58 (1H, d, J=2.4 Hz), 6.83 (1H, dd, J=2.4, 8.7 Hz), 7.30 (5H, m), 8.02 (1H, d, J=8.7 Hz).

TSIMS (M/Z): 422 (M+H)$^+$.

(c) The compound (0.10 g) prepared just above in step (b) was dissolved in methylene chloride (5 ml). Trifluoroacetic acid (2 ml) was added to the solution, and the mixture was stirred at room temperature overnight. The reaction solution was evaporated to dryness under the reduced pressure. The solid thus obtained as such was used in a next reaction without any purification.

(d) Step (c) of Example 92 was repeated, except that the compound prepared just above in step (c) was used as the starting compound. Thus, the title compound was obtained.

$^1$H-NMR (CDCl$_3$) δ: 0.70–1.50 (6H, m), 2.17 (1H, m), 2.42 (6H, m), 2.87 (2H, m), 3.21 (2H, m), 3.45 (3H, m), 3.69 (2H, m), 4.76 (2H, s), 5.35 (1H, m), 6.55 (1H, m), 6.81 (1H, m), 7.29–7.45 (9H, m), 7.53 (2H, d, J=7.5 Hz), 7.76 (2H, d, J=7.5 Hz), 8.01 (1H, dd, J=8.5, 20.9 Hz).

TSIMS (M/Z): 667 (M+H)$^+$.

EXAMPLE 135

2-Cyclohexyl-6-[4-[4-[10-oxo-9-(2,2,2-trifluoroethylcarbamoyl)-9,10-dihydro-10λ$^4$-thioxanthen-9-yl]butyl]piperazin-1-yl]-2,3-dihydro-1H-isoindol-1-one (a) The compound (46 mg) prepared in step (d) of Example 133 was dissolved in dichloromethane (1 ml). m-Chloroperbenzoic acid (19 mg) was added to the solution at 0° C., and the mixture was stirred at 0° C. for one hr. Water was added to the reaction solution, and the mixture was extracted with chloroform. The extract was dried over anhydrous MgSO$_4$, and the solvent was then removed by distillation under the reduced pressure. The residue was purified by preparative TLC (n-hexane:ethyl acetate=1:4) to give 4-[10-oxo-9-(2,2,2-trifluoroethylcarbamoyl)-9,10-dihydro-10λ$^4$-thioxanthen-9-yl]butyl bromide (38 mg).

$^1$H-NMR (CDCl$_3$) δ: 0.87–0.95 (2H, m), 1.65–1.72 (2H, m), 2.27–2.32 (2H, m), 3.22 (2H, t, J=6.7 Hz), 3.81 (2H, dq, J=9.0, 2.5 Hz), 6.24 (1H, t, J=6.4 Hz), 7.47–7.52 (2H, m), 7.58–7.62 (4H, m), 8.01–8.05 (2H, m).

FABMS (M/Z): 474 (M+H)$^+$.

(b) Step (c) of Example 92 was repeated, except that the compound prepared just above in step (a) was used as the starting compound. Thus, the title compound was prepared.

$^1$H-NMR (CDCl$_3$) δ: 0.75–0.82 (2H, m), 1.24–1.30 (2H, m), 1.32–1.40 (2H, m), 1.43–1.48 (3H, m), 1.70–1.73 (1H, m), 1.85 (4H, m), 2.17–2.20 (2H, m), 2.31–2.35 (2H, m), 2.46 (4H, m), 3.14 (4H, m), 3.77–3.85 (2H, m), 4.22–4.25 (1H, m), 4.25 (2H, s), 6.25 (1H, t, J=6.4 Hz), 7.06 (1H, dd, J=8.5, 2.4 Hz), 7.27 (1H, m), 7.30 (1H, d, J=2.4 Hz), 7.51 (2H, dd, J=5.9, 3.3 Hz), 7.59 (4H, dd, J=5.9, 3.3 Hz), 8.03 (2H, dd, J=5.9, 3.3 Hz).

TSIMS (M/Z): 693 (M+H)$^+$.

EXAMPLE 136

2-Cyclohexyl-6-[4-[4-[10,10-dioxo-9-(2,2,2-trifluoroethylcarbamoyl)-9,10-dihydro-10λ$^6$-thioxanthen-9-yl]butyl]piperazin-1-yl]-2,3-dihydro-1H-isoindol-1-one (a) The compound (46 mg) prepared in step (d) of Example 133 was dissolved in dichloromethane (1 ml). m-Chloroperbenzoic acid (76 mg) was added to the solution at 0° C. The mixture was stirred at 0° C. for 30 min and then at room temperature for one hr. A saturated aqueous NaHCO$_3$ solution was added to the reaction solution, and the mixture was extracted with chloroform. The extract was dried over anhydrous MgSO$_4$, and the solvent was then removed by distillation under the reduced pressure. The residue was purified by preparative TLC (n-hexane:ethyl acetate=1:4) to give 4-[10,10-dioxo-9-(2,2,2-trifluoroethylcarbamoyl)-9,10-dihydro-10λ$^6$-thio-xanthen-9-yl]butyl bromide (50 mg).

$^1$H-NMR (CDCl$_3$) δ: 1.00–1.08 (2H, m), 1.65–1.72 (2H, m), 2.45–2.49 (2H, m), 3.21 (2H, t, J=7.0 Hz), 3.81 (2H, dq, J=8.9, 2.3 Hz), 5.41 (1H, t, J=6.2 Hz), 7.48 (2H, dd, J=7.6, 1.4 Hz), 7.62 (2H, dt, J=7.6, 1.4 Hz), 7.67 (2H, dt, J=7.6, 1.4 Hz), 8.17 (2H, dd, J=7.6, 1.4 Hz).

TSIMS (M/Z): 490 (M+H)$^+$.

(b) Step (c) of Example 92 was repeated, except that the compound prepared just above in step (a) was used as the starting compound. Thus, the title compound was obtained.

$^1$H-NMR (CDCl$_3$) δ: 0.87–0.94 (2H, m), 1.14–1.30 (2H, m), 1.33–1.40 (2H, m), 1.43–1.50 (3H, m), 1.70–1.73 (1H, m), 1.84–1.85 (4H, m), 2.20 (2H, t, J=7.4 Hz), 2.46–2.52 (6H, m), 3.14 (4H, m), 3.76–3.84 (2H, m), 4.21 (1H, m), 4.25 (2H, s), 5.51 (1H, t, J=6.5 Hz), 7.06 (1H, dd, J=8.3, 2.2 Hz), 7.26–7.29 (2H, m), 7.49 (2H, d, J=7.9 Hz), 7.58–7.68 (4H, m), 8.13 (2H, dd, J=7.9, 1.4 Hz).

TSIMS (M/Z): 709 (M+H)$^+$.

EXAMPLE 137

2-Benzyl-7-[4-[4-[9-(2,2,2-trifluoroethylcarbamoyl)-9H-fluoren-9-yl]butyl]piperazin-1-yl]-2H-phthalazin-1-one (a) 3-Bromo-6-nitrophthalide was synthesized using 6-nitrophthalide as a starting compound according to the method described in J. Chem. Soc., 5275 (1961).

¹H-NMR (CDCl₃) δ: 7.48 (1H, s), 7.84 (1H, d, J=8.5 Hz), 8.65 (1H, dd, J=8.5, 1.9 Hz), 8.77 (1H, d, J=1.9 Hz).

TSIMS (M/Z): 258 (M+H)⁺.

(b) 1,2-Dihydro-7-nitro-1-oxophthalazine was synthesized using the compound prepared just above in step (a) as a starting compound according to the method described in J. Chem. Soc., 5275 (1961).

¹H-NMR (CD₃OD) δ: 8.13 (1H, d, J=8.8 Hz), 8.44 (1H, s), 8.67 (1H, dd, J=8.8, 2.4 Hz), 9.09 (1H, d, J=2.4 Hz).

TSIMS (M/Z): 190 (M+H)⁺.

(c) Step (b) of Example 125 was repeated, except that the compound prepared just above in step (b) and benzyl bromide were used as the starting compounds. Thus, 2-benzyl-7-nitro-2H-phthalazin-1-one was obtained.

¹H-NMR (CDCl₃) δ: 5.43 (2H, s), 7.27–7.36 (3H, m), 7.47–7.49 (2H, m), 7.86 (1H, d, J=8.6 Hz), 8.26 (1H, s), 8.58 (1H, dd, J=8.6, 2.3 Hz), 9.27 (1H, d, J=2.3 Hz).

ESIMS (M/Z): 281 (M+H)⁺.

(d) The compound prepared just above in step (c) was reduced in the same manner as described in WO 9854135 to give 7-amino-2-benzyl-2H-phthalazin-1-one.

¹H-NMR (CDCl₃) δ: 4.30 (2H, brs), 5.38 (2H, s), 7.04 (1H, dd, J=8.5, 2.5 Hz), 7.23–7.33 (3H, m), 7.43–7.45 (2H, m), 7.47 (1H, d, J=8.5 Hz), 7.57 (1H, d, J=2.5 Hz), 7.99 (1H, s).

TSIMS (M/Z): 252 (M+H)⁺.

(e) The compound prepared just above in step (d) was piperazinated in the same manner as described in WO 9854135. Thus, 2-benzyl-7-piperazinyl-2H-phthalazin-1-one was obtained.

¹H-NMR (CDCl₃) δ: 3.03–3.05 (4H, m), 3.37–3.39 (4H, m), 5.39 (2H, s), 7.23–7.34 (4H, m), 7.44–7.46 (2H, m), 7.54 (1H, d, J=9.0 Hz), 7.73 (1H, d, J=2.7 Hz), 8.02 (1H, s).

ESIMS (M/Z): 320 (M+H)⁺.

(f) Step (c) of Example 92 was repeated, except that the compound prepared just above in step (e) was used as the starting compound. Thus, the title compound was obtained.

¹H-NMR (CDCl₃) δ: 0.69–0.77 (2H, m), 1.33–1.43 (2H, m), 2.18 (2H, t, J=7.7 Hz), 2.44–2.48 (6H, m), 3.34 (4H, t, J=5.0 Hz), 3.69 (2H, dq, J=8.9, 2.4 Hz), 5.36–5.38 (3H, m), 7.23–7.32 (4H, m), 7.36–7.40 (2H, m), 7.43–7.47 (4H, m), 7.51–7.57 (3H, m), 7.68 (1H, d, J=2.5 Hz), 7.78 (2H, d, J=7.5 Hz), 8.01 (1H, s).

TSIMS (M/Z): 666 (M+H)⁺.

EXAMPLE 138

2-Benzyl-7-[4-[4-[9-(2,2,2-trifluoroethylcarbamoyl)-9H-xanthen-9-yl]butyl]piperazin-1-yl]-2H-phthalazin-1-one (a) Step (b) of Example 96 was repeated, except that the compound prepared in step (e) of Example 137 was used as the starting compound. Thus, the title compound was obtained.

¹H-NMR (CDCl₃) δ: 0.80–0.88 (2H, m), 1.32–1.40 (2H, m), 2.16–2.20 (2H, m), 2.27–2.31 (2H, m), 2.44 (4H, t, J=4.9 Hz), 3.32 (4H, t, J=4.9 Hz), 3.80 (2H, dq, J=8.9, 2.2 Hz), 5.37 (2H, s), 5.49 (1H, t, J=6.6 Hz), 7.08–7.12 (4H, m), 7.22–7.32 (8H, m), 7.41–7.44 (2H, m), 7.52 (1H, d, J=8.8 Hz), 7.67 (1H, d, J=2.6 Hz), 7.99 (1H, s).

TSIMS (M/Z): 682 (M+H)⁺.

EXAMPLE 139

2-Benzyl-7-[4-[3-[9-(2,2,2-trifluoroethylcarbamoyl)-9H-fluoren-9-yl]propyl]piperazin-1-yl]-2H-phthalazin-1-one (a) Step (b) of Example 93 was repeated, except that the compound prepared in step (e) of Example 137 was used as the starting compound. Thus, the title compound was obtained.

¹H-NMR (CDCl₃) δ: 0.87–0.95 (2H, m), 2.21 (2H, t, J=7.3 Hz), 2.35–2.37 (4H, m), 2.47–2.51 (2H, m), 3.30–3.33 (4H, m), 3.65–3.74 (2H, m), 5.36–5.39 (3H, m), 7.24–7.32 (4H, m), 7.36–7.48 (6H, m), 7.51 (1H, d, J=9.0 Hz), 7.56 (2H, d, J=7.5 Hz), 7.66 (1H, d, J=2.5 Hz), 7.78 (2H, d, J=7.5 Hz), 8.00 (1H, s).

TSIMS (M/Z): 652 (M+H)⁺.

EXAMPLE 140

2-Benzyl-7-[4-[3-[9-(2,2,2-trifluoroethylcarbamoyl)-9H-xanthen-9-yl]propyl]piperazin-1-yl]-2H-phthalazin-1-one Step (c) of Example 92 was repeated, except that the compound prepared in step (b) of Example 114 and the compound prepared in step (e) of Example 137 were used as the starting compounds. Thus, the title compound was obtained.

¹H-NMR (CDCl₃) δ: 1.03–1.07 (2H, m), 2.21 (2H, t, J=7.1 Hz), 2.31–2.35 (6H, m), 3.30 (4H, m), 3.81 (2H, dq, J=9.0, 2.2 Hz), 5.37 (2H, s), 5.48 (1H, t, J=6.5 Hz), 7.09–7.13 (4H, m), 7.22–7.33 (8H, m), 7.42–7.44 (2H, m), 7.51 (1H, d, J=9.1 Hz), 7.65 (1H, d, J=2.4 Hz), 8.00 (1H, s).

TSIMS (M/Z): 668 (M+H)⁺.

EXAMPLE 141

2-(Tetrahydropyran-2-yl)methyl-7-[4-[4-[9-(2,2,2-trifluoroethylcarbamoyl)-9H-fluoren-9-yl]butyl]piperazin-1-yl]-2H-phthalazin-1-one (a) Step (b) of Example 125 was repeated, except that the compound prepared in step (b) of Example 137 and tetrahydro-2H-pyran-2-methyl bromide were used as the starting compounds. Thus, 7-nitro-2-(tetrahydropyran-2-yl)methyl-2H-phthalazin-1-one was obtained.

¹H-NMR (CDCl₃) δ: 1.37–1.67 (4H, m), 1.71–1.74 (1H, m), 1.87–1.91 (1H, m), 3.34 (1H, dt, J=11.6, 2.2 Hz), 3.85–3.92 (1H, m), 3.94–3.98 (1H, m), 4.29–4.31 (2H, m), 7.88 (1H, d, J=8.6 Hz), 8.28 (1H, s), 8.59 (1H, dd, J=8.6, 2.3 Hz), 9.27 (1H, d, J=2.3 Hz).

TSIMS (M/Z): 290 (M+H)⁺.

(b) The compound prepared just above in step (a) was reduced in the same manner as described in WO 9854135 to give 7-amino-2-(tetrahydropyran-2-yl)methyl-2H-phthalazin-1-one.

¹H-NMR (CDCl₃) δ: 1.38–1.70 (5H, m), 1.83–1.87 (1H, m), 3.35 (1H, dt, J=11.6, 2.1 Hz), 3.84–3.90 (1H, m), 3.95–3.99 (1H, m), 4.23–4.25 (2H, m), 4.30 (2H, brs), 7.06 (1H, dd, J=8.4, 2.4 Hz), 7.49 (1H, d, J=8.4 Hz), 7.55 (1H, d, J=2.4 Hz), 8.01 (1H, s).

TSIMS (M/Z): 260 (M+H)⁺.

(c) The compound prepared just above in step (b) was piperazinated in the same manner as described in WO 9854135 to give 7-piperazinyl-2-(tetrahydropyran-2-yl)methyl-2H-phthalazin-1-one.

¹H-NMR (CDCl₃) δ: 1.38–1.63 (4H, M), 1.67–1.70 (1H, m), 1.83–1.87 (1H, m), 3.04–3.07 (4H, m), 3.32–3.40 (5H, m), 3.84–3.91 (1H, m), 3.95–3.99 (1H, m), 4.21–4.31 (2H, m), 7.35 (1H, dd, J=8.9, 2.6 Hz), 7.56 (1H, d, J=8.9 Hz), 7.72 (1H, d, J=2.6 Hz), 8.03 (1H, s).

TSIMS (M/Z): 329 (M+H)⁺.

(d) Step (c) of Example 92 was repeated, except that the compound prepared just above in step (c) was used as the starting compound. Thus, the title compound was obtained.

¹H-NMR (CDCl₃) δ: 0.72–0.76 (2H, m), 1.33–1.62 (7H, m), 1.83 (1H, m), 2.20 (2H, t, J=7.7 Hz), 2.44–2.48 (6H, m), 3.32–3.38 (5H, m), 3.65–3.74 (2H, m), 3.85–3.88 (1H, m), 3.94–3.97 (1H, m), 4.20–4.26 (2H, m), 5.38 (1H, t, J=6.5 Hz), 7.30 (1H, dd, J=8.9, 2.6 Hz), 7.38 (2H, dt, J=7.5, 1.1 Hz), 7.45 (2H, dt, J=7.5, 1.1 Hz), 7.53 (1H, d, J=8.9 Hz), 7.56 (2H, d, J=7.5 Hz), 7.68 (1H, d, J=2.6 Hz), 7.78 (2H, d, J=7.5 Hz), 8.01 (1H, s).

TSIMS (M/Z): 674 (M+H)⁺.

EXAMPLE 142

2-(Tetrahydropyran-2-yl)methyl-7-[4-[4-[9-(2,2,2-trifluoroethylcarbamoyl)-9H-xanthen-9-yl]butyl]piperazin-1-yl]-2H-phthalazin-1-one (a) Step (b) of Example 96 was repeated, except that the compound prepared in step (c) of Example 141 was used as the starting compound. Thus, the title compound was obtained.

¹H-NMR (CDCl₃) δ: 0.82–0.86 (2H, m), 1.35–1.61 (7H, m), 1.83 (1H, m), 2.18 (2H, t, J=7.7 Hz), 2.28–2.32 (2H, m), 2.44–2.46 (4H, m), 3.31–3.38 (5H, m), 3.77–3.87 (3H, m), 3.94–3.98 (1H, m), 4.22–4.25 (2H, m), 5.48 (1H, t, J=6.5 Hz), 7.08–7.12 (4H, m), 7.24–7.32 (5H, m), 7.53 (1H, d, J=8.8 Hz), 7.66 (1H, d, J=2.7 Hz), 8.01 (1H, s).

TSIMS (M/Z): 690 (M+H)⁺.

EXAMPLE 143

2-(Pyridin-2-yl)methyl-7-[4-[3-[9-(2,2,2-trifluoroethylcarbamoyl)-9H-fluoren-9-yl]propyl]piperazin-1-yl]-2H-phthalazin-1-one (a) Step (b) of Example 125 was repeated, except that the compound prepared in step (b) of Example 137 and 2-(chloromethyl)pyridine hydrochloride were used as the starting compounds. Thus, 7-nitro-2-(pyridin-2-yl)methyl-2H-phthalazin-1-one was obtained.

¹H-NMR (CDCl₃) δ: 5.58 (2H, s), 7.21 (1H, ddd, J=7.6, 4.9, 1.2 Hz), 7.37 (1H, d, J=7.6 Hz), 7.68 (1H, dt, J=7.6, 1.8 Hz), 7.90 (1H, d, J=8.7 Hz), 8.33 (1H, d, J=0.5 Hz), 8.57 (1H, ddd, J=4.9, 1.8, 0.8 Hz), 8.61 (1H, dd, J=8.7, 2.2 Hz), 9.27 (1H, d, J=2.2 Hz).

ESIMS (M/Z): 282 (M+H)⁺.

(b) The compound prepared just above in step (a) was reduced in the same manner as described in WO 9854135 to give 7-amino-2-(pyridin-2-yl)methyl-2H-phthalazin-1-one.

¹H-NMR (CDCl₃) δ: 4.32 (2H, brs), 5.54 (2H, s), 7.07 (1H, dd, J=8.4, 2.4 Hz), 7.17 (1H, ddd, J=7.9, 4.9, 1.2 Hz), 7.25 (1H, d, J=7.9 Hz), 7.51 (1H, d, J=8.4 Hz), 7.57 (1H, d, J=2.4 Hz), 7.62 (1H, dt, J=7.9, 1.8 Hz), 8.05 (1H, d, J=0.7 Hz), 8.58 (1H, ddd, J=4.9, 1.8, 1.0 Hz).

TSIMS (M/Z): 253 (M+H)⁺.

(c) The compound prepared just above in step (b) was piperazinated in the same manner as described in WO 9854135 to give 7-piperazinyl-2-(pyridin-2-yl)methyl-2H-phthalazin-1-one.

¹H-NMR (CD₃OD) δ: 3.04–3.06 (4H, m), 3.44–3.46 (4H, m), 5.51 (2H, s), 7.24 (1H, d, J=7.9 Hz), 7.29–7.33 (1H, m), 7.58 (1H, dd, J=8.8, 2.7 Hz), 7.65 (1H, d, J=2.7 Hz), 7.77 (1H, dt, J=7.9, 1.8 Hz), 7.77 (1H, d, J=8.8 Hz), 8.22 (1H, s), 8.46–8.48 (1H, m).

TSIMS (M/Z): 322 (M+H)⁺.

(d) Step (b) of Example 93 was repeated, except that the compound prepared just above in step (c) was used as the starting compound. Thus, the title compound was obtained.

¹H-NMR (CDCl₃) δ: 0.88–0.92 (2H, m), 2.21 (2H, t, J=7.5 Hz), 2.35 (4H, t, J=5.1 Hz), 2.47–2.51 (2H, m), 3.32 (4H, t, J=5.1 Hz), 3.70 (2H, dq, J=9.0, 2.5 Hz), 5.39 (1H, t, J=6.6 Hz), 5.53 (2H, s), 7.16 (1H, ddd, J=7.7, 4.9, 1.0 Hz), 7.24 (1H, d, J=7.7 Hz), 7.29 (1H, dd, J=8.9, 2.6 Hz), 7.38 (2H, dt, J=7.5, 1.1 Hz), 7.46 (2H, dt, J=7.5, 1.1 Hz), 7.54 (1H, d, J=8.9 Hz), 7.57 (1H, d, J=7.7 Hz), 7.61 (2H, dt, J=7.7, 1.8 Hz), 7.66 (1H, d, J=2.6 Hz), 7.78 (2H, d, J=7.3 Hz), 8.05 (1H, s), 8.56 (1H, ddd, J=4.9, 1.8, 1.0 Hz).

FABMS (M/Z): 653 (M+H)⁺.

EXAMPLE 144

2-(Pyridin-2-yl)methyl-7-[4-[3-[9-(2,2,2-trifluoroethylcarbamoyl)-9H-xanthen-9-yl]propyl]piperazin-1-yl]-2H-phthalazin-1-one (a) Step (b) of Example 92 was repeated, except that the compound prepared in step (b) of Example 114 and the compound prepared in step (c) of Example 143 were used as the starting compounds. Thus, the title compound was obtained.

¹H-NMR (CDCl₃) δ: 1.05–1.07 (2H, m), 2.21 (2H, t, J=7.1 Hz), 2.31–2.35 (6H, m), 3.31 (4H, m), 3.81 (2H, dq, J=9.0, 2.4 Hz), 5.50 (1H, t, J=6.6 Hz), 5.53 (2H, s), 7.09–7.17 (5H, m), 7.23–7.33 (6H, m), 7.54 (1H, d, J=9.0 Hz), 7.61 (1H, dt, J=7.7, 1.8 Hz), 7.66 (1H, d, J=2.7 Hz), 8.05 (1H, s), 8.56 (1H, ddd, J=4.9, 1.8, 1.0 Hz).

TSIMS (M/Z): 669 (M+H)⁺.

EXAMPLE 145

2-(Pyridin-3-yl)methyl-7-[4-[3-[9-(2,2,2-trifluoroethylcarbamoyl)-9H-fluoren-9-yl]propyl]piperazin-1-yl]-2H-phthalazin-1-one (a) Step (b) of Example 125 was repeated, except that the compound prepared in step (b) of Example 137 and 3-(chloromethyl)pyridine hydrochloride were used as the starting compounds. Thus, 7-nitro-2-(pyridin-3-yl)methyl-2H-phthalazin-1-one was obtained.

¹H-NMR (CDCl₃) δ: 5.44 (2H, s), 7.28 (1H, ddd, J=7.8, 4.9, 0.7 Hz), 7.85 (1H, dt, J=7.8, 2.0 Hz), 7.89 (1H, d, J=8.5 Hz), 8.28 (1H, d, J=0.5 Hz), 8.56 (1H, dd, J=4.9, 1.7 Hz), 8.60 (1H, dd, J=8.5, 2.4 Hz), 8.76 (1H, d, J=2.0 Hz), 9.26 (1H, d, J=2.4 Hz).

TSIMS (M/Z): 283 (M+H)⁺.

(b) The compound prepared just above in step (a) was reduced in the same manner as described in WO 9854135 to give 7-amino-2-(pyridin-3-yl)methyl-2H-phthalazin-1-one.

¹H-NMR (CD₃OD) δ: 5.39 (2H, s), 7.15 (1H, dd, J=8.6, 2.4 Hz), 7.37 (1H, d, J=2.4 Hz), 7.40 (1H, ddd, J=7.9, 5.0, 0.8 Hz), 7.58 (1H, d, J=8.6 Hz), 7.87 (1H, ddd, J=7.9, 2.2, 1.6 Hz), 8.11 (1H, d, J=0.7 Hz), 8.44 (1H, dd, J=5.0, 1.6 Hz), 8.60 (1H, d, J=2.2 Hz).

TSIMS (M/Z): 253 (M+H)⁺.

(c) The compound just above prepared in step (b) was piperazinated in the same manner as described in WO 9854135 to give 7-piperazinyl-2-(pyridin-3-yl)methyl-2H-phthalazin-1-one.

¹H-NMR (CD₃OD) δ: 2.98–3.01 (4H, m), 3.40–3.42 (4H, m), 5.42 (2H, s), 7.40 (1H, dd, J=8.0, 4.9 Hz), 7.55 (1H, dd, J=9.0, 2.6 Hz), 7.62 (1H, d, J=2.6 Hz), 7.73 (1H, d, J=9.0 Hz), 7.88 (1H, dt, J=8.0, 1.8 Hz), 8.19 (1H, s), 8.45 (1H, dd, J=4.9, 1.8 Hz), 8.61 (1H, d, J=1.8 Hz).

TSIMS (M/Z): 322 (M+H)⁺.

(d) Step (b) of Example 93 was repeated, except that the compound prepared just above in step (c) was used as the starting compound. Thus, the title compound was obtained.

$^1$H-NMR (CDCl$_3$) δ: 0.86–0.92 (2H, m), 2.20 (2H, t, J=7.3 Hz), 2.35 (4H, t, J=4.8 Hz), 2.47–2.51 (2H, m), 3.32 (4H, t, J=4.8 Hz), 3.69 (2H, dq, J=9.0, 2.4 Hz), 5.37 (3H, m), 7.21–7.30 (2H, m), 7.38 (2H, dt, J=7.5, 1.1 Hz), 7.46 (2H, dt, J=7.5, 1.1 Hz), 7.51–7.57 (3H, m), 7.63 (1H, d, J=2.5 Hz), 7.78 (3H, d, J=7.5 Hz), 8.00 (1H, s), 8.50 (1H, dd, J=4.8, 1.7 Hz), 8.72 (1H, d, J=1.7 Hz).

FABMS (M/Z): 653 (M+H)$^+$.

EXAMPLE 146

3-(4-Bromo-2-methylphenyl)-6-[4-(3,3-diphenylpropyl)-piperazin-1-yl]-2-methyl-3H-quinazolin-4-one (a) Acetic anhydride (200 ml) was added to 2-amino-5-nitrobenzoic acid (18.12 g), and the mixture was stirred at room temperature overnight. The reaction solution was concentrated under the reduced pressure. A saturated aqueous NaHCO$_3$ solution was then added to the residue, and the mixture was extracted with ethyl acetate, followed by washing with water. The extract was dried over anhydrous Na$_2$SO$_4$, and the solvent was then removed by distillation under the reduced pressure. The residue was collected by filtration (and washed with n-hexane) to give 2-acetamide-5-nitrobenzoic acid (17.17 g).

$^1$H-NMR (CDCl$_3$) δ: 2.54 (3H, s), 7.71 (1H, d, J=8.8 Hz), 8.60 (1H, dd, J=8.8, 2.6 Hz), 9.04 (1H, d, J=2.6 Hz).

ESIMS (M/Z): 224 (M+H)$^+$.

(b) 3-(4-Bromo-2-methylphenyl)-2-methyl-6-nitro-3H-quinazolin-4-one was synthesized using the compound prepared just above in step (a) and 4-bromo-2-methylaniline as the starting compounds according to the method described in J. Med. Chem., Vol. 33, 161–166 (1990).

$^1$H-NMR (CDCl$_3$) δ: 2.12 (3H, s), 2.25 (3H, s), 7.05 (1H, d, J=8.3 Hz), 7.55 (1H, dd, J=8.3, 2.1 Hz), 7.61 (1H, d, J=2.1 Hz), 7.81 (1H, d, J=8.9 Hz), 8.57 (1H, dd, J=8.9, 2.7 Hz), 9.13 (1H, d, J=2.7 Hz).

TSIMS (M/Z): 374 (M+H)$^+$.

(c) The compound prepared just above in step (b) was reduced in the same manner as described in WO 9854135 to give 6-amino-3-(4-bromo-2-methylphenyl)-2-methyl-3H-quinazolin-4-one.

$^1$H-NMR (CDCl$_3$) δ: 2.10 (3H, s), 2.13 (3H, s), 3.96 (2H, brs), 7.03 (1H, d, J=8.5 Hz), 7.13 (1H, dd, J=8.5, 2.8 Hz), 7.44 (1H, d, J=2.8 Hz), 7.50 (1H, dd, J=8.8, 2.1 Hz), 7.52 (1H, d, J=8.8 Hz), 7.56 (1H, d, J=2.1 Hz).

TSIMS (M/Z): 344 (M+H)$^+$.

(d) The compound prepared just above in step (c) was piperazinated in the same manner as described in WO 9854135 to give 3-(4-bromo-2-methylphenyl)-2-methyl-6-piperazinyl-3H-quinazolin-4-one.

$^1$H-NMR (CDCl$_3$) δ: 2.10 (3H, s), 2.14 (3H, s), 3.05–3.07 (4H, m), 3.25–3.28 (4H, m), 7.03 (1H, d, J=8.3 Hz), 7.44 (1H, dd, J=8.9, 3.1 Hz), 7.50 (1H, dd, J=8.3, 2.1 Hz), 7.56 (1H, d, J=2.1 Hz), 7.60 (1H, d, J=8.9 Hz), 7.61 (1H, d, J=3.1 Hz).

TSIMS (M/Z): 413 (M+H)$^+$.

(e) The title compound was prepared in the same manner as described in WO 9854135, except that the compound prepared just above in step (d) was used as the starting compound.

$^1$H-NMR (CDCl$_3$) δ: 2.09 (3H, 9), 2.14 (3H, s), 2.30–2.34 (4H, m), 2.59 (4H, m), 3.32 (4H, m), 4.02 (1H, t, J=7.4 Hz), 7.03 (1H, d, J=8.3 Hz), 7.15–7.20 (2H, m), 7.25–7.30 (8H, m), 7.42 (1H, dd, J=8.8, 3.0 Hz), 7.50 (1H, dd, J=8.3, 2.1 Hz), 7.56 (1H, d, J=2.1 Hz), 7.58 (1H, d, J=8.8 Hz), 7.59 (1H, d, J=3.0 Hz).

TSIMS (M/Z): 607 (M+H)$^+$.

EXAMPLE 147

3-Benzyl-6-[4-(3,3-diphenylpropyl)piperazin-1-yl]-2-methyl-3H-quinazolin-4-one (a) 3-Benzyl-2-methyl-6-nitro-3H-quinazolin-4-one was synthesized using the compound prepared in step (a) of Example 146 and benzylamine as the starting compounds according to the method described in J. Med. Chem., Vol. 33, 161–166 (1990).

$^1$H-NMR (CDCl$_3$) δ: 2.61 (3H, s), 5.42 (2H, s), 7.20–7.22 (2H, m), 7.29–7.38 (3H, m), 7.74 (1H, d, J=8.9 Hz), 8.53 (1H, dd, J=8.9, 2.7 Hz), 9.18 (1H, d, J=2.7 Hz).

TSIMS (M/Z): 296 (M+H)$^+$.

(b) The compound prepared just above in step (a) was reduced in the same manner as described in WO 9854135 to give 6-amino-3-benzyl-2-methyl-3H-quinazolin-4-one.

$^1$H-NMR (CDCl$_3$) δ: 2.50 (3H, s), 3.95 (2H, brs), 5.38 (2H, s), 7.11 (1H, dd, J=8.6, 2.8 Hz), 7.17–7.19 (2H, m), 7.23–7.34 (3H, m), 7.46–7.49 (2H, m).

TSIMS (M/Z): 266 (M+H)$^+$.

(c) The compound prepared just above in step (b) was piperazinated in the same manner as described in WO 9854135 to give 3-benzyl-2-methyl-6-piperazinyl-3H-quinazolin-4-one.

$^1$H-NMR (CDCl$_3$) δ: 2.52 (3H, s), 3.07–3.10 (4H, m), 3.28–3.30 (4H, m), 5.40 (2H, s), 7.18–7.20 (2H, m), 7.24–7.34 (3H, m), 7.42 (1H, dd, J=9.0, 2.7 Hz), 7.55 (1H, d, J=9.0 Hz), 7.66 (1H, d, J=2.7 Hz).

TSIMS (M/Z): 335 (M+H)$^+$.

(d) The title compound was prepared using the compound prepared just above in step (c) as a starting compound according to the method described in WO 9854135.

$^1$H-NMR (CDCl$_3$) δ: 2.34–2.38 (4H, m), 2.51 (3H, s), 2.64 (4H, m), 3.35 (4H, m), 4.02 (1H, t, J=7.4 Hz), 5.39 (2H, s), 7.16–7.19 (4H, m), 7.27–7.33 (11H, m), 7.40 (1H, dd, J=9.0, 2.9 Hz), 7.54 (1H, d, J=9.0 Hz), 7.64 (1H, d, J=2.9 Hz).

TSIMS (M/Z): 529 (M+H)$^+$.

EXAMPLE 148

3-(4-Bromo-2-methylphenyl)-6-[4-(3,3-diphenylpropyl)piperazin-1-yl]-3H-quinazolin-4-one (a) 2-Nitro-5-piperazinylbenzoic acid was synthesized using 5-chloro-2-nitrobenzoic acid as a starting compound according to the method described in J. Med. Chem., Vol. 39, 4583–4591 (1996).

$^1$H-NMR (D$_2$O) δ: 3.24–3.27 (4H, m), 3.59–3.61 (4H, m), 6.73 (1H, d, J=2.9 Hz), 6.87 (1H, dd, J=9.4, 2.9 Hz), 7.97 (1H, d, J=9.4 Hz).

ESIMS (M/Z): 251 (M+H)$^+$.

(b) 5-[(4-Tert-butoxycarbonyl)-piperazin-1-yl]-2-nitrobenzoic acid was synthesized using the compound prepared just above in step (a) according to the method described in J. Med. Chem., Vol. 39, 4583–4591 (1996).

¹H-NMR (CDCl₃) δ: 1.50 (9H, s), 3.45–3.47 (4H, m), 3.61–3.64 (4H, m), 6.86 (1H, dd, J=9.4, 2.8 Hz), 6.95 (1H, d, J=2.8 Hz), 8.03 (1H, d, J=9.4 Hz).

TSIMS (M/Z): 350 (M–H)⁻.

(c) The compound (1.05 g) prepared just above in step (b) was dissolved in dichloromethane (24 ml). Triethylamine (0.46 ml) and isobutyl chloroformate (0.43 ml) were added to the solution at 0° C. The mixture was stirred at 0° C. for 45 min. Thereafter, 4-dimethylaminopyridine (0.04 g) and 4-bromo-2-methylaniline (0.61 g) were added thereto, and the mixture was stirred at room temperature overnight. The reaction solution was diluted with chloroform, and the dilution was washed with water, dilute hydrochloric acid, and water in that order, and was then dried over anhydrous MgSO₄. The solvent was then removed by distillation under the reduced pressure. The residue was purified by column chromatography on silica gel (n-hexane:ethyl acetate=2:1) to give N-(4-bromo-2-methylphenyl)-5-[(4-tert-butoxycarbonyl)-piperazin-1-yl]-2-nitrobenzamide (0.57 g).

¹H-NMR (CDCl₃) δ: 1.49 (9H, s), 2.62 (3H, s), 3.46 (4H, m), 3.62 (4H, m), 6.86 (1H, s), 7.12 (1H, s), 7.36–7.39 (2H, m), 7.82 (1H, d, J=8.6 Hz), 8.12 (1H, d, J=9.5 Hz).

ESIMS (M/Z): 520 (M+H)⁺.

(d) The compound (0.52 g) prepared just above in step (c) was dissolved in acetic acid (20 ml). Zinc (1.23 g) was added to the solution, and the mixture was stirred at room temperature for 45 min. The reaction solution was filtered through Celite, and the filtrate was concentrated under the reduced pressure. The residue was diluted with chloroform. The dilution was then washed with water, a saturated aqueous NaHCO₃ solution, and saturated brine and was dried over anhydrous MgSO₄. The solvent was then removed by distillation under the reduced pressure. The residue was purified by column chromatography on silica gel (n-hexane:ethyl acetate=2:1) to give 2-amino-N-(4-bromo-2-methylphenyl)-5-[(4-tert-butoxycarbonyl)piperazin-1-yl] benzamide (0.39 g).

¹H-NMR (CDCl₃) δ: 1.48 (9H, s), 2.31 (3H, s), 3.02 (4H, m), 3.62 (4H, m), 6.74 (1H, d, J=8.3 Hz), 7.02 (1H, m), 7.35–7.38 (2H, m), 7.76 (1H, d, J=8.0 Hz), 7.87 (1H, s).

TSIMS (M/Z): 489 (M+H)⁺.

(e) 3-(4-Bromo-2-methylphenyl)-6-[(4-tert-butoxycarbonyl)piperazin-1-yl]-3H-quinazolin-4-one was synthesized using the compound prepared just above in step (d) according to the method described in J. Med. Chem., Vol. 39, 4583–4591 (1996).

¹H-NMR (CDCl₃) δ: 1.49 (9H, s), 2.17 (3H, s), 3.28–3.31 (4H, m), 3.61–3.63 (4H, m), 7.12 (1H, d, J=8.3 Hz), 7.45 (1H, dd, J=9.0, 2.9 Hz), 7.49 (1H, dd, J=8.3, 2.2 Hz), 7.56 (1H, d, J=2.2 Hz), 7.68–7.71 (2H, m), 7.80 (1H, s).

TSIMS (M/Z): 499 (M+H)⁺.

(f) The compound prepared just above in step (e) was dissolved in dichloromethane. Trifluoroacetic acid was added to the solution, and the mixture was stirred at room temperature for one hr. A saturated aqueous NaHCO₃ solution was added to the reaction solution, followed by extraction with ethyl acetate. The extract was dried over anhydrous MgSO₄. The solvent was then removed by distillation under the reduced pressure. The title compound was then prepared using the compound thus obtained and 3,3-diphenylpropyl bromide as starting compounds according to the method described in WO 9854135.

¹H-NMR (CDCl₃) δ: 2.17 (3H, s), 2.30–2.35 (4H, m), 2.59–2.61 (4H, m), 3.34–3.36 (4H, m), 4.03 (1H, t, J=7.3 Hz), 7.11 (1H, d, J=8.2 Hz), 7.16–7.20 (2H, m), 7.25–7.30 (8H, m), 7.43 (1H, dd, J=9.1, 2.8 Hz), 7.49 (1H, dd, J=8.2, 1.9 Hz), 7.55 (1H, d, J=1.9 Hz), 7.66–7.68 (2H, m), 7.78 (1H, s).

TSIMS (M/Z): 593 (M+H)⁺.

EXAMPLE 149

2-Benzyl-7-[4-(3,3-diphenylpropyl)piperazin-1-yl]-2H-phthalazin-1-one

The title compound was prepared using the compound prepared in step (e) of Example 137 and 3,3-diphenylpropyl bromide as starting compounds according to the method described in WO 9854135.

¹H-NMR (CDCl₃) δ: 2.26–2.37 (4H, m), 2.55–2.57 (4H, m), 3.40–3.43 (4H, m), 4.02 (1H, t, J=7.3 Hz), 5.39 (2H, s), 7.16–7.20 (2H, m), 7.22–7.32 (12H, m), 7.43–7.45 (2H, m), 7.53 (1H, d, J=8.8 Hz), 7.71 (1H, d, J=2.5 Hz), 8.01 (1H, s).

TSIMS (M/Z): 515 (M+H)⁺.

EXAMPLE 150

N-Allyl-N-cyclohexyl-4-[4-[3-[9-(2,2,2-trifluoroethylcarbamoyl)-9H-fluoren-9-yl]propyl]piperazin-1-yl]benzamide (a) Step (b) of Example 1 was repeated, except that the compound prepared in step (a) of Example 80 and the compound prepared in step (a) of Example 93 were used as the starting compounds. Thus, ethyl 4-[4-[3-[9-(2,2,2-trifluoroethylcarbamoyl)-9H-fluoren-9-yl]propyl]piperazin-1-yl]benzoate was obtained.

¹H-NMR (CDCl₃) δ: 0.89–0.93 (2H, m), 1.35 (3H, t, J=7.2 Hz), 2.20 (2H, t, J=7.3 Hz), 2.34 (4H, t, J=5.0 Hz), 2.46–2.50 (2H, m), 3.21 (4H, t, J=5.0 Hz), 3.69 (2H, dq, J=8.9, 2.4 Hz), 4.31 (2H₁ q, J=7.2 Hz), 5.36 (1H, t, J=6.6 Hz), 6.80 (2H, d, J=9.2 Hz), 7.38 (2H, dt, J=7.5, 1.2 Hz), 7.46 (2H, dt, J=7.5, 1.2 Hz), 7.56 (2H, d, J=7.5 Hz), 7.78 (2H, d, J=7.5 Hz), 7.89 (2H, d, J=9.2 Hz).

FABMS (M/Z): 566 (M+H)⁺.

(b) Step (c) of Example 87 was repeated, except that the compound prepared just above in step (a) was used as the starting compound. Thus, the title compound was obtained.

¹H-NMR (CDCl₃) δ: 0.88–0.98 (2H, m), 1.04–1.22 (3H, m), 1.48–1.60 (3H, m), 1.73–1.76 (4H, m), 2.21 (2H, t, J=7.4 Hz), 2.36 (4H, t, J=4.8 Hz), 2.46–2.50 (2H, m), 3.13 (4H, t, J=4.8 Hz), 3.64–3.74 (2H, m), 3.96 (3H, m), 5.09 (1H, d, J=10.2 Hz), 5.14 (1H, d, J=17.6 Hz), 5.37 (1H, t, J=6.5 Hz), 5.87 (1H, brs), 6.81 (2H, d, J=8.8 Hz), 7.27 (2H, d, J=8.8 Hz), 7.38 (2H, dt, J=7.6, 1.1 Hz), 7.45 (2H, dt, J=7.6, 1.1 Hz), 7.56 (2H, d, J=7.6 Hz), 7.78 (2H, d, J=7.6 Hz).

TSIMS (M/Z): 659 (M+H)⁺.

EXAMPLE 151

N-Allyl-N-cyclohexyl-4-[4-[4-[9-(2,2,2-trifluoroethylcarbamoyl)-9H-xanthen-9-yl]butyl]piperazin-1-yl]benzamide (a) Step (b) of Example 1 was repeated, except that the compound prepared in step (a) of Example 80 and the compound prepared in step (a) of Example 96 were used as the starting compounds. Thus, ethyl 4-[4-[4-[9-(2,2,2-trifluoroethylcarbamoyl)-9H-xanthen-9-yl]butyl]piperazin-1-yl]benzoate was obtained.

¹H-NMR (CDCl₃) δ: 0.79–0.87 (2H, m), 1.32–1.40 (2H, m), 1.36 (3H, t, J=7.1 Hz), 2.17 (2H, t, J=7.7 Hz), 2.27–2.31

(2H, m), 2.42 (4H, t, J=5.1 Hz), 3.22 (4H, t, J=5.1 Hz), 3.81 (2H, dq, J=9.0, 2.5 Hz), 4.32 (2H, q, J=7.1 Hz), 5.44 (1H, t, J=6.6 Hz), 6.82 (2H, d, J=9.2 Hz), 7.08–7.12 (4H, m), 7.24–7.32 (4H, m), 7.90 (2H, d, J=9.2 Hz).

FABMS (M/Z): 596 (M+H)$^+$.

(b) Step (c) of Example 87 was repeated, except that the compound prepared just above in step (a) was used as the starting compound. Thus, the title compound was obtained.

$^1$H-NMR (CDCl$_3$) δ: 0.81–0.87 (2H, m), 1.07–1.22 (3H, m), 1.33–1.40 (2H, m), 1.51–1.57 (3H, m), 1.74–1.76 (4H, m), 2.18 (2H, t, J=7.7 Hz), 2.27–2.32 (2H, m), 2.45 (4H, t, J=4.8 Hz), 3.15 (4H, t, J=4.8 Hz), 3.80 (2H, dq, J=9.0, 2.4 Hz), 3.97 (3H, m), 5.09 (1H, dd, J=10.4, 1.4 Hz), 5.12–5.17 (1H, m), 5.47 (1H, t, J=6.6 Hz), 5.88 (1H, brs), 6.84 (2H, d, J=.8.8 Hz), 7.08–7.12 (4H, m), 7.24–7.32 (6H, m).

TSIMS (M/Z): 689 (M+H)$^+$.

EXAMPLE 152

N-Allyl-2-chloro-N-cyclohexyl-4-[4-[4-[9-(2,2,2-trifluoroethylcarbamoyl)-9H-fluoren-9-yl]butyl]piperazin-1-yl]benzamide (a) Step (a) of Example 1 was repeated, except that ethyl 4-amino-2-chlorobenzoate was used instead of ethyl 3-aminobenzoate. Step (b) of Example 87 was then repeated. Thus, ethyl 2-chloro-4-[4-[4-[9-(2,2,2-trifluoroethylcarbamoyl)-9H-fluoren-9-yl]butyl]piperazin-1-yl]benzoate was obtained.

$^1$H-NMR (CDCl$_3$) δ: 0.73 (2H, m), 1.31 (2H, m), 1.38 (3H, t, J=7.0 Hz), 2.44 (6H, m), 2.77 (2H, m), 3.23 (4H, m), 3.25 (2H, q, J=7.0 Hz), 5.37 (1H, t, J=6.5 Hz), 6.70 (1H, dd, J=2.3, 9.0 Hz), 6.83 (1H, d, J=2.3 Hz), 7.37 (1H, t, J=7.3 Hz), 7.46 (1H, t, J=7.3 Hz), 7.56 (2H, d, J=7.4 Hz), 7.78 (2H, d, J=7.4 Hz), 7.82 (1H, d, J=9.0 Hz).

TSIMS (M/Z): 615 (M+H)$^+$.

(b) Hydrolysis was carried out in the same manner as in step (c) of Example 1, except that the compound prepared just above in step (a) was used. Thus, 2-chloro-4-[4-[4-[9-(2,2,2-trifluoroethylcarbamoyl)-9H-fluoren-9-yl]butyl]piperazin-1-yl]benzoic acid was obtained.

TSIMS (M/Z): 586 (M+H)$^+$.

(c) Step (c) of Example 87 was repeated, except that the compound prepared just above in step (b) was used instead of 3-[4-[4-[9-(2,2,2-trifluoroethylcarbamoyl)-9H-fluoren-9-yl]butyl]piperazin-1-yl]benzoic acid. Thus, the title compound was obtained.

$^1$H-NMR (CDCl$_3$) δ: 0.65 (2H, m), 1.01 (2H, m), 1.20–2.00 (10H, m), 2.19 (2H, m), 2.45 (6H, m), 3.13 (4H, m), 3.30+4.45 (1H, m), 3.74 (2H, m), 4.05 (2H, m), 5.14 (2H, m), 5.37 (1H, m), 5.80 (1H, m), 6.76 (1H, m), 6.84 (1H, d, J=2.5 Hz), 7.08 (1H, d, J=8.3 Hz), 7.38 (2H, t, J=7.3 Hz), 7.46 (2H, t, J=7.3 Hz), 7.56 (2H, d, J=7.7 Hz), 7.89 (2H, d, J=7.7 Hz).

TSIMS (M/Z): 707 (M+H)$^+$.

EXAMPLE 153

N-Benzyl-N-cyclohexyl-4-[4-[4-[9-(2,2,2-trifluoroethylcarbamoyl)-9H-fluoren-9-yl]butyl]piperazin-1-yl]benzamide (a) Step (b) of Example 1 was repeated, except that the compound prepared in step (a) of Example 80 was used as the starting compound and 4-[9-(2,2,2-trifluoroethylcarbamoyl)-9H-fluoren-9-yl]butyl bromide was used instead of 3,3-diphenyl bromide. Thus, ethyl 4-[4-[4-[9-(2,2,2-trifluoroethylcarbamoyl)-9H-fluoren-9-yl]butyl]piperazin-1-yl]benzoate was obtained.

$^1$H-NMR (CDCl$_3$) δ: 0.73 (2H, m), 1.36 (3H, t, J=7.1 Hz), 2.18 (2H, m), 2.45 (6H, m), 3.25 (4H, m), 3.70 (2H, m), 4.32 (2H, q, J=7.1 Hz), 5.38 (1H, t, J=6.6 Hz), 6.82 (1H, d, J=9.0 Hz), 7.37 (2H, m), 7.46 (2H, m), 7.56 (2H, m), 7.78 (2H, d, J=7.4 Hz), 7.91 (2H, d, J=9.0 Hz).

TSIMS (M/Z): 580 (M+H)$^+$.

(b) Hydrolysis was carried out in the same manner as in step (c) of Example 1, except that the compound prepared just above in step (a) was used as the starting compound. Thus, 4-[4-[4-[9-(2,2,2-trifluoroethylcarbamoyl)-9H-fluoren-9-yl]butyl]piperazin-1-yl]benzoic acid was obtained.

TSIMS (M/Z): 552 (M+H)$^+$.

(c) Step (d) of Example 1 was repeated, except that the compound prepared just above in step (b) was used instead of 3-[4-(3,3-diphenyl-1-propyl)piperazin-1-yl]benzoic acid and N-benzylcyclohexylamine was used instead of N-methylbenzylamine. Thus, the title compound was obtained.

$^1$H-NMR (CDCl$_3$) δ: 0.73 (2H, m), 1.28 (12H, m), 2.15 (2H, m), 2.45 (6H, m), 3.16 (4H, m), 3.69 (2H, m), 3.90 (1H, m), 4.64 (2H, brs), 5.39 (1H, m), 6.83 (2H, m), 7.43 (I1H, m), 7.58 (2H, d, J=7.4 Hz), 7.79 (2H, d, J=7.4 Hz).

TSIMS (M/Z): 723 (M+H)$^+$.

EXAMPLE 154

N-Benzyl-N-isopropyl-4-[4-[4-[9-(2,2,2-trifluoroethylcarbamoyl)-9H-fluoren-9-yl]butyl]piperazin-1-yl]benzamide Step (c) of Example 153 was repeated, except that N-benzylisopropylamine was used instead of N-benzylcyclohexylamine. Thus, the title compound was obtained.

$^1$H-NMR (CDCl$_3$) δ: 0.74 (2H, m), 1.14 (6H, d, J=6.6 Hz), 1.40 (2H, m), 2.17 (2H, m), 2.42 (6H, m), 3.16 (4H, m), 3.69 (2H, m), 4.35 (1H, m), 4.62 (2H, brs), 5.38 (1H, m), 6.84 (2H, d, J=8.5 Hz), 7.38 (11H, m), 7.56 (2H, d, J=7.5 Hz), 7.79 (2H, d, J=7.5 Hz).

TSIMS (M/Z): 683 (M+H)$^+$.

EXAMPLE 155

N-Allyl-N-cyclohexyl-2-methyl-3-[4-[3-[9-(2,2,2-trifluoroethylcarbamoyl)-9H-xanthen-9-yl]propyl]piperazin-1-yl]benzamide (a) Step (b) of Example 1 was repeated, except that the compound prepared in step (a) of Example 53 and the compound prepared in step (b) of Example 114 were used as the starting compounds. Thus, ethyl 2-methyl-3-[4-[3-[9-(2,2,2-trifluoroethylcarbamoyl)-9H-xanthen-9-yl]propyl]piperazin-1-yl]benzoate was obtained.

$^1$H-NMR (CDCl$_3$) δ: 1.01–1.09 (2H, m), 1.37 (3H, t, J=7.2 Hz), 2.21–2.25 (2H, m), 2.31–2.35 (6H, m), 2.42 (3H, s), 2.79 (4H, t, J=4.7 Hz), 3.81 (2H, dq, J=8.9, 2.3 Hz), 4.33 (2H, q, J=7.2 Hz), 5.45 (1H, t, J=6.6 Hz), 7.08–7.19 (6H, m), 7.25–7.33 (4H, m), 7.49 (1H, dd, J=7.5, 1.4 Hz).

FABMS (M/Z): 596 (M+H)$^+$.

(b) Step (c) of Example 87 was repeated, except that the compound prepared just above in step (a) was used as the starting compound. Thus, the title compound was obtained.

¹H-NMR (CDCl₃) δ: 0.98–1.06 (4H, m), 1.44–1.53 (5H, m), 1.60–1.68 (3H, m), 1.82–1.83 (2H, m), 2.17+2.20 (3H, s), 2.21–2.25 (2H, m), 2.30–2.34 (4H, m), 2.74–2.85 (4H, m), 3.56–3.74 (1H, m), 3.81 (2H, dq, J=9.0, 2.5 Hz), 3.97+4.14 (1H, dd, J=16.1, 5.7 Hz), 3.24+4.45 (1H, tt, J=11.8, 3.5 Hz), 4.96+5.13 (1H, dd, J=10.3, 1.3 Hz), 4.85+5.24 (1H, dd, J=17.6, 1.4 Hz), 5.46 (1H, t, J=6.6 Hz), 5.61+5.98 (1H, m), 6.82 (1H, d, J=7.6 Hz), 6.96 (1H, t, J=8.2 Hz), 7.08–7.15 (4H, m), 7.25–7.31 (5H, m).

TSIMS (M/Z): 689 (M+H)⁺.

EXAMPLE 156

N-Allyl-N-cyclohexyl-4-[4-[5-[9-(2,2,2-trifluoroethylcarbamoyl)-9H-fluoren-9-yl]pentyl]piperazin-1-yl]benzamide (a) Step (b) of Example 1 was repeated, except that the compound prepared in step (a) of Example 80 and the compound prepared in step (a) of Example 94 were used as the starting compounds. Thus, ethyl 4-[4-[5-[9-(2,2,2-trifluoroethylcarbamoyl)-9H-fluoren-9-yl]pentyl]piperazin-1-yl]benzoate was obtained.

¹H-NMR (CDCl₃) δ: 0.71–0.78 (2H, m), 1.14–1.21 (2H, m), 1.36 (3H, t, J=7.1 Hz), 1.30–1.38 (2H, m), 2.20 (2H, t, J=7.7 Hz), 2.39–2.44 (2H, m), 2.47 (4H, t, J=5.0 Hz), 3.26 (4H, t, J=5.0 Hz), 3.69 (2H, dq, J=9.0, 2.4 Hz), 4.32 (2H, q, J=7.1 Hz), 5.39 (1H, t, J=6.4 Hz), 6.83 (2H, d, J=9.0 Hz), 7.37 (2H, dt, J=7.5, 1.2 Hz), 7.45 (2H, dt, J=7.5, 1.2 Hz), 7.56 (2H, d, J=7.5 Hz), 7.77 (2H, d, J=7.5 Hz), 7.91 (2H, d, J=9.0 Hz).

TSIMS (M/Z): 594 (M+H)⁺.

(b) Step (c) of Example 87 was repeated, except that the compound prepared just above in step (a) was used as the starting compound. Thus, the title compound was obtained.

¹H-NMR (CDCl₃) δ: 0.74 (2H, m), 1.07–1.26 (5H, m), 1.34 (2H, m), 1.52–1.58 (3H, m), 1.74–1.77 (4H, m), 2.21 (2H, m), 2.40–2.44 (2H, m), 2.49 (4H, m), 3.19 (4H, m), 3.65–3.75 (2H, m), 3.97 (3H, m), 5.08–5.17 (2H, m), 5.38 (1H, m), 5.88 (1H, brs), 6.85 (2H, d, J=8.0 Hz), 7.27–7.30 (2H, m), 7.37 (2H, t, J=7.3 Hz), 7.45 (2H, t, J=7.3 Hz), 7.56 (2H, d, J=7.3 Hz), 7.77 (2H, d, J=7.3 Hz).

TSIMS (M/Z): 687 (M+H)⁺.

EXAMPLE 157

N-Allyl-N-cyclohexyl-4-[4-[4-[9-(2,2,2-trifluoroethylcarbamoyl)-9H-fluoren-9-yl]butyl]piperazin-1-yl]-2-trifluoromethylbenzamide (a) Step (a) of Example 80 was repeated, except that ethyl 4-fluoro-2-trifluoromethylbenzoate was used instead of ethyl 4-fluorobenzoate. Thus, ethyl 4-(piperazin-1-yl)-2-trifluoromethylbenzoate was obtained.

¹H-NMR (CDCl₃) δ: 1.37 (3H, t, J=7.1 Hz), 2.62 (1H, s), 3.03 (4H, m), 3.30 (4H, m), 4.35 (2H, q, J=7.1 Hz), 6.96 (1H, dd, J=2.8, 8.8 Hz), 7.19 (1H, d, J=2.8 Hz), 7.83 (1H, d, J=8.8 Hz).

EIMS (M/Z): 302 (M⁺).

(b) Step (b) of Example 1 was repeated, except that the compound prepared just above in step (a) was used as the starting compound and 4-[9-(2,2,2-trifluoroethylcarbamoyl)-9H-fluoren-9-yl]butyl bromide was used instead of 3,3-diphenyl bromide. Thus, ethyl 4-[4-[4-[9-(2,2,2-trifluoroethylcarbamoyl)-9H-fluoren-9-yl]butyl]piperazin-1-yl]-2-trifluoromethylbenzoate was obtained.

¹H-NMR (CDCl₃) δ: 0.74 (2H, m), 1.36 (3H, t, J=7.1 Hz), 1.52 (2H, m), 2.18 (2H, m), 2.46 (6H, m), 3.24 (4H, m), 3.70 (2H, m), 4.33 (2H, q, J=7.1 Hz), 5.37 (1H, m), 6.92 (1H, dd, J=2.4, 8.5 Hz), 7.15 (1H, d, J=2.4 Hz), 7.38 (2H, m), 7.46 (2H, m), 7.56 (2H, d, J=7.2 Hz), 7.79 (3H, m).

TSIMS (M/Z): 648 (M+H)⁺.

(c) Step (c) of Example 1 was repeated, except that the hydrolysis of the compound prepared just above in step (b) was carried out. Thus, 4-[4-[4-[9-(2,2,2-trifluoroethylcarbamoyl)-9H-fluoren-9-yl]butyl]piperazin-1-yl]-2-trifluoromethylbenzoic acid was obtained.

FABMS (M/Z): 620 (M+H)⁺.

(d) Step (c) of Example 87 was repeated, except that the compound prepared just above in step (c) was used instead of 3-[4-[4-[9-(2,2,2-trifluoroethylcarbamoyl)-9H-fluoren-9-yl]butyl]piperazin-1-yl]benzoic acid. Thus, the title compound was obtained.

¹H-NMR (CDCl₃) δ: 0.75 (2H, m), 1.20–1.80 (12H, m), 2.19 (2H, m), 2.45 (6H, m), 3.20 (4H, m), 3.73 (2H, m), 4.05 (2H, m), 4.36 (1H, m), 4.90–5.27 (2H, m), 5.38 (1H, m), 5.61–6.00 (1H, m), 6.98 (1H, m), 7.09 (2H, dd, J=2.1, 11.5 Hz), 7.40 (2H, m), 7.46 (2H, m), 7.50 (2H, d, J=7.4 Hz), 7.89 (2H, d, J=7.4 Hz).

TSIMS (M/Z): 741 (M+H)⁺.

EXAMPLE 158

N-Allyl-N-cyclohexyl-2-fluoro-4-[4-[4-[9-(2,2,2-trifluoroethylcarbamoyl)-9H-fluoren-9-yl]butyl]piperazin-1-yl]-2-trifluoromethylbenzamide (a) Step (a) of Example 157 was repeated, except that the reaction was carried out using ethyl 2,4-difluorobenzoate instead of ethyl 4-fluoro-2-trifluoromethylbenzoate to give ethyl 2-fluoro-4-(piperazin-1-yl)benzoate. Step (b) of Example 157 was repeated, except that the reaction was carried out using the ethyl 2-fluoro-4-(piperazin-1-yl)benzoate thus obtained. Thus, ethyl 2-fluoro-4-[4-[4-[9-(2,2,2-trifluoroethylcarbamoyl)-9H-fluoren-9-yl]butyl]piperazin-1-yl]benzoate was obtained.

¹H-NMR (CDCl₃) δ: 0.72 (2H, m), 1.36 (3H, t, J=7.1 Hz), 2.17 (2H, m), 2.46 (6H, m), 3.20 (1H, m), 3.25 (4H, m), 3.49 (1H, m), 3.72 (2H, m), 4.36 (2H, q, J=7.1 Hz), 5.38 (1H, m), 6.55 (2H, m), 7.38 (2H, m), 7.46 (2H, m), 7.56 (2H, d, J=7.4 Hz), 7.62 (2H, d, J=7.4 Hz).

TSIMS (M/Z): 598 (M+H)⁺.

(b) Step (c) of Example 1 was repeated, except that the hydrolysis of the compound prepared just above in step (a) was carried out. Thus, 2-fluoro-4-[4-[4-[9-(2,2,2-trifluoroethylcarbamoyl)-9H-fluoren-9-yl]butyl]piperazin-1-yl]-2-benzoic acid was obtained.

TSIMS (M/Z): 570 (M+H)⁺.

(c) Step (c) of Example 87 was repeated, except that the reaction was carried out using the compound prepared just above in step (b) instead of 3-[4-[4-[9-(2,2,2-trifluoroethylcarbamoyl)-9H-fluoren-9-yl]butyl]piperazin-1-yl]benzoic acid. Thus, the title compound was obtained.

¹H-NMR (CDCl₃) δ: 0.70–2.00 (14H, m), 2.18 (2H, m), 2.43 (4H, m), 2.48 (2H, m), 3.14 (4H, m), 3.45+4.40 (1H, m), 3.69 (2H, m), 3.80–4.10 (2H, m), 5.12 (2H, m), 5.40 (1H, m), 5.89 (1H, m), 6.57 (2H, m), 7.18 (1H, m), 7.41 (4H, m), 7.56 (2H, d, J=7.5 Hz), 7.78 (2H, d, J=7.5 Hz).

TSIMS (M/Z): 691 (M+H)⁺.

EXAMPLE 159

N-Benzyl-N-(2-tetrahydrofurfuryl)-4-[4-[4-[9-(2,2,2-trifluoroethylcarbamoyl)-9H-fluoren-9-yl]butyl]piperazin-1-yl]benzamide Step (c) of Example 153 was repeated, except that the reaction was carried out using N-(2-tetrahydrofurfuryl)

benzylamine instead of N-benzylcyclohexylamine. Thus, the title compound was obtained.

¹H-NMR (CDCl₃) δ: 0.89 (2H, m), 1.36 (6H, m), 1.84 (2H, m), 2.15 (2H, m), 2.45 (4H, m), 2.69 (2H, m), 3.15 (4H, m), 3.67–4.30 (5H, m), 4.83 (2H, brs), 5.40 (1H, brs), 6.65–7.46 (13H, m), 7.56 (2H, d, J=7.4 Hz), 7.78 (2H, d, J=7.4 Hz).

TSIMS (M/Z): 725 (M+H)⁺.

EXAMPLE 160

N-Cyclohexyl-N-(pyridin-2-yl)methyl-4-[4-[4-[9-(2,2,2-trifluoroethylcarbamoyl)-9H-fluoren-9-yl]butyl]piperazin-1-yl]benzamide (a) Step (c) of Example 153 was repeated, except that the reaction was carried out using N-(2-pyridylmethyl)cyclohexylamine instead of N-benzylcyclohexylamine. Thus, the title compound was obtained.

¹H-NMR (CDCl₃) δ: 0.72–1.79 (14H, m), 2.18 (2H, m), 2.45 (6H, m), 3.17 (4H, m), 3.68 (2H, m), 3.84 (1H, m), 4.77 (2H, brs), 5.37 (1H, t, J,=6.3 Hz), 6.84 (2H, brs), 7.12 (1H, dd, J=5.0, 7.1 Hz), 7.35 (5H, m), 7.44 (2H, t, J=7.3 Hz), 7.54 (2H, d, J=7.3 Hz), 7.60 (1H, m), 7.76 (2H, d, J=7.5 Hz), 8.48 (1H, d, J=5.0 Hz).

TSIMS (M/Z): 724 (M+H)⁺.

EXAMPLE 161

N-Cyclohexyl-N-(2-furfuryl)-4-[4-[4-[9-(2,2,2-trifluoroethylcarbamoyl)-9H-fluoren-9-yl]butyl]piperazin-1-yl]benzamide Step (c) of Example 153 was repeated, except that the reaction was carried out using N-(2-furfuryl)cyclohexylamine instead of N-benzylcyclohexylamine. Thus, the title compound was obtained.

¹H-NMR (CDCl₃) δ: 0.72 (2H, m), 0.88 (2H, m), 1.02–1.90 (10H, m), 2.17 (2H, m), 2.45 (6H, m), 3.16 (4H, m), 3.68 (2H, m), 3.80 (1H, m), 4.53 (2H, brs), 5.38 (1H, t, J=6.1 Hz), 6.20–6.28 (2H, m), 6.82 (2H, d, J=8.5 Hz), 7.31 (3H, m), 7.36 (2H, t, J=7.3 Hz), 7.44 (2H, t, J=7.3 Hz), 7.54 (2H, d, J=7.5 Hz), 7.75 (2H, d, J=7.5 Hz).

TSIMS (M/Z): 713 (M+H)⁺.

EXAMPLE 162

N-Cyclohexyl-N-(2-thienyl)methyl-4-[4-[4-[9-(2,2,2-trifluoroethylcarbamoyl)-9H-fluoren-9-yl]butyl]piperazin-1-yl]benzamide (a) Step (c) of Example 153 was repeated, except that the reaction was carried out using N-[(2-thienyl)methyl]cyclohexylamine instead of N-benzylcyclohexylamine. Thus, the title compound was obtained.

¹H-NMR (CDCl₃) δ: 0.72–1.73 (14H, m), 2.17 (2H, m), 2.45 (6H, m), 3.16 (4H, m), 3.69 (2H, m), 3.80 (1H, m), 4.73 (2H, s), 5.36 (1H, m), 6.83 (1H, d, J=8.6 Hz), 6.89 (1H, dd, J=3.4, 5.1 Hz), 6.94 (1H, m), 7.15 (2H, d, J=5.1 Hz), 7.31 (2H, d, J=8.6 Hz), 7.36 (2H, d, J=7.5 Hz), 7.44 (2H, d, J=7.5 Hz), 7.54 (2H, d, J=7.5 Hz), 7.76 (2H, d, J=7.5 Hz).

TSIMS (M/Z): 729 (M+H)⁺.

EXAMPLE 163

N-Allyl-N-cyclohexyl-5-[4-[3-[9-(2,2,2-trifluoroethylcarbamoyl)-9H-fluoren-9-yl]propyl]piperazinyl]-2-methylbenzamide (a) Ethyl 2-methyl-5-piperazinylbenzoate (1.8 g, 9.1 mmol) was dissolved in 20 ml of anhydrous DMF. Potassium carbonate (1.7 g) and 3-[9-(2,2,2-trifluoroethylcarbamoyl)-9H-fluoren-9-yl]propyl bromide (2.5 g, 6.1 mmol) were added to the solution, and the mixture was stirred at 75° C. for 7 hr. The temperature of the reaction solution was returned to room temperature, and the reaction solution was then diluted with ethyl acetate. The dilution was washed twice with water and was then dried over anhydrous magnesium sulfate. The solvent was removed by distillation under the reduced pressure. The residue was purified by column chromatography (development system, n-hexane:ethyl acetate=2:1) to give 2.1 g (yield 59%) of ethyl 5-[4-[3-[9-(2,2,2-trifluoroethylcarbamoyl)-9H-fluoren-9-yl]propyl]piperazinyl]-2-methylbenzoate as a pale yellow foam.

¹H-NMR (CDCl₃) δ: 0.87–0.95 (2H, m), 1.37 (3H, t, J=7.1 Hz), 2.21 (2H, t, J=7.6 Hz), 2.36 (4H, t, J=4.9 Hz), 2.45–2.50 (5H, m), 3.07 (4H, t, J=4.9 Hz), 3.65–3.74 (2H, m), 4.33 (2H, q, J=7.1 Hz), 5.38 (1H, t, J=6.6 Hz), 6.91 (1H, dd, J=2.8, 8.4 Hz), 7.08 (1H, d, J=8.4 Hz), 7.35–7.41 (3H, m), 7.43–7.48 (2H, m), 7.56 (2H, d, J=7.6 Hz), 7.78 (2H, d, J=7.6 Hz).

TSIMS (M/Z): 580 (M+H)⁺.

(b) The compound (1.8 g, 3.1 mmol) prepared just above in step (a) was dissolved in 10 ml of methanol and 10 ml of THF. A 1 N aqueous sodium hydroxide solution (10 ml) was added to the solution, and the mixture was stirred at 70° C. for 5 hr. The reaction solution was concentrated to about 10 ml. The residue was diluted with methylene chloride, and water was added thereto. The mixture was acidified by the addition of a 1 N aqueous hydrochloric acid solution, followed by extraction twice with methylene chloride. The organic layer was dried over anhydrous magnesium sulfate. The solvent was removed by distillation under the reduced pressure to give 1.7 g (yield 100%) of 5-[4-[3-[9-(2,2,2-trifluoroethylcarbamoyl)-9H-fluoren-9-yl]propyl]piperazinyl]-2-methylbenzoic acid as a pink foam.

¹H-NMR (CDCl₃) δ: 1.29–1.36 (2H, m), 2.41–2.49 (5H, m), 2.66 (2H, t, J=7.6 Hz), 2.87 (4H, brs), 3.34 (4H, brs), 3.63–3.73 (2H, m), 5.46 (1H, t, J=6.6 Hz), 6.89 (1H, dd, J=2.7, 8.3 Hz), 7.09 (1H, d, J=8.3 Hz), 7.32–7.37 (2H, m), 7.40–7.46 (3H, m), 7.56 (2H, d, J=7.6 Hz), 7.76 (1H, d, J=7.6 Hz).

TSIMS (M/Z): 552 (M+H)⁺.

(c) The compound (1.9 g, 3.1 mmol) prepared just above in step (b) was dissolved in 20 ml of methylene chloride. A BOP reagent (1.6 g) and 1.6 ml of diisopropylethylamine were added to the solution. The mixture was stirred at room temperature for one hr. Allylcyclohexylamine (0.54 ml) was then added thereto, and the mixture was stirred at room temperature overnight. Allylcyclohexylamine (0.14 ml) was further added thereto, and the mixture was stirred at 45° C. for 4 hr. The reaction solution was diluted with methylene chloride, and the dilution was washed with water and was then dried over anhydrous magnesium sulfate. The solvent was removed by distillation under the reduced pressure. The residue was purified by column chromatography (development system, methylene chloride methanol=50:1) to give 1.1 g (yield 51%) of the title compound as a pale orange foam.

¹H-NMR (CDCl₃) δ: 0.88–1.88 (12H, m), 1.89, 1.92 (3H, s), 2.37–4.17 (17H, m), 4.83–5.11 (2H, m), 5.41 (1H, t, J=6.6 Hz), 5.53–5.78 (1H, m), 6.54–6.61 (2H, m), 7.04, 7.09 (1H, d, J=8.4 Hz), 7.42 (2H, t, J=7.4 Hz), 7.50 (2H, q, J=7.4 Hz), 7.57 (2H, dd, J=4.1, 7.4 Hz), 7.81 (2H, dd, J=4.1, 7.4 Hz).

TSIMS (M/Z): 673 (M+H)⁺.

EXAMPLE 164

N-Allyl-N-cyclohexyl-3-[4-[3-[9-(2,2,2-trifluoroethylcarbamoyl)-9H-fluoren-9-yl]propyl]piperazin-1-yl]benzamide (a) Step (b) of Example 1 was repeated, except that the reaction was carried out using the compound prepared in step (a) of Example 93 instead of 3,3-diphenylpropyl bromide. Thus, ethyl 3-[4-[3-[9-(2,2,2-trifluoroethylcarbamoyl)-9H-fluoren-9-yl]propyl]piperazin-1-yl]benzoate was obtained.

$^1$H-NMR (CDCl$_3$) δ: 1.37 (3H, t, J=7.3 Hz), 2.19–2.49 (7H, m), 3.11–3.18 (6H, m), 3.68 (2H, m), 3.84 (1H, t, J=6.1 Hz), 4.11 (2H, q, J=7.3 Hz), 5.36 (1H, t, J=6.1 Hz), 7.01 (1H, m), 7.26–7.56 (9H, m), 7.70–7.78 (2H, m).

TSIMS (M/Z): 566 (M+H)$^+$.

(b) Step (c) of Example 1 was repeated, except that the hydrolysis of the compound prepared just above in step (a) was carried out. Thus, 3-[4-[3-[9-(2,2,2-trifluoroethylcarbamoyl)-9H-fluoren-9-yl]propyl]piperazin-1-yl]benzoic acid was obtained.

FABMS (M/Z): 537 (M+H)$^+$.

(c) Step (d) of Example 1 was repeated, except that the compound prepared just above in step (b) was used instead of 3-[4-(3,3-diphenyl-1-propyl)piperazin-1-yl]benzoic acid and N-allylcyclohexylamine was used instead of N-benzylmethylamine. Thus, the title compound was obtained.

$^1$H-NMR (CDCl$_3$) δ: 1.02–1.81 (14H, m), 2.10 (2H, m), 2.33 (2H, m), 2.49 (4H, m), 3.12 (4H, m), 3.52–3.78 (4H, m), 4.28 (1H, m), 5.10–5.50 (3H, m), 5.92 (1H, m), 6.76 (1H, d, J=7.3 Hz), 6.86 (2H, m), 7.22 (1H, m), 7.30 (2H, t, J=7.3 Hz), 7.35 (2H, t, J=6.9 Hz), 7.50 (2H, d, J=7.3 Hz), 7.74 (2H, m).

FABMS (M/Z): 659 (M+H)$^+$.

EXAMPLE 165

N-Cyclohexyl-3-[4-(3,3-diphenyl-1-propyl)piperazin-1-yl]-N-(pyridin-2-yl)methyl-2-methylbenzamide Step (d) of Example 53 was repeated, except that the reaction was carried out using N-(2-pyridylmethyl)cyclohexylamine instead of N-isopropylcyclohexylamine. Thus, the title compound was obtained.

$^1$H-NMR (CDCl$_3$) δ: 0.95–1.49 (10H, m), 2.20–2.38 (7H, m), 2.58 (4H, m), 2.93 (4H, m), 3.36+4.58 (1H, m), 4.02 (1H, t, J=7.5 Hz), 4.42+4.94 (2H, m), 6.87–7.65 (16H, m), 8.40+8.51 (1H, m).

TSIMS (M/Z): 587 (M+H)$^+$.

EXAMPLE 166

N-Allyl-4-[4-[4,4-bis(4-fluorophenyl)-1-butyl]piperazin-1-yl]-N-cyclohexylbenzamide (a) Step (b) of Example 1 was repeated, except that 4,4-bis(4-fluorophenyl)butyl bromide was used instead of 3,3-diphenylpropyl bromide and the compound prepared in step (a) of Example 80 was used instead of ethyl 3-piperazin-1-yl-benzoate. Thus, ethyl 4-[4-[4,4-bis(4-fluorophenyl)-1-butyl]piperazin-1-yl]benzoate was obtained.

$^1$H-NMR (CDCl$_3$) δ: 1.36 (3H, t, J=7.1 Hz), 1.48 (2H, m), 2.02 (2H, m), 2.38 (2H, m), 2.50 (4H, m), 3.29 (4H, m), 3.88 (1H, t, J=7.5 Hz), 4.32 (2H, q, J=7.1 Hz), 6.83 (2H, d, J=9.0 Hz), 6.96 (4H, m), 7.15 (4H, m), 7.90 (2H, d, J=9.0 Hz).

TSIMS (M/Z): 479 (M+H)$^+$.

(b) Step (c) of Example 1 was repeated, except that the hydrolysis of the compound prepared just above in step (a) was carried out. Thus, 4-[4-[4,4-bis(4-fluorophenyl)-1-butyl]piperazin-1-yl]benzoic acid was obtained.

TSIMS (M/Z): 451 (M+H)$^+$.

(c) Step (d) of Example 1 was repeated, except that the compound prepared just above in step (b) was used instead of 3-[4-(3,3-diphenyl-1-propyl)piperazin-1-yl]benzoic acid and N-allylcyclohexylamine was used instead of N-benzylmethylamine. Thus, the title compound was obtained.

$^1$H-NMR (CDCl$_3$) δ: 1.07–1.74 (10H, m), 2.05 (4H, m), 2.41 (2H, m), 2.53 (4H, m), 3.22 (4H, m), 3.40 (1H, m), 3.89 (3H, m), 5.11 (2H, m), 5.88 (1H, m), 6.85–7.28 (12H, m).

TSIMS (M/Z): 572 (M+H)$^+$.

EXAMPLE 167

N-Allyl-N-cyclohexyl-4-[4-[4-[9-(2,2,2-trifluoroethylcarbamoyl)-9H-thioxanthen-9-yl]butyl]piperazin-1-yl]benzamide (a) Step (b) of Example 1 was repeated, except that the compound prepared in step (a) of Example 80 and the compound prepared in step (d) of Example 133 were used as the starting compounds. Thus, ethyl 4-[4-[4-[9-(2,2,2-trifluoroethylcarbamoyl)-9H-thioxanthen-9-yl]butyl]piperazin-1-yl]benzoate was obtained.

$^1$H-NMR (CDCl$_3$) δ: 1.05–1.13 (2H, m), 1.36 (3H, t, J=7.1 Hz), 1.34–1.41 (2H, m), 2.18–2.24 (4H, m), 2.46 (4H, t, J=4.9 Hz), 3.24 (4H, t, J=4.9 Hz), 3.88 (2H, dq, J=9.0, 2.2 Hz), 4.32 (2H, q, J=7.1 Hz), 5.41 (1H, t, J=6.6 Hz), 6.82 (2H, d, J=9.1 Hz), 7.17–7.29 (8H, m), 7.90 (2H, d, J=9.1 Hz).

TSIMS (M/Z): 612 (M+H)$^+$.

(b) Step (c) of Example 87 was repeated, except that the compound prepared just above in step (a) was used as the starting compound. Thus, the title compound was obtained.

$^1$H-NMR (CDCl$_3$) δ: 1.05–1.20 (5H, m), 1.34–1.41 (2H, m), 1.48–1.60 (3H, m), 1.73–1.76 (4H, m), 2.18–2.24 (4H, m), 2.47 (4H, t, J=4.9 Hz), 3.17 (4H, t, J=5.4 Hz), 3.88 (2H, dq, J=9.0, 2.2 Hz), 3.96 (3H, m), 5.09 (1H, dd, J=10.4, 1.4 Hz), 5.12–5.17 (1H, m), 5.44 (1H, t, J=6.6 Hz), 5.88 (1H, brs), 6.84 (2H, d, J=8.7 Hz), 7.17–7.29 (10H, m).

TSIMS (M/Z): 705 (M+H)$^+$.

EXAMPLE 168

N-Cyclohexyl-3-[4-(3,3-diphenyl-1-propyl)piperazin-1-yl]-N-(pyridin-2-yl)methylbenzamide The procedure of Example 1 was repeated, except that the reaction was carried out using N-(2-pyridylmethyl)cyclohexylamine instead of N-methylbenzylamine. Thus, the title compound was obtained.

$^1$H-NMR (CDCl$_3$) δ: 0.87–1.57 (10H, m), 2.31 (4H, m), 2.52 (4H, m), 3.13 (4H, m), 3.68 (1H, m), 4.01 (1H, m), 4.58–4.82 (2H, m), 6.92 (2H, m), 7.26 (14H, m), 7.63 (1H, m), 8.50 (1H, m).

TSIMS (M/Z): 573 (M+H)$^+$.

EXAMPLE 169

N-Allyl-3-[4-[3,3-bis(4-fluorophenyl)-1-propyl]piperazin-1-yl]-N-cyclohexylbenzamide (a) Step (b) of Example 1 was repeated, except that the reaction was carried out using 3,3-bis(4-fluorophenyl)propyl bromide instead of 3,3-diphenylpropyl bromide. Thus, ethyl 3-[4-[3,3-bis(4-fluorophenyl)-1-propyl]piperazin-1-yl]benzoate was obtained.

$^1$H-NMR (CDCl$_3$) δ: 1.39 (3H, t, J=7.2 Hz), 2.27 (4H, m), 2.58 (4H, m), 3.27 (4H, m), 4.02 (1H, t, J=7.8 Hz), 4.38 (2H, q, J=7.2 Hz), 6.98 (4H, m), 7.18 (4H, m), 7.31 (1H, m), 7.56 (3H, m).

TSIMS (M/Z): 465 (M+H)$^+$.

(b) Step (c) of Example 1 was repeated, except that the hydrolysis of the compound prepared just above in step (a) was carried out. Thus, 3-[4-[3,3-bis(4-fluorophenyl)-1-propyl]piperazin-1-yl]benzoic acid was obtained.

(c) Step (d) of Example 1 was repeated, except that the compound prepared just above in step (b) was used instead of 3-[4-(3,3-diphenyl-1-propyl)piperazin-1-yl]benzoic acid and N-allylcyclohexylamine was used instead of N-benzylmethylamine. Thus, the title compound was obtained.

TSIMS (M/Z): 558 (M+H)$^+$.

EXAMPLE 170

1-Methyl N-allyl-N-cyclohexyl-6-[4-(3,3-diphenylpropyl)piperazin-1-yl]phthalaminate (a) A solution of 3-nitrophthalic anhydride (5.0 g) in methanol (90 ml) was heated under reflux overnight, and the solvent was then removed by distillation under the reduced pressure to give 2-methyl 3-nitrophthalate (5.85 g).

$^1$H-NMR (CD$_3$OD) δ: 3.36 (1H, s), 3.89 (3H, s), 7.75 (1H, t, J=7.7 Hz), 8.34 (2H, m).

FABMS (M/Z): 226 (M+H)$^+$.

(b) Triethylamine (0.328 ml) and benzyloxycarbonyl chloride (368 mg) were added in that order to a solution of the compound (485 mg, 2.15 mmol), prepared just above in step (a), in anhydrous dichloroethane (10 ml) at 0° C., and the mixture was stirred at 0° C. for 5 min. N,N-Dimethylaminopyridine (26.3 mg) was then added thereto, and the mixture was stirred at room temperature overnight. Water and dichloromethane were added to the reaction mixture, followed by extraction. The organic layer was washed with a saturated aqueous sodium chloride solution and was then dried over sodium sulfate. The solvent was removed by distillation under the reduced pressure. The residue was purified by column chromatography on silica gel (n-hexane:ethyl acetate=4:1) to give 1-benzyl-2-methyl 3-nitrophthalate (207.6 mg) as an oil.

$^1$H-NMR (CDCl$_3$) δ: 3.84 (3H, 9), 5.36 (2H, s), 7.40 (5H, m), 7.68 (1H, dd, J=8.0, 8.0 Hz), 8.35 (2H, d, J=8.0 Hz).

FABMS (M/Z): 316 (M+H)$^+$.

(c) Finely powdered iron (100 mg) and acetic acid (1 ml) were added to a solution of the compound (104 mg, 0.33 mmol), prepared just above in step (b), of MeOH (10 ml) at room temperature, and the mixture was heated under reflux for 2 hr. The solvent was concentrated under the reduced pressure. Thereafter, ethyl acetate and an aqueous sodium hydrogencarbonate solution were added to the residue, and the mixture was stirred. The insolubles were removed by filtration, followed by extraction. The organic layer was washed with a saturated aqueous sodium chloride solution and was dried over anhydrous sodium sulfate. The solvent was removed by distillation under the reduced pressure to give 1-benzyl-2-methyl 3-aminophthalate (68.3 mg) as a white solid.

$^1$H-NMR (CDCl$_3$) δ: 3.58 (3H, s), 5.30 (2H, s), 6.8–7.40 (8H, m).

TSIMS (M/Z): 286 (M+H)$^+$.

(d) Water (10 ml) was added to the compound (600 mg) prepared just above in step (c). 47% hydrobromic acid (3 ml) and sodium nitrite (160 mg) were added thereto, and the mixture was stirred at 0° C. for one hr. Separately, copper(I) bromide (332 mg) was dissolved in water (3 ml), hydrobromic acid (3 ml) was added to the solution, and the mixture was stirred. The above reaction solution was added to this stirred mixture, and the mixture was then stirred at 80° C. for 2 hr. The reaction solution was cooled to room temperature. Water was then added to the cooled reaction solution, and the mixture was extracted with ethyl acetate. The organic layer was dried over anhydrous sodium sulfate. The solvent was then removed by distillation under the reduced pressure. The residue was purified by preparative TLC (hexane:ethyl acetate=4:1) to give 1-benzyl-2-methyl 3-bromophthalate as a brown solid.

$^1$H-NMR (CDCl$_3$) δ: 3.79 (3H, s), 5.34 (2H, s), 7.33–7.40 (6H, m), 7.76 (1H, d, J=8.0 Hz), 8.01 (1H, d, J=8.0 Hz).

EIMS (M/Z): 348,350 (M$^+$).

(e) The procedure of step (i) of Example 106 was repeated, except that the compound prepared just above in step (d) was used as the starting compound. Thus, 1-benzyl-2-methyl 3-[4-(3,3-diphenyl-propyl)piperazin-1-yl]phthalate was obtained as a yellow solid.

$^1$H-NMR (CDCl$_3$) δ: 2.20–2.49 (8H, m), 2.98 (4H, brs), 3.71 (3H, s), 4.08 (1H, t, J=6.3 Hz), 7.20–7.42 (18H, m).

FABMS (M/Z): 549 (M+H)$^+$.

(f) The compound as an ester prepared just above in step (e) was hydrolyzed in the same manner as in step (c) of Example 1. Thus, 2-methyl 3-[4-(3,3-diphenylpropyl)piperazin-1-yl]phthalate was obtained as a yellow solid.

$^1$H-NMR (CDCl$_3$) δ: 2.17–2.63 (8H, m), 3.10 (4H, brs), 3.74 (3H, s), 4.17 (1H, t, J=6.3 Hz), 7.09–7.37 (11H, m), 7.82 (2H, m).

TSIMS (M/Z): 459 (M+H)$^+$.

(g) The procedure of step (d) of Example 1 was repeated, except that the compound prepared just above in step (f) was used as the starting compound and N-allylcyclohexylamine was used instead of N-methylbenzylamine. Thus, the title compound was obtained as a yellow solid.

$^1$H-NMR (CDCl$_3$) δ: 1.01–2.34 (14H, m), 2.53 (4H, brs), 3.05 (4H, brs), 3.80 (3H, s), 3.96 (1H, t, J=5.9 Hz), 4.00 (1H, m), 4.88 (1/2H, dd, J=1.5, 16.1 Hz), 5.01 (1/2H, dd, J=1.5, 10.3 Hz), 5.18 (1/2H, dd, J=1.5, 10.3 Hz), 5.27 (1/2H, dd, J=1.5, 16.1 Hz), 5.36 (2H, t, J=6.0 Hz), 5.61 (1/2H, m), 5.95 (1/2H, m), 6.90–7.29 (13H, m).

TSIMS (M/Z): 580 (M+H)$^+$.

EXAMPLE 171

N-Allyl-N-cyclohexyl-3-[4-[4-[9-[allyl-(2,2,2-trifluoroethylcarbamoyl)]-9H-fluoren-9-yl]butyl]piperazin-1-yl]benzamide A reaction was carried out in the same manner as in Example 121, except that the compound prepared in Example 87 was used as the starting compound. Thus, the title compound was obtained.

¹H-NMR (CDCl₃) δ: 0.60 (2H, m), 1.01–1.27 (10H, m), 2.12 (2H, m), 2.31 (2H, m), 2.43 (4H, m), 2.89 (2H, m), 3.11 (6H, m), 3.50–4.10 (5H, m), 4.30–4.85 (3H, m), 5.14 (2H, m), 5.65–6.02 (1H, m), 6.78 (1H, d, J=7.1 Hz), 6.84 (2H, m), 7.23 (1H, m), 7.43 (6H, m), 7.79 (2H, d, J=7.4 Hz).

TSIMS (M/Z): 713 (M+H)⁺.

EXAMPLE 172

N-Allyl-N-cyclohexyl-3-[4-[4-[9-(2,2,2-trifluoroethylcarbamoyl)-9H-fluoren-9-yl]butyl]piperazin-1-yl]-2-methylbenzamide (a) The procedure of step (b) of Example 1 was repeated, except that the compound prepared in step (a) of Example 87 was used instead of 3,3-diphenylpropyl bromide and the compound prepared in step (a) of Example 53 was used instead of ethyl 3-piperazin-1-yl-benzoate. Thus, ethyl 3-[4-[4-[9-(2,2,2-trifluoroethylcarbamoyl)-9H-fluoren-9-yl]butyl]piperazin-1-yl]-2-methylbenzoate was obtained.

¹H-NMR (CDCl₃) δ: 1.38 (3H, t, J=7.1 Hz), 1.58 (3H, s), 2.20 (2H, m), 2.46 (6H, m), 2.85 (4H, m), 3.70 (2H, m), 4.35 (2H, q, J=7.1 Hz), 5.39 (1H, m), 7.17 (3H, m), 7.39 (2H, m), 7.47 (2H, m), 7.57 (2H, d, J=7.0 Hz), 7.78 (2H, d, J=7.0 Hz).

TSIMS (M/Z): 594 (M+H)⁺.

(b) The compound prepared just above in step (a) was hydrolyzed in the same manner as in step (c) of Example 1 to give 3-[4-[4-[9-(2,2,2-trifluoroethylcarbamoyl)-9H-fluoren-9-yl]butyl]piperazin-1-yl]-2-methylbenzoic acid.

¹H-NMR (CDCl₃) δ: 0.88 (2H, m), 1.72 (2H, m), 2.58 (5H, m), 3.06 (2H, m), 3.20 (4H, m), 3.50 (4H, m), 3.78 (2H, m), 7.35 (2H, m), 7.48 (2H, dt, J=0.83, 7.4 Hz), 7.56 (2H, m), 7.62 (2H, d, J=7.4 Hz), 7.68 (1H, m), 7.96 (2H, d, J=7.4 Hz).

TSIMS (M/Z): 566 (M+H)⁺.

(c) The procedure of step (d) of Example 1 was repeated, except that the compound prepared just above in step (b) was used instead of 3-[4-(3,3-diphenyl-1-propyl)piperazin-1-yl]benzoic acid and N-allylcyclohexylamine was used instead of N-benzylmethylamine. Thus, the title compound was obtained.

¹H-NMR (CDCl₃) δ: 0.73–1.96 (12H, m), 2.27 (3H, d), 2.43 (2H, m), 2.53 (4H, m), 2.94 (6H, m), 3.23+4.33 (1H, m), 3.50 (2H, m), 4.05 (2H, m), 4.84–5.35 (2H, m), 5.38 (2H, m), 5.43 (1H, m), 5.80 (1H, m), 6.86 (1H, d, J=7.1 Hz), 6.99 (1H, t, J=8.3 Hz), 7.16 (1H, m), 7.40 (2H, t, J=7.4 Hz), 7.47 (2H, t, J=7.4 Hz), 7.56 (2H, d, J=7.6 Hz), 7.79 (2H, d, J=7.6 Hz).

TSIMS (M/Z): 687 (M+H)⁺.

EXAMPLE 173

N-Allyl-N-cyclohexyl-2-methyl-3-[4-[4-[9-(2,2,2-trifluoroethylcarbamoyl)-9H-xanthen-9-yl]butyl]piperazin-1-yl]benzamide (a) The procedure of step (b) of Example 1 was repeated, except that the compound prepared in step (a) of Example 53 and the compound prepared in step (a) of Example 96 were used as the starting compounds. Thus, ethyl 2-methyly-3-[4-[4-[9-(2,2,2-trifluoroethylcarbamoyl)-9H-xanthen-9-yl]butyl]piperazin-1-yl]benzoate was obtained.

¹H-NMR (CDCl₃) δ: 0.79–0.87 (2H, m), 1.33–1.41 (5H, m), 2.17–2.21 (2H, m), 2.28–2.32 (2H, m), 2.45 (7H, m), 2.82 (4H, t, J=4.6 Hz), 3.81 (2H, dq, J=8.9, 2.2 Hz), 4.34 (2H, q, J=7.1 Hz), 5.44 (1H, t, J=6.6 Hz), 7.09–7.20 (4H, m), 7.25–7.32 (4H, m), 7.50 (1H, dd, J=7.8, 1.5 Hz).

TSIMS (M/Z): 610 (M+H)⁺.

(b) The procedure of step (c) of Example 87 was repeated, except that the compound prepared just above in step (a) was used as the starting compound. Thus, the title compound was obtained.

¹H-NMR (CDCl₃) δ: 0.81–0.90 (2H, m), 0.97–1.44 (5H, m), 1.50 (2H, m), 1.66 (3H, m), 1.83 (2H, m), 2.15+2.20 (3H, s), 2.20 (2H, m), 2.28–2.32 (2H, m), 2.46 (4H, m), 2.79–2.88 (4H, m), 3.58–3.74 (1H, m), 3.81 (2H, dq, J=9.0, 2.4 Hz), 3.98+4.16 (1H, dd, J=15.5, 5.7 Hz), 3.25+4.46 (1H, tt, J=11.9, 3.5 Hz), 4.96+5.14 (1H, dd, J=10.2, 1.2 Hz), 4.85+5.25 (1H, dd, J=17.1, 1.3 Hz), 5.46 (1H, t, J=.6.5 Hz), 5.62+5.98 (1H, m), 6.83 (1H, d, J=7.6 Hz), 6.95–7.00 (1H, m), 7.09–7.16 (4H, m), 7.25–7.32 (5H, m).

TSIMS (M/Z): 703 (M+H)⁺.

EXAMPLE 174

N-Allyl-N-cyclohexyl-2-methyl-3-[4-[3-[9-(2,2,2-trifluoroethylcarbamoyl)-9H-fluoren-9-yl]propyl]piperazin-1-yl]benzamide (a) The procedure of step (b) of Example 1 was repeated, except that the compound prepared in step (a) of Example 53 and the compound prepared in step (a) of Example 93 were used as the starting compound. Thus, ethyl 2-methyly-3-[4-[3-[9-(2,2,2-trifluoroethylcarbamoyl)-9H-fluoren-9-yl]propyl]piperazin-1-yl]benzoate was obtained.

¹H-NMR (CDCl₃) δ: 0.87–0.95 (2H, m), 1.37 (3H, t, J=7.1 Hz), 2.23 (2H, t, J=7.6 Hz), 2.38 (4H, m), 2.43 (3H, s), 2.47–2.51 (2H, m), 2.80 (4H, t, J=4.6 Hz), 3.70 (2H, dq, J=9.0, 2.5 Hz), 4.33 (2H, q, J=7.1 Hz), 5.37 (1H, t, J=6.5 Hz), 7.12 (1H, dd, J=7.8, 1.5 Hz), 7.17 (1H, t, J=7.8 Hz), 7.37 (2H, dt, J=7.5, 1.2 Hz), 7.45 (2H, dt, J=7.5, 1.2 Hz), 7.49 (1H, dd, J=7.8, 1.5 Hz), 7.57 (2H, d, J=7.5 Hz), 7.78 (2H, d J=7.5 Hz).

TSIMS (M/Z): 580 (M+H)⁺.

(b) The procedure of step (c) of Example 87 was repeated, except that the compound prepared just above in step (a) was used as the starting compound. Thus, the title compound was obtained.

¹H-NMR (CDCl₃) δ: 0.88–0.92 (2H, m), 0.96–1.43 (5H, m), 1.47–1.53 (2H, m), 1.63–1.68 (3H, m), 1.82 (2H, m), 2.13+2.17 (3H, s), 2.23–2.37 (4H, m), 2.46–2.50 (2H, m), 2.76–2.85 (4H, m), 3.62 (1H, m), 3.70 (2H, dq, J=8.9, 2.3 Hz), 3.97+4.15 (1H, dd, J=15.4, 5.7 Hz), 3.24+4.45 (1H, tt, J=11.9, 3.3 Hz), 4.96+5.13 (1H, dd, J=10.3, 1.3 Hz), 4.85+5.24 (1H, dd, J=17.2, 1.4 Hz), 5.37 (1H, t, J=6.4 Hz), 5.61+5.98 (1H, m), 6.82 (1H, d, J=7.6 Hz), 6.96 (1H, t, J=8.3 Hz), 7.12 (1H, q, J=7.9 Hz), 7.37 (2H, dt, J=7.5, 1.2 Hz), 7.45 (2H, dt, J=7.5, 1.2 Hz), 7.57 (2H, d, J=7.5 Hz), 7.78 (2H, d, J=7.5 Hz).

TSIMS (M/Z): 673 (M+H)⁺.

EXAMPLE 175

N-Allyl-N-cyclohexyl-6-[4-(3,3-diphenylpropyl)-piperazin-1-yl]-2-phthalaminate The compound as an ester prepared in Example 170 was hydrolyzed in the same manner as in step (c) of Example 1. Thus, the title compound was obtained as a yellow solid.

¹H-NMR (CDCl₃) δ: 0.85–1.98 (11H, m), 2.17 (2H, brs), 2.39 (2H, brs), 2.66 (4H, brs), 3.08 (4H, brs), 4.01 (1H, t, J=7.1 Hz), 4.10 (1H, m), 4.45 (1H, m), 4.78 (1H, d, J=6.7

Hz), 4.92 (1H, d, J=9.9 Hz), 5.13 (1H, d, J=9.9 Hz), 5.31 (1H, d, J=6.7 Hz), 5.66 (2H, m), 6.10 (2H, m), 7.18–7.31 (12H, m), 7.44 (1H, m), 7.56 (1H, m).

TSIMS (M/Z): 566 (M+H)$^+$.

EXAMPLE 176

N-Cyclohexyl-3-[4-(3,3-diphenyl-1-propyl)piperazin-1-yl]-N-(3-pyridyl)methyl-2-methylbenzamide A reaction was carried out in the same manner as in step (d) of Example 53, except that N-(2-pyridylmethyl)cyclohexylamine was used instead of N-isopropylcyclohexylamine. Thus, the title compound was obtained.

TSIMS (M/Z): 587 (M+H)$^+$.

EXAMPLE 177

N-Cyclohexyl-3-(4-(3,3-diphenyl-1-propyl)piperazin-1-yl]-N-(4-pyridyl)methyl-2-methylbenzamide A reaction was carried out in the same manner as in step (d) of Example 53, except that N-(4-pyridylmethyl)cyclohexylamine was used instead of N-isopropylcyclohexylamine. Thus, the title compound was obtained.

TSIMS (M/Z): 587 (M+H)$^+$.

| Preparation Example 1: Tablets | |
|---|---|
| Compound of Example 8 | 2.5 g |
| Lactose | 12 g |
| 6% HPC lactose | 8 g |
| Potato starch | 2 g |
| Magnesium stearate | 0.5 g |
| Total | 25 g |

All the above ingredients were intimately mixed with each other, and the mixture was compressed into 1000 tablets.

| Preparation Example 2: Capsules | |
|---|---|
| Compound of Example 127 | 2.5 g |
| Lactose | 18 g |
| Potato starch | 4 g |
| Magnesium stearate | 0.5 g |
| Total | 25 g |

All the above ingredients were intimately mixed with each other, and the mixture was filled into hard capsules to prepare 1000 capsules.

Test 1: Triglyceride Biosynthesis Inhibitory Activity

The triglyceride biosynthesis inhibitory activity of compounds according to the present invention was examined using human hepatoma-derived cell line, Hep G2.

The test was carried out by partially modifying the method of Nagata et al. (Biochem. Pharmacol., 40, 843 (1990)) and the method of Furukawa et al. (J. Biol. Chem., 267, 22630 (1992)). Specifically, Hep G2 cells were cultivated in a Dulbecco modified Eagles's medium (DMEM) containing 10% fetal calf serum (FCS), 100 units/ml penicillin, and 100 µg/ml streptomycin on a 96-well plate. Thereafter, the medium was replaced by DMEM containing 1% bovine serum albumin. At the same time, the test compound was added to a final concentration of 1 µM, followed by cultivation, or cultivation was carried out without the addition of the test compound. Three hours after the replacement of the medium, $^{14}$C-acetic acid was added to a final concentration of 1 mM, and cultivation was continued for additional 4 hours. After the cells were washed with a phosphate buffer (pH 7.5) containing 150 mM sodium chloride, lipids within the cells were extracted with n-butanol. After the extraction, the extract was evaporated to dryness under a nitrogen stream. The solid obtained by the evaporation to dryness was dissolved in a minor amount of chloroform. The solution was developed by thin layer chromatography (development solvent: petroleum ether/diethyl ether/acetic acid=90/15/3) to separate a $^{14}$C-triglyceride fraction, and the amount of $^{14}$C-triglyceride produced was then determined with a liquid scintillation counter (Beckman, LS-6500).

The inhibition (%) of biosynthesis of triglyceride was calculated by the following equation.

Inhibition of biosynthesis of triglyceride (%)={1−(amount of $^{14}$C-triglyceride produced in the presence of test compound)/(amount of $^{14}$C-triglyceride produced in the absence of test compound)}×100

Test 2: Apolipoprotein B Secretion Inhibitory Activity

The apolipoprotein B secretion inhibitory activity of compounds according to the present invention was examined using human hepatoma-derived cell line, Hep G2.

The test was carried out by partially modifying the method of Nagata et al. (Biochem. Pharmacol., 40, 843 (1990)) and the method of Furukawa et al. (J. Biol. Chem., 267, 22630 (1992)). Specifically, Hep G2 cells were cultivated in a Dulbecco modified Eagles's medium (DMEM) containing 10% fetal calf serum (FCS), 100 units/ml penicillin, and 100 µg/ml streptomycin on a 96-well plate. Thereafter, the medium was replaced by DMEM containing 1% bovine serum albumin. At the same time, the test compound was added to a final concentration of 1 µM, followed by cultivation, or cultivation was carried out without the addition of the test compound. Three hours after the replacement of the medium, acetic acid was added to a final concentration of 1 mM, and cultivation was continued for additional 4 hours. The amount of apolipoprotein B secreted in the supernatant of the culture thus obtained was determined by the sandwich ELISA method. Goat anti-human apolipoprotein B polyclonal antibody (CHEMICON) was used as the primary antibody, and mouse anti-human apolipoprotein B monoclonal antibody peroxydase conjugate (BIOSYS) was used as the secondary antibody.

The inhibition (%) of secretion of apolipoprotein B was calculated by the following equation.

Inhibition (%) of secretion of apolipoprotein B={1−(amount of apolipoprotein B secreted in the presence of test compound)/(amount of apolipoprotein B secreted in the absence of test compound)}×100

For the compounds prepared in Example 5, 99, 102, 104, and 149, the inhibition of secretion of apolipoprotein B and the inhibition of biosynthesis of triglyceride as the results of the tests in Test Examples 1 and 2 described above were as follows.

| Example compound | Inhibition, % | |
|---|---|---|
| | Apolipoprotein B | Triglyceride |
| 5 | 92 | 8 |
| 99 | ≧80 | 11 |
| 102 | 80 | 89 |
| 104 | 84 | 83 |
| 149 | 70 | 74 |

Test 3: Acute Toxicity Test

For the compound prepared in Example 104, an acute toxicity test was carried out using mice and rats according to a conventional method. Specifically, the compound prepared in Example 104 was orally administered to ddY mice (male) and wistar rats (male) at a dose of 200 mg/kg, and these animals were observed for 8 days. As a result, all the animals survived, and, in addition, any change in general conditions, such as a change in weight, did not occur.

What is claimed is:

1. A compound represented by formula (I) or a pharmacologically acceptable salt or solvate thereof:

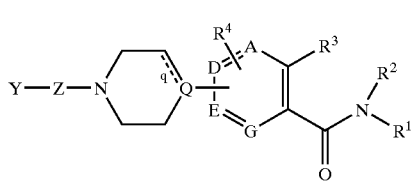

(I)

wherein $R^1$ and $R^2$, which may be the same or different, represent alkyl having 1 to 6 carbon atoms which is optionally substituted by hydroxyl; halogen; amino; alkoxy having 1 to 6 carbon atoms; alkoxycarbonyl having 2 to 5 carbon atoms; $C_{3-8}$ cycloalkyl; phenyl; biphenyl; amino substituted by alkyl having 1 to 6; or five- or six-membered saturated or unsaturated heteroaromatic ring containing one hetero-atom, alkoxy having 1 to 6 carbon atoms which is optionally substituted by hydroxyl; halogen; amino; alkoxy having 1 to 6 carbon atoms; alkoxycarbonyl having 2 to 5 carbon atoms; $C_{3-8}$ cycloalkyl; phenyl; biphenyl; amino substituted by alkyl having 1 to 6; or five- or six-membered saturated or unsaturated heteroaromatic ring containing one hetero-atom, cycloalkyl having 3 to 8 carbon atoms which is optionally substituted by alkyl having 1 to 6 carbon atoms; hydroxyl; halogen atom; amino; alkoxy having 1 to 6 carbon atoms; alkoxycarbonyl having 2 to 5 carbon atoms; $C_{3-8}$ cycloalkyl; phenyl; benzyl; or alkylcarbonyloxy having 2 to 5 carbon atoms, phenyl which is optionally substituted by alkyls having 1 to 6 carbon atoms; hydroxyl; halogen; amino; alkoxy having 1 to 6 carbon atoms; alkylcarbonyl having 2 to 5 carbon atoms; alkoxycarbonyl having 2 to 5 carbon atoms; $C_{3-8}$ cycloalkyl; phenyl; biphenyl; amino substituted by alkyl having 1 to 6; five- or six-membered saturated or unsaturated heteroaromatic ring containing one hetero-atom; trifluoromethyl; or nitro, alkenyl having 2 to 6 carbon atoms which is optionally substituted by hydroxyl; halogen; amino; alkoxy having 1 to 6 carbon atoms; alkoxycarbonyl having 2 to 5 carbon atoms; $C_{3-8}$ cycloalkyl; phenyl; biphenyl; amino substituted by alkyl having 1 to 6; or five- or six-membered saturated or unsaturated heteroaromatic rings containing one hetero-atom, alkynyl having 2 to 6 carbon atoms which is optionally substituted by hydroxyl; halogen; amino; alkoxy having 1 to 6 carbon atoms; alkoxycarbonyl having 2 to 5 carbon atoms; $C_{3-8}$ cycloalkyl; phenyl; biphenyl; amino substituted by alkyl having 1 to 6; or five- or six-membered saturated or unsaturated heteroaromatic rings containing one hetero-atom, or a heterocyclic ring which is selected from pyridine, thiophene, pyrrole, furan, pyrazole, imidazole, oxazole, thiazole, pyran, pyridazine, pyrimidine, pyrazine, and oxane, wherein one of more hydrogen atoms on the ring are optionally subsititeud by alkyls having 1 to 6 carbon atoms; hydroxyl; halogen; amino; alkoxy having 1 to 6 carbon atoms; alkoxycarbonyl having 2 to 5 carbon atoms; $C_{3-8}$ cycloalkyl; and benzyl or $R^1$ and $R^2$, together with a nitrogen atom to which $R^1$ and $R^2$ are attached, may form a piperazine, piperidine, or 3,4-dihydro-1H-isoquinolinone ring where one of more hydrogen atoms on the ring may be substituted by alkyl having 1 to 6 carbon atoms; hydroxyl; halogen; amino; alkoxy having 1 to 6 carbon atoms; alkoxycarbonyl having 2 to 5 carbon atoms; $C_{3-8}$ cycloalkyls; or benzyl;

$R^3$ and $R^4$, which may be the same or different, represent a hydrogen atom, alkyl having 1 to 6 carbon atoms which is optionally substituted by hydroxyl; halogen; amino; alkoxy having 1 to 6 carbon atoms; alkoxycarbonyl having 2 to 5 carbon atoms; $C_{3-8}$ cycloalkyl; phenyl; biphenyl; amino substituted by alkyl having 1 to 6; or five- or six-membered saturated or unsaturated heteroaromatic ring containing one hetero-atom, a halogen atom, hydroxyl, nitrile, alkoxycarbonyl having 2 to 5 carbon atoms, alkoxy having 1 to 6 carbon atoms, or carboxyl, A, D, E, and G each represent a carbon atom, Q represents a nitrogen atom, q represents a single bond;

Y represents a group represented by formula (II):

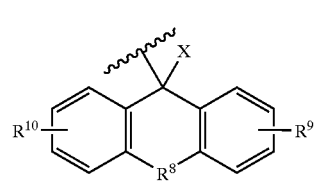

(II)

wherein

X represents a hydrogen atom; group —C(=O)N($R^5$)$R^6$ wherein $R^5$ and $R^6$, which may be the same or different, represent a hydrogen atom, alkyl having 1 to 6 carbon atoms (which is optionally substituted by hydroxyl; halogen; amino; alkoxy having 1 to 6 carbon atoms; alkoxycarbonyl having 2 to 5 carbon atoms; $C_{3-8}$ cycloalkyl; phenyl; biphenyl; amino substituted by alkyl having 1 to 6; or five- or six-membered saturated or unsaturated heteroaromatic ring containing one hetero-atom), cycloalkyl having 3 to 8 carbon atoms (which is optionally substituted by alkyl having 1 to 6 carbon atoms; hydroxyl; halogen atom; amino; alkoxy having 1 to 6 carbon atoms; alkoxycarbonyl having 2 to S carbon atoms; $C_{3-8}$ cycloalkyl; phenyl; benzyl; or alkylcarbonyloxy having 2 to 5 carbon atoms), phenyl (which is optionally substituted by alkyls having 1 to 6 carbon atoms; hydroxyl; halogen; amino; alkoxy having 1 to 6 carbon atoms; alkylcarbonyl having 2 to 5 carbon atoms; alkoxycarbonyl having 2 to 5 carbon atoms; $C_{3-8}$ cycloalkyl; phenyl; biphenyl; amino substituted by alkyl having 1 to 6; five- or six-membered saturated or unsaturated heteroaromatic ring containing one hetero-atom; trifluoromethyl; or nitro), alkenyl having 2 to 6 carbon atoms (which is optionally substituted by hydroxyl; halogen; amino; alkoxy having 1 to 6 carbon atoms; alkoxycarbonyl having 2 to 5 carbon atoms; $C_{3-8}$ cycloalkyl; phenyl; biphenyl; amino substituted by alkyl having 1 to 6; or five- or six-membered saturated or unsaturated heteroaromatic rings containing one hetero-atom), or alkynyl having 2 to 6 carbon atoms (which is optionally substituted by hydroxyl; halogen; amino; alkoxy having 1 to 6 carbon atoms; alkoxycarbonyl having 2 to 5 carbon atoms; $C_{3-8}$ cycloalkyl; phenyl; biphenyl; amino substituted by alkyl having 1 to 6; or five- or six-membered saturated or unsaturated heteroaromatic rings containing one hetero-atom); or group —C(=O)OR$^7$ wherein R$^7$ represents a hydrogen atom or alkyl having 1 to 6 carbon atoms (which is optionally substituted by hydroxyl; halogen; amino; alkoxy having 1 to 6 carbon atoms; alkoxycarbonyl having 2 to 5 carbon atoms; $C_{3-8}$ cycloalkyl; phenyl; biphenyl; amino substituted by alkyl having 1 to 6; or five- or six-membered saturated or unsaturated heteroaromatic ring containing one hetero-atom), R$^8$ represents two hydrogen atoms to make the group of formula (II) diphenylmethyl or represents a bond, an oxygen atom, a sulfur atom, —SO$_2$—, —SO—, —CH$_2$—CH$_2$—, or —CH=CH—, and R$^9$ and R$^{10}$, which may be the same or different, represent a hydrogen atom, alkyl having 1 to 6 carbon atoms (which is optionally substituted by hydroxyl; halogen; amino; alkoxy having 1 to 6 carbon atoms; alkoxycarbonyl having 2 to 5 carbon atoms; $C_{3-8}$ cycloalkyl; phenyl; biphenyl; amino substituted by alkyl having 1 to 6; or five- or six-membered saturated or unsaturated heteroaromatic ring containing one hetero-atom), alkoxy having 1 to 6 carbon atoms, a halogen atom, or hydroxyl; and Z represents —(CH$_2$)$_n$—, wherein n is an integer of 0 to 6, —O—(CH$_2$)$_i$—, or —C(=O)NH—(CH$_2$)$_i$— wherein i is an integer of 1 to 6.

2. The compound or pharmacologically acceptable salt or solvate thereof according to claim 1, wherein R$^1$ and R$^2$, which may be the same or different, represent optionally substituted alkyl having 1 to 6 carbon atoms, optionally substituted alkoxy having 1 to 6 carbon atoms, optionally substituted cycloalkyl having 3 to 8 carbon atoms, optionally substituted phenyl, optionally substituted alkenyl having 2 to 6 carbon atoms, alkynyl having 2 to 6 carbon atoms, or an optionally substituted five- or six-membered saturated or unsaturated heterocyclic ring containing not more than two hetero-atoms, or R$^1$ and R$^2$, together with a nitrogen atom to which R$^1$ and R$^2$ are attached, may form a five- or six-membered monocyclic ring which may further contain one hetero-atom or may be substituted or an eight- to ten-membered condensed ring which may further contain one hetero-atom or may be substituted;

R$^3$ and R$^4$, which may be the same or different, represent a hydrogen atom, optionally substituted alkyl having 1 to 6 carbon atoms, a halogen atom, hydroxyl, nitrile, alkoxycarbonyl having 2 to 5 carbon atoms, alkoxy having 1 to 6 carbon atoms, or carboxyl, A, D, E, and G each represent a carbon atom, Q represents a nitrogen atom, q represents a single bond;

Y represents a group represented by formula (II) wherein X represents a hydrogen atom, group —C(=O)N(R$^5$)R$^6$ wherein R$^5$ and R$^6$, which may be the same or different, represent a hydrogen atom, optionally substituted alkyl having 1 to 6 carbon atoms, optionally substituted cycloalkyl having 3 to 8 carbon atoms, optionally substituted phenyl, optionally substituted alkenyl having 2 to 6 carbon atoms, or alkynyl having 2 to 6 carbon atoms, or group —C(=O)OR$^7$ wherein R$^7$ represents a hydrogen atom or optionally substituted alkyl having 1 to 6 carbon atoms; R$^8$ is absent or represents a bond, an oxygen atom, a sulfur atom, —SO$_2$—, —SO—, —CH$_2$—CH$_2$—, or —CH=CH—; and R$^9$ and R$^{10}$, which may be the same or different, represent a hydrogen atom, optionally substituted alkyl having 1 to 6 carbon atoms, alkoxy having 1 to 6 carbon atoms, a halogen atom, or hydroxyl; and Z represents —(CH$_2$)$_n$— wherein n is an integer of 0 to 6.

3. The compound or pharmacologically acceptable salt or solvate thereof according to claim 1, wherein R$^1$ and R$^2$, which may be the same or different, represent optionally substituted alkyl having 1 to 6 carbon atoms, optionally substituted alkoxy having 1 to 6 carbon atoms, optionally substituted cycloalkyl having 3 to 8 carbon atoms, optionally substituted phenyl, optionally substituted alkenyl having 2 to 6 carbon atoms, alkynyl having 2 to 6 carbon atoms, or an optionally substituted five- or six-membered saturated or unsaturated heterocyclic ring containing not more than two hetero-atoms, or R$^1$ and R$^2$, together with a nitrogen atom to which R$^1$ and R$^2$ are attached, may form a five- or six-membered monocyclic ring which may further contain one hetero-atom or may be substituted or an eight- to ten-membered condensed ring which may further contain one hetero-atom or may be substituted;

$R^3$ and $R^4$, which may be the same or different, represent
a hydrogen atom,
optionally substituted alkyl having 1 to 6 carbon atoms,
a halogen atom,
hydroxyl,
nitrile,
alkoxycarbonyl having 2 to 5 carbon atoms,
alkoxy having 1 to 6 carbon atoms, or
carboxyl;
A, D, E, and G each represent a carbon atom,
Q represents a nitrogen atom,
q represents a single bond;
Y represents a group represented by formula (II) wherein
  X represents group —C(=O)N($R^5$)$R^6$ wherein $R^5$ and $R^6$, which may be the same or different, represent a hydrogen atom, optionally substituted alkyl having 1 to 6 carbon atoms, optionally substituted cycloalkyl having 3 to 8 carbon atoms, optionally substituted phenyl, optionally substituted alkenyl having 2 to 6 carbon atoms, or alkynyl having 2 to 6 carbon atoms; $R^8$ represents a bond, an oxygen atom, a sulfur atom, —$SO_2$—, —SO—, —$CH_2$—$CH_2$—, or —CH=CH—; and $R^9$ and $R^{10}$, which may be the same or different, represent a hydrogen atom, optionally substituted alkyl having 1 to 6 carbon atoms, alkoxy having 1 to 6 carbon atoms, a halogen atom, or hydroxyl; and
  Z represents —$(CH_2)_n$— wherein n is an integer of 0 to 6.

4. The compound or pharmacologically acceptable salt or solvate thereof according to claim 1, wherein
$R^1$ and $R^2$, which may be the same or different, represent
optionally substituted alkyl having 1 to 6 carbon atoms,
optionally substituted alkoxy having 1 to 6 carbon atoms,
optionally substituted cycloalkyl having 3 to 8 carbon atoms,
optionally substituted phenyl,
optionally substituted alkenyl having 2 to 6 carbon atoms,
alkynyl having 2 to 6 carbon atoms, or
an optionally substituted five- or six-membered saturated or unsaturated heterocyclic ring containing not more than two hetero-atoms, or
$R^1$ and $R^2$, together with a nitrogen atom to which $R^1$ and $R^2$ are attached, may form a five- or six-membered monocyclic ring which may further contain one hetero-atom or may be substituted or an eight- to ten-membered condensed ring which may further contain one hetero-atom or may be substituted;
$R^3$ and $R^4$, which may be the same or different, represent
a hydrogen atom,
optionally substituted alkyl having 1 to 6 carbon atoms,
a halogen atom,
hydroxyl,
nitrile,
alkoxycarbonyl having 2 to 5 carbon atoms,
alkoxy having 1 to 6 carbon atoms, or
carboxyl;
A, D, E, and G each represent a carbon atom,
Q represents a nitrogen atom,
q represents a single bond;
Y represents a group represented by formula (II) wherein
  X represents a hydrogen atom; $R^8$ is absent; $R^9$ and $R^{10}$, which may be the same or different, represent a hydrogen atom, optionally substituted alkyl having 1 to 6 carbon atoms, alkoxy having 1 to 6 carbon atoms, a halogen atom, or hydroxyl; and
  Z represents —$(CH_2)_n$— wherein n is an integer of 0 to 6.

5. The compound or pharmacologically acceptable salt or solvate thereof according to claim 1, wherein
$R^1$ and $R^2$, which may be the same or different, represent
optionally substituted alkyl having 1 to 6 carbon atoms,
alkoxy,
optionally substituted cycloalkyl having 3 to 8 carbon atoms,
optionally substituted phenyl,
optionally substituted alkenyl having 2 to 6 carbon atoms,
alkynyl having 2 to 6 carbon atoms, or
$R^1$ and $R^2$, together with a nitrogen atom to which $R^1$ and $R^2$ are attached, may form a five- or six-membered monocyclic ring which may further contain one hetero-atom or may be substituted or an eight- to ten-membered condensed ring which may further contain one hetero-atom or may be substituted;
$R^3$ and $R^4$, which may be the same or different, represent
a hydrogen atom,
optionally substituted alkyl having 1 to 6 carbon atoms,
a halogen atom,
hydroxyl,
nitrile,
alkoxycarbonyl having 2 to 5 carbon atoms,
alkoxy having 1 to 6 carbon atoms, or
carboxyl, or
A, D, E, and G each represent a carbon atom,
Q represents a nitrogen atom,
q represents a single bond;
Y represents a group represented by formula (II) wherein
  X represents a hydrogen atom, group —C(=O)N($R^5$)$R^6$ wherein $R^5$ and $R^6$, which may be the same or different, represent a hydrogen atom, optionally substituted alkyl having 1 to 6 carbon atoms, or group —C(=O)O$R^7$ wherein $R^7$ represents a hydrogen atom or alkyl having 1 to 6 carbon atoms; $R^8$ is absent or represents a bond or an oxygen atom; and $R^9$ and $R^{10}$, which may be the same or different, represent a hydrogen atom or a halogen atom; and
  Z represents —$(CH_2)_n$— wherein n is an integer of 0 to 6.

6. A pharmaceutical composition comprising an effective amount of the compound according to claim 1 or a pharmacologically acceptable salt or solvate thereof in combination with a pharmacologically acceptable carrier.

7. A method for inhibiting the secretion of an apolipoprotein B-containing lipoprotein, comprising the step of administering an effective amount of the compound according to claim 1 or a pharmacologically acceptable salt or solvate thereof to an animal including a human.

8. A method for inhibiting the biosynthesis of triglycerides, comprising the step of administering an effective amount of the compound according to claim 1 or a pharmacologically acceptable salt or solvate thereof to an animal including a human.

9. A method for or treating hyperlipidemia, comprising the step of administering an effective amount of the compound according to claim 1 or a pharmacologically acceptable salt or solvate thereof to an animal including a human.

10. A method for or treating arteriosclerotic diseases, comprising the step of administering an effective amount of the compound according to claim 1 or a pharmacologically acceptable salt or solvate thereof to an animal including a human.

11. A method for treating pancreatitis, comprising the step of administering an effective amount of the compound according to claim 1 or a pharmacologically acceptable salt or solvate thereof to an animal including a human.

12. A compound represented by formula (III) or a pharmacologically acceptable salt or solvate thereof:

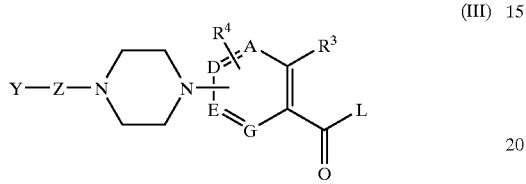

(III)

wherein $R^3$ and $R^4$, which may be the same or different, represent a hydrogen atom,
alkyl having 1 to 6 carbon atoms which is optionally substituted by hydroxyl; halogen; amino; alkoxy having 1 to 6 carbon atoms; alkoxycarbonyl having 2 to 5 carbon atoms; $C_{3-8}$ cycloalkyl; phenyl; biphenyl; amino substituted by alkyl having 1 to 6; or five- or six-membered saturated or unsaturated heteroaromatic ring containing one hetero-atom,
a halogen atom,
hydroxyl,
nitrile,
alkoxycarbonyl having 2 to 5 carbon atoms,
alkoxy having 1 to 6 carbon atoms, or
carboxyl,
A, D, E, and G each represent a carbon atom,
L represents group —O—$R^{11}$ wherein $R^{11}$ represents a hydrogen atom or alkyl having 1 to 6 carbon atoms,
Y represents a group represented by formula (II):

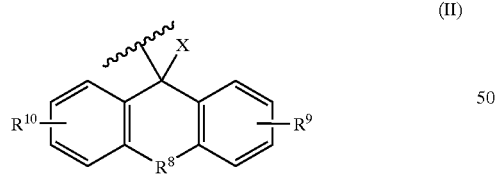

(II)

wherein

X represents a hydrogen atom, group —C(=O)N($R^5$)$R^6$ wherein $R^5$ and $R^6$, which may be the same or different, represent a hydrogen atom, alkyl having 1 to 6 carbon atoms (which is optionally substituted by hydroxyl; halogen; amino; alkoxy having 1 to 6 carbon atoms; alkoxycarbonyl having 2 to 5 carbon atoms; $C_{3-8}$ cycloalkyl; phenyl; biphenyl; amino substituted by alkyl having 1 to 6; or five- or six-membered saturated or unsaturated heteroaromatic ring containing one hetero-atom), cycloalkyl having 3 to 8 carbon atoms (which is optionally substituted by alkyl having 1 to 6 carbon atoms; hydroxyl; halogen atom; amino; alkoxy having 1 to 6 carbon atoms; alkoxycarbonyl having 2 to 5 carbon atoms; $C_{3-8}$ cycloalkyl; phenyl; benzyl; or alkylcarbonyloxy having 2 to 5 carbon atoms), phenyl (which is optionally substituted by alkyls having 1 to 6 carbon atoms; hydroxyl; halogen; amino; alkoxy having 1 to 6 carbon atoms; alkylcarbonyl having 2 to 5 carbon atoms; alkoxycarbonyl having 2 to 5 carbon atoms; $C_{3-8}$ cycloalkyl; phenyl; biphenyl; amino substituted by alkyl having 1 to 6; five- or six-membered saturated or unsaturated heteroaromatic ring containing one hetero-atom; trifluoromethyl; or nitro), alkenyl having 2 to 6 carbon atoms (which is optionally substituted by hydroxyl; halogen; amino; alkoxy having 1 to 6 carbon atoms; alkoxycarbonyl having 2 to 5 carbon atoms; $C_{3-8}$ cycloalkyl; phenyl; biphenyl; amino substituted by alkyl having 1 to 6; or five- or six-membered saturated or unsaturated heteroaromatic rings containing one hetero-atom), or alkynyl having 2 to 6 carbon atoms (which is optionally substituted by hydroxyl; halogen; amino; alkoxy having 1 to 6 carbon atoms; alkoxycarbonyl having 2 to 5 carbon atoms; $C_{3-8}$ cycloalkyl; phenyl; biphenyl; amino substituted by alkyl having 1 to 6; or five- or six-membered saturated or unsaturated heteroaromatic rings containing one hetero-atom), or group —C(=O)O$R^7$ wherein $R^7$ represents a hydrogen atom or alkyl having 1 to 6 carbon atoms (which is optionally substituted by hydroxyl; halogen; amino; alkoxy having 1 to 6 carbon atoms; alkoxycarbonyl having 2 to 5 carbon atoms; $C_{3-8}$ cycloalkyl; phenyl; biphenyl; amino substituted by alkyl having 1 to 6; or five- or six-membered saturated or unsaturated heteroaromatic ring containing one hetero-atom), $R^8$ represents two hydrogen atoms to make the group of formula (II) diphenylmethyl or represents a bond, an oxygen atom, a sulfur atom, —$SO_2$—, —SO—, —$CH_2$—$CH_2$—, or —CH=CH—, and $R^9$ and $R^{10}$, which may be the same or different, represent a hydrogen atom, alkyl having 1 to 6 carbon atoms (which is optionally substituted by hydroxyl; halogen; amino; alkoxy having 1 to 6 carbon atoms; alkoxycarbonyl having 2 to 5 carbon atoms; $C_{3-8}$ cycloalkyl; phenyl; biphenyl; amino substituted by alkyl having 1 to 6; or five- or six-membered saturated or unsaturated heteroaromatic ring containing one hetero-atom), alkoxy having 1 to 6 carbon atoms, a halogen atom, or hydroxyl, and Z represents —$(CH_2)_n$—, wherein n is an integer of 0 to 6, —O—$(CH_2)_i$—, or —C(=O)NH—$(CH_2)_i$— wherein i is an integer of 1 to 6.

13. A method for producing a pharmaceutical composition, which comprises mixing a compound of claim 1 or a pharmaceutically acceptable salt or solvate thereof with a pharmaceutically acceptable carrier.

* * * * *